(12) United States Patent
Moseley et al.

(10) Patent No.: US 11,224,637 B2
(45) Date of Patent: Jan. 18, 2022

(54) METHODS FOR TREATING HYPOPHOSPHATASIA (HPP) IN ADULTS AND ADOLESCENTS

(71) Applicant: Alexion Pharmaceuticals, Inc., Boston, MA (US)

(72) Inventors: Scott Edward Moseley, Arlington, MA (US); Andrew E. Denker, Boston, MA (US); Wei-Jian Pan, Boston, MA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 208 days.

(21) Appl. No.: 16/498,143

(22) PCT Filed: Mar. 29, 2018

(86) PCT No.: PCT/US2018/025206
§ 371 (c)(1),
(2) Date: Sep. 26, 2019

(87) PCT Pub. No.: WO2018/183720
PCT Pub. Date: Oct. 4, 2018

(65) Prior Publication Data
US 2020/0101141 A1 Apr. 2, 2020

Related U.S. Application Data

(60) Provisional application No. 62/480,213, filed on Mar. 31, 2017, provisional application No. 62/502,255, filed on May 5, 2017, provisional application No. 62/643,953, filed on Mar. 16, 2018.

(51) Int. Cl.
| | |
|---|---|
| *C12N 9/16* | (2006.01) |
| *A61K 38/46* | (2006.01) |
| *A61P 19/08* | (2006.01) |
| *A61K 9/00* | (2006.01) |
| *A61K 47/02* | (2006.01) |

(52) U.S. Cl.
CPC .......... *A61K 38/465* (2013.01); *A61K 9/0019* (2013.01); *A61K 47/02* (2013.01); *A61P 19/08* (2018.01); *C12N 9/16* (2013.01); *C12Y 301/03001* (2013.01)

(58) Field of Classification Search
CPC .. A61P 19/00; A61P 19/08; C12Y 301/03001; C12N 9/00; C12N 9/16
See application file for complete search history.

(56) References Cited

U.S. PATENT DOCUMENTS

| | | | |
|---|---|---|---|
| 5,336,759 A | 8/1994 | Matsuo et al. | |
| 5,338,830 A | 8/1994 | Matsuo et al. | |
| 5,340,920 A | 8/1994 | Matsuo et al. | |
| 5,352,770 A | 10/1994 | Matsuo | |
| 5,428,130 A | 6/1995 | Capon et al. | |
| 5,434,133 A | 7/1995 | Tanaka et al. | |
| 5,583,108 A | 12/1996 | Wei et al. | |
| 5,665,704 A | 9/1997 | Lowe et al. | |
| 5,714,147 A | 2/1998 | Capon et al. | |
| 5,767,239 A | 6/1998 | Immer et al. | |
| 5,846,932 A | 12/1998 | Lowe et al. | |
| 5,948,761 A | 9/1999 | Seilhamer et al. | |
| 5,973,134 A | 10/1999 | Matsuo et al. | |
| 6,020,168 A | 2/2000 | Matsuo et al. | |
| 6,028,055 A | 2/2000 | Lowe et al. | |
| 6,034,231 A | 3/2000 | Tanaka et al. | |
| 6,290,952 B1 | 9/2001 | Poelstra et al. | |
| 6,406,697 B1 | 6/2002 | Capon et al. | |
| 6,407,211 B1 | 6/2002 | Burnett, Jr. et al. | |
| 6,420,384 B2 | 7/2002 | Weigele et al. | |
| 6,436,386 B1 | 8/2002 | Roberts et al. | |
| 6,455,495 B1 | 9/2002 | Orgel et al. | |
| 6,458,579 B2 | 10/2002 | Hopwood et al. | |
| 6,525,022 B1 | 2/2003 | Lowe et al. | |
| 6,541,610 B1 | 4/2003 | Smith | |
| 6,743,425 B2 | 6/2004 | Nakao | |
| 6,790,649 B1 | 9/2004 | Crine et al. | |
| 6,818,619 B2 | 11/2004 | Burnett, Jr. et al. | |
| 6,830,885 B1 | 12/2004 | Lanctot et al. | |
| 6,849,714 B1 | 2/2005 | Bridon et al. | |
| 6,887,470 B1 | 5/2005 | Bridon et al. | |
| 6,905,689 B2 | 6/2005 | Schneidinger et al. | |
| 6,946,484 B2 | 9/2005 | Adams et al. | |

(Continued)

FOREIGN PATENT DOCUMENTS

| | | |
|---|---|---|
| EP | 0478797 B1 | 4/1995 |
| EP | 0769554 A2 | 4/1997 |

(Continued)

OTHER PUBLICATIONS

Strensiq, 2015a. World wide web at globalgenes.org/2015/11/05/alexion-announces-fda-approval-for-strensiq/?gclid=CjwKCAjwwqaGBhBKEiwAMk-FtFQOKvuVN-WmNcDVyu9Q9X3f6QB-V0Two0x216TR2H4_Qc6jSlhvxoCiLMQAvD_BwE. One page.*

(Continued)

*Primary Examiner* — Karen Cochrane Carlson
(74) *Attorney, Agent, or Firm* — Clark & Elbing LLP

(57) ABSTRACT

The disclosure features methods for treating hypophosphatasia (HPP) in a patient (e.g., an adult having HPP, such as an adult having pediatric-onset HPP, or an adolescent having HPP) exhibiting decreased pyrophosphate (PPi) or pyridoxal 5'-phosphate (PLP) concentrations in, e.g., a plasma sample, physical impairments, or decreased walking ability by administering a soluble alkaline phosphatase (sALP) to the patient.

20 Claims, 23 Drawing Sheets
Specification includes a Sequence Listing.

(56) References Cited

U.S. PATENT DOCUMENTS

| | | | |
|---|---|---|---|
| 7,026,293 B2 | 4/2006 | Kitakaze | |
| 7,033,997 B2 | 4/2006 | Forssmann et al. | |
| 7,070,974 B1 | 7/2006 | Desgroseillers et al. | |
| 7,105,539 B2 | 9/2006 | Gravel et al. | |
| 7,179,903 B2 | 2/2007 | McArthur et al. | |
| 7,256,253 B2 | 8/2007 | Bridon et al. | |
| 7,271,149 B2 | 9/2007 | Glaesner et al. | |
| 7,276,481 B2 | 10/2007 | Golembo et al. | |
| 7,341,838 B2 | 3/2008 | Buechler et al. | |
| 7,365,091 B2 | 4/2008 | Gravel et al. | |
| 7,384,917 B2 | 6/2008 | Burnett, Jr. et al. | |
| 7,399,466 B2 | 7/2008 | Boileau | |
| 7,414,107 B2 | 8/2008 | Larsen | |
| 7,425,531 B2 | 9/2008 | Lanctot et al. | |
| 7,427,498 B2 | 9/2008 | Crine et al. | |
| 7,470,668 B2 | 12/2008 | Lanctot et al. | |
| 7,488,713 B2 | 2/2009 | Vesely | |
| 7,527,939 B2 | 5/2009 | Davey et al. | |
| 7,563,769 B2 | 7/2009 | Bogin et al. | |
| 7,625,564 B2 | 12/2009 | Wang et al. | |
| 7,642,243 B2 | 1/2010 | Nakao et al. | |
| 7,648,962 B2 | 1/2010 | James et al. | |
| 7,662,773 B2 | 2/2010 | James et al. | |
| 7,678,391 B2 | 3/2010 | Graham et al. | |
| 7,732,406 B2 | 6/2010 | Mitrovic et al. | |
| 7,736,653 B2 | 6/2010 | Kim et al. | |
| 7,754,852 B2 | 7/2010 | Burnett, Jr. et al. | |
| 7,763,712 B2 | 7/2010 | Crine et al. | |
| 7,803,769 B2 | 9/2010 | Sullivan et al. | |
| 7,803,901 B2 | 9/2010 | Burnett, Jr. et al. | |
| 7,825,092 B2 | 11/2010 | Vesely | |
| 7,846,900 B2 | 12/2010 | Vesely | |
| 7,858,560 B2 | 12/2010 | Koster et al. | |
| 7,919,591 B2 | 4/2011 | Sheffer et al. | |
| 7,943,126 B2 | 5/2011 | Tomatsu et al. | |
| 7,960,529 B2 | 6/2011 | Crine et al. | |
| 8,058,242 B2 | 11/2011 | Alewood et al. | |
| 8,691,208 B2 | 4/2014 | Tomatsu et al. | |
| 9,266,939 B2 | 2/2016 | Crine et al. | |
| 9,908,932 B2 | 3/2018 | Malanson et al. | |
| 9,988,620 B2 | 6/2018 | Crine et al. | |
| 10,000,532 B2 | 6/2018 | Crine et al. | |
| 10,052,366 B2 | 8/2018 | Crine et al. | |
| 10,449,236 B2 | 10/2019 | Marozsan et al. | |
| 10,603,361 B2 * | 3/2020 | Odrljin | A61K 38/465 |
| 2002/0183276 A1 | 12/2002 | Millan et al. | |
| 2003/0158132 A1 | 8/2003 | Kovesdi | |
| 2004/0023916 A1 | 2/2004 | Millan et al. | |
| 2004/0077537 A1 | 4/2004 | Schreiner | |
| 2004/0234518 A1 | 11/2004 | Crine et al. | |
| 2005/0113286 A1 | 5/2005 | Schreiner et al. | |
| 2005/0142217 A1 | 6/2005 | Adams et al. | |
| 2005/0202442 A1 | 9/2005 | Morris et al. | |
| 2005/0244904 A1 | 11/2005 | Ng | |
| 2005/0276796 A1 | 12/2005 | Tomatsu et al. | |
| 2006/0014687 A1 | 1/2006 | Crine et al. | |
| 2006/0019890 A1 | 1/2006 | Kapoun et al. | |
| 2006/0074009 A1 | 4/2006 | James et al. | |
| 2006/0110359 A1 | 5/2006 | Sanchez-Ramos et al. | |
| 2006/0172929 A1 | 8/2006 | Rappold-Hoerbrand et al. | |
| 2006/0228710 A1 | 10/2006 | Morris et al. | |
| 2007/0041972 A1 | 2/2007 | Rother et al. | |
| 2007/0042957 A1 | 2/2007 | Burnett et al. | |
| 2007/0081984 A1 | 4/2007 | Tomatsu et al. | |
| 2007/0081986 A1 | 4/2007 | Tomatsu et al. | |
| 2007/0197434 A1 | 8/2007 | Nakao et al. | |
| 2007/0281887 A1 | 12/2007 | Pan | |
| 2007/0292966 A1 | 12/2007 | Prickett et al. | |
| 2007/0293418 A1 | 12/2007 | Larsen | |
| 2008/0032933 A1 | 2/2008 | Burnett et al. | |
| 2008/0081768 A1 | 4/2008 | Watt et al. | |
| 2008/0085862 A1 | 4/2008 | Kim et al. | |
| 2008/0113411 A1 | 5/2008 | Sheffer et al. | |
| 2008/0113412 A1 | 5/2008 | Sheffer et al. | |
| 2008/0125574 A1 | 5/2008 | Sheffer et al. | |
| 2008/0153747 A1 | 6/2008 | Alewood et al. | |
| 2008/0161243 A1 | 7/2008 | Rosen et al. | |
| 2008/0181903 A1 | 7/2008 | Bhaskar et al. | |
| 2008/0182299 A1 | 7/2008 | Colocaru et al. | |
| 2008/0194481 A1 | 8/2008 | Rosen et al. | |
| 2008/0194682 A1 | 8/2008 | Golembo et al. | |
| 2008/0227713 A1 | 9/2008 | Protter | |
| 2008/0293632 A1 | 11/2008 | Rappold-Hoerbrand et al. | |
| 2008/0312142 A1 | 12/2008 | Nakao et al. | |
| 2009/0011997 A1 | 1/2009 | Peri et al. | |
| 2009/0023652 A1 | 1/2009 | Bell et al. | |
| 2009/0053192 A1 | 2/2009 | Millan et al. | |
| 2009/0069243 A1 | 3/2009 | Burnett, Jr. et al. | |
| 2009/0092582 A1 | 4/2009 | Bogin et al. | |
| 2009/0142347 A1 | 6/2009 | Millan | |
| 2009/0170756 A1 | 7/2009 | Burnett, Jr. et al. | |
| 2009/0221803 A1 | 9/2009 | Dall'Acqua et al. | |
| 2009/0238814 A1 | 9/2009 | Tomatsu et al. | |
| 2009/0240031 A1 | 9/2009 | Immer et al. | |
| 2009/0247462 A1 | 10/2009 | Bogin et al. | |
| 2009/0252729 A1 | 10/2009 | Farrington et al. | |
| 2009/0258018 A1 | 10/2009 | Medich et al. | |
| 2009/0275506 A1 | 11/2009 | Bakis et al. | |
| 2009/0325195 A1 | 12/2009 | Davey et al. | |
| 2010/0008979 A1 | 1/2010 | Tomatsu et al. | |
| 2010/0055150 A1 | 3/2010 | Golembo et al. | |
| 2010/0093678 A1 | 4/2010 | Della-Fera et al. | |
| 2010/0160212 A1 | 6/2010 | Sheffer et al. | |
| 2010/0168443 A1 | 7/2010 | Geysen | |
| 2010/0184680 A1 | 7/2010 | Bevec | |
| 2010/0197574 A1 | 8/2010 | Chen et al. | |
| 2010/0204094 A1 | 8/2010 | Simari et al. | |
| 2010/0204109 A1 | 8/2010 | Bevec | |
| 2010/0204446 A1 | 8/2010 | Forssmann | |
| 2010/0209958 A1 | 8/2010 | Nakao et al. | |
| 2010/0216714 A1 | 8/2010 | James et al. | |
| 2010/0221234 A1 | 9/2010 | Crine et al. | |
| 2010/0240125 A1 | 9/2010 | Crine et al. | |
| 2010/0249017 A1 | 9/2010 | Bevec et al. | |
| 2010/0260706 A1 | 10/2010 | Bogin et al. | |
| 2010/0261248 A1 | 10/2010 | Kim et al. | |
| 2010/0297021 A1 | 11/2010 | Wendt et al. | |
| 2010/0297119 A1 * | 11/2010 | Crine | A61P 1/02 424/134.1 |
| 2010/0305031 A1 | 12/2010 | Wakabayashi et al. | |
| 2010/0305051 A1 | 12/2010 | Burnett, Jr. et al. | |
| 2010/0310561 A1 | 12/2010 | Canada et al. | |
| 2010/0311660 A1 | 12/2010 | Simari et al. | |
| 2010/0317600 A1 | 12/2010 | Immer et al. | |
| 2010/0331256 A1 | 12/2010 | Wendt et al. | |
| 2011/0152194 A1 | 6/2011 | Burnett, Jr. et al. | |
| 2011/0250187 A1 | 10/2011 | Tomatsu et al. | |
| 2011/0269684 A1 | 11/2011 | Burnett, Jr. et al. | |
| 2011/0300143 A1 | 12/2011 | Sly et al. | |
| 2012/0088771 A1 | 4/2012 | Millan | |
| 2012/0164142 A1 | 6/2012 | Crine et al. | |
| 2013/0108635 A1 | 5/2013 | Crine et al. | |
| 2013/0323244 A1 | 12/2013 | Crine et al. | |
| 2014/0193388 A1 | 7/2014 | Velders et al. | |
| 2014/0194484 A1 | 7/2014 | Coats et al. | |
| 2015/0353633 A1 | 12/2015 | Kakkis et al. | |
| 2016/0052968 A1 | 2/2016 | Crine et al. | |
| 2016/0097100 A1 | 4/2016 | Trent et al. | |
| 2017/0175094 A1 | 6/2017 | Hatch | |
| 2017/0360899 A1 | 12/2017 | Marozsan et al. | |
| 2018/0230445 A1 | 8/2018 | Jaluria et al. | |

FOREIGN PATENT DOCUMENTS

| | | |
|---|---|---|
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1502604 A1 | 2/2005 |
| EP | 1623994 A2 | 2/2006 |
| EP | 1759710 A1 | 3/2007 |

(56) References Cited

FOREIGN PATENT DOCUMENTS

| | | |
|---|---|---|
| EP | 0771875 B1 | 2/2008 |
| EP | 1985697 A1 | 10/2008 |
| EP | 1759001 B1 | 4/2011 |
| EP | 2158319 B1 | 12/2011 |
| JP | H08-70875 A | 3/1996 |
| JP | 2000-327583 A | 11/2000 |
| JP | 2002-541776 A | 12/2002 |
| JP | 2007-511209 A | 5/2007 |
| JP | 2007-537725 A | 12/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| JP | 2015-502336 A | 1/2015 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/087802 A2 | 9/2005 |
| WO | WO-2005/094890 A1 | 10/2005 |
| WO | WO-2005/098490 A1 | 10/2005 |
| WO | WO-2005/103263 A1 | 11/2005 |
| WO | WO-2005/105156 A1 | 11/2005 |
| WO | WO-2005/110435 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2007/130113 A2 | 11/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/015011 A1 | 1/2009 |
| WO | WO-2009/023270 A2 | 2/2009 |
| WO | WO-2009/006732 A9 | 3/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A2 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/130229 A1 | 10/2011 |
| WO | WO-2011/134084 A1 | 11/2011 |
| WO | WO-2012/088608 A1 | 7/2012 |
| WO | WO-2012/099851 A2 | 7/2012 |
| WO | WO-2013/059491 A1 | 4/2013 |
| WO | WO-2013/058833 A1 | 4/2013 |
| WO | WO-2013/071262 A1 | 5/2013 |
| WO | WO-2015/112015 A1 | 7/2015 |
| WO | WO-2015/112017 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2016/153191 A1 | 9/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |
| WO | WO-2018/164995 A1 | 9/2018 |

OTHER PUBLICATIONS

Strinsiq, 2015b; European Medicines Agency. www.ema.europa.eu/en/medicines/human/EPAR/strensiq. pp. 1-8.*
Millan et al. 2016; Alkaline phosphatase and hypophosphatasia. Calcif. Tissue. Int. 98:398-416.*
ClinicalTrials.gov. 2008; NCT00739505, pp. 1-8.*
ClinicalTrials.gov. 2010; NCT01163149, pp. 1-8.*
Kishnani et al. 2019; Five-year efficacy and safety of asfotase alfa therapy for adults and adolescents with hypophosphatasia. Bone . 121: 149-162.*
Williams et al., "Solute transport in growth plate cartilage: In vitro and in vivo," Biophys J. 93(3):1039-1050 (2007).
Yasoda et al., "Systemic administration of C-type natriuretic peptide as a novel therapeutic strategy for skeletal dysplasias," Endocrinology. 150(7):3138-3144 (2009).
Potter et al., "Natriuretic peptides, their receptors, and cyclic guanosine monophosphate-dependent signaling functions," Endocr Rev. 27(1):47-72 (2006).

(56) References Cited

OTHER PUBLICATIONS

Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol Cell Physiol. 270:C1311-18 (1996) (9 pages).
Suda et al., "C-type natriuretic peptide as an autocrine/paracrine regulator of osteoblast: evidence for possible presence of bone natriuretic peptide system," Biochem Biophys Res Commun. 223:1-6(1996).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Mericq et al., "Regulation of fetal rat bone growth by C-type natriuretic peptide and cGMP," Pediatr Res. 47(2):189-193 (2000) (9 pages).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
Kalra et al., "The role of C-type natriuretic peptide in cardiovascular medicine," Eur Heart J. 22:997-1007 (2001).
Pfeifer et al., "Intestinal secretory defects and dwarfism in mice lacking cGMP-dependent protein kinase II," Science. 274:2082-2086 (1996).
Chusho et al., "Dwarfism and early death in mice lacking C-type natriuretic peptide," Proc Natl Acad Sci USA. 98(7):4016-4021 (2001).
Yoder et al., "Reduced ability of C-type natriuretic peptide (CNP) to activate natriuretic peptide receptor B (NPR-B) causes dwarfism in lbab$^{-/-}$ mice," Peptides. 29(9):1575-1581 (2008).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Tamura et al., "Critical roles of the guanylyl cyclase B receptor in endochondral ossification and development of female reproductive organs," Proc Natl Acad Sci USA. 101(49): 17300-17305 (2004).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Miyazawa et al., "Cyclic GMP-dependent protein kinase II plays a critical role in C-type natriuretic peptide-mediated endochondral ossification," Endocrinology. 143(9):3604-3610 (2002).
Teixeira et al., "Nitric oxide, C-type natriuretic peptide and cGMP as regulators of endochondral ossification," Dev Biol. 319:171-178 (2008).
Horton et al., "Achondroplasia," Lancet. 370:162-72 (2007).
Nakao et al., "The pharmacokinetics of alpha-human atrial natriuretic polypeptide in healthy subjects," Eur J Clin Pharmacol. 31:101-103 (1986).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Cleland et al., "Emerging protein delivery methods," Curr Opin Biotechnol. 12:212-219 (2001).
Guo et al., "Protein tolerance to random amino acid change," Proc Natl Acad Sci USA. 101(25):9205-9210 (2004).
Hardy et al., "Dissection of a carboxy-terminal region of the yeast regulatory protein RAP1 with effects on both transcriptional activation and silencing," Mol Cell Biol. 12(3):1209-1217 (1992).
Hult et al., "Engineered enzymes for improved organic synthesis," Curr Opin Biotechnol. 14:395-400 (2003).
Tomatsu, Declaration Under 37 C.F.R. § 1.132 for U.S. Appl. No. 11/484,870, dated Nov. 27, 2007 (2 pages).

Inoue et al., "Four functionally distinct C-type natriuretic peptides found in fish reveal evolutionary history of the natriuretic peptide system," Proc Natl Acad Sci USA. 100(17):10079-10084 (2003).
Furuya et al., "Structural requirements of C-type natriuretic peptide for elevation of cyclic GMP in cultured vascular smooth muscle cells," Biochem Biophys Res Commun. 183(3):964-969 (1992).
Choe et al., "Substrate profiling of cysteine proteases using a combinatorial peptide library identifies functionally unique specificities," J Biol Chem. 281(18):12824-12832 (2006).
Takano et al., "Molecular evolution of shark C-type natriuretic peptides," Zoolog Sci. 11:451-454 (1994).
Shukla et al., "RNA interference and inhibition of MEK-ERK signaling prevent abnormal skeletal phenotypes in a mouse model of craniosynostosis," Nat Genet. 39(9):1145-1150 (2007).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Lo et al., "High level expression and secretion of Fc-X fusion proteins in mammalian cells," Protein Eng. 11(6):495-500(1998).
Anderson et al., "The role of matrix vesicles in growth plate development and biomineralization," Front Biosci. 10:822-37 (2005).
Anderson et al., "Pyrophosphate stimulation of calcium uptake into cultured embryonic bones. Fine structure of matrix vesicles and their role in calcification," Dev Biol. 34:211-227 (1973).
Beertsen et al., "Root development in mice lacking functional tissue non-specific alkaline phosphatase gene: Inhibition of acellular cementum formation," J Dent Res. 78(6): 1221-1229 (1999) (10 pages).
Bernard, "Ultrastructural localization of alkaline phosphatase in initial intramembranous osteogenesis," Clin Orthop Relat Res. 135:218-225 (1978).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Greenberg et al., "A homoallelic Gly$^{317}$ to Asp mutation in *ALPL* causes the perinatal (lethal) form of hypophosphatasia in Canadian Mennonites," Genomics. 17:215-217 (1993).
Jansonius, "Structure, evolution and action of vitamin B$_6$-dependent enzymes," Curr Opin Struct Biol. 8:759-769 (1998).
Mahmood et al., "Selection of the first-time dose in humans: comparison of different approaches based on interspecies scaling of clearance," J Clin Pharmacol. 43:692-697 (2003).
Morris et al., "Immunolocalization of alkaline phosphatase in osteoblasts and matrix vesicles of human fetal bone," Bone Miner. 19:287-298 (1992).
Bonilla, "Pharmacokinetics of immunoglobulin administered via intravenous or subcutaneous routes," Immunol Allergy Clin N Am. 28:803-819 (2008).
Byers et al., "Effect of enzyme replacement therapy on bone formation in a feline model of mucopolysaccharidosis type VI," Bone. 21(5):425-431 (1997).
Garg, "Investigation of the role of FcRn in the absorption, distribution, and elimination of monoclonal antibodies," Dissertation: State University of New York at Buffalo, 2007 (Abstract only) (2 pages).
Kochendoerfer, "Protein & Peptide Drug Delivery—Third International Conference: Minimally invasive delivery methods, Sep. 22-23, Philadelphia, PA, USA," IDrugs. 6(11):1043-5 (2003).
Wang et al., "Structure-based chemical modification strategy for enzyme replacement treatment of phenylketonuria," Mol Genet Metab. 86:134-140 (2005).
Zierhut et al., "Population PK-PD model for Fc-osteoprotegerin in healthy postmenopausal women," J Pharmacokinet Pharmacodyn. 35:379-399 (2008).
Engel et al., "Characterization of the hormone binding site of natriuretic peptide receptor-C," FEBS Lett. 360:169-172 (1995).
Jin et al., "Novel analog of atrial natriuretic peptide selective for receptor-A produces increased diuresis and natriuresis in rats," J Clin Invest. 98(4):969-976 (1996).
Tye et al., "Delineation of the hydroxyapatite-nucleating domains of bone sialoprotein," J Biol Chem. 278(10):7949-7955 (2003).

(56) References Cited

OTHER PUBLICATIONS

Kostenuik et al., "Infrequent delivery of a long-acting PTH-Fc fusion protein has potent anabolic effects on cortical and cancellous bone," J Bone Miner Res. 22(10):1534-1547 (2007).
Bennett et al., "Extracellular domain-IgG fusion proteins for three human natriuretic peptide receptors," J Biol Chem. 266(34):23060-23067 (1991).
Ali et al., "Isolation and characterization of calcifying matrix vesicles from epiphyseal cartilage," Proc Natl Acad Sci USA. 67(3):1513-20 (1970).
Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Harmey et al., "Elevated skeletal osteopontin levels contribute to the hypophosphatasia phenotype in $Akp2^{-/-}$ mice," J Bone Miner Res. 21 (9):1377-1386 (2006).
Harmey et al., "Concerted regulation of inorganic pyrophosphate and osteopontin by *Akp2, Enpp1,* and *Ank,*" Am J Pathol. 164(4):1199-1209 (2004).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glycoprotein-1 are central antagonistic regulators of bone mineralization," Proc Natl Acad Sci USA. 99(14): 9445-9449 (2002).
Johnson et al., "Matrix vesicle plasma cell membrane glycoprotein-1 regulates mineralization by murine osteoblastic MC3T3 cells," J Bone Miner Res. 14(6):883-892 (1999).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
Nosjean et al., "Human tissue non-specific alkaline phosphatases: sugar-moiety-induced enzymatic and antigenic modulations and genetic aspects," Biochem J. 321:297-303 (1997).
Urlaub et al., "Deletion of the diploid dihydrofolate reductase locus from cultured mammalian cells," Cell. 33:405-412 (1983).
Weiss et al., "A missense mutation in the human liver/bone/kidney alkaline phosphatase gene causing a lethal form of hypophosphatasia," Proc Natl Acad Sci USA. 85:7666-7669 (1988).
Whyte et al., "Markedly increased circulating pyridoxal-5'-phosphate levels in hypophosphatasia," J Clin Invest. 76:752-756 (1985).
Zurutuza et al., "Correlations of genotype and phenotype in hypophosphatasia," Hum Mol Genet. 8(6):1039-1046 (1999).
NCBI Protein Database Accession No. P09487. Retrieved on Apr. 16, 2013 (4 pages).
NCBI Protein Database Accession No. Q29486. Retrieved on Apr. 16, 2013 (3 pages).
NCBI Protein Database Accession No. P09242. Retrieved on Apr. 16, 2013 (6 pages).
NCBI Protein Database Accession No. P08289. Retrieved on Apr. 16, 2013 (5 pages).
NCBI Protein Database Accession No. Q9N0V0. Retrieved on Apr. 16, 2013 (1 page).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. P05187. Retrieved on Apr. 16, 2013 (10 pages).
NCBI Protein Database Accession No. P05186. Retrieved on Apr. 16, 2013 (19 pages).
NCBI Protein Database Accession No. NP_112603. Retrieved on Apr. 16, 2013 (3 pages).
NCBI Protein Database Accession No. NP_001623. Retrieved on Apr. 16, 2013 (3 pages).
NCBI Protein Database Accession No. NP_000469. Retrieved on Apr. 16, 2013 (3 pages).
NCBI Protein Database Accession No. AAI10910. Retrieved on Apr. 16, 2013 (2 pages).
NCBI Protein Database Accession No. AAH90861. Retrieved on Apr. 16, 2013 (2 pages).
NCBI Protein Database Accession No. AAH66116. Retrieved on Apr. 16, 2013 (2 pages).
NCBI Protein Database Accession No. AAH21289, <www.ncbi.nlm.nih.gov/protein/AAH21289>, retrieved Apr. 16, 2013 (2 pages).
NCBI Protein Database Accession No. AAI26166. Retrieved on Apr. 16, 2013 (2 pages).
NCBI Protein Database Accession No. AAF64516, <www.ncbi.nlm.nih.gov/protein/AAF64516>, retrieved Apr. 16, 2013 (2 pages).
NCBI Protein Database Accession No. AAN64273. Retrieved on Apr. 16, 2013 (1 page).
NCBI Protein Database Accession No. AAI18209. Retrieved on Apr. 17, 2013 (2 pages).
NCBI Protein Database Accession No. AAC33858, <www.ncbi.nlm.nih.gov/protein/AAC33858>, retrieved Apr. 16, 2013 (1 page).
NCBI Protein Database Accession No. NP 001036028. Retrieved on Apr. 16, 2013 (2 pages).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Wang et al., "A mouse model for achondroplasia produced by targeting fibroblast growth factor receptor 3," Proc Natl Acad Sci USA. 96:4455-4460 (1999).
Clemens et al., "Pharmacokinetics and biological actions of subcutaneously administered human brain natriuretic peptide," J Pharmacol Exp Ther. 287(1):67-71 (1998).
Cameron et al., "Minireview: Natriuretic peptides during development of the fetal heart and circulation," Endocrinology. 144(6):2191-2194 (2003).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
Altarescu et al., "The efficacy of enzyme replacement therapy in patients with chronic neuronopathic Gaucher's disease," J Pediatr. 138(4):539-547 (2001).
Boskey, "Amorphous calcium phosphate: The contention of bone," J Dent Res. 76:1433-1436 (1997).
Furbish et al., "Uptake and distribution of placental glucocerebrosidase in rat hepatic cells and effects of sequential deglycosylation," Biochim Biophys Acta. 673:425-434 (1981).
Leone et al., "Allosteric modulation of pyrophosphatase activity of rat osseous plate alkaline phosphatase by magnesium ions," Int J Biochem Cell Biol. 30:89-97 (1998).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).

(56) References Cited

OTHER PUBLICATIONS

Moss et al., "Association of inorganic-pyrophosphatase activity with human alkaline-phosphatase preparations," Biochem J. 102:53-57 (1967).
Murray, "Lectin-specific targeting of lysosomal enzymes to reticuloendothelial cells," Methods Enzymol. 149:25-42 (1987).
Narisawa et al., "Inactivation of two mouse alkaline phosphatase genes and establishment of a model of infantile hypophosphatasia," Dev Dyn. 208:432-446 (1997).
Narisawa et al., "Abnormal vitamin B6 metabolism in alkaline phosphatase knock-out mice causes multiple abnormalities, but not the impaired bone mineralization," J Pathol. 193:125-133 (2001).
Russell et al., "Inorganic pyrophosphate in plasma in normal persons and in patients with hypophosphatasia, osteogenesis imperfecta, and other disorders of bone," J Clin Invest. 50:961-969 (1971).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Bobé et al., "Fas-mediated liver damage in MRL hemopoietic chimeras undergoing lpr-mediated graft-versus-host disease," J Immunol. 159:4197-4204 (1997).
Data Sheet for pFUSE-SEAP-hFC "Plasmid designed for the expression of a SEAP-Fc Fusion protein," Invivogen, San Diego, CA (4 pages) (1989).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Hailing Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).
Hunter et al., "Modulation of crystal formation by bone phosphoproteins: structural specificity of the osteopontin-mediated inhibition of hydroxyapatite formation," Biochem J. 300:723-728 (1994).
Kasugai et al., "Selective drug delivery system to bone: small peptide $(Asp)_6$ conjugation," J Bone Miner Res. 15(5):936-943 (2000).
Rowe et al., "MEPE, a new gene expressed in bone marrow and tumors causing osteomalacia," Genomics. 67:54-68 (2000).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Symersky et al., "Structure of the collagen-binding domain from a *Staphylococcus aureus* adhesin," Nat Struct Biol. 4(10):833-838 (1997).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
NCBI Protein Database Accession No. XP_001109717. Retrieved on Apr. 17, 2013 (1 page).
Wang et al., "Mice lacking Nf1 in osteochondroprogenitor cells display skeletal dysplasia similar to patients with neurofibromatosis type 1," Hum Mol Genet. 20(20):3910-3924 (2011).
Addison et al., "Pyrophosphate inhibits mineralization of osteoblast cultures by binding to mineral, up-regulating osteopontin, and inhibiting alkaline phosphatase activity," J Biol Chem. 282(21):15872-83 (2007).
Ikezawa, "Glycosylphosphatidylinositol (GPI)-anchored proteins," Biol Pharm Bull. 25(4):409-17 (2002).
Murshed et al., "Unique coexpression in osteoblasts of broadly expressed genes accounts for the spatial restriction of ECM mineralization to bone," Genes Dev. 19:1093-1104 (2005).
Nishioka et al., "Enhancement of drug delivery to bone: characterization of human tissue-nonspecific alkaline phosphatase tagged with an acidic oligopeptide," Mol Genet Metab. 88:244-255 (2006).
Rezende et al., "Inorganic pyrophosphate-phosphohydrolytic activity associated with rat osseous plate alkaline phosphatase," Cell Mol Biol. 44(2):293-302 (1998).
Weninger et al., "Biochemical and morphological effects of human hepatic alkaline phosphatase in a neonate with hypophosphatasia," Acta Paediatr Scand. Suppl. 360:154-160 (1989).
Whyte, "Hypophosphatasia and the role of alkaline phosphatase in skeletal mineralization," Endocr Rev. 15(4):439-461 (1994).
Meyer, "Can biological calcification occur in the presence of pyrophosphate?" Arch Biochem Biophys. 231(1):1-8 (1984).
Yasoda et al., "Overexpression of CNP in chondrocytes rescues achondroplasia through a MAPK-dependent pathway," Nat Med. 10(1):80-86 (2004).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
NCBI Protein Database Accession No. Q6PYX1. Retrieved on Oct. 15, 2013 (2 pages).
Yadav et al., "Dose response of bone-targeted enzyme replacement for murine hypophosphatasia," available in PMC Aug. 1, 2012, published in final edited form as: Bone. 49(2):250-6 (2011) (20 pages).
EBI Blast for Accession No. ATD17216. Entered Oct. 16, 2008 (1 page).
Siris et al., "Paget's disease of bone," Trends Endocrinol Metab. 2(6):207-12 (1991).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (1 page) (Abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int. 60(3):309-15 (1997).
Ciancaglini et al., "Contribution of matrix vesicles and alkaline phosphatase to ectopic bone formation," Braz J Med Biol Res. 39(5):603-10 (2006).
Crawley et al., "Enzyme replacement therapy in a feline model of Maroteaux-Lamy syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).

(56) References Cited

OTHER PUBLICATIONS

Eng et al., "Safety and efficacy of recombinant human alpha-galactosidase A replacement therapy in Fabry's disease," N Engl J Med. 345(1):9-16 (2001).

Gilbert et al., "Chimeric peptides of statherin and osteopontin that bind hydroxyapatite and mediate cell adhesion," J Biol Chem. 275(21):16213-8 (2000).

Henthorn et al., "Missense mutations of the tissue-nonspecific alkaline phosphatase gene in hypophosphatasia," Clin Chem. 38(12):2501-5 (1992).

Hosain et al., "Targeted delivery of antineoplastic agent to bone: biodistribution studies of technetium-99m-labeled gem-bisphosphonate conjugate of methotrexate," J Nucl Med. 37(1):105-7 (1996).

Kakkis et al., "Enzyme-replacement therapy in mucopolysaccharidosis I," N Engl J Med. 344(3):182-8 (2001).

Kaufmann et al., "Influence of low temperature on productivity, proteome and protein phosphorylation of CHO cells," Biotechnol Bioeng. 63(5):573-82 (1999).

Millán et al., "Enzyme replacement therapy for murine hypophosphatasia," J Bone Miner Res. 23(6):777-87 (2008).

Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).

Pedersen et al., "Removal of N-terminal polyhistidine tags from recombinant proteins using engineered aminopeptidases," Protein Expr Purif. 15(3):389-400 (1999).

Salih et al., "Identification of the phosphorylated sites of metabolically $^{32}$P-labeled osteopontin from cultured chicken osteoblasts," J Biol Chem. 272(21):13966-73 (1997).

Sands et al., "Enzyme replacement therapy for murine mucopolysaccharidosis type VII," J Clin Invest. 93(6):2324-31 (1994).

Sekido et al., "Novel drug delivery system to bone using acidic oligopeptide: pharmacokinetic characteristics and pharmacological potential," J Drug Target. 9(2):111-21 (2001).

Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).

Tomatsu, Declaration Under 37 C.F.R. § 1.132 for U.S. Appl. No. 11/484,870, dated Jun. 1, 2009 (3 pages).

Uludag et al., "Bone affinity of a bisphosphonate-conjugated protein in vivo," Biotechnol Prog. 16(6):1115-8 (2000).

Waymire et al., "Mice lacking tissue non-specific alkaline phosphatase die from seizures due to defective metabolism of vitamin B-6," Nat Genet. 11(1):45-51 (1995).

Weinberg, "An overview of infliximab, etanercept, efalizumab, and alefacept as biologic therapy for psoriasis," Clin Ther. 25(10):2487-505 (2003).

Weiss et al., "Isolation and characterization of a cDNA encoding a human liver/bone/kidney-type alkaline phosphatase," Proc Natl Acad Sci USA. 83(19):7182-6 (1986) (6 pages).

Weiss et al., "Structure of the human liver/bone/kidney alkaline phosphatase gene," J Biol Chem. 263(24):12002-10 (1988).

Whyte et al., "Infantile hypophosphatasia: enzyme replacement therapy by intravenous infusion of alkaline phosphatase-rich plasma from patients with Paget bone disease," J Pediatr. 101(3):379-86 (1982).

Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).

Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).

Whyte, "Hypophosphatasia," in The Metabolic and Molecular Bases of Inherited Disease (8th ed.), pp. 5313-5329, 2001 (McGraw-Hill Book Company) (epub pp. 1-41).

Whyte et al., "Marrow cell transplantation for infantile hypophosphatasia," J Bone Miner Res. 18(4):624-36 (2003).

Yamamoto et al., "Prolonged survival and phenotypic correction of $Akp2^{-/-}$ hypophosphatasia mice by lentiviral gene therapy," J Bone Miner Res. 26(1):135-42 (2011).

Harris, "The human alkaline phosphatases: what we know and what we don't know," Clin Chim Acta. 186:133-50 (1989).

Orimo, "The mechanism of mineralization and the role of alkaline phosphatase in health and disease," J Nippon Med Sch. 77(1):4-12 (2010).

Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).

Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).

Alexion Pharma International, "Product Monograph, Including Patient Medication Information. Strensiq™ (asfotase alfa), Solution for Injection 40 mg/mL & 100 mg/mL," <alexionpharma.ca/documents/Strensiq-PM-asfotase-alfa-14Aug2015.aspx>, prepared Aug. 14, 2015 (32 pages).

Graham et al., "Characteristics of a human cell line transformed by DNA from human adenovirus type 5," J Gen Virol. 36(1):59-72 (1977).

Mather, "Establishment and characterization of two distinct mouse testicular epithelial cell lines," Biol Reprod. 23(1):243-52 (1980).

Urlaub et al., "Isolation of Chinese hamster cell mutants deficient in dihydrofolate reductase activity," Proc Natl Acad Sci U S A. 77(7):4216-20 (1980).

Madson et al., "Asfotase alfa: sustained efficacy and tolerability in children with hypophosphatasia treated for 5 years," ESPE Abstracts. 84:FC2.4 (2015) (2 pages).

Center for Drug Evaluation and Research, "Application No. 125513Orig1s000," <www.accessdata.fda.gov/drugsatfda_docs/nda/2015/125513Orig1s000MedR.pdf>, review completed Oct. 20, 2015; retrieved on Jun. 1, 2016 (254 pages).

Skolnick et al., "From genes to protein structure and function: novel applications of computational approaches in the genomic era," Trends Biotechnol. 18(1):34-9 (2000).

Nahabet et al., "Postnatal pancraniosynostosis in a patient with infantile hypophosphatasia," Cleft Palate Craniofac J. 53(6):741-4, doi: 10.1597/15-027 (2016).

Srinivas et al., "Assessment of dose proportionality, absolute bioavailability, and immunogenicity response of CTLA4lg (BMS-188667), a novel immunosuppressive agent, following subcutaneous and intravenous administration to rats," Pharm Res. 14(7):911-6 (1997).

De la Croix Ndong et al., "Asfotase-alpha improves bone growth, mineralization and strength in mouse models of neurofibromatosis type-1," Nat Med. 20(8):904-10 (2014) (10 pages).

Ratner, "Alexion pays big for Synageva's rare disease drug candidate," Nat Biotechnol. 33(7):679 (2015).

Highlights of Prescribing Information for Strensiq™ (asfotase alfa) Injection, Alexion Pharmaceuticals, Inc., <www.alexion.com/Documents/strensiq_pi-10-2015.aspx> (2015) (19 pages).

"View of NCT02235493 on 2015_11_19," ClinicalTrials.gov archive, updated Nov. 19, 2015, retrieved Jan. 27, 2017 (4 pages).

Epps, "Application No. 125513Orig1s000 Medical Review(s)," Center for Drug Evaluation and Research, <www.accessdata.fda.gov/drugsatfda_docs/nda/2015/125513Orig1s000MedR.pdf>, Oct. 20, 2015 (254 pages).

Whyte et al., "Enzyme-replacement therapy in life-threatening hypophosphatasia," N Engl J Med. 366(10):904-13 (2012).

Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).

(56) References Cited

OTHER PUBLICATIONS

Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Millán et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).
Park et al., "Ex vivo assessment of contractility, fatigability and alternans in isolated skeletal muscles," J Vis Exp. 69:e4198 (2012) (8 pages).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Li et al., "Standard reference for the six-minute-walk test in healthy children aged 7 to 16 years," Am J Respir Crit Care Med. 176(2):174-80 (2007).
Matsumoto et al., "Rescue of severe infantile hypophosphatasia mice by AAV-mediated sustained expression of soluble alkaline phosphatase," Hum Gene Ther. 22(11):1355-64 (2011).
Hofmann et al., "Clinical aspects of hypophosphatasia: an update," Clinic Rev Bone Miner Metab. 11(2):60-70 (2013).
Taketani et al., "Clinical and genetic aspects of hypophosphatasia in Japanese patients," Arch Dis Child. 99(3):211-5 (2014) (6 pages).
Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts," J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)-->Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).
Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).
Sawai et al., "Severe perinatal hypophosphatasia due to homozygous deletion of T at nucleotide 1559 in the tissue nonspecific alkaline phosphatase gene," Prenat Diagn. 23(9):743-6 (2003).
Wickramasinghe et al., "A case of hypophosphatasia," Ceylon Med J. 48(3):94-5 (2003) (2 pages).
Yamamoto et al., "A successful treatment with pyridoxal phosphate for West syndrome in hypophosphatasia," Pediatr Neurol. 30(3):216-8 (2004).
Millán et al., "Hypophosphatasia—pathophysiology and treatment," available in PMC Sep. 22, 2014, published in final edited form as: Actual Osteol. 8(3):164-182 (2012) (21 pages).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research, www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2016).
Bloch-Zupan, "Hypophosphatasia: diagnosis and clinical signs—a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).
Güzel Nur et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl-/-mice by administration of soluble (non-targeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26):1003-1007 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Bare). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).
Mornet et al., "Hypophosphatasia," GeneReviews. www.ncbi.nlm.nih.gov/books/NBK1150/, retrieved Dec. 6, 2017, initially published Nov. 20, 2007, last updated Feb. 4, 2016 (25 pages).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).
Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).

(56) References Cited

OTHER PUBLICATIONS

Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Whyte, "Physiological role of alkaline phosphatase explored in hypophosphatasia," Ann N Y Acad Sci. 1192:190-200 (2010).
Hofmann et al., "Compound heterozygosity of two functional null mutations in the ALPL gene associated with deleterious neurological outcome in an infant with hypophosphatasia," Bone. 55:150-7 (2013).
Alexion Third Quarter 2017 Earnings Call, "files.shareholder.com/downloads/ALXN/5636824573x0x961197/3B361D6E-80E2-463E-B0E5-3EAD7FC5B9D0/Alexion_Q3_2017_Earnings_Slides.pdf" (43 pages).
Stec et al., "A revised mechanism for the alkaline phosphatase reaction involving three metal ions," J Mol Biol. 299(5):1303-11 (2000).
Alexion, "Highlights of Prescribing Information" for Strensiq®, 2018 (8 pages).
UniProtKB Accession No. P05186. Retrieved May 2, 2018 (19 pages).
UniProtKB Accession No. P01857. Retrieved May 2, 2018 (13 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," *Neuronal Tissue-Nonespecific Alkaline Phosphatase (TNAP): Subcellular Biochemistry*. Caroline Fonta and Laszlo Negyessy, 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).

Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in *ALPL* and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of *ALPL* in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL (1 page).
Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).

(56) References Cited

OTHER PUBLICATIONS

Lazdunski et al., "Structure-function relationships for some metalloalkaline phosphatases of *E. coli*" Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
Sugano et al., "Successful gene therapy *in utero* for lethal murine hypophosphatasia," Hum Gene Ther. 23(4):399-406 (2012).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
"Sequence 4," SCORE Search Results for U.S. Appl. No. 12/599,679, retrieved Nov. 17, 2018 (2 pages).
Anderson et al., "Impaired calcification around matrix vesicles of growth plate and bone in alkaline phosphatase-deficient mice," Am J Pathol. 164(3):841-7 (2004).
Attwood, "The Babel of Bioinformatics," Science. 290(5491):471-3 (2000).
Barranger et al., "Lessons learned from the development of enzyme therapy for Gaucher disease," J Inherit Metab Dis. 24(Suppl. 2):89-96 (2001).
Campbell et al., "Insulin-like growth factor (IGF)-binding protein-5-(201-218) region regulates hydroxyapatite and IGF-I binding," Am J Physiol Endocrinol Metab. 273:E1005-1013 (1997).
Declaration of Dr. Philippe Crine for European Patent Application No. 08757088.3, executed Jan. 14, 2011 (6 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Salzburg, Austria. Bone Abstracts. 4:OC18 (2015) (3 pages).
Mayer, "Chapter 4: Immunoglobulins: Structure and Function," *Microbiology and Immunology On-line*, University of South Carolina School of Medicine, <pathmicro.med.sc.edu/mayer/IgStruct2000.htm> (2009) (12 pages).
Millán, *Mammalian Alkaline Phosphatases: From Biology to Applications in Medicine and Biotechnology*, Wiley-VCH Verlag GmbH & Co., Weinheim, Germany (2006) (324 pages).
Millan, Chapter 7: The in vivo role of TNAP. Mammalian alkaline phosphatases: From Biology to Applications in Medicine and Biotechnology. Wiley-VCH Verlag GmbH & Co., 107-185 (2006).
NCBI Protein Database Accession No. NP_001253798, Retrieved on Apr. 17, 2013 (2 pages).
Ngo et al., Chapter 14: Computational Complexity, Protein Structure Prediction, and the Levinthal Paradox. *The Protein Folding Problem and Tertiary Structure Prediction*. Merz et al. (eds.), 433, 492-495 (1994).
Oikawa et al., "Enzyme replacement therapy on hypophosphatasia mouse model," J Inherit Metab Dis. 37(2):309-17 (2013).
Patti et al., "Critical residues in the ligand-binding site of the *Staphylococcus aureus* collagen-binding adhesin (MSCRAMM)," J Biol Chem. 270(20):12005-11 (1995).
Phillips et al., "A modified performance-oriented mobility assessment tool for assessing clinically relevant gait impairments and change in children with hypophosphatasia: development and validation," 7th International Conference on Children's Bone Health, Jun. 27-30, Salzburg, Austria. Bone Abstracts. 4:P136 (2015) (2 pages).
Phillips et al., "Gait assessment in children with childhood hypophosphatasia: impairments in muscle strength and physical function," The Endocrine Society's 97th Annual Meeting & Expo, Mar. 5-8, San Diego, California. Poster LBS-039 (2015) (2 pages).
Whyte, Chapter 207: Hypophosphatasia. *The Online Metabolic and Molecular Bases for Inherited Disease*. McGraw-Hill Book Company, Valle et al. (eds.) (2001) (41 pages).
Whyte, Chapter 18: Heritable Forms of Rickets and Osteomalacia. *Connective Tissue and Its Heritable Disorders*. Wiley-Liss, Inc., eds. R.M. Royce and B. Steinmann, 765-87 (2002).
Whyte, "Chapter 70: Hypophosphatasia: Nature's window on alkaline phosphatase function in man," *Principles of Bone Biology*, 2nd ed., Bilezikian, Raisz, and Rodan. 2:1229-1248 (2002).
Wroblewski et al., "Pharmacokinetics, metabolic stability, and subcutaneous bioavailability of a genetically engineered analog of DcR3, FLINT [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009) (2 pages).
Le Du et al., "Crystal structure of alkaline phosphatase from human placenta at 1.8 Å resolution. Implication for a substrate specificity," J Biol CheM. 276(12):9158-65 (2001) (9 pages).
European Collection of Authenticated Cell Cultures (ECACC), General Cell Collection: NS0, Catalogue No. 85110503. Retrieved May 2, 2018 (3 pages).
Belkhouribchia et al., "Osteomalacia with low alkaline phosphatase: a not so rare condition with important consequences," BMJ Case Rep, doi: 10.1136/bcr-2015-212827 (2016) (4 pages).
Buchet et al., "Chapter 3: Multisystemic functions of alkaline phosphatases," *Phosphatase Modulators, Methods in Molecular Biology*, vol. 1053. José Luis Millán (ed.), 27-51 (2013).
Sather, "Case Study: 3 year old female with hypophosphatasia, treated with asfotase alfa replacement," J Pediatr Nurs. 34:104 (Abstract 008) (2017) (1 page).
De Roo et al., "Infantile hypophosphatasia without bone deformities presenting with severe pyridoxine-resistant seizures," Mol Genet Metab. 111 (3):404-7 (2014).
Phillips et al., "Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, Mar. 5-8, San Diego, California. Poster Abstract FRI-224 (2015) (1 page).
National Institute for Health and Care Excellence, "Highly Specialised Technology Evaluation: Asfotase alfa for treating paediatric-onset hypophosphatasia [ID 758]," Oct. 21, 2015, <www.nice.org.uk/guidance/hst6/documents/committee-papers-8> (99 pages).
Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <abstracts.eurospe.org/hrp/0086/hrp0086FC2.5.htm> (2016) (4 pages).
Agochukwu et al., "Hearing loss in syndromic craniosynostoses: Introduction and consideration of mechanisms," available in PMC Aug. 13, 2014, published in final edited form as: Am J Audiol. 23(2):135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).
Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigi et al., "Pyridoxine-responsive seizures as the first symptom of infantile hypophosphatasia caused by two novel missense mutations (c.677T>C, p. M226T; c.1112C>T, p. T371I) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).

(56) References Cited

OTHER PUBLICATIONS

Boulet et al., "A population-based study of craniosynostosis in metropolitan Atlanta, 1989-2003," Am J Med Genet A. 146A(8): 984-91 (2008).
Chan et al., "Endoscope-assisted versus open repair of craniosynostosis: a comparison of perioperative cost and risk," J Craniofac Surg. 24(1):170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3(Suppl 3):S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugía. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-9 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: Craniosynostosis," BBA Clin. 6:165-76 (2016).
Khanna et al., "Pictorial essay: the many faces of craniosynostosis," Indian J Radiol J. 21 (1 ):49-56 (2011).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976) (15 pages).
Krakow et al., "Clinical and radiographic delineation of bent bone dysplasia-FGFR2 type or bent bone dysplasia with distinctive clavicles and angel-shaped phalanges," Am J Med Genet A. 170(10):2652-61 (2016).

Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring-assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with *FGFR3 P250R* mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c.1559delT in *ALPL*, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).

(56) References Cited

OTHER PUBLICATIONS

Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology, vol. 1, Third Edition*. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices In: Recognizing and Diagnosing Hypophosphatasia," Clinical Endocrinology News. <www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: A Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Dortschy et al., "Bevölkerungsbezogene verteilungswerte ausgewählter laborparameter aus der studie zur gesundheit von kindern und jugendlichen in Deutschland (KiGGS)," Gesundheitsberichterstattung des Bundes, Robert Koch Institute (2009) (136 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).
Di Rocco et al., "Craniosynostosis and hypophosphatasia," Arch Pediatr. 24(5S2):5S89-5S92 (2017).
Whyte et al., "Natural history of perinatal and infantile hypophosphatasia: a retrospective study," J Pediatr. 209:116-124.e4 (2019) (13 pages).
Leung et al., "Outcome of perinatal hypophosphatasia in manitoba mennonites: a retrospective cohort analysis," JIMP Rep. 11:73-78 (2013).
Taketani et al., Chapter 9: Hypophosphatasia. *Human Pathobiochemistry*. T. Oohashi et al. (eds.), 91-100 (2019).
Morrison et al., "Mitigation of tracheobronchomalacia with 3D-printed personalized medical devices in pediatric patients," available in PMC Apr. 29, 2016, published in final edited form as: Sci Transl Med. 7(285):285ra264 (2015) (23 pages).
Whyte et al., "Asfotase alfa for infants and young children with hypophosphatasia: 7 year outcomes of a single-arm, open-label, phase 2 extension trial," Lancet Diabetes Endocrinol. 7(2):93-105 (2019) (52 pages).
Mornet, "The tissue nonspecific alkaline phosphatase gene mutations database," <www.sesep.uvsq.fr/03_hypo_mutations.php>, last updated Nov. 28, 2019 (14 pages).
Hancarova et al., "Hypophosphatasia due to uniparental disomy," Bone. 81:765-766 (2015).
Carden et al., "Tracheomalacia and tracheobronchomalacia in children and adults: an in-depth review," Chest. 127(3):984-1005 (2005).
Murgu et al., "Tracheobronchomalacia and excessive dynamic airway collapse," Respirology. 11(4):388-406 (2006).
Whyte et al., "Hypophosphatasia (HPP) in Children: Enzyme Replacement Therapy (EzRT) Using Bone-Targeted, Tissue-Nonspecific Alkaline Phosphatase (TNSALP)," Ann Neurol. 68(Suppl 14):S70 Abstract WIP-28 (2010) (1 page).
Park et al. "The effect of alendronate loaded biphasic calcium phosphate scaffolds on bone regeneration in a rat tibial defect model," Int J Mol Sci. 16(11):26738-53 (2015) (17 pages).
Li et al. "Timing of the initiation of bisphosphonates after surgery for fracture healing: a systematic review and meta-analysis of randomized controlled trials," Osteoporos Int. 26(2):431-41 (2015) (11 pages).
International Search Report and Written Opinion for International Application No. PCT/US2019/045963, dated Jan. 30, 2020 (26 pages).
Rodionova et al., "Hypophosphatasia in adults: clinical cases and literature review," Osteoporosis and Bone Diseases. 18(2):25-7 (2015) (4 pages).
Search Report and Translation for Russian Application No. 2018109368, dated Feb. 5, 2020 (4 pages).
Wang et al. "The effects of tissue-non-specific alkaline phosphatase gene therapy on craniosynostosis and craniofacial morphology in the FGFR2$^{C342Y/+}$ mouse model of Crouzon craniosynostosis," Orthod Craniofac Res. 18 Suppl. 1(01):196-206 (2015).
Abrams et al., "Calcium and Vitamin D Requirements of Enterally Fed Preterm Infants," Pediatrics. 131(5): e1676-e1683 (2013) (9 pages).
Kishnani et al., "Hypophosphatasia: enzyme replacement therapy (ENB-0040) decreases TNSALP substrate accumulation and improves functional outcome in affected adolescents and adults," Endocrine Society's 15th International & 14th European Congress of Endocrinology, May 5-9, Florence, Italy. Abstract OC8.1 (2012) (4 pages).
Notice of Reasons for Rejection for Japanese Application No. 2018-508754, dated Jun. 30, 2020 (11 pages).
Phillips et al., "Gait Assessment in Children with Childhood Hypophosphatasia: Impairments in Muscle Strength and Physical Function," The Endocrine Society's 97th Annual Meeting & Expo, Mar. 5-8, San Diego, CA (2015) (2 pages).
Office Action for European Patent Application No. 16739617.5, dated May 11, 2020 (10 pages).
Office Action for Russian Patent Application No. 2018137822, dated Jul. 24, 2020 (20 pages).
Bishop et al., "Life-threatening hypophosphatasia (HPP): Results of up to two years bone-targeted Enzyme Replacement Therapy (ERT) in infants and young children," Bone. 48:S82 (2011).
Kim et al., "Comparison of phenylketonuria (PKU) patients' height, weight and body mass index (BMI) to the general population," Mol Genet Metab. 105:328-329, 2012.
Whyte et al., "Treatment of children with hypophosphatasia (HPP) with ENB-0040: radiographic and DXA outcomes after 6 months of therapy," Horm Res Paediatr. 76(Suppl 2):26 (2011).
Office Action for Japanese Patent Application No. 2018-515934, dated Jul. 28, 2020 (7 pages).
Dbfetch, "Bone targeted alkaline phosphatase, kits and methods of use thereof," Database No. HI520929, last updated Nov. 2, 2010 (1 page).

(56) References Cited

OTHER PUBLICATIONS

Seefried et al., "Long-term Effectiveness of Asfotase Alfa Treatment in Adults with Pediatric-onset Hypophosphatasia in Routine Clinical Practice" 2020 American Society for Bone and Mineral Research Virtual Conference, Sep. 11-15, 2020.
Seefried et al., "Real-world Clinical Profiles of Adults with Hypophosphatasia (HPP) from the Global HPP Registry," The American Society for Bone and Mineral Research 2020 Annual Meeting, Sep. 11-15, virtually (2020).
Seefried et al., "Bone Turnover and Mineral Metabolism in Adult Patients with Pediatric-Onset Hypophosphatasia Treated With Asfotase Alfa," The American Society for Bone and Mineral Research 2020 Annual Meeting, Sep. 11-15, virtually (2020).
Seefried et al., "Long-term Effectiveness of Asfotase Alfa Treatment in Adults with Pediatric-onset Hypophosphatasia in Routine Clinical Practice" 22nd European Congress of Endocrinology, Sep. 5-9, virtual (2020).
Seefried et al., "Bone Turnover and Mineral Metabolism in Adult Patients with Pediatric-Onset Hypophosphatasia Treated With Asfotase Alfa" 2020 World Congress on Osteoporosis, Osteoarthritis, and Muscoloskeletal Diseases, Aug. 20-23, Barcelona, Spain (2020).
"Scale-up of CHO fed-batch cultures in HyClone (TM) ActiPro (TM) medium supplemented with Cell Boost (TM) 7a and 7b," GE Healthcare Bio-Sciences AB, dated Sep. 2016 (4 pages).
Fu-Hang et al., "Preliminary study on the effect of Zn2+ on the activities of peptidase and alkaline phosphatase," Marine Sciences. 27(3):64-65 (2003).
Office Action for Chinese Patent Application No. 201680048588.5, dated Jan. 18, 2021 (28 pages).
Dutta et al., "Men and mice: Relating their ages," Life Sci. 152:244-8 (2015) (5 pages).
Zhang et al., "Engineering *E. coli* Alkaline Phosphatase Yields Changes of Catalytic Activity, Thermal Stability and Phosphate Inhibition," Biocatal Biotransfor. 20(6):381-389 (2002).
Nangia et al., "Disorders of Calcium Metabolism in Newborns," Journal of Neonatology. 17(2):43-49 (2003).
Kochanowski et al., "Medium and feed optimization for fed-batch production of a monoclonal antibody in CHO cells," BMC Proc. 5(Suppl 8):P75 (2011) (3 pages).

"Data file 29-0929-25 AA. Xcellerex™ XDR cell culture bioreactor systems," GE Healthcare Life Sciences, published Feb. 2014 (4 pages).
Yagasaki et al., "Animal Cell Technology: Basic & Applied Aspects," Proceedings of the Fifteenth Annual Meeting of the Japanese Association for Animal Cell Technology (JAACT), vol. 13, Fuchu, Nov. 11-15, 2002 (461 pages).
Kozlenkov et al., "Residues determining the binding specificity of uncompetitive inhibitors to tissue-nonspecific alkaline phosphatase," J Bone Miner Res. 19(11):1862-72 (2004).
NCBI Protein Database Accession No. NM_000478.2, retrieved on Feb. 23, 2021 (7 pages).
Pradhan et al., "Exposure-Response Modeling and Simulation to Support Evaluation of Efficacious and Safe Exposure and Dose Range for Asfotase alfa in Pateints with Hypophosphatasia," ASBMR 2015 Annual Meeting Abstracts. J Bone and Med Res. SU0380:S316 (2015) (1 page).
Abbruzzese, "The Tinetti Performance-Oriented Mobility Assessment Tool," Am J Nursing. 98(12):16J-16L (1998) (3 pages).
International Search Report and Written Opinion for International Patent Application No. PCT/US20/64140, dated Apr. 23, 2021 (70 pages).
Hofmann et al. "Efficacy and safety of asfotase alfa in infants and young children with hypophosphatasia: a phase 2 open-label study," J Clin Endocrinol Metab. 104(7): 2735-2747 (2019) (14 pages).
Examination Report No. 1 for Australian Patent Application No. 2016308624, dated Aug. 27, 2021 (6 pages).
Kim et al., "CHO cells in biotechnology for production of recombinant proteins: current state and further potential," Appl Microbiol Biotechnol. 93(3): 917-30 (2012).
Office Action for Chinese Patent Application No. 201780021666.7, dated Jul. 21, 2021 (34 pages).
McCormack et al., "Is bigger better? An argument for very low starting doses," CMAJ. 183(1):65-9 (2011).
Rush, "Childhood hypophosphatasia: to treat or not to treat," Orphanet J Rare Dis. 13(1):116 (2018) (5 pages).
Phillips et al., "Clinical Outcome Assessments: Use of Normative Data in a Pediatric Rare Disease," Value Health. 21(5):508-514 (2018).

\* cited by examiner

FIG. 17B

| Run-In Period | Week | Sampling Times | Dosing[2] | PK, PPi and PLP | ADA |
|---|---|---|---|---|---|
| | Week -1 | Day -7: -168h, -156h pre-dose<br>Day -1: -24h, -12h pre-dose | NA | PPi and PLP only | NA |
| Single Dose | Week 1 | Day 1: pre=dose; post-dose 6h, 12h | D1 (single-dose) | All | Day 1: pre-dose |
| No Dosing | Week 1 | Day 2: post-D1 dose 24h, 32h, 36h<br>Day 3: pst-D1 dose 48h, 56h, 60h<br>Day 4: post-D1 dose 72h<br>Day 5: post-D1 dose 96h<br>Day 6: post-D1 dose 120h<br>Day 7: post-D1 dose 144h | None | All | |
| No Dosing | Week 2 | Day 8: post-D1 dose 168h<br>Day 11: post-D1 dose 240h | None | All | Day 8: post-D1 dose 168h |
| Weekly Dosing<br>(3 times per week) | Week 3 | Day 15: pre-dose, post-dose 6h | D15, D17, D19 | All | Day 15: pre-dose |
| | Week 4 | Day 22: pre-dose, post-dose 6h | D22, D24, D26 | All | Day 22: pre-dose |
| | Week 5 | Day 29: pre-üose (trough), post-dose 6h | D29, D31, D33 | All | Day 29: pre-dose |
| | Week 6 | None | D36, D38, D40 | None | None |
| | Week 7 | Day 43: pre-dose (trough), post-dose 6h | D43, D45, D47 | All | Day 43: pre-dose |
| | Week 8 | Day 50: pre=dose (trough), post-dose 6h | D50, D52, D54 | All | Day 50: pre-dose |
| | Week 9 | Day 57: pre-dose<br>Day 61: pre-dose (trough), post-dose 6h, 12h<br>Day 62: post-D61 dose 24h, 32h, 36h<br>Day 63: post-D61 dose 48h, 56h, 60h | D57, D59, D61 | All | Day 61: pre-dose |
| No Dosing | Week 10 | Day 64: post-D61 dose 72h<br>Day 65: post-D61 dose 96h<br>Day 66: post-D61 dose 120h<br>Day 67: post-D61 dose 144h<br>Day 68: post-D61 dose 168h | None | All | Day 68: post-D61 dose 168h |
| | Week 11 | Day 71: post-D61 dose 240h<br>Day 75: post-D61 dose 336h | None | All | Day 75: post-D61 dose 336h |
| | Week 12 | Day 80: post-D61 dose 456h | None | All | Day 80: post-D61 dose 456h |
| | Week 13 | Day 87: post-D61 dose 624h | None | All | Day 87: post-D61 dose 624h |

METHODS FOR TREATING HYPOPHOSPHATASIA (HPP) IN ADULTS AND ADOLESCENTS

FIELD

The disclosure features methods for treating hypophosphatasia (HPP).

BACKGROUND

Hypophosphatasia (HPP) is a rare, heritable skeletal disease with an incidence of 1 per 100,000 births for the most severe forms of the disease. The disorder results from loss-of-function mutations in the gene coding for tissue-nonspecific alkaline phosphatase (TNALP). HPP exhibits a remarkable range of symptoms and severity, from rickets to almost complete absence of bone mineralization in utero.

The presentation of HPP varies among patients, and varies between patient age. Most patients having HPP display skeletal changes, short stature, chronic pain, painful lower limbs, gait disturbance, and premature, atraumatic tooth loss. For instance, common symptoms of adults with HPP can include osteomalacia, poorly mineralized bones, elevated blood and/or urine levels of inorganic pyrophosphate (PPi), pyridoxal 5'-phosphate (PLP), or phosphoethanolamine (PEA), hypomineralization, hypercalciuria, short stature, skeletal deformity, waddling gait, bone pain, bone fracture, calcium pyrophosphate dihydrate crystal deposition, arthritis, and pyrophosphate arthropathy. Common symptoms of adolescents with HPP can include elevated blood or urine levels of PPi, PEA, or PLP, osteomalacia, skeletal deformity, hypotonia, muscle weakness, rheumatoid complications, arthritis, pseudogout, waddling gait, ambulatory difficulties, bone pain, pain, premature loss of teeth, hypomineralization, pulmonary hypoplasia, respiratory insufficiency, seizures, hypercalciuria, short stature, and growth delay.

Due to physical impairments associated with HPP, adult patients afflicted with HPP often exhibit decreased walking ability relative to healthy subjects (Weinstein R S, Whyte M P, *Arch Intern Med.* 1981; 141(6): 727-731). Adult HPP patients may suffer from Calcium Pyrophosphate Deposition Disease (CPPD), pseudogout, chondrocalcinosis, calcific periarthritis, vertebral crush fractures, subtrochanteric fractures, metatarsal fractures, and/or pseudofractures (Coe J D, et al., *J Bone Joint Surg Am.* 1986; 68(7):981-990; Sutton, R A L, et al., *J Bone Miner Res.* 2012; 27(5): 987-994). Other symptoms, such as rickets, rachitic ribs, severe hypomineralization, failure to thrive, delayed motor development, inadequate weight gain, pulmonary hypoplasia, respiratory insufficiency, respiratory failure, craniosynostosis (including complications of craniosynostosis), and seizures, occur in young children or in infants with HPP, but not in adults with HPP.

Notably, the efficacy and safety of treatment of HPP, particularly the particular physiological and physical impairments and the decreased walking ability associated with adult and adolescent forms of HPP, with a therapeutic for an extended period of time, is unknown. Thus, there exists a need for methods that can be used to treat and monitor HPP in adult and adolescent patients, for extended durations so that these patients can live with decreased physical and physiological impairments and can regain appropriate levels of walking ability.

SUMMARY

Disclosed are (1) methods to identify adults having HPP (e.g., adults having HPP of about 18 years of age or older, such as adults having pediatric-onset HPP) and/or adolescents having HPP (e.g., adolescents having HPP of about 13 years of age to about 17 years of age) for treatment with a soluble alkaline phosphatase (sALP; e.g., SEQ ID NO: 1), and (2) treatment of such patients with an sALP. Symptoms of adult HPP as defined herein include, e.g., elevated blood and/or urine levels of phosphoethanolamine (PEA), hypomineralization, hypercalciuria, skeletal deformity, waddling gait, bone pain, bone fracture, calcium pyrophosphate dihydrate crystal deposition, arthritis, pyrophosphate arthropathy, chondrocalcinosis, calcific periarthritis, and pseudofracture. Symptoms of adolescent HPP as defined herein include, e.g., elevated blood or urine levels of PPi, PEA, or PLP, osteomalacia, one or more skeletal deformities, hypotonia, muscle weakness, rheumatoid complications, arthritis, pseudogout, waddling gait, ambulatory difficulties, bone pain, pain, premature loss of teeth, hypomineralization, pulmonary hypoplasia, respiratory insufficiency, seizures, hypercalciuria, short stature, and growth delay.

Exemplary metrics useful for evaluating the need for or the efficacy of treatment using an sALP (e.g., SEQ ID NO: 1) include (1) plasma PPi and PLP concentrations, (2) the Six Minute Walk Test (6MWT), (3) the Bruininks-Oseretsky Test of Motor Proficiency $2^{nd}$ Edition (BOT-2), (4) Hand-held Dynamometry (HHD), (5) the Lower Extremity Function Scale (LEFS), and (6) the Brief Pain Inventory-Short Form (BPI-SF). Additional testing and metrics could include the Tinetti Performance Oriented Mobility Assessment (POMA; optionally modified) and temporo-spatial gait analysis software and hardware, such as GAITRITE® (Clinical Image Retrieval System Inc.). The methods further include the use of one or more of the described metrics (e.g., the BOT-2, 6MWT, plasma PPi and PLP concentrations, HHD, LEFS, or BPI-SF) singly or in combination to assess treatment efficacy using an sALP (e.g., SEQ ID NO: 1) for a patient having HPP in which improvements relative to a certain score or value demonstrate that the sALP is effective for treating HPP. In addition, the activity level of ALP in a sample (e.g., a plasma sample) from the patient having HPP may also be used singly or in combination with one or each of these metrics to assess treatment efficacy of the sALP (e.g., SEQ ID NO: 1) for the patient. Additionally, methods further include changing the dosage and/or frequency of sALP (e.g., SEQ ID NO: 1) administration in order to determine the effective amount of the sALP to administer to an adult having HPP (e.g., an adult having pediatric-onset HPP) or an adolescent having HPP.

A first aspect features a method of treating HPP in a pediatric-onset HPP patient of about 18 years of age or older (e.g., a human) characterized as having symptoms of adult HPP, which includes administering an sALP (e.g., SEQ ID NO: 1) to the patient in a treatment regimen providing about 1 mg/kg/week to about 9 mg/kg/week, preferably 6 mg/kg/week, of the sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). Preferably, the adult patient is naïve (i.e., treatment naïve) with respect to treatment with the sALP. In particular, the sALP includes an amino acid sequence having at least 95% sequence identity to the amino acid sequence of SEQ ID NO: 1 (e.g., asfotase alfa). Administration of the sALP (e.g., SEQ ID NO: 1) results in one or more of the following: (i) a statistically significant decrease in PPi concentration in a plasma sample from the patient of at least about 1 μM relative to PPi concentration in a plasma sample from an untreated pediatric-onset HPP subject of about 18 years of age or older; (ii) a statistically significant decrease in PLP concentration in a plasma sample from the patient of at least about 100 ng/ml relative to PLP concentration in a plasma sample from an untreated pediatric-onset HPP subject of about 18 years of age or older; and (iii) a statistically significant increase of at least 50 meters in walking distance of the patient, as assessed by a 6MWT, relative to the walking distance in 6 minutes of the patient without administration. Additionally, there may be an increase in the activity of ALP in a sample (e.g., a plasma sample) after administration of the sALP (e.g., SEQ ID NO: 1).

As a result of the methods, the decrease in PPi concentration in the plasma sample from the patient (e.g., a naïve, pediatric-onset HPP patient of about 18 years of age or older), the decrease in PLP concentration in the plasma sample from the patient, and/or the increase in the walking distance of the patient is sustained during the treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

Prior to administration of the sALP (e.g., SEQ ID NO: 1), the patient (e.g., a naïve, pediatric-onset HPP patient of about 18 years of age or older) may be characterized as having a plasma PPi concentration of up to about 6 μM (e.g., about 3.5 μM, about 4 μM, about 4.5 μM, about 5 μM, or about 5.5 μM or a plasma PPi concentration within the range of about 3.5 μM to about 6 μM), a plasma PLP concentration of up to 1300 ng/ml (e.g., a plasma PLP concentration of about 200 ng/ml, 300 ng/ml, 400 ng/ml, 500 ng/ml, 600 ng/ml, 700 ng/ml, 800 ng/ml, 900 ng/ml, 1000 ng/ml, 1100 ng/ml, 1200 ng/ml, or 1300 ng/ml or a plasma PLP concentration within the range of about 200 ng/ml to about 1300 ng/ml), and/or a walking distance in six minutes of about 350 meters or less (e.g., an walking distance in six minutes of about 50 meters, 75 meters, 100 meters, 125 meters, 150 meters, 175 meters, 200 meters, 225 meters, 250 meters, 275 meters, or 350 meters or a walking distance in six minutes within the range of about 50 meters to about 350 meters). Following administration of the sALP for a treatment period, the decrease in PPi concentration in the plasma sample from the patient can be at least about 2 μM (e.g., the patient exhibits a plasma PPi concentration in the range of about 2 μM to about 5 μM after administration of the sALP), the decrease in PLP concentration in the sample from the patient is at least about 200 ng/ml (e.g., the patient exhibits a plasma PLP concentration in the range of about 2 ng/ml to about 150 ng/ml after administration of the sALP), and/or the increase in the walking distance in six minutes of at least 100 meters or more (e.g., the patient exhibits a walking distance in six minutes of about 420 meters or more after administration of the sALP). The patient may also exhibit decreased reliance on an assistive mobility device (e.g., a walker, a wheelchair, braces, crutches, and orthotics) and/or a decreased incidence of fractures (e.g., vertebral crush fracture, subtrochanteric fracture, or metatarsal fracture) after administration of the sALP (SEQ ID NO: 1). Patients may also be excluded from treatment with a sALP for, e.g., serum calcium levels below the range of a healthy subject (e.g., about 8.5 to about 10.2 mg/dl), serum phosphate levels below the range of a healthy subject (e.g., about 2.5 to about 4.5 mg/dl), serum vitamin D levels below the range of a healthy subject (e.g, about 20 ng/ml), serum creatinine above the range of a healthy subject (e.g., about 0.6 mg/dl to 1.2 mg/dl), and/or parathyroid hormone levels above the range of a healthy subject (e.g., about 10 to about 65 pg/ml).

A second aspect features a method of treating HPP in a patient of about 13 years of age or older (e.g., a human), which includes administering a sALP (e.g., SEQ ID NO: 1) to the patient in a treatment regimen providing about 1 mg/kg/week to about 9 mg/kg/week, preferably 6 mg/kg/week, of the sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). The patient may be naïve with respect to treatment with the sALP. In particular, the sALP includes an amino acid sequence having at least 95% sequence identity to the amino acid sequence of SEQ ID NO: 1 (e.g., asfotase alfa). Administration of the sALP (e.g., SEQ ID NO: 1) results in one or more of the following: (i) a change in the percentage (%) predicted HHD score of the patient of about 5% or more (e.g., about 5%, 6%, 7%, 8%, 9%, 10%, 11%, 12%, 13%, 14%, 15%, 16%, 17%, 18%, 19%, or 20% or more) relative to the % predicted HHD score of the patient prior to treatment with the sALP; (ii) a change in a LEFS score of the patient of about 3 or more (e.g., about 3, 4, 5, 6, 7, 8, 9, or 10 or more) relative to the LEFS score of the patient prior to treatment with the sALP; and (iii) a change in a BPI-SF score of the patient of about −2 or more (e.g., about −2, about −3, about −4, about −5, about −6, or about −7 or more) relative to the BPI-SF score of the patient prior to treatment with the sALP.

In the first or second aspect, the sALP (e.g., SEQ ID NO: 1) may be administered one or more times per day, week, month, or year (e.g., twice a week, three times a week, four times a week, five times a week, six times a week, or seven times a week). In particular, the sALP may be administered in multiple doses on two days a week, three days a week, four days a week, five days a week, six days a week, or seven days a week. For example, the sALP (e.g., SEQ ID NO: 1) is administered at an initial dosage of about 2.1 mg/kg/week to about 3.5 mg/kg/week (e.g., an initial dosage of about 0.3 mg/kg/day to about 0.5 mg/kg/day of the sALP) and subsequently is increased to a dosage of about 6 mg/kg/week or more (e.g., 9 mg/kg/week). In particular, the initial dosage may be increased after a treatment period of at least six months, at least one year, at least two years, at least three years, or at least four years or longer (e.g., at least five years, at least six years, at least seven years, at least eight years, at least nine years, at least ten years, or more than ten years, such as for the lifetime of the patient). Moreover, the sALP (e.g., SEQ ID NO: 1) may be administered at a dosage of about 1.3 mg/kg/week, about 2.7 mg/kg/week, or about 6 mg/kg/week or more (e.g., about 9 mg/kg/week), such as the sALP is administered at a dosage of about 2 mg/kg three times a week, about 3 mg/kg two times a week, about 3 mg/kg three times a week, or about 1 mg/kg six times a week. Additionally, the sALP may be administered once daily on consecutive or alternating days. Furthermore, the sALP (e.g., SEQ ID NO: 1) may be administered in an amount that is therapeutically effective to treat at least one symptom of adult HPP (e.g., one or more of elevated blood and/or urine levels of phosphoethanolamine (PEA), hypomineralization, hypercalciuria, skeletal deformity, waddling gait, bone pain, bone fracture (e.g., vertebral crush fracture, subtrochanteric fracture, or metatarsal fracture), calcium pyrophosphate dihydrate crystal deposition, arthritis, pyrophosphate arthropathy, chondrocalcinosis, calcific periarthritis, and pseudofracture).

In the first or second aspect, the sALP (e.g., SEQ ID NO: 1) is administered in a composition including at least one pharmaceutically acceptable carrier, diluent, or excipient, such as saline or sodium chloride and sodium phosphate. For example, at least one pharmaceutically acceptable carrier, diluent, or excipient includes 150 mM sodium chloride and 25 mM sodium phosphate. Moreover, the pharmaceutical composition may be administered subcutaneously, intramuscularly, intravenously, orally, nasally, sublingually, intrathecally, or intradermally. In particular, the pharmaceutical composition is administered subcutaneously.

A third aspect features an sALP including an amino acid sequence having at least 95% sequence identity to the amino acid sequence of SEQ ID NO: 1 (e.g., asfotase alfa) for treating hypophosphatasia (HPP) in a naïve, pediatric-onset HPP patient of about 18 years of age or older (e.g., a human). In particular, the sALP is formulated for administration in a treatment regimen providing about 1 mg/kg/week to about 9 mg/kg/week, preferably 6 mg/kg/week, of the sALP for a treatment period of at least two weeks e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). The sALP (e.g., SEQ ID NO: 1) is characterized in that administration of the sALP to the patient results in one or more of the following: (i) a statistically significant decrease in PPi concentration in a plasma sample from the patient of at least about 1 μM relative to PPi concentration in a plasma sample from an untreated pediatric-onset HPP subject of about 18 years of age or older; (ii) a statistically significant decrease in PLP concentration in a plasma sample from the patient of at least about 100 ng/ml relative to PLP concentration in a plasma sample from an untreated pediatric-onset HPP subject of about 18 years of age or older; and (iii) a statistically significant increase of at least 50 meters in walking distance of the patient, as assessed by a 6MWT, relative to the walking distance in 6 minutes of the patient without administration.

In the third aspect, the sALP may be characterized in that the decrease in PPi concentration in the plasma sample from the patient (e.g., a naïve, pediatric-onset HPP patient of about 18 years of age or older), the decrease in PLP concentration in the plasma sample from the patient, and/or the increase in the walking distance of the patient is sustained during the treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

In the third aspect, the sALP (e.g., SEQ ID NO: 1) may be characterized in that, prior to administration of the sALP, the patient (e.g., a naïve, pediatric-onset HPP patient of about 18 years of age or older) exhibits a plasma PPi concentration of about 6 μM, a plasma PLP concentration of up to 1300 ng/ml, and/or a walking distance in six minutes of about 350 meters or less. In particular, the sALP is characterized in that the decrease in PPi concentration in the plasma sample from the patient is at least about 2 μM (e.g., the patient exhibits a plasma PPi concentration of about 2 μM to about 5 μM after administration of the sALP), the decrease in PLP concentration in the sample from the patient is at least about 200 ng/ml (e.g., the patient exhibits a plasma PLP concentration of about 2 ng/ml to about 150 ng/ml after administration of the sALP), and/or administration of the sALP for a treatment period of at least one year results in an increase in the walking distance in six minutes of at least 100 meters or more (e.g., the patient exhibits a walking distance in six minutes of about 420 meters or more after administration of the sALP). The patient may also exhibit decreased reliance on an assistive mobility device (e.g., a walker, a wheelchair, braces, crutches, and orthotics) and/or a decreased incidence of fractures (e.g., vertebral crush fracture, subtrochanteric fracture, or metatarsal fracture) after administration of the sALP (e.g., SEQ ID NO: 1).

In the third aspect, the sALP (e.g., SEQ ID NO: 1) may be formulated for administration one or more times per day, week, month, or year (e.g., twice a week, three times a week, four times a week, five times a week, six times a week, or seven times a week). In particular, the sALP is formulated for administration in multiple doses on two days a week, three days a week, four days a week, five days a week, six days a week, or seven days a week. For example, the sALP (e.g., SEQ ID NO: 1) is formulated for administration at an initial dosage of about 2.1 mg/kg/week to about 3.5 mg/kg/week (e.g., an initial dosage of about 0.3 mg/kg/day to about 0.5 mg/kg/day of the sALP) and subsequently is increased to a dosage of about 6 mg/kg/week or more (e.g., 9 mg/kg/week). In particular, the initial dosage may be increased after a treatment period of at least six months, at least one year, at least two years, at least three years, or at least four years or longer (e.g., at least five years, at least six years, at least seven years, at least eight years, at least nine years, at least ten years, or more than ten years, such as for the lifetime of the patient). Moreover, the sALP (e.g., SEQ ID NO: 1) may be formulated for administration at a dosage of about 1.3 mg/kg/week, about 2.7 mg/kg/week, or about 6 mg/kg/week or more (e.g., about 9 mg/kg/week), such as the sALP is formulated for administration at a dosage of about 2 mg/kg three times a week, about 3 mg/kg two times a week, about 3 mg/kg three times a week, or about 1 mg/kg six times a week. Additionally, the sALP may be formulated for administration once daily on consecutive or alternating days. Furthermore, the sALP (e.g., SEQ ID NO: 1) may be formulated for administration in an amount that is therapeutically effective to treat at least one symptom of adult HPP (e.g., one or more of elevated blood and/or urine levels of phosphoethanolamine (PEA), hypomineralization, hypercalciuria, skeletal deformity, waddling gait, bone pain, bone fracture (e.g., vertebral crush fracture, subtrochanteric fracture, or metatarsal fracture), calcium pyrophosphate dihydrate crystal deposition, arthritis, pyrophosphate arthropathy, chondrocalcinosis, calcific periarthritis, and pseudofracture).

In the third aspect, the sALP (e.g., SEQ ID NO: 1) may be formulated for administration in a composition including at least one pharmaceutically acceptable carrier, diluent, or excipient, such as saline or sodium chloride and sodium phosphate. For example, at least one pharmaceutically acceptable carrier, diluent, or excipient includes 150 mM sodium chloride and 25 mM sodium phosphate. Moreover, the pharmaceutical composition may be formulated for subcutaneous, intramuscular, intravenous, oral, nasal, sublingual, intrathecal, or intradermal administration. In particular, the pharmaceutical composition is formulated for subcutaneous administration.

In any of the above aspects, the patient (e.g., a naïve, pediatric-onset HPP patient of about 18 years of age or older) may be one that was not diagnosed based on presence of symptoms of perinatal, infantile, or childhood HPP, such as rickets, rachitic ribs, severe hypomineralization, failure to thrive, delayed motor development, inadequate weight gain, pulmonary hypoplasia, respiratory insufficiency, respiratory failure, craniosynostosis (including complications of craniosynostosis), and seizures In any of the above aspects, the patient is a human. The patient (e.g., a naïve, pediatric-onset HPP patient of about 18 years of age or older) may not exhibit ectopic calcification after administration of the sALP (e.g., SEQ ID NO: 1). For example, the patient does not exhibit ectopic calcification after administration of the sALP for at least one year, at least two years, at least three years, at least four years, at least five years, at least six years, at least seven years, at least eight years, at least nine years, or at least ten years or longer, such as for the lifetime of the patient. Moreover, the patient (e.g., an HPP patient of about 13 years of age or older, such has a naïve, pediatric-onset HPP patient of about 18 years of age or older) may exhibit tolerability to administration of the sALP (e.g., SEQ ID NO: 1), such as a lack of or decreased incidence of adverse events selected from the group consisting of injection site erythema, decrease in hemoglobin, pyrexia, pneumonia, upper respiratory tract infection, otitis media, vomiting, constipation, diarrhea, tooth loss, nasopharyngitis, rash, dental carries, and irritability.

In any of the above aspects, the sALP (e.g., SEQ ID NO: 1) includes or consists of the amino acid sequence of SEQ ID NO: 1. For example, the sALP (e.g., SEQ ID NO: 1) is physiologically active toward PEA, PPi, and PLP, catalytically competent to improve skeletal mineralization in bone, and/or is the soluble extracellular domain of an alkaline phosphatase.

In any of the above aspects, administration of the sALP may result in a statistically significant change in the least squares mean from baseline of PPi and/or PLP concentrations in a plasma sample from the patient. Administration of the sALP may result in an $AUC_{last}$ of about 2,000 U×day/L to about 7,000 U×day/L, wherein the $AUC_{last}$ is equal to the area under a concentration-time curve from time zero to time of a last observed concentration in a dosing interval. The administration of the sALP may result in an $AUC_{inf}$ of about 4,000 U×day/L to about 10,000 U×day/L, wherein the $AUC_{inf}$ is equal to the area under a concentration-time curve from time zero to infinity. Administration of the sALP may result in a $t_{1/2}$ of about 3 days to about 8 days.

Definitions

As used herein, "a" or "an" means "at least one" or "one or more" unless otherwise indicated. In addition, the singular forms "a", "an", and "the" include plural referents unless the context clearly dictates otherwise.

As used herein, "about" refers to an amount that is ±10% of the recited value and is preferably ±5% of the recited value, or more preferably ±2% of the recited value.

As used herein, "at least" refers to an amount that is ≤10% of the recited value and is preferably ≤5% of the recited value, or more preferably ≤2% of the recited value.

By "asfotase alfa" is meant a human TNALP (hTNALP) fusion protein formulated for the treatment of HPP. Asfotase alfa (STRENSIQ®, Alexion Pharmaceuticals, Inc.) is a fusion protein including a soluble glycoprotein of two identical polypeptide chains, in which each polypeptide chain includes amino acid residues 1-726 of SEQ ID NO: 1. The structure of each polypeptide chain includes the catalytic domain of hTNALP, the human immunoglobulin $G_1$ Fc domain, and a deca-aspartate peptide used as a bone targeting domain (the structure hTNALP-Fc-$D_{10}$). The two polypeptide chains are covalently linked by two disulfide bonds. Asfotase alfa has been approved throughout the world under the trade name STRENSIQ®, including in the United States, Europe, Japan, Canada, Israel, Australia, and Korea.

As used herein, "average" refers to a numerical value expressing the mean or median of a data set. The mean of a data set is calculated by dividing the sum of the values in the set by their number. The median of a date set is calculated by determining the middle value in a list of odd numbers or by determining the mean of the two data values in the middle in a list of even numbers.

The term "bone-targeting moiety," as used herein, refers to an amino acid sequence of between 1 and 50 amino acid residues in length having a sufficient affinity to the bone matrix, such that the bone-targeting moiety, singularly, has an in vivo binding affinity to the bone matrix that is about $10^{-6}$ M to about $10^{-15}$ M (e.g., $10^{-7}$ M, $10^{-8}$ M, $10^{-9}$ M, $10^{-10}$ M, $10^{-11}$ M, $10^{-12}$ M, $10^{-13}$ M, $10^{-14}$ M, or $10^{-15}$ M).

The terms "Brief Pain Inventory-Short Form" and "BPI-SF" as used interchangeably herein refer to a method to measure pain of patients, in particular, patients having HPP (e.g., patients of about 13 years of age or older). The BPI-SF is a self-reported pain measure described in Cleeland & Ryan (*Ann Acad Med Singapore*, 23(2), 129-138; 1994), hereby incorporated by reference in its entirety. The BPI-SF is a questionnaire designed to assess the severity of pain and the impact of pain on daily functions. The BPI-SF consists of 11 items that utilize a numeric rating scale to assess pain severity (4 items) and pain interference (7 items) in the 24 hours prior to questionnaire administration. The BPI-SF questionnaire provides information on the intensity of pain and degree to which the pain interferes with daily functions of the patient (e.g., a HPP patient of about 13 years of age or older) on a numeric rating scale from 0 (no pain) to 10 (severe pain or significant interference caused by pain); lower scores indicate better quality of life outcomes and reduced pain. For instance, BPI-SF scores of the HPP adolescents and adults are a composite of 11 pain assessments.

The terms "Bruininks-Oseretsky Test of Motor Proficiency 2nd Edition" or "BOT-2," as used herein, refer to the second edition of a standardized test of gross and fine motor performance for patients, e.g., adults having HPP, such as adults having pediatric-onset HPP. See Bruininks, R. H. (2005). *Bruininks-Oseretsky Test of Motor Proficiency*, (BOT-2). Minneapolis, Minn.: Pearson Assessment, hereby incorporated by reference in its entirety. The BOT-2 is administered individually to assess gross and fine motor skills of a range of patients. The BOT-2, for example, can be used to evaluate physical impairments and mobility restrictions in patients having HPP (e.g., adults having HPP, such as adults having pediatric-onset HPP). The BOT-2 provides composite BOT-2 scores in the following exemplary areas: strength, running speed and agility, fine motor precision, fine motor integration, manual dexterity, bilateral coordination, balance, and upper-limb coordination. For example, a BOT-2 strength total score can be determined by having a patient perform sit-ups, v-ups, standing long jump, wall sit, and push-ups. A running speed and agility total score can be determined by having a patient step over a balance beam or perform a shuttle run, two-legged side hop, or one-legged side hop. Both BOT-2 total strength and BOT-2 running speed and agility total scores range from 0 to 25, in which a score of about 10 to 25 is considered representative of healthy subjects. Normative scores for the strength and running speed and agility are 15+/−5. Adult scores are not normed (does not use the scaled score), and thus higher point values represent better performance. Either average or median scores may be used, with median scores preferred for smaller sample sizes or smaller data sets.

The term "catalytically competent," as used herein, refers to an sALP that hydrolyzes the bone mineralization inhibitor inorganic pyrophosphate (PPi) to provide inorganic phosphate (Pi), thereby decreasing the extracellular concentrations of PPi. Thus, the catalytically competent sALP improves skeletal mineralization in bone by regulating the concentration of PPi.

By "extracellular domain" is meant any functional extracellular portion of the native protein, e.g., alkaline phosphatase. In particular, the extracellular domain lacks the signal peptide.

By "Fc" is meant a fragment crystallizable region of an immunoglobulin, e.g., IgG-1, IgG-2, IgG-3, IgG-3 or IgG-4, including the CH2 and CH3 domains of the immunoglobulin heavy chain. Fc may also include any portion of the hinge region joining the Fab and Fc regions. The Fc can be of any mammal, including human, and may be post-translationally modified (e.g., by glycosylation). In a non-limiting example, Fc can be the fragment crystallizable region of human IgG-1 having the amino acid sequence of SEQ ID NO: 20.

By "fragment" is meant a portion of a polypeptide or nucleic acid molecule that contains, preferably, at least 10%, 20%, 30%, 40%, 50%, 60%, 70%, 75%, 80%, 85%, 90%, 95%, 96%, 97%, 98%, 99%, or more of the entire length of the reference nucleic acid molecule or polypeptide. A fragment may contain, e.g., 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 400, 500, 600, 700, or more amino acid residues, up to the entire length of the polypeptide. Exemplary sALP fragments have amino acid residues 18-498, 18-499, 18-500, 18-501, 18-502, 18-503, 18-504, 18-505, 18-506, 18-507, 18-508, 18-509, 18-510, 18-511, or 18-512 of a ALP (e.g., SEQ ID NOs: 2-6), and may include additional C-terminal and/or N-terminal portions.

The terms "Hand Held Dynamometry" and "HHD" as used interchangeably herein refer to a method to measure the grip and muscle strength of subjects, in particular, subjects having HPP of about 13 years of age or older. A dynamometer can be used to assess grip strength, knee flexion, knee extension, hip flexion, hip extension, and hip abduction of a subject having HPP. For example, knee flexion and extension and also hip flexion, extension, and abduction of a subject having HPP of about 13 years of age or older can be measured using, e.g., a MICROFET2™ Dynamometer, while grip strength of the subject can be measured using, e.g., a JAMAR® Grip Dynamometer. In particular, the administrator holds the dynamometer stationary, and the subject exerts a maximal force against the dynamometer. Peak force data is collected in pounds, then converted to Newtons (N). Torque values are then calculated using limb length in N-meters. The torque value can then be compared to the value of, e.g., a normal subject of about the same age, the same gender, and/or the same height, and expressed as a percentage value to generate the HHD score of the subject.

The terms "hypophosphatasia" or "HPP," as used herein, refer to a rare, heritable skeletal disorder caused by, e.g., one or more loss-of-function mutations in the ALPL (alkaline phosphatase, liver/bone/kidney) gene, which encodes tissue-nonspecific alkaline phosphatase (TNALP). HPP may be further characterized as infantile HPP, childhood HPP, perinatal HPP (e.g., benign perinatal HPP or lethal perinatal HPP), odonto-HPP, adolescent HPP, or adult HPP. For instance, "adult HPP" describes a patient having HPP that is 18 years of age or older. "Adolescent HPP" describes a patient having HPP that is about 13 years of age to about 17 years of age. The term "adult HPP," as used herein, refers to a condition or phenotype characterized by the presence of one or more of the following symptoms: elevated blood and/or urine levels of inorganic pyrophosphate (PPi), phosphoethanolamine (PEA), or pyridoxal 5'-phosphate (PLP), hypomineralization, hypercalciuria, skeletal deformity, waddling gait, bone pain, bone fracture (e.g., vertebral crush fracture, subtrochanteric fracture, or metatarsal fracture), calcium pyrophosphate dihydrate crystal deposition, arthritis, pyrophosphate arthropathy, chondrocalcinosis, calcific periarthritis, and pseudofracture. The term "adolescent HPP," as used herein, refers to a condition or phenotype characterized by the presence of one or more of the following symptoms: elevated blood or urine levels of PPi, PEA, or PLP, osteomalacia, one or more skeletal deformities, hypotonia, muscle weakness, rheumatoid complications, arthritis, pseudogout, waddling gait, ambulatory difficulties, bone pain, pain, premature loss of teeth, hypomineralization, pulmonary hypoplasia, respiratory insufficiency, seizures, hypercalciuria, short stature, and growth delay.

The terms "Lower Extremity Function Scale" and "LEFS" as used interchangeably herein refer to a method to measure the functional disability in the lower extremities of patients, in particular, patients having HPP (e.g., patients of about 13 years of age or older). The LEFS is a self-reported measure described in Binkley et al. (*Phys Ther.* 79:371-83, 1999), hereby incorporated by reference in its entirety. Total LEFS scores range from 0 to 80 with higher scores indicative of better lower extremity functioning. A LEFS score change of about 9 points is considered a clinically meaningful change. A licensed physical therapist can administer the LEFS to HPP patients (e.g., HPP patients of about 13 years of age or older) in interview format. Higher LEFS scores are indicative of improved lower extremity functioning including transitional movements (e.g., getting out of bath or rolling in bed), locomotion (e.g., walking or running on uneven ground), climbing stairs, and squatting. The LEFS can be used to evaluate the functional impairment of one or both lower extremities of an HPP patient, including the ability to monitor the patient over time and evaluate the effectiveness of asfotase alfa treatment.

By "naïve patient" or "naïve subject" is meant a patient or subject having pediatric-onset HPP that has not previously received treatment with an alkaline phosphatase, or a polypeptide having alkaline phosphatase activity, such as a sALP (e.g., TNALP, for example the sALP polypeptide of SEQ ID NO: 1 or a polypeptide variant having at least 95% sequence identity to the sequence of SEQ ID NO: 1, e.g., asfotase alfa).

The terms "pediatric-onset hypophosphatasia" and "pediatric-onset HPP" refer to the occurrence of HPP symptoms prior to about 18 years of age in a subject.

The terms "polypeptide" and "protein" are used interchangeably and refer to any chain of two or more natural or unnatural amino acid residues, regardless of post-translational modification (e.g., glycosylation or phosphorylation), constituting all or part of a naturally-occurring or non-naturally occurring polypeptide or peptide, as is described herein.

By "pharmaceutically acceptable carrier, diluent, or excipient" is meant a carrier, diluent, or excipient, respectively, that is physiologically acceptable to the subject (e.g., a human) while retaining the therapeutic properties of the pharmaceutical composition with which it is administered. One exemplary pharmaceutically acceptable carrier, diluent, or excipient is physiological saline. For instance, the pharmaceutically acceptable carrier, diluent, or excipient can include sodium chloride (e.g., 150 mM sodium chloride) and sodium phosphate (e.g., 25 mM sodium phosphate). Other physiologically acceptable carriers, diluents, or excipients and their formulations are known to one skilled in the art.

By "pharmaceutical composition" is meant a composition containing a polypeptide (e.g., compositions including an sALP, such as asfotase alfa) as described herein formulated with at least one pharmaceutically acceptable carrier, diluent, or excipient. The pharmaceutical composition may be manufactured or sold with the approval of a governmental regulatory agency as part of a therapeutic regimen for the treatment or prevention of a disease or event in a patient. Pharmaceutical compositions can be formulated, for example, for subcutaneous administration, intravenous administration (e.g., as a sterile solution free of particulate emboli and in a solvent system suitable for intravenous use), for oral administration (e.g., a tablet, capsule, caplet, gelcap, or syrup), or any other formulation described herein, e.g., in unit dosage form.

The term "physical impairments," as used herein, refers to a physiological condition, such as bone weakness and muscle weakness, associated with HPP that can restrict or eliminate, e.g., walking ability, functional endurance, and ability to perform activities of daily living (ADL) of a patient (e.g., an adult having HPP, such as an adult having pediatric-onset HPP). In particular, physical impairments may restrict or eliminate a patient's ability to perform ADL, which are routine activities that healthy subjects perform on a daily basis without requiring assistance, such as functional mobility or transferring (e.g., walking), bathing and showering, dressing, self-feeding, and personal hygiene and grooming. As described herein, therapeutic compositions (e.g., compositions including an sALP, such as asfotase alfa) can be administered to a patient (e.g., an adult having HPP, such as an adult having pediatric-onset HPP) to decrease the severity and/or frequency of physical impairments associated with an HPP phenotype and/or to increase the walking ability of the patient (e.g., the walking ability determined from the distance walked by the patient over six minutes).

The term "physiologically active," as used herein, refers to an sALP (e.g., SEQ ID NO: 1) that hydrolyzes phosphoethanolamine (PEA), inorganic pyrophosphate (PPi), and pyridoxal 5'-phosphate (PLP) to provide Pi, thereby decreasing extracellular concentrations of PEA, PPi, and PLP.

The terms "sALP," "soluble alkaline phosphatase," and "extracellular domain of an alkaline phosphatase" are used interchangeably and refer to a soluble, non-membrane-bound alkaline phosphatase or a domain, biologically active fragment, or biologically active variant thereof. sALPs include, for example, an alkaline phosphatase lacking a C-terminal glycolipid anchor (GPI signal sequence, e.g., polypeptides including or consisting of the amino acid residues 18-502 of a human TNALP (SEQ ID NOs: 2, 3, 4, 5, or 6)). In particular, a TNALP may include, e.g., a polypeptide including or consisting of amino acid residues 1-485 of SEQ ID NO: 1, such as asfotase alfa, or a polypeptide variant having at least 95% sequence identity to the amino acid residues 1-485 of SEQ ID NO: 1. sALPs further include, for example, mammalian orthologs of human TNALP, such as a rhesus TNALP (SEQ ID NO: 7), a rat TNALP (SEQ ID NO: 8), a canine TNALP (SEQ ID NO: 9), a porcine TNALP (SEQ ID NO: 10), a murine TNALP (SEQ ID NO: 11), a bovine TNALP (SEQ ID NOs: 12-14), or a feline TNALP (SEQ ID NO: 15). sALPs also include soluble, non-membrane-bound forms of human PALP (e.g., polypeptides including or consisting of amino acid residues 18-502 of SEQ ID NOs: 16 or 17), GCALP (e.g., polypeptides including or consisting of amino acid residues 18-502 of SEQ ID NO: 18), and IALP (e.g., polypeptides including or consisting of amino acid residues 18-502 of SEQ ID NO: 19), and additional variants and analogs thereof that retain alkaline phosphatase activity, e.g., the ability to hydrolyze PPi. An sALP, in particular, lacks the N-terminal signal peptide (e.g., aa 1-17 of SEQ ID NOs: 2-6, 8, 11-13, or 15 or aa 1-25 of SEQ ID NO: 7).

By "sALP polypeptide" is meant a polypeptide having the structure A-sALP-B, wherein sALP is as defined herein and each of A and B is absent or is an amino acid sequence of at least one amino acid (e.g., any sALP fusion polypeptide described herein (for example the sALP fusion polypeptide of SEQ ID NO: 1 or a polypeptide variant having at least 95% sequence identity to the sequence of SEQ ID NO: 1, e.g., asfotase alfa).

By "signal peptide" is meant a short peptide (5-30 amino acids long) at the N-terminus of a polypeptide that directs a polypeptide towards the secretory pathway (e.g., the extracellular space). The signal peptide is typically cleaved during secretion of the polypeptide. The signal sequence may direct the polypeptide to an intracellular compartment or organelle, e.g., the Golgi apparatus. A signal sequence may be identified by homology, or biological activity, to a peptide with the known function of targeting a polypeptide to a particular region of the cell. One of ordinary skill in the art can identify a signal peptide by using readily available software (e.g., Sequence Analysis Software Package of the Genetics Computer Group, University of Wisconsin Biotechnology Center, 1710 University Avenue, Madison, Wis. 53705, BLAST, or PILEUP/PRETTYBOX programs). A signal peptide can be one that is, for example, substantially identical to amino acid residues 1-17 of SEQ ID NOs: 2-6 or amino acid residues 1-25 of SEQ ID NO: 7.

As used herein, when a polypeptide or nucleic acid sequence is referred to as having "at least X % sequence identity" to a reference sequence, wherein "X" is a real number, it is meant that at least X percent of the amino acid residues or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., *J. Mol. Biol.* 147:195-7, 1981) and BLAST (Basic Local Alignment Search Tool; Altschul et al., *J. Mol. Biol.* 215: 403-10, 1990). These and other alignment algorithms are accessible using publicly available computer software such as "Best Fit" (Smith and Waterman, *Advances in Applied Mathematics*, 482-489, 1981) as incorporated into GeneMatcher Plus (Schwarz and Dayhoff, *Atlas of Protein Sequence and Structure*, Dayhoff, M. O., Ed. pp 353-358, 1979), BLAST, BLAST-2, BLAST-P, BLAST-N, BLAST-X, WU-BLAST-2, ALIGN, ALIGN-2, CLUSTAL, Megalign (DNASTAR), or other software/hardware for alignment. In addition, those skilled in the art can determine appropriate parameters for measuring alignment, including any algorithms needed to achieve optimal alignment over the length of the sequences being compared.

The terms "patient" or "subject" refer to a mammal, including, but not limited to, a human or a non-human mammal, such as a bovine, equine, canine, ovine, or feline. Of particular interest are human patients.

"Parenteral administration," "administered parenterally," and other grammatically equivalent phrases, as used herein, refer to modes of administration other than enteral and topical administration, usually by injection, and include, without limitation, subcutaneous, intradermal, intravenous, intranasal, intraocular, pulmonary, intramuscular, intra-arterial, intrathecal, intracapsular, intraorbital, intracardiac, intradermal, intrapulmonary, intraperitoneal, transtracheal, subcuticular, intraarticular, subcapsular, subarachnoid, intraspinal, epidural, intracerebral, intracranial, intracarotid, and intrasternal injection and infusion.

As used herein, "Six Minute Walk Test" and "6MWT" refer to a standardized test to assess walking ability of a patient (e.g., an adult having HPP, such as an adult having pediatric-onset HPP), in particular, the ability of the patient to lift and set down each foot in turn. See the American Thoracic Society statement: guidelines for the six-minute walk test (American Journal of Respiratory and Critical Care Medicine, 166(1):111-7, 2002), hereby incorporated by reference in its entirety. The 6MWT is determined from the distance (e.g., in meters) that a patient walks on a flat, hard surface in a period of six minutes. The 6MWT distance can then be compared to the 6MWT distance of the patient at baseline, the 6MWT distance of an untreated subject (e.g., an untreated subject of about the same age, height, and/or gender), or the 6MWT distance of a healthy subject (e.g., a healthy subject of about the same age, height, and/or gender) and expressed as a percentage to determine the 6MWT value.

By "therapeutically effective amount" is meant an amount of a polypeptide (e.g., an sALP, such as SEQ ID NO: 1) or nucleic acid molecule described herein that is sufficient to substantially improve, treat, prevent, delay, suppress, or arrest at least one symptom of adult HPP (e.g., elevated blood and/or urine levels of PPi, PLP, and PEA, hypomineralization, hypercalciuria, skeletal deformity, waddling gait, bone pain, bone fracture, calcium pyrophosphate dihydrate crystal deposition, arthritis, pyrophosphate arthropathy, chondrocalcinosis, calcific periarthritis, and pseudofracture). A therapeutically effective amount of a composition described herein may depend on the severity of the disorder being treated and the condition, weight, and general state of the patient and can be determined by an ordinarily-skilled artisan with consideration of such factors. A therapeutically effective amount of a composition described herein can be administered to a patient in a single dose or in multiple doses administered over a period of time.

By "treating," "treat," or "treatment" is meant the medical management of a patient with the intent to cure, ameliorate, stabilize, reduce the likelihood of, or prevent adult HPP and/or management of a patient exhibiting or likely to have adult HPP, e.g., by administering a pharmaceutical composition (e.g., an sALP, such as SEQ ID NO: 1). This term includes active treatment, that is, treatment directed specifically toward the improvement or associated with the cure of a disease, pathological condition, disorder, or event, and also includes causal treatment, that is, treatment directed toward removal of the cause of the associated disease, pathological condition, disorder, or event. In addition, this term includes palliative treatment, that is, treatment designed for the relief or improvement of at least one symptom rather than the curing of the disease, pathological condition, disorder, or event; symptomatic treatment, that is, treatment directed toward constitutional symptoms of the associated disease, pathological condition, disorder, or event; preventative treatment, that is, treatment directed to minimizing or partially or completely inhibiting the development of the associated disease, pathological condition, disorder, or event, e.g., in a patient who is not yet ill, but who is susceptible to, or otherwise at risk of, a particular disease, pathological condition, disorder, or event; and supportive treatment, that is, treatment employed to supplement another specific therapy directed toward the improvement of the associated disease, pathological condition, disorder, or event.

Other features and advantages of the present disclosure will be apparent from the following Detailed Description, the drawings, and the claims.

BRIEF DESCRIPTION OF THE DRAWINGS

FIG. 1A) and pyridoxal 5'-phosphate (PLP; FIG. 1B) concentrations in plasma samples from adult pediatric-onset hypophosphatasia (HPP) patients from baseline to six months of treatment with asfotase alfa. Data are presented as median (minimum, maximum). $^a$The P value compares the combined asfotase-alfa treated group (adult HPP patients receiving dosages of 0.3 mg/kg/day and 0.5 mg/kg/day of asfotase alfa) with the untreated control group. The number (n) of treated patients and untreated control subjects assessed for plasma PPi and PLP concentrations is shown.

FIG. 9A) and inorganic pyrophosphate (PPi; FIG. 9B) concentrations in plasma samples from adolescent and adult HPP patients from baseline to six months of treatment with asfotase alfa. Data are presented as median (minimum, maximum). $^a$The P value compares the combined asfotase-alfa treated group (adult and adolescent HPP patients receiving dosages of 0.3 mg/kg/day and 0.5 mg/kg/day of asfotase alfa) with the untreated control group. The number (n) of treated patients and untreated control subjects assessed for plasma PPi and PLP concentrations is shown.

FIGS. 17A-17B are schematic diagrams showing the dosing schedule of each dosage cohort (FIG. 17A) and the schedule of pharmacokinetic, pharmacodynamics, and immunogenicity assessments (FIG. 17B).

DETAILED DESCRIPTION

Figure 1A:
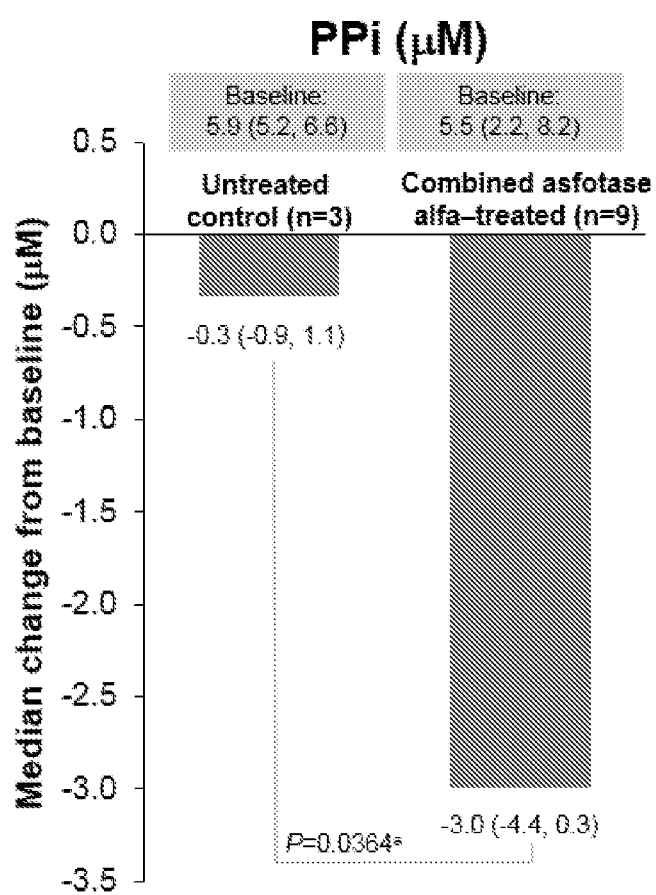
FIGS. 1A-1B are graphs showing the median change in inorganic pyrophosphate (PPi.

We have discovered that asfotase alfa (SEQ ID NO: 1, STRENSIQ®, Alexion Pharmaceuticals, Inc.) can be used effectively to treat hypophosphatasia (HPP), its symptoms, and physical impairments associated therewith, in adults having HPP (e.g., adults having HPP of about 18 years of age or older, such as adults having pediatric-onset HPP) or adolescents having HPP (e.g., adolescents having HPP of about 13 years to about 17 years of age) for an extended period of time (e.g., at least one year, at least two years, at least three years, at least four years, at least five years, at least six years, at least seven years, at least eight years, at least nine years, at least ten years, or longer than ten years, such as for the lifetime of the patient). In particular, asfotase alfa (SEQ ID NO: 1) can be administered to treat adults or adolescents with HPP exhibiting physical impairments (e.g., bone or muscle weakness), decreased walking ability relative to a healthy subject (e.g., a subject without HPP of about the same age, gender, and/or height), decreased alkaline phosphatase (ALP) level in a sample (e.g., a plasma sample) relative to a healthy subject (e.g., a subject without HPP of about the same age, same gender, and/or height), decreased grip and muscle strength relative to a healthy subject (e.g., a subject without HPP of about the same age, same gender, and/or height), decreased functional disability in the lower extremities relative to a healthy subject (e.g., a subject without HPP of about the same age, same gender, and/or height), or increased pain relative to a healthy subject (e.g., a subject without HPP of about the same age, same gender, and/or height). Furthermore, the adult or adolescent having HPP can be a naïve patient that has not previously received treatment with asfotase alfa (SEQ ID NO: 1).

Methods for administering asfotase alfa (SEQ ID NO: 1) to an adult having HPP (e.g., an adult having HPP of about 18 years of age or older, such as an adult having pediatric-onset HPP) or an adolescent having HPP (e.g., adolescents having HPP of about 13 years of age to about 17 years of age) that exhibits elevated inorganic pyrophosphate (PPi) or pyridoxal 5'-phosphate (PLP) concentrations in a plasma sample from the adult or adolescent having HPP, relative to PPi or PLP concentrations in a plasma sample from an untreated adult or adolescent having HPP, are described. Prior to administration of the sALP, the HPP patient may be characterized as having a plasma PPi concentration of up to about 6 μM and/or a PLP concentration of up to 1300 ng/ml. Additionally, methods for administering asfotase alfa (SEQ ID NO: 1) to an adult having HPP (e.g., an adult having pediatric-onset HPP) or an adolescent having HPP (e.g., adolescents having HPP of about 13 years of age to about 17 years of age) that results in an improvement in walking ability of the adult having HPP are described. For example, asfotase alfa (SEQ ID NO: 1) can be administered to an adult or adolescent having HPP with decreased walking ability, such that, prior to administration of the sALP, the patient is characterized as having a walking distance in six minutes of about 350 meters or less. For instance, the adult having HPP exhibits decreased reliance on an assistive mobility device, such as a walker, a wheelchair, braces, crutches, and orthotics, after administration of the sALP.

Methods for administering asfotase alfa (SEQ ID NO: 1) to an adult having HPP (e.g., an adult having pediatric-onset HPP) or an adolescent having HPP (e.g., adolescents having HPP of about 13 years of age to about 17 years of age) having a total Bruininks-Oseretsky Test of Motor Proficiency $2^{nd}$ Edition (BOT-2) running speed and agility test or strength score indicative of physical impairments (e.g., a BOT-2 score of less than about 7 in one or more BOT-2 score areas of strength, running speed and agility, fine motor precision, fine motor integration, manual dexterity, bilateral coordination, balance, and upper-limb coordination) are also described. For example, asfotase alfa (SEQ ID NO: 1) can be administered to an adult having HPP with a BOT-2 running speed and agility score of less than about 6. Furthermore, asfotase alfa (SEQ ID NO: 1) can be administered to an adult having HPP having a BOT-2 strength score of less than about 12.

Methods for administering asfotase alfa (SEQ ID NO: 1) to an adult having HPP (e.g., an adult having pediatric-onset HPP) or an adolescent having HPP (e.g., adolescents having HPP of about 13 years of age to about 17 years of age) having a Handheld Dynamometry (HHD) score indicative of decreased grip and muscle strength (e.g., a HHD score of less than about 50, such as about 10, 20, 30, 40, or 50), a Lower Extremity Functional Scale (LEFS) score indicative of decreased functional disability in the lower extremities (e.g., a LEFS score of less about 40, such as about 10, 20, 30, or 40), and/or a Brief Pain Inventory-Short Form (BPI-SF) indicative of pain (e.g., a score of greater than about 10, such as about 10, about 15, about 20, about 25, or about 30 or more) are also described.

In any of these methods, asfotase alfa (SEQ ID NO: 1) may be administered to an adult having HPP (e.g., an adult having pediatric-onset HPP) or an adolescent having HPP for an extended period of time, e.g., at least one year, at least two years, at least three years, at least four years, at least five years, at least six years, at least seven years, at least eight years, at least nine years, at least ten years, or longer than ten years, such as for the lifetime of the patient). Furthermore, given the results described herein using asfotase alfa, other sALPs (such as a polypeptide variant having at least 95% sequence identity to the sequence of SEQ ID NO: 1) may be used to treat an adult having HPP (e.g., an adult having pediatric-onset HPP) for an extended period of time, e.g., at least one year, at least two years, at least three years, at least four years, at least five years, at least six years, at least seven years, at least eight years, at least nine years, at least ten years, or longer than ten years, such as for the lifetime of the patient).

Methods of Treatment

Provided herein are methods for treating an adult having HPP (e.g., an adult having HPP of about 18 years of age or older, such as an adult having pediatric-onset HPP) or an adolescent having HPP (e.g., an adolescent having HPP of about 13 years of age to about 17 years of age). Adults having HPP (e.g., an adult having pediatric-onset HPP) or adolescents having HPP (e.g., adolescents having HPP of about 13 years of age to about 17 years of age) can be treated by administering an sALP (such as TNALP, for example, an sALP fusion polypeptide, such as the sALP fusion polypeptide of SEQ ID NO: 1 or a polypeptide variant having at least 95% sequence identity to the sequence of SEQ ID NO: 1, e.g., asfotase alfa) across a range of ages, e.g., about 18 to about 20 years of age, about 20 to about 25 years of age, about 25 to about 30 years of age, about 30 to about 35 years of age, about 35 to about 40 years of age, about 40 to about 45 years of age, about 45 to about 50 years of age, about 50 to about 55 years of age, about 60 to about 65 years of age, about 20 to about 30 years of age, about 30 to about 40 years of age, about 40 to about 50 years of age, about 50 to about 60 years of age, about 60 to about 70 years of age, about 20 to about 65 years of age, about 30 to about 65, years of age, or older than 65 years of age.

Adults (e.g., an adult having HPP of about 18 years of age or older, such as an adult having pediatric-onset HPP) or adolescents (e.g., adolescents having HPP of about 13 years of age to about 17 years of age) can be diagnosed with HPP prior to administration of an sALP (such as TNALP, for example, an sALP fusion polypeptide, such as the sALP fusion polypeptide of SEQ ID NO: 1 or a polypeptide variant having at least 95% sequence identity to the sequence of SEQ ID NO: 1, e.g., asfotase alfa). An adult having HPP (e.g., an adult having pediatric-onset HPP) or an adolescent having HPP can exhibit, e.g., physical impairments and impaired walking ability relative to an adult without HPP.

Additionally, the adult having HPP (e.g., an adult having HPP of about 18 years of age or older, such as an adult having pediatric-onset HPP) or the adolescent having HPP (e.g., adolescent having HPP of about 13 years of age to about 17 years of age) can be a naïve patient that has not previously received treatment with an sALP (such as TNALP, for example, an sALP fusion polypeptide, such as the sALP fusion polypeptide of SEQ ID NO: 1 or a polypeptide variant having at least 95% sequence identity to the sequence of SEQ ID NO: 1, e.g., asfotase alfa). The method involves administering an sALP (such as TNALP, for example, an sALP fusion polypeptide, such as the sALP fusion polypeptide of SEQ ID NO: 1 or a polypeptide variant having at least 95% sequence identity to the sequence of SEQ ID NO: 1, e.g., asfotase alfa) to an adult having HPP or an adolescent having HPP, such as administering an sALP for a treatment period of at least one year (e.g., at least two years, at least three years, at least four years, at least five years, at least six years, at least seven years, at least eight years, at least nine years, at least ten years, or longer than ten years, such as for the lifetime of the patient).

In particular, an sALP, such as asfotase alfa, can be administered for a treatment period to an adult having HPP (e.g., an adult having HPP of about 18 years of age or older, such as an adult having pediatric-onset HPP) or an adolescent having HPP (e.g., an adolescent having HPP of about 13 years of age to about 17 years of age) previously determined to have a plasma PPi concentration of up to about 6 µM (e.g., about 3.5 µM, about 4 µM, about 4.5 µM, about 5 µM, or about 5.5 µM), a plasma PLP concentration of up to 1300 ng/ml (e.g., a plasma PLP concentration of about 200 ng/ml, 300 ng/ml, 400 ng/ml, 500 ng/ml, 600 ng/ml, 700 ng/ml, 800 ng/ml, 900 ng/ml, 1000 ng/ml, 1100 ng/ml, 1200 ng/ml, or 1300 ng/ml), a walking distance in six minutes of about 350 meters or less (e.g., a walking distance in six minutes of about 50 meters, 75 meters, 100 meters, 125 meters, 150 meters, 175 meters, 200 meters, 225 meters, 250 meters, 275 meters, or 350 meters), a total BOT-2 running speed and agility score of less than about 6.0, a total BOT-2 strength score of less than about 12, a HHD score of less than about 80% of the predicted HHD score (e.g., about 30%, about 35%, about 40%, about 45%, about 50%, about 55%, about 60%, about 65%, about 70%, or about 75% of the predicted HHD score), a LEFS score of less about 40 (e.g., a LEFS score of less about 10, about 20, about 30, or about 40), and/or a BPI-SF score of less than about 12 (e.g., a BPI-SF score of less than about 0, about 1, about 2, about 3, about 4, about 5, about 6, about 7, about 8, about 9, or about 10). Moreover, the plasma PPi concentration, plasma PLP concentration, walking distance in six minutes, BOT-2 strength score, BOT-2 running speed and agility score, HHD score, LEFS score, and BPI-SF score of the adult or adolescent having HPP can be compared to the plasma PPi concentration, plasma PLP concentration, walking distance in six minutes, BOT-2 strength score, BOT-2 running speed and agility score, HHD score, LEFS score, and BPI-SF score, respectively, at baseline of the patient to assess an effect in the adult or adolescent following treatment with the sALP.

Additionally, the plasma PPi concentration, plasma PLP concentration, walking distance in six minutes, BOT-2 strength score, BOT-2 running speed and agility score, HHD score, LEFS score, and BPI-SF score of the adult having HPP (e.g., an adult having HPP of about 18 years of age or older, such as an adult having pediatric-onset HPP) or adolescent having HPP (e.g., an adolescent having HPP of about 13 years of age to about 17 years of age) can be compared to the plasma PPi concentration, plasma PLP concentration, walking distance in six minutes, BOT-2 strength score, BOT-2 running speed and agility score, HHD score, LEFS score, and BPI-SF score of a healthy patient to determine a treatment effect in the adult or adolescent administered an sALP (e.g., asfotase alfa). In particular, the sALP can be administered for a treatment period of least one year (e.g., at least two years, at least three years, at least four years, at least five years, at least six years, at least seven years, at least eight years, at least nine years, at least ten years, or longer than ten years, such as for the lifetime of the patient). Alternatively, the methods can include determining the plasma PPi concentration, plasma PLP concentration, walking distance in six minutes, BOT-2 strength score, BOT-2 running speed and agility score, HHD score, LEFS score, and BPI-SF score prior to administering an sALP, such as asfotase alfa, as described herein to assess an effect in the adult or adolescent of treatment with the sALP.

Additionally, each of the described metrics (e.g., the plasma PPi concentration, plasma PLP concentration, walking distance in six minutes, BOT-2 strength score, BOT-2 running speed and agility score, HHD score, LEFS score, and BPI-SF score) can be used singly or in any combination to assess treatment efficacy using an sALP (such as TNALP, for example the sALP fusion polypeptide of SEQ ID NO: 1 or a polypeptide variant having at least 95% sequence identity to the sequence of SEQ ID NO: 1, e.g., asfotase alfa) in an adult having HPP (e.g., an adult having HPP of about 18 years of age or older, such as an adult having pediatric-onset HPP) or an adolescent having HPP (e.g., an adolescent having HPP of about 13 years of age to about 17 years of age), in which improvements relative to a certain value or score of the metric tested can be used to show a treatment effect in the HPP patient using the sALP.

Hypophosphatasia in Adults and Adolescents

Patients having adult HPP (e.g., adults having HPP of about 18 years of age or older, such as adults having pediatric-onset HPP) or adolescent HPP (e.g., adolescents having HPP of about 13 years of age to about 17 years of age) can be treated with an sALP (such as a TNALP, for example the sALP fusion polypeptide of SEQ ID NO: 1 or a polypeptide variant having at least 95% sequence identity to the sequence of SEQ ID NO: 1, e.g., asfotase alfa) for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). In particular, asfotase alfa (STRENSIQ®) can be administered, as described herein, to treat pediatric-onset HPP in an adult patient (e.g., a naïve patient). Accordingly, the methods are useful for alleviating one or more, or all, of any of the symptoms of HPP described herein, particularly when the sALP (such as TNALP, for example the sALP fusion polypeptide of SEQ ID NO: 1 or a polypeptide variant having at least 95% sequence identity to the sequence of SEQ ID NO: 1, e.g., asfotase alfa) is administered for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years). In particular, the treatment period is at least six weeks.

For instance, the methods are useful for treating symptoms of adult HPP, including, but not limited to, elevated blood and/or urine levels of phosphoethanolamine (PEA), hypomineralization, hypercalciuria, skeletal deformity, waddling gait, bone pain, bone fracture (e.g., vertebral crush fracture, subtrochanteric fracture, or metatarsal fracture), calcium pyrophosphate dihydrate crystal deposition, arthritis, pyrophosphate arthropathy, chondrocalcinosis, calcific periarthritis, and pseudofracture. The methods are also useful for treating symptoms of adolescent HPP, including, but not limited to, elevated blood or urine levels of PPi, PEA, or PLP, osteomalacia, one or more skeletal deformities, hypotonia, muscle weakness, rheumatoid complications, arthritis, pseudogout, waddling gait, ambulatory difficulties, bone pain, pain, premature loss of teeth, hypomineralization, pulmonary hypoplasia, respiratory insufficiency, seizures, hypercalciuria, short stature, and growth delay.

Exemplary metrics useful for evaluating the need for or the efficacy of treatment using an sALP (such as TNALP, for example the sALP fusion polypeptide of SEQ ID NO: 1 or a polypeptide variant having at least 95% sequence identity to the sequence of SEQ ID NO: 1, e.g., asfotase alfa) include (1) plasma PPi and/or PLP concentrations, (2) the Six Minute Walk Test (6MWT), (3) the Bruininks-Oseretsky Test of Motor Proficiency 2nd Edition (BOT-2), (4) Handheld Dynamometry (HHD), (5) the Lower Extremity Functional Scale (LEFS), and (6) the Brief Pain Inventory-Short Form (BPI-SF), which are described in further detail below. Plasma Inorganic Pyrophosphate (PPi) and Pyridoxal 5'-Phosphate (PLP) Concentrations Patients having HPP (e.g., adults having HPP of about 18 years of age or older, such as adults having pediatric-onset HPP, or adolescents having HPP of about 13 years of age to about 17 years of age) can be identified for treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa) by determining the PPi and/or PLP concentrations in a sample, such as a plasma or urine sample, from the patient. Any method known to those of skill in the art can be used to quantify the PPi and PLP concentrations in a plasma sample or alternatively in a urine sample, as described in detail in Whyte et al., 1995 (*J. Clin. Invest.* 95(4): 1440-1445), hereby incorporated by reference in its entirety. Methods to quantify PPi concentrations in a plasma or urine sample are also described in Cheung et al., 1977 (*Anal. Biochem.* 83: 61-63), Cook et al., 1978 (*Anal. Biochem.* 91: 557-565), and Johnson et al, 1968 (*Anal. Biochem.* 26: 137-145), which are each hereby incorporated by reference in their entirety. In particular, PPi and PLP concentrations in a plasma sample can be used to evaluate ALP activity for the patient (e.g., an adult having HPP of about 18 years of age or older, such as an adult having pediatric-onset HPP, or an adolescent having HPP of about 13 years of age to about 17 years of age).

In comparison to healthy subjects (e.g., healthy subjects of about the same age, same gender, and/or same height), HPP patients typically exhibit elevated plasma concentrations of PPi and PLP, such as a PPi concentration of up to about 6 µM (e.g., about 3.5 µM, about 4 µM, about 4.5 µM, about 5 µM, or about 5.5 µM) and/or a PLP concentration of up to about 1300 ng/ml (e.g., a plasma PLP concentration of about 200 ng/ml, 300 ng/ml, 400 ng/ml, 500 ng/ml, 600 ng/ml, 700 ng/ml, 800 ng/ml, 900 ng/ml, 1000 ng/ml, 1100 ng/ml, 1200 ng/ml, or 1300 ng/ml). The lower normal limit for plasma PPi concentrations of healthy adults is about 1 µM, while the upper normal limit is about 5.9 µM. The lower normal limit for plasma PLP concentrations of healthy adults is less than about 10 ng/ml, while the upper normal limit is about 60 ng/ml. The lower normal limit for plasma PPi concentrations of healthy adolescents is less than about 0.75 µM, while the upper normal limit is about 4.78 µM. The lower normal limit for plasma PLP concentrations of healthy adolescents is less than about 5.74 ng/ml, while the upper normal limit is about 61.15 ng/ml.

HPP patients (e.g., adults having HPP of about 18 years of age or older, such as adults having pediatric-onset HPP, or adolescents having HPP of about 13 years of age to about 17 years of age) with elevated plasma concentrations of PPi and/or PLP can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as by administering an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For example, an HPP patient (e.g., an adult having HPP of about 18 years of age or older, such as an adult having pediatric-onset HPP, or an adolescent having HPP of about 13 years of age to about 17 years of age) with a PPi concentration of up to about 6 µM can be treated with an sALP during the treatment period. Likewise, an HPP patient with a PLP concentration of up to about 1300 ng/ml can be treated with an sALP during the treatment period.

The methods result in a statistically significant decrease in PPi and/or PLP concentrations in a sample (e.g., a plasma sample) from the patient. For example, treatment with an sALP results in a decrease in PPi concentrations in a sample (e.g., a plasma sample) from the patient of about 1 µM, about 1.5 µM, about 2 µM, about 2.5 µM, or about 3 µM or 25% or greater (e.g., 30%, 35%, 40%, 45%, 50%, 55%, 60%, or more than 60%) relative to PPi concentrations in a sample (e.g., a plasma sample) from an untreated HPP patient (e.g., a pediatric-onset HPP subject of about 18 years of age or older). Thus, the patient exhibits a plasma PPi concentration of, e.g., about 2 µM to about 5 µM, about 3 µM to about 5 µM, about 2 µM to about 4 µM, or about 2 µM to about 3 µM after administration of the sALP.

Likewise, treatment with an sALP results in a decrease in PLP concentrations in a sample (e.g., a plasma sample) from the patient of about 100 ng/ml, 125 ng/ml, 150 ng/ml, 175 ng/ml, 200 ng/ml, 225 ng/ml, or 250 ng/ml or 50% or greater (e.g., 55%, 60%, 65%, 70%, 75%, 80%, 85%, 90%, 95%, or more than 95%) relative to PLP concentrations in a sample (e.g., a plasma sample) from an untreated HPP patient (e.g., a pediatric-onset HPP subject of about 18 years of age or older). Thus, the patient exhibits a plasma PLP concentration of, e.g., about 2 ng/ml to about 150 ng/ml, about 4 ng/ml to about 100 ng/ml, about 10 ng/ml to about 75 ng/ml, or about 1 ng/ml to about 50 ng/ml after administration of the sALP.

The decrease in the plasma PPi and/or PLP concentrations of the HPP patient (e.g., an adult having HPP of about 18 years of age or older, such as an adult having pediatric-onset HPP, or an adolescent having HPP of about 13 years of age to about 17 years of age) can be sustained throughout administration of the sALP. For instance, the plasma PPi concentration decreases by about 25% and remains at ±10% of the decreased plasma PPi concentration during treatment with the sALP and/or the plasma PLP concentration decreases by about 50% and remains at ±10% of the decreased plasma PLP concentration during treatment with the sALP Alternatively, when administration of an sALP does not result in a decrease in PPi concentrations in a plasma sample from the HPP patient (e.g., an adult having HPP of about 18 years of age or older, such as an adult having pediatric-onset HPP, or an adolescent having HPP of about 13 years of age to about 17 years of age) by about 25% or greater, the dosage and/or frequency of sALP administration can be changed in order to determine the effective amount of the sALP for the HPP patient (e.g., an adult having HPP of about 18 years of age or older, such as an adult having pediatric-onset HPP). Likewise, when administration of an sALP does not result in a decrease in PLP concentrations in a plasma sample from the patient by about 50% or greater, the dosage and/or frequency of sALP administration can be changed in order to determine the effective amount of the sALP for the HPP patient (e.g., an adult having HPP of about 18 years of age or older, such as an adult having pediatric-onset HPP, or an adolescent having HPP of about 13 years of age to about 17 years of age). For instance, the dosage of the sALP can be increased from, e.g., about 2.1 mg/kg/week or about 3.5 mg/kg/week to about 6 mg/kg/week or about 9 mg/kg/week.

Six Minute Walk Test (6MWT)

Adults having HPP (e.g., adults having HPP of about 18 years of age or older, such as adults having pediatric-onset HPP, or an adolescent having HPP of about 13 years of age to about 17 years of age) can be identified for treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa) using the 6MWT. In particular, the 6MWT can be used to evaluate walking ability in an adult having HPP (e.g., an adult having HPP of about 18 years of age or older, such as an adult having pediatric-onset HPP) or an adolescent having HPP (e.g., an adolescent having HPP of about 13 years of age to about 17 years of age) to generate a 6MWT value for the adult or adolescent.

The 6MWT can be performed indoors or outdoors using a flat, straight, enclosed corridor (e.g., of about 30 meters in length) with a hard surface. A stopwatch or other timer can be used to track the time and a mechanical counter or other device can be used to determine the distance (e.g., in meters) that the HPP patient (e.g., an adult having HPP of about 18 years of age or older, such as an adult having pediatric-onset HPP, or an adolescent having HPP (e.g., adolescents having HPP of about 13 years of age to about 17 years of age) walks. For instance, the length of the corridor can be marked every three meters to determine the number of meters walked by the HPP patient, with the turnaround point at 30 meters and the starting line also marked. The distance walked by the patient in six minutes can then be compared to the predicted number of meters walked, e.g., by an untreated subject of about the same age, the same gender, and/or the same height, and expressed as a percentage value to generate the 6MWT value of the patient. The 6MWT value of the patient (e.g., an adult having HPP of about 18 years of age or older, such as an adult having pediatric-onset HPP, or an adolescent having HPP of about 13 years of age to about 17 years of age) can be compared to the 6MWT value at baseline of the patient. Additionally, the 6MWT value of the adult or adolescent having HPP can be compared to the 6MWT value of a healthy patient.

HPP patients (e.g., adults having HPP of about 18 years of age or older, such as adults having pediatric-onset HPP, or adolescents having HPP of about 13 years of age to about 17 years of age) with a 6MWT of less than about 80% of the predicted 6MWT value can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as by administering an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For example, an HPP patient with a 6MWT of less than about 80% of the predicted 6MWT value (e.g., about 50%, about 55%, about 60%, about 65%, about 70%, or about 75% of the predicted 6MWT value) can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa) for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods can result in an improvement in the 6MWT value of a HPP patient (e.g., an adult having HPP of about 18 years of age or older, such as an adult having pediatric-onset HPP, or an adolescent having HPP of about 13 years of age to about 17 years of age). For example, treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in a increase in the 6MWT value to about 80% or greater of the predicted 6MWT value of the patient (e.g. about 82%, about 84%, about 86%, about 88%, about 90%, about 92%, about 94%, about 96%, about 98%, or more of the predictive 6MWT value).

The increase in the 6MWT value of the HPP patient (e.g., an adult having HPP of about 18 years of age or older, such as an adult having pediatric-onset HPP, or an adolescent having HPP of about 13 years of age to about 17 years of age) can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For instance, the 6MWT value increases to greater than about 80% of the predicted 6 MWT value of the patient and remains at ±10% of the increased 6MWT value during treatment with the sALP (e.g., asfotase alfa).

Likewise, the improvement in walking ability of the HPP patient (e.g., an adult having HPP of about 18 years of age or older, such as an adult having pediatric-onset HPP, or an adolescent having HPP of about 13 years of age to about 17 years of age) can be sustained throughout administration of the sALP, e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). For instance, the HPP patient exhibits decreased reliance on an assistive mobility device, such as a walker, a wheelchair, braces, crutches, or orthotics, during treatment with the sALP.

Alternatively, when administration of an sALP does not result in an increase in the 6MWT value to greater than 80% of the predicted 6MWT value (e.g., of an untreated subject having HPP of about the same age, same gender, and/or height), the dosage and/or frequency of sALP administration can be changed in order to determine the effective amount of the sALP for the HPP patient (e.g., an adult having HPP of about 18 years of age or older, such as an adult having pediatric-onset HPP, or an adolescent having HPP of about 13 years of age to about 17 years of age). For instance, the dosage of the sALP (such as TNALP, for example the sALP fusion polypeptide of SEQ ID NO: 1 or a polypeptide variant having at least 95% sequence identity to the sequence of SEQ ID NO: 1, e.g., asfotase alfa) can be increased from, e.g., about 2.1 mg/kg/week or about 3.5 mg/kg/week to about 6 mg/kg/week or about 9 mg/kg/week.

Bruininks-Oseretsky Test of Motor Proficiency 2nd Edition (BOT-2)

Adults having HPP (e.g., an adult having HPP of about 18 years of age or older, such as an adult having pediatric-onset HPP) or adolescents having HPP (e.g., adolescents having HPP of about 13 years of age to about 17 years of age) can be identified for treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa) using the BOT-2 running speed and agility and BOT-2 strength tests. In particular, the BOT-2 speed and agility and BOT-2 strength tests can be used to evaluate physical impairments and mobility restrictions in an adult having HPP to generate a total BOT-2 speed and agility score and/or total BOT-2 strength score for the adult.

The BOT-2 includes a range of tests to evaluate physical impairments of a patient having HPP (e.g., an adult having HPP of about 18 years of age or older, such as an adult having pediatric-onset HPP, or an adolescent having HPP of about 13 years of age to about 17 years of age), which can be performed with, e.g., a kit including the tests. The BOT-2 provides composite BOT-2 scores in the following areas: strength, running speed and agility, fine motor precision, fine motor integration, manual dexterity, bilateral coordination, balance, and upper-limb coordination. For example, the adult or adolescent having HPP can perform sit-ups, v-ups, standing long jump, wall sit, and/or push-ups to determine the BOT-2 strength score; the adult or adolescent having HPP can step over a balance beam and/or perform a shuttle run, two-legged side hop, and/or one-legged side hop to determine the BOT-2 running speed and agility score; the adult or adolescent having HPP can cut out a circle and/or connect dots to determine the BOT-2 fine motor precision score; the adult or adolescent having HPP can copy a star and/or copy a square to determine the BOT-2 fine motor integration score; the adult or adolescent having HPP can transfer pennies, sort cards, and/or string blocks to determine the manual dexterity score; the adult or adolescent having HPP can tap his or her foot and finger and/or perform jumping jacks to determine the BOT-2 bilateral coordination score; the adult or adolescent having HPP can walk forward on a line and/or stand on one leg on a balance beam to determine the BOT-2 balance score; and the adult or adolescent having HPP can throw a ball at a target and/or catch a tossed ball to determine the BOT-2 upper-limb coordination score. The BOT-2 score is an additive total of each area assessed. Moreover, the BOT-2 score used to assess the physical proficiency of the patient can be the raw additive score or a normative score.

An adult having HPP (e.g., an adult having HPP of about 18 years of age or older, such as an adult having pediatric-onset HPP), or an adolescent having HPP (e.g., an adolescent having HPP of about 13 years of age to about 17 years of age) could perform tests in one or more of described areas (strength, running speed and agility, fine motor precision, fine motor integration, manual dexterity, bilateral coordination, balance, and upper-limb coordination) to generate a BOT-2 score indicative of physical impairments in the adult or adolescent. Within each BOT-2 area (strength, running speed and agility, fine motor precision, fine motor integration, manual dexterity, bilateral coordination, balance, and upper-limb coordination), an adult or adolescent having HPP could perform one or more tests to determine the BOT-2 score of the adult or adolescent, e.g., the adult or adolescent could perform one or more of sit-ups, v-ups, standing long jump, wall sit, and push-ups to determine the BOT-2 strength score. If desired, only a single test (e.g., one test selected from the group of sit-ups, v-ups, standing long jump, wall sit, and push-ups) can be performed to determine the BOT-2 score (e.g., a BOT-2 strength score) of an adult or adolescent having HPP.

Each of the BOT-2 scores (strength, running speed and agility, fine motor precision, fine motor integration, manual dexterity, bilateral coordination, balance, and upper-limb coordination) of the patient having HPP (e.g., an adult having HPP of about 18 years of age or older, such as an adult having pediatric-onset HPP or an adolescent having HPP of about 13 years of age to about 17 years of age) can be compared to the BOT-2 score of patients without HPP (e.g., an adult without HPP of about 18 years of age or older or an adolescent having HPP of about 13 years of age to about 17 years of age) to, e.g., determine the standard deviation of the BOT-2 score. Each of the BOT-2 scores (e.g., strength, running speed and agility, fine motor precision, fine motor integration, manual dexterity, bilateral coordination, balance, and upper-limb coordination) of the patient having HPP can be compared to the BOT-2 score of other HPP patients (e.g., HPP patients of about the same age, height, and/or gender) to, e.g., determine the BOT-2 score for the HPP patient.

BOT-2 scores (e.g., strength, running speed and agility, fine motor precision, fine motor integration, manual dexterity, bilateral coordination, balance, and upper-limb coordination scores) range from about 0 to equal to or less than about 25, in which a score of greater than about 10 is considered representative of healthy subjects (e.g., patients without HPP). Patients with a BOT-2 score (e.g., strength, running speed and agility, fine motor precision, fine motor integration, manual dexterity, bilateral coordination, balance, and upper-limb coordination scores) of less than about 10 can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as by administering an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

For example, an HPP patient (e.g., an adult having HPP of about 18 years of age or older, such as an adult having pediatric-onset HPP or an adolescent having HPP of about 13 years of age to about 17 years of age) with a BOT-2 running speed and agility score of less than 10 (e.g, about 0, about 1, about 2, about 3, about 4, about 5, about 6, about 7, about 8, about 9, or about 10) can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa) for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). Similarly, an HPP patient (e.g., an adult having HPP of about 18 years of age or older, such as an adult having pediatric-onset HPP, or an adolescent having HPP of about 13 years of age to about 17 years of age) with a BOT-2 strength score of less than 12 (e.g, about 0, about 1, about 2, about 3, about 4, about 5, about 6, about 7, about 8, about 9, about 10, about 11, about 12, about 13, or about 14) can then be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa) for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods result in an improvement in the BOT-2 score (e.g., strength, running speed and agility, fine motor precision, fine motor integration, manual dexterity, bilateral coordination, balance, and/or upper-limb coordination score) of a HPP patient (e.g., an adult having HPP of about 18 years of age or older, such as an adult having pediatric-onset HPP, or an adolescent having HPP of about 13 years of age to about 17 years of age). For example, treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in an increase in the BOT-2 strength score to about 10 to about 20 or greater (e.g. about 9, about 10, about 11, about 12, about 13, about 14, about 15, about 16, about 17, about 18, about 19, about 20, about 21, about 22, about 23, about 24, or about 25). Additionally, treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in an increase in the BOT-2 running speed and agility score to about 9 to about 20 or greater (e.g. about 9, about 10, about 11, about 12, about 13, about 14, about 15, about 16, about 17, about 18, about 19, about 20, about 21, about 22, about 23, about 24, or about 25).

The increase in the BOT-2 score (e.g., strength, running speed and agility, fine motor precision, fine motor integration, manual dexterity, bilateral coordination, balance, and/or upper-limb coordination score) can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks). Likewise, the decrease in physical impairments can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The BOT-2 scores (strength, running speed and agility, fine motor precision, fine motor integration, manual dexterity, bilateral coordination, balance, and upper-limb coordination scores) of a HPP patient (e.g., an adult having HPP of about 18 years of age or older, such as an adult having pediatric-onset HPP, or an adolescent having HPP of about 13 years of age to about 17 years of age) can be used singly or in combination to assess treatment efficacy using an sALP (such as TNALP, for example the sALP fusion polypeptide of SEQ ID NO: 1 or a polypeptide variant having at least 95% sequence identity to the sequence of SEQ ID NO: 1, e.g., asfotase alfa), in which improvements relative to a certain test score demonstrate that the sALP is effective for treating physical impairments associated with HPP. For example, when administration of an sALP to a HPP patient (e.g., an adult having HPP of about 18 years of age or older, such as an adult having pediatric-onset HPP, or an adolescent having HPP of about 13 years of age to about 17 years of age) results in an increase in the BOT-2 running speed and agility score to about 9 or greater, in which the patient previously had a BOT-2 running speed and agility score of less than about 7, then the sALP is considered to be effective at, e.g., treating physical impairments associated with HPP. Alternatively, an increase of at least two points or more (e.g., 2, 3, 4, 5, 6, 7, 8, 9, or 10 points) over the BOT-2 running speed and agility score prior to treatment indicates efficacy (e.g., when coupled with a sustained high score for greater than 1 year of treatment).

Additionally, within each BOT-2 area (strength, running speed and agility, fine motor precision, fine motor integration, manual dexterity, bilateral coordination, balance, and upper-limb coordination), a HPP patient (e.g., an adult having HPP of about 18 years of age or older, such as an adult having pediatric-onset HPP, or an adolescent having HPP of about 13 years of age to about 17 years of age) could perform one or more tests to determine the BOT-2 score of the patient. For instance, the adult or adolescent having HPP could perform one or more of sit-ups, v-ups, standing long jump, wall sit, and push-ups to determine the BOT-2 strength score and assess the treatment efficacy of sALP administration. The adult or adolescent having HPP could perform one or more of balance beam, a shuttle run, two-legged side hop, and/or one-legged side hop to determine the BOT-2 running speed and agility score and assess the treatment efficacy of sALP administration. The adult or adolescent having HPP can cut out a circle and/or connect dots to determine the BOT-2 fine motor precision score and assess the treatment efficacy of sALP administration. The adult or adolescent having HPP can copy a star and/or copy a square to determine the BOT-2 fine motor integration score and assess the treatment efficacy of sALP administration. The adult or adolescent having HPP could perform one or more of transferring pennies, sorting cards, and stringing blocks to determine the BOT-2 manual dexterity score and assess the treatment efficacy of sALP administration. The adult or adolescent having HPP can tap his or her foot and finger and/or perform jumping jacks to determine the BOT-2 bilateral coordination score and assess the treatment efficacy of sALP administration. The adult or adolescent having HPP can walk forward on a line and/or stand on one leg on a balance beam to determine the BOT-2 balance score and assess the treatment efficacy of sALP administration. The adult or adolescent having HPP can throw a ball at a target and/or catch a tossed ball to determine the BOT-2 upper-limb coordination score and assess the treatment efficacy of sALP administration.

Alternatively, when administration of an sALP does not result in an increase in the BOT-2 running speed and agility score to greater than about 9 (e.g., an increase of at least 2 to 10 points (e.g., 2, 3, 4, 5, 6, 7, 8, 9, or 10 points) over the BOT-2 running speed and agility score prior to treatment with the sALP), the dosage and/or frequency of sALP administration can be changed in order to determine an effective amount of the sALP for the HPP patient (e.g., an adult having HPP of about 18 years of age or older, such as an adult having pediatric-onset HPP, or an adolescent having HPP of about 13 years of age to about 17 years of age). For instance, the dosage of the sALP (such as TNALP, for example the sALP fusion polypeptide of SEQ ID NO: 1 or a polypeptide variant having at least 95% sequence identity to the sequence of SEQ ID NO: 1, e.g., asfotase alfa) can be increased from, e.g., about 2.1 mg/kg/week or about 3.5 mg/kg/week to about 6 mg/kg/week or to about 9 mg/kg/week.

Handheld Dynamometry (HHD)

The grip and muscle strength of an HPP patient (e.g., an adult having HPP of about 18 years of age or older, such as an adult having pediatric-onset HPP, or an adolescent having HPP of about 13 years of age to about 17 years of age) can be assessed using Hand Held Dynamometry (HHD). For example, knee flexion and extension and also hip flexion, extension, and abduction of an HPP patient can be measured using, e.g., a MICROFET2™ Dynamometer, while grip strength of the HPP patient can be measured using, e.g., a JAMAR® Grip Dynamometer. In particular, the administrator holds the dynamometer stationary, and the patient exerts a maximal force against the dynamometer. Peak force data is collected in pounds, then converted to Newtons (N). Torque values are then calculated using limb length in N-meters. The torque value can then be compared to the torque value of, e.g., a normal subject of about the same age, the same gender, and/or the same height, and expressed as a percentage value to generate the HHD score of the subject.

An HPP patient (e.g., an adult having HPP of about 18 years of age or older, such as an adult having pediatric-onset HPP, or an adolescent having HPP of about 13 years of age to about 17 years of age) with an HHD score of less than about 80% of the predicted HHD score (e.g., relative to a normal subject of about the same age, the same gender, and/or the same height) can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa). For example, an HPP patient with an HHD of less than about 80% of the predicted HHD score can be treated with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods can result in an improvement in the HHD score of an HPP patient (e.g., an adult having HPP of about 18 years of age or older, such as an adult having pediatric-onset HPP, or an adolescent having HPP of about 13 years of age to about 17 years of age). For example, treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in an increase in the HHD score by about 5% or greater of the predicted HHD score of the patient (e.g., an increase of about 5%, about 10%, about 15%, about 20%, about 25%, about 30%, about 35%, about 40%, about 45%, or about 50%).

The increase in the HHD score of the HPP patient (e.g., an adult having HPP of about 18 years of age or older, such as an adult having pediatric-onset HPP, or an adolescent having HPP of about 13 years of age to about 17 years of age) can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the HPP patient; particularly at least six weeks). For instance, the HHD score increases by about 5% or greater of the predicted HHD score and remains at ±10% of the increased HHD score during treatment with the sALP. Alternatively, when administration of an sALP does not result in an increase in the HHD score by about 5% or greater of the predicted HHD score (e.g., of a HPP patient of about the same age, same gender, and/or height), the dosage and/or frequency of sALP administration can be changed in order to determine an effective amount of the sALP for the HPP patient. For instance, the dosage of the sALP can be increased from, e.g., about 2.1 mg/kg/week or about 3.5 mg/kg/week to about 6 mg/kg/week or about 9 mg/kg/week.

Lower Extremity Functional Scale (LEFS)

The decreased functional disability in the lower extremities of an HPP patient (e.g., an adult having HPP of about 18 years of age or older, such as an adult having pediatric-onset HPP, or an adolescent having HPP of about 13 years of age to about 17 years of age) can be assessed using the Lower Extremity Function Scale (LEFS). The LEFS can be used to evaluate the functional impairment of one or both lower extremities of an HPP patient, including the ability to monitor the patient over time and evaluate the effectiveness of asfotase alfa treatment. A licensed physical therapist can administer the LEFS to an HPP patient (e.g., an HPP patient of about 13 years of age or older) in interview format.

An HPP patient (e.g., an adult having HPP of about 18 years of age or older, such as an adult having pediatric-onset HPP, or an adolescent having HPP of about 13 years of age to about 17 years of age) with an LEFS score of less than about 40 (e.g., a LEFS score of about 10, about 15, about 20, about 25, about 30, about 35, or about 40) can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa). For example, an HPP patient with a LEFS score of less than about 40 (e.g., a LEFS score of about 10, about 15, about 20, about 25, about 30, about 35, or about 40) can be treated with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods can result in an improvement in the LEFS score of an HPP patient (e.g., an adult having HPP of about 18 years of age or older, such as an adult having pediatric-onset HPP, or an adolescent having HPP of about 13 years of age to about 17 years of age). For example, treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in an increase in the LEFS score by about 3 or more (e.g., about 3, about 4, about 5, about 6, about 7, about 8, about 9, or about 10).

The increase in the LEFS score of the HPP patient (e.g., an adult having HPP of about 18 years of age or older, such as an adult having pediatric-onset HPP, or an adolescent having HPP of about 13 years of age to about 17 years of age) can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the HPP patient; particularly at least six weeks). For instance, the LEFS score can increase by about 3 or more (e.g., about 3, about 4, about 5, about 6, about 7, about 8, about 9, or about 10) and remains at ±10% of the increased LEFS score during treatment with the sALP. Alternatively, when administration of an sALP does not result in an increase in the LEFS score by about 3 or more (e.g., about 3, about 4, about 5, about 6, about 7, about 8, about 9, or about 10), the dosage and/or frequency of sALP can be changed in order to determine an effective amount of sALP for the HPP patient. For instance, the dosage of the sALP can be increased from, e.g., about 2.1 mg/kg/week or about 3.5 mg/kg/week to about 6 mg/kg/week or about 9 mg/kg/week.

Brief Pain Inventory-Short Form (BPI-SF)

Pain of an HPP patient (e.g., an adult having HPP of about 18 years of age or older, such as an adult having pediatric-onset HPP, or an adolescent having HPP of about 13 years of age to about 17 years of age) can be assessed using the Brief Pain Inventory-Short Form (BPI-SF). The BPI-SF is a questionnaire designed to assess the severity of pain and the impact of pain on daily functions. The BPI-SF consists of 11 items that utilize a numeric rating scale to assess pain severity (4 items) and pain interference (7 items) in the 24 hours prior to questionnaire administration. The BPI-SF questionnaire provides information on the intensity of pain and degree to which the pain interferes with daily functions of the HPP patient (e.g., an HPP patient of about 13 years of age or older) on a numeric rating scale from 0 (no pain) to 10 (severe pain or significant interference caused by pain); lower scores indicate better quality of life outcomes and reduced pain. For instance, BPI-SF scores of the HPP adolescents and adults are a composite of 11 pain assessments.

An HPP patient (e.g., an adult having HPP of about 18 years of age or older, such as an adult having pediatric-onset HPP, or an adolescent having HPP of about 13 years of age to about 17 years of age) with a BPI-SF score of greater than about 10 (e.g., a BPI-SF score of about 10, about 15, about 20, about 25, or about 30 or more) can be treated with an sALP (such as TNALP, for example the sALP fusion polypeptide of SEQ ID NO: 1 or a polypeptide variant having at least 95% sequence identity to the sequence of SEQ ID NO: 1, e.g., asfotase alfa). For example, an HPP patient with a BPI-SF score of greater than about 10 (e.g., a BPI-SF score of about 10, about 15, about 20, about 25, or about 30 or more) can be treated with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks).

The methods can result in an improvement in the BPI-SF score of an HPP patient (e.g., an adult having HPP of about 18 years of age or older, such as an adult having pediatric-onset HPP, or an adolescent having HPP of about 13 years of age to about 17 years of age). For example, treatment with an sALP (such as TNALP, for example the sALP fusion polypeptide of SEQ ID NO: 1 or a polypeptide variant having at least 95% sequence identity to the sequence of SEQ ID NO: 1, e.g., asfotase alfa), such as treatment with an sALP for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the patient; particularly at least six weeks), can result in decrease in the BPI-SF score by about −2 or more (e.g., about −2, about −3, about −4, about −5, about −6, or about −7 or more).

The decrease in the BPI-SF score of the HPP patient (e.g., an adult having HPP of about 18 years of age or older, such as an adult having pediatric-onset HPP, or an adolescent having HPP of about 13 years of age to about 17 years of age) can be sustained throughout administration of the sALP (such as TNALP, for example the sALP fusion polypeptide of SEQ ID NO: 1 or a polypeptide variant having at least 95% sequence identity to the sequence of SEQ ID NO: 1, e.g., asfotase alfa), e.g., for a treatment period of at least two weeks (e.g., at least three weeks, at least four weeks, at least five weeks, at least six weeks, at least seven weeks, at least eight weeks, at least nine weeks, at least ten weeks, at least three months, at least four months, at least five months, at least six months, at least seven months, at least eight months, at least nine months, at least one year, at least two years, at least three years, at least four years, at least five years, at least six years, at least seven years, at least eight years, at least nine years, or at least ten years, or the lifetime of the HPP patient; particularly at least six weeks). For instance, the BPI-SF score decreases by about −2 or more (e.g., about −2, about −3, about −4, about −5, about −6, or about −7 or more) and remains at ±10% of the decreased BPI-SF score during treatment with the sALP.

Alternatively, when administration of an sALP (such as TNALP, for example the sALP fusion polypeptide of SEQ ID NO: 1 or a polypeptide variant having at least 95% sequence identity to the sequence of SEQ ID NO: 1, e.g., asfotase alfa) does not result in a decrease in the BPI-SF score by about −2 or more (e.g., about −2, about −3, about −4, about −5, about −6, or about −7 or more), the dosage and/or frequency of sALP can be changed in order to determine an effective amount of sALP for the HPP patient. For instance, the dosage of the sALP can be increased from, e.g., about 2.1 mg/kg/week or about 3.5 mg/kg/week to about 6 mg/kg/week or about 9 mg/kg/week.

Alkaline Phosphatase

Asfotase alfa is a human TNALP (hTNALP; SEQ ID NO: 1) fusion polypeptide formulated for the treatment of HPP. In particular, asfotase alfa (SEQ ID NO: 1) can be used effectively to treat hypophosphatasia (HPP), its symptoms, and physical impairments associated therewith in an adult having HPP ((e.g., an adult having HPP of about 18 years of age or older, such as an adult having pediatric-onset HPP, or an adolescent having HPP of about 13 years of age to about 17 years of age) for an extended period of time (e.g., at least six months, at least one year, at least two years, at least three years, at least four years, at least five years, at least six years, at least seven years, at least eight years, at least nine years, at least ten years, or longer than ten years, such as for the lifetime of the patient).

Given the results described herein, the treatment methods are not limited to administration of a particular alkaline phosphatase (ALP) or nucleic acid sequence encoding an ALP. Alkaline phosphatases encompass a group of enzymes that catalyze the cleavage of a phosphate moiety (e.g., hydrolysis of pyrophosphate, $PP_i$). There are four known mammalian alkaline phosphatase (ALP) isozymes: tissue nonspecific alkaline phosphatase (TNALP; described further below), placental alkaline phosphatase (PLALP) (e.g., Accession Nos. P05187, NP_112603, and NP_001623), germ cell alkaline phosphatase (GALP) (e.g., Accession No. P10696), and intestinal alkaline phosphatase (IALP) (e.g., Accession Nos. P09923 and NP_001622). In addition to the exemplary ALPs discussed above, any polypeptide having the identical or similar catalytic site structure and/or enzymatic activity of ALP can be used (e.g., as an sALP or an sALP fusion polypeptide as defined herein) for treating HPP patients, such as adults having HPP (e.g., adults having HPP of about 18 years of age or older, such as adults having pediatric-onset HPP) or adolescents having HPP (e.g., adolescents having HPP of about 13 years of age to about 17 years of age). Bone delivery conjugates including sALP are further described in International Publication Nos: WO 2005/103263 and WO 2008/138131.

TNALPs that can be used according to the methods described herein include, e.g., human TNALP (Accession Nos. NP_000469, AAI10910, AAH90861, AAH66116, AAH21289, and AAI26166); rhesus TNALP (Accession No. XP_01109717); rat TNALP (Accession No. NP_037191); dog TNALP (Accession No. AAF64516); pig TNALP (Accession No. AAN64273), mouse (Accession No. NP_031457), cow TNALP (Accession Nos. NP_789828, NP_776412, AAM 8209, and AAC33858), and cat TNALP (Accession No. NP_001036028). In particular, TNALP can be a recombinant human TNALP (e.g., SEQ ID NO: 1, asfotase alfa; see U.S. Pat. Nos. 7,763,712 and 7,960,529, incorporated herein by reference in their entirety) used for the treatment of HPP patients, such adults with HPP (e.g., adults having HPP of about 18 years of age or older, such as adults having pediatric-onset HPP) or adolescents having HPP (e.g., adolescents having HPP of about 13 years of age to about 17 years of age). The TNALP can also be one that exhibits at least about 95% sequence identity to the polypeptide or nucleic acid sequence of the above-noted TNALPs.

Soluble Alkaline Phosphatases

The ALPs that can be used in the methods described herein include soluble (e.g., extracellular or non-membrane-bound) forms of any of the alkaline phosphatases described herein. The sALP can be, for example, a soluble form of human tissue non-specific alkaline phosphatase (human TNALP (hTNALP)). The methods are not limited to a particular sALP and can include any sALP that is physiologically active toward, e.g., phosphoethanolamine (PEA), inorganic pyrophosphate (PPi), and pyridoxal 5′-phosphate (PLP). In particular, an sALP is one that is catalytically competent to improve skeletal mineralization in bone. The methods further include nucleic acids encoding the sALPs described herein that can be used to treat the conditions described herein, e.g., HPP, such as adults with HPP (e.g., adults having HPP of about 18 years of age or older, such as adults having pediatric-onset HPP) or adolescents having HPP (e.g., adolescents having HPP of about 13 years of age to about 17 years of age).

TNALP is a membrane-bound protein anchored by a glycolipid moiety at the C-terminal (Swiss-Prot, P05186). This glycolipid anchor (GPI) is added post-translationally after the removal of a hydrophobic C-terminal end, which serves both as a temporary membrane anchor and as a signal for the addition of the GPI. While the GPI anchor is located in the cell membrane, the remaining portions of TNALP are extracellular. In particular, TNALP (e.g., human TNALP (hTNALP)) can be engineered to replace the first amino acid of the hydrophobic C-terminal sequence (an alanine) with a stop codon, thereby producing an engineered hTNALP that contains all amino acid residues of the native anchored form of TNALP and lacks the GPI membrane anchor. One skilled in the art will appreciate that the position of the GPI membrane anchor will vary in different ALPs and can include, e.g., the last 10, 12, 14, 16, 18, 20, 21, 22, 23, 24, 25, 26, 27, 28, 29, 30, 32, 34, 36, 38, 40, 45, 50, or more amino acid residues on the C-terminus of the polypeptide. Recombinant sTNALP can include, e.g., amino acids 1 to 502 (18 to 502 when secreted), amino acids 1 to 501 (18 to 501 when secreted), amino acids 1 to 504 (18 to 504 when secreted), amino acids 1 to 505 (18-505 when secreted), or amino acids 1 to 502. Thus, the C-terminal end of the native ALP can be truncated by certain amino acids without affecting ALP activity.

In addition to the C-terminal GPI anchor, TNALP also has an N-terminal signal peptide sequence. The N-terminal signal peptide is present on the synthesized protein when it is synthesized, but cleaved from TNALP after translocation into the ER. The sALPs include both secreted (i.e., lacking the N-terminal signal) and non-secreted (i.e., having the N-terminal signal) forms thereof. One skilled in the art will appreciate that the position of the N-terminal signal peptide will vary in different alkaline phosphatases and can include, for example, the first 5, 8, 10, 11, 12, 13, 14, 15, 16, 17, 18, 19, 20, 21, 22, 23, 24, 25, 27, 30, or more amino acid residues on the N-terminus of the polypeptide. One of skill in the art can predict the position of a signal sequence cleavage site, e.g., by an appropriate computer algorithm such as that described in Bendtsen et al. (*J. Mol. Biol.* 340(4):783-795, 2004) and available on the Web at www.cbs.dtu.dk/services/SignalP/.

The methods can also be performed using sALP consensus sequences derived from the extracellular domain of ALP isozymes (e.g., TNALP, PALP, GCALP, IALP, etc.). Thus, similar to sTNALP discussed above, the present disclosure also provides other soluble human ALP isozymes, i.e., without the peptide signal, preferably comprising the extracellular domain of the ALPs. The sALPs also include polypeptide sequences satisfying a consensus sequence derived from the ALP extracellular domain of human ALP isozymes and of mammalian TNALP orthologs (human, mouse, rat, cow, cat, and dog) or a consensus derived from the ALP extracellular domain of just mammalian TNALP orthologs (human, mouse, rat, cow, cat, and dog). The sALPs also include those which satisfy similar consensus sequences derived from various combinations of these TNALP orthologs or human ALP isozymes. Such consensus sequences are given, for example, in WO 2008/138131.

sALPs of the present methods can include not only the wild-type sequence of the sALPs described above, but any polypeptide having at least 50% (e.g., 55%, 60%, 65%, 70%, 75%, 80%, 85%, 86%, 87%, 88%, 89%, 90%, 91%, 92%, 93%, 94%, 95%, 96%, 97%, 98%, 99%, or more) sequence identity to these alkaline phosphatases (e.g., SEQ ID NOs: 1-24; for example the sALP fusion polypeptide of SEQ ID NO: 1 or a polypeptide variant having at least 95% sequence identity to the sequence of SEQ ID NO: 1, e.g., asfotase alfa). Examples of mutations that can be introduced into an ALP sequence are described in US Publication No. 2013/0323244, hereby incorporated by reference in its entirety. An sALP can optionally be glycosylated at any appropriate one or more amino acid residues. In addition, an sALP can have at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to any of the sALPs described herein (such as TNALP, for example the sALP fusion polypeptide of SEQ ID NO: 1 or a polypeptide variant having at least 95% sequence identity to the sequence of SEQ ID NO: 1, e.g., asfotase alfa). An sALP can have 1, 2, 3, 4, 5, 6, 7, 8, 9, 10, or more additions, deletions, or substitutions relative to any of the sALPs described herein (such as TNALP, for example the sALP fusion polypeptide of SEQ ID NO: 1 or a polypeptide variant having at least 95% sequence identity to the sequence of SEQ ID NO: 1, e.g., asfotase alfa).

sALP Fusion Polypeptides

Any of the sALPs and linkers described herein can be combined in an sALP polypeptide, e.g., an sALP polypeptide of A-sALP-B, wherein each of A and B is absent or is an amino acid sequence of at least one amino acid (such as TNALP, for example the sALP polypeptide of SEQ ID NO: 1 or a polypeptide variant having at least 95% sequence identity to the sequence of SEQ ID NO: 1, e.g., asfotase alfa). When present, A and/or B can be any linker described herein. In some sALP polypeptides, A is absent, B is absent, or A and B are both absent. The sALP polypeptides of the invention can optionally include an Fc region to provide an sALP fusion polypeptide, as described herein. The sALP polypeptide can optionally include a bone-targeting moiety, as described herein. In some sALP polypeptides, a linker, e.g., a flexible linker, can be included between the bone-targeting moiety and the sALP, such as a dipeptide sequence (e.g., leucine-lysine or aspartic acid-isoleucine). Further exemplary Fc regions, linkers, and bone-targeting moieties are described below.

Any of the sALPs, linkers, and Fc regions described herein can be combined in a fusion polypeptide, e.g., a recombinant fusion polypeptide, which includes the structure Z-sALP-Y-spacer-X-$W_n$-V, Z-$W_n$-X-spacer-Y-sALP-V, Z-sALP-Y-$W_n$-X-spacer-V, and Z-$W_n$-X-sALP-Y-spacer-V (such as TNALP, for example the sALP polypeptide of SEQ ID NO: 1 or a polypeptide variant having at least 95% sequence identity to the sequence of SEQ ID NO: 1, e.g., asfotase alfa). In particular, the structure can be Z-sALP-Y-spacer-X-$W_n$-V or Z-$W_n$-X-spacer-Y-sALP-V. The sALP can be the full-length or functional fragments of ALPs, such as the soluble, extracellular domain of the ALP, as is described herein (e.g., TNALP, PALP, GCALP and IALP). Any one of X, Y, Z, and V and/or the spacer can be absent or an amino acid sequence of at least one amino acid. $W_n$ can be a bone-targeting moiety, e.g., having a series of consecutive Asp or Glu residues, in which n=1 to 50, e.g., n=3-30, e.g., 5-15, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 36, 38, 39, 40, 41, 42, 43, 44, 45, 46, 47, 48, 49, or 50. The bone-targeting moiety, if present, can be positioned anywhere in the fusion polypeptide, e.g., at or near the N-terminal or C-terminal end, and/or in the linker region. For instance, the bone-targeting moiety is at the C-terminal end. sALP polypeptides and fusion polypeptides can also not include a bone-targeting moiety.

sALP fusion polypeptides of the present invention can be of the structure hTNALP-Fc-$D_{10}$. In particular, sALP fusion polypeptides can include an amino acid sequence of SEQ ID NO: 1 or a polypeptide variant having at least 95% sequence identity to the sequence of SEQ ID NO: 1, e.g., asfotase alfa.

Useful spacers include, but are not limited to, polypeptides comprising a Fc, and hydrophilic and flexible polypeptides able to alleviate the repulsive forces caused by the presence of the terminal highly negatively charged peptide (e.g., $W_n$). For example, an sALP can be a fusion polypeptide including an Fc region of an immunoglobulin at the N-terminal or C-terminal domain. An immunoglobulin molecule has a structure that is well known in the art. It includes two light chains (~23 kD each) and two heavy chains (~50-70 kD each) joined by inter-chain disulfide bonds. Immunoglobulins are readily cleaved proteolytically (e.g., by papain cleavage) into Fab (containing the light chain and the VH and CH1 domains of the heavy chain) and Fc (containing the CH2 and CH3 domains of the heavy chain, along with adjoining sequences). Useful Fc fragments as described herein include the Fc fragment of any immunoglobulin molecule, including IgG, IgM, IgA, IgD, or IgE, and their various subclasses (e.g., IgG-1, IgG-2, IgG-3, IgG-4, IgA-1, IgA-2), from any mammal (e.g., human). For instance, the Fc fragment is human IgG-1. The Fc fragments of the invention can include, for example, the CH2 and CH3 domains of the heavy chain and any portion of the hinge region. The Fc region can optionally be glycosylated at any appropriate one or more amino acid residues known to those skilled in the art. In particular, the Fc fragment of the fusion polypeptide has the amino acid sequence of SEQ ID NO: 20, or has at least 50% (e.g., 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more) sequence identity to SEQ ID NO: 20. Engineered, e.g., non-naturally occurring, Fc regions can be utilized in the methods of the invention, e.g., as described in International Application Pub. No. WO2005/007809, which is hereby incorporated by reference. An Fc fragment as described herein can have 1, 2, 3, 4, 5, 6, 7, 8, 9, 10, 11, 12, 13, 14, 15, 16, 17, 18, 19, 20, 25, 30, 35, 40, 50, or more additions, deletions, or substitutions relative to any of the Fc fragments described herein.

The sALP fusion polypeptides described herein (such as TNALP, for example the sALP polypeptide of SEQ ID NO: 1 or a polypeptide variant having at least 95% sequence identity to the sequence of SEQ ID NO: 1, e.g., asfotase alfa) can include a peptide linker region between the Fc fragment. In addition, a peptide linker region can be included between the Fc fragment and the optional bone-targeting moiety. The linker region can be of any sequence and length that allows the sALP to remain biologically active, e.g., not sterically hindered. Exemplary linker lengths are between 1 and 200 amino acid residues, e.g., 1-5, 6-10, 11-15, 16-20, 21-25, 26-30, 31-35, 36-40, 41-45, 46-50, 51-55, 56-60, 61-65, 66-70, 71-75, 76-80, 81-85, 86-90, 91-95, 96-100, 101-110, 111-120, 121-130, 131-140, 141-150, 151-160, 161-170, 171-180, 181-190, or 191-200 amino acid residues. For instance, linkers include or consist of flexible portions, e.g., regions without significant fixed secondary or tertiary structure. Exemplary flexible linkers are glycine-rich linkers, e.g., containing at least 50%, 60%, 65%, 70%, 75%, 80%, 85%, 90%, 95%, or even 100% glycine residues. Linkers can also contain, e.g., serine residues. In some cases, the amino acid sequence of linkers consists only of glycine and serine residues. A linker can optionally be glycosylated at any appropriate one or more amino acid residues. Additionally, a linker as described herein can include any other sequence or moiety, attached covalently or non-covalently. The linker can also be absent, in which the Fc fragment and the sALP are fused together directly, with no intervening residues. Certain Fc-sALP or sALP-Fc fusion polypeptides can be viewed, according to the present disclosure, either as 1) having no linker, or as 2) having a linker which corresponds to a portion of the sALP. For example, Fc fused directly to hsTNALP (1-502) can be viewed, e.g., either as having no linker, in which the hsTNALP is amino acids 1-502, or as having a 17-amino acid linker, in which the hsTNALP (18-502).

Additional amino acid residues can be introduced into the polypeptide according to the cloning strategy used to produce the fusion polypeptides. For instance, the additional amino acid residues do not provide an additional GPI anchoring signal so as to maintain the polypeptide in a soluble form. Furthermore, any such additional amino acid residues, when incorporated into the polypeptide of the invention, do not provide a cleavage site for endoproteases of the host cell. The likelihood that a designed sequence would be cleaved by the endoproteases of the host cell can be predicted as described, e.g., by Ikezawa (*Biol. Pharm. Bull.* 25:409-417, 2002).

The sALPs and sALP fusion polypeptides of the invention (such as TNALP, for example the sALP polypeptide of SEQ ID NO: 1 or a polypeptide variant having at least 95% sequence identity to the sequence of SEQ ID NO: 1, e.g., asfotase alfa) can be associated into dimers or tetramers. For example, two sALP-Fc monomers can covalently be linked through two disulfide bonds located in the hinge regions of the Fc fragments. Additionally, the polypeptide or fusion polypeptide of the invention (e.g., an sALP polypeptide or fusion polypeptide) can be glycosylated or PEGylated.

Production of Nucleic Acids and Polypeptides

The nucleic acids encoding sALPs and sALP fusion polypeptides (such as TNALP, for example the sALP fusion polypeptide of SEQ ID NO: 1 or a polypeptide variant having at least 95% sequence identity to the sequence of SEQ ID NO: 1, e.g., asfotase alfa) can be produced by any method known in the art. Typically, a nucleic acid encoding the desired fusion polypeptide is generated using molecular cloning methods, and is generally placed within a vector, such as a plasmid or virus. The vector is used to transform the nucleic acid into a host cell appropriate for the expression of the fusion polypeptide. Representative methods are disclosed, for example, in Maniatis et al. (Cold Springs Harbor Laboratory, 1989). Many cell types can be used as appropriate host cells, although mammalian cells are preferable because they are able to confer appropriate post-translational modifications. Host cells can include, e.g., Chinese Hamster Ovary (CHO) cell, L cell, C127 cell, 3T3 cell, BHK cell, COS-7 cell or any other suitable host cell known in the art. For example, the host cell is a Chinese Hamster Ovary (CHO) cell (e.g., a CHO-DG44 cell).

The sALPs and sALP fusion polypeptides (such as TNALP, for example the sALP fusion polypeptide of SEQ ID NO: 1 or a polypeptide variant having at least 95% sequence identity to the sequence of SEQ ID NO: 1, e.g., asfotase alfa) can be produced under any conditions suitable to effect expression of the sALP polypeptide in the host cell. Such conditions include appropriate selection of a media prepared with components such as a buffer, bicarbonate and/or HEPES, ions like chloride, phosphate, calcium, sodium, potassium, magnesium, iron, carbon sources like simple sugars, amino acids, potentially lipids, nucleotides, vitamins and growth factors like insulin; regular commercially available media like alpha-MEM, DMEM, Ham's-F12, and IMDM supplemented with 2-4 mM L-glutamine and 5% Fetal bovine serum; regular commercially available animal protein free media like Hyclone™ SFM4CHO, Sigma CHO DHFR−, Cambrex POWER™ CHO CD supplemented with 2-4 mM L-glutamine. These media are desirably prepared without thymidine, hypoxanthine and L-glycine to maintain selective pressure, allowing stable protein-product expression.

Pharmaceutical Compositions and Formulations

A composition that can be used in the methods described herein (e.g., including an sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) can be administered by a variety of methods known in the art. As will be appreciated by the skilled artisan, the route and/or mode of administration will vary depending upon the desired results. The route of administration can depend on a variety of factors, such as the environment and therapeutic goals. In particular, the polypeptides and fusion polypeptides described herein can be administration by any route known in the art, e.g., subcutaneous (e.g., by subcutaneous injection), intravenously, orally, nasally, intramuscularly, sublingually, intrathecally, or intradermally. By way of example, pharmaceutical compositions that can be used in the methods described herein can be in the form of a liquid, solution, suspension, pill, capsule, tablet, gelcap, powder, gel, ointment, cream, nebulae, mist, atomized vapor, aerosol, or phytosome.

Dosage

Any amount of a pharmaceutical composition (e.g., including an sALP or sALP fusion polypeptide, such as TNALP, for example the sALP polypeptide of SEQ ID NO: 1 or a polypeptide variant having at least 95% sequence identity to the sequence of SEQ ID NO: 1, e.g., asfotase alfa) can be administered to adults having HPP (e.g., adults having HPP of about 18 years of age or older, such as adults having pediatric-onset HPP) or adolescents having HPP (e.g., adolescents having HPP of about 13 years of age to about 17 years of age). The dosages will depend on many factors including the mode of administration and the age of the patient. For example, the sALP polypeptides (such as TNALP, for example the sALP polypeptide of SEQ ID NO: 1 or a polypeptide variant having at least 95% sequence identity to the sequence of SEQ ID NO: 1, e.g., asfotase alfa) described herein can be administered to an HPP patient, such as an adult having HPP (e.g., an adult having HPP of about 18 years of age or older, such as an adult having pediatric-onset HPP) or an adolescent having HPP (e.g., an adolescent having HPP of about 13 years of age to about 17 years of age), in individual doses ranging, e.g., from 0.01 mg/kg to 500 mg/kg of the patient (e.g., from 0.05 mg/kg to 500 mg/kg, from 0.1 mg/kg to 20 mg/kg, from 5 mg/kg to 500 mg/kg, from 0.1 mg/kg to 100 mg/kg, from 10 mg/kg to 100 mg/kg, from 0.1 mg/kg to 50 mg/kg, 0.5 mg/kg to 25 mg/kg, 1.0 mg/kg to 10 mg/kg, 1.5 mg/kg to 5 mg/kg, or 2.0 mg/kg to 3.0 mg/kg) or from 1 µg/kg to 1,000 µg/kg (e.g., from 5 µg/kg to 1,000 µg/kg, from 1 µg/kg to 750 µg/kg, from 5 µg/kg to 750 µg/kg, from 10 µg/kg to 750 µg/kg, from 1 µg/kg to 500 µg/kg, from 5 µg/kg to 500 µg/kg, from 10 µg/kg to 500 µg/kg, from 1 µg/kg to 100 µg/kg, from 5 µg/kg to 100 µg/kg, from 10 µg/kg to 100 µg/kg, from 1 µg/kg to 50 µg/kg, from 5 µg/kg to 50 µg/kg, or from 10 µg/kg to 50 µg/kg of the patient).

Exemplary doses of an sALP include, e.g., 0.01, 0.05, 0.1, 0.5, 1, 2, 2.5, 5, 10, 20, 25, 50, 100, 125, 150, 200, 250, or 500 mg/kg; or 1, 2, 2.5, 5, 10, 20, 25, 50, 100, 125, 150, 200, 250, 500, 750, 900, or 1,000 µg/kg. In particular, compositions (e.g., including sALP (such as TNALP, for example the sALP polypeptide of SEQ ID NO: 1 or a polypeptide variant having at least 95% sequence identity to the sequence of SEQ ID NO: 1, e.g., asfotase alfa)) in accordance with the present disclosure can be administered to patients in doses ranging from about 0.001 mg/kg/day to about 500 mg/kg/day, about 0.01 mg/kg/day to about 100 mg/kg/day, or about 0.01 mg/kg/day to about 20 mg/kg/day. For example, the sALP compositions (such as TNALP, for example the sALP polypeptide of SEQ ID NO: 1 or a polypeptide variant having at least 95% sequence identity to the sequence of SEQ ID NO: 1, e.g., asfotase alfa) can be administered to patients in a weekly dosage ranging, e.g., from about 0.5 mg/kg/week to about 140 mg/kg/week, e.g., about 0.8 mg/kg/week to about 50 mg/kg/week, or about 1 mg/kg/week to about 10 mg/kg/week (e.g., about 6 or about 9 mg/kg/week). In particular, the sALP (such as TNALP, for example the sALP polypeptide of SEQ ID NO: 1 or a polypeptide variant having at least 95% sequence identity to the sequence of SEQ ID NO: 1, e.g., asfotase alfa) can be administered at a dosage of 2 mg/kg three times a week (total dose 6 mg/kg/week), 1 mg/kg six times a week (total dose 6 mg/kg/week), 3 mg/kg three times a week (total dose 9 mg/kg/week), 0.5 mg/kg three times a week (total dose of 1.5 mg/kg/week), or 9.3 mg/kg three times a week (total dose 28 mg/kg/week). The dosage will be adapted by the clinician in accordance with conventional factors such as the extent of the disease and different parameters from the HPP patient, such as an adult having HPP (e.g., an adult having HPP of about 18 years of age or older, such as an adult having pediatric-onset HPP) or an adolescent having HPP (e.g., an adolescent having HPP of about 13 years of age to about 17 years of age).

Dosages of compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be provided in either a single or multiple dosage regimens. Doses can be administered, e.g., hourly, bihourly, daily, bidaily, twice a week, three times a week, four times a week, five times a week, six times a week, weekly, biweekly, monthly, bimonthly, or yearly. Alternatively, doses can be administered, e.g., twice, three times, four times, five times, six times, seven times, eight times, nine times, 10 times, 11 times, or 12 times per day. In particular, the dosing regimen is once weekly. The duration of the dosing regimen can be, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 day(s), week(s), or month(s), or even for the remaining lifespan of the HPP patient, such as adult having HPP (e.g., an adult having HPP of about 18 years of age or older, such as an adult having pediatric-onset HPP) or an adolescent having HPP (e.g., an adolescent having HPP of about 13 years of age to about 17 years of age). The amount, frequency, and duration of dosage will be adapted by the clinician in accordance with conventional factors such as the extent of the disease and different parameters from the HPP patient, such as an adult having HPP (e.g., an adult having HPP of about 18 years of age or older, such as an adult having pediatric-onset HPP) or an adolescent having HPP (e.g., an adolescent having HPP of about 13 years of age to about 17 years of age).

For example, an sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection, which is a clear, colorless to slightly yellow, aqueous solution, pH 7.4. The sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) may be formulated at a concentration of 12 mg/0.3 mL, 18 mg/0.45 mL, 28 mg/0.7 mL, 40 mg/1 ml, or 80 mg/0.8 mL. In particular, the composition can be formulated as a 40 mg/ml solution for injection, in which each ml of solution contains 40 mg of sALP or sALP polypeptide (e.g., each vial contains 0.3 ml solution and 12 mg of sALP (40 mg/ml), each vial contains 0.45 ml solution and 18 mg of sALP (40 mg/ml), each vial contains 0.7 ml solution and 28 mg of sALP (40 mg/ml), or each vial contains 1.0 ml solution and 40 mg of asfotase alfa (40 mg/ml)). An sALP or sALP polypeptide (such as TNALP, for example the sALP polypeptide of SEQ ID NO: 1 or a polypeptide variant having at least 95% sequence identity to the sequence of SEQ ID NO: 1, e.g., asfotase alfa) can be formulated as a solution for injection at a concentration of 100 mg/ml, in which each 1 ml of solution contains 100 mg of sALP or sALP polypeptide (e.g., each vial contains 0.8 ml solution and 80 mg of asfotase alfa (100 mg/ml)). The volume of the sALP injected in the patient may be, e.g., 0.15 ml, 0.18 ml, 0.20 ml, 0.23 ml, 0.25 ml, 0.28 ml, 0.30 ml, 0.33 ml, 0.35 ml, 0.38 ml, 0.40 ml, 0.43 ml, 0.45 ml, 0.48 ml, 0.50 ml, 0.63 ml, 0.75 ml, 0.88 ml, or 1.00 ml.

For example, the recommended dosage of an sALP or sALP fusion polypeptide ((such as TNALP, for example the sALP polypeptide of SEQ ID NO: 1 or a polypeptide variant having at least 95% sequence identity to the sequence of SEQ ID NO: 1, e.g., asfotase alfa) is 2 mg/kg of body weight administered subcutaneously three times per week, or a dosage regimen of 1 mg/kg of body weight administered subcutaneously six times per week. Additional dosage information is provided below (Table 1). In particular, a 40 kg patient administered a dosage of 6 mg/kg/week would receive an injection of 80 mg of the sALP in 0.8 ml three times a week or 40 mg of the sALP in 1.00 ml six times a week, while a 50 kg patient administered a dosage of 6 mg/kg/week would receive an injection of 50 mg of the sALP in 0.05 ml six times a week.

TABLE 1

DOSING OF ASFOTASE ALFA

| Body Weight (kg) | If injecting 3x per week | | | If injecting 6x per week | | |
|---|---|---|---|---|---|---|
| | Dose to be injected | Volume to be injected | Vial type used for injection | Dose to be injected | Volume to be injected | Vial type used for injection |
| 3 | 6 mg | 0.15 ml | 0.3 ml | | | |
| 4 | 8 mg | 0.20 ml | 0.3 ml | | | |
| 5 | 10 mg | 0.25 ml | 0.3 ml | | | |
| 6 | 12 mg | 0.30 ml | 0.3 ml | 6 mg | 0.15 ml | 0.3 ml |
| 7 | 14 mg | 0.35 ml | 0.45 ml | 7 mg | 0.18 ml | 0.3 ml |
| 8 | 16 mg | 0.40 ml | 0.45 ml | 8 mg | 0.20 ml | 0.3 ml |
| 9 | 18 mg | 0.45 ml | 0.45 ml | 9 mg | 0.23 ml | 0.3 ml |
| 10 | 20 mg | 0.50 ml | 0.7 ml | 10 mg | 0.25 ml | 0.3 ml |
| 11 | 22 mg | 0.55 ml | 0.7 ml | 11 mg | 0.28 ml | 0.3 ml |
| 12 | 24 mg | 0.60 ml | 0.7 ml | 12 mg | 0.30 ml | 0.3 ml |
| 13 | 26 mg | 0.65 ml | 0.7 ml | 13 mg | 0.33 ml | 0.45 ml |
| 14 | 28 mg | 0.70 ml | 0.7 ml | 14 mg | 0.35 ml | 0.45 ml |
| 15 | 30 mg | 0.75 ml | 1 ml | 15 mg | 0.38 ml | 0.45 ml |
| 16 | 32 mg | 0.80 ml | 1 ml | 16 mg | 0.40 ml | 0.45 ml |
| 17 | 34 mg | 0.85 ml | 1 ml | 17 mg | 0.43 ml | 0.45 ml |
| 18 | 36 mg | 0.90 ml | 1 ml | 18 mg | 0.45 ml | 0.45 ml |
| 19 | 38 mg | 0.95 ml | 1 ml | 19 mg | 0.48 ml | 0.7 ml |
| 20 | 40 mg | 1.00 ml | 1 ml | 20 mg | 0.50 ml | 0.7 ml |
| 25 | 50 mg | 0.50 ml | 0.8 ml | 25 mg | 0.63 ml | 0.7 ml |
| 30 | 60 mg | 0.60 ml | 0.8 ml | 30 mg | 0.75 ml | 1 ml |
| 35 | 70 mg | 0.70 ml | 0.8 ml | 35 mg | 0.88 ml | 1 ml |
| 40 | 80 mg | 0.80 ml | 0.8 ml | 40 mg | 1.00 ml | 1 ml |
| 50 | | | | 50 mg | 0.50 ml | 0.8 ml |
| 60 | | | | 60 mg | 0.60 ml | 0.8 ml |
| 70 | | | | 70 mg | 0.70 ml | 0.8 ml |
| 80 | | | | 80 mg | 0.80 ml | 0.8 ml |
| 90 | | | | 90 mg | 0.90 ml | 0.8 ml (x2) |
| 100 | | | | 100 mg | 1.00 ml | 0.8 ml (x2) |

Formulations

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be formulated according to standard methods. Pharmaceutical formulation is a well-established art, and is further described in, e.g., Gennaro (2000) *Remington: The Science and Practice of Pharmacy*, 20th Edition, Lippincott, Williams & Wilkins (ISBN: 0683306472); Ansel et al. (1999) *Pharmaceutical Dosage Forms and Drug Delivery Systems*, 7th Edition, Lippincott Williams & Wilkins Publishers (ISBN: 0683305727); and Kibbe (2000) *Handbook of Pharmaceutical Excipients American Pharmaceutical Association*, 3$^{rd}$ Edition (ISBN: 091733096X). For instance, an sALP composition (such as TNALP, for example the sALP polypeptide of SEQ ID NO: 1 or a polypeptide variant having at least 95% sequence identity to the sequence of SEQ ID NO: 1, e.g., asfotase alfa) can be formulated, for example, as a buffered solution at a suitable concentration and suitable for storage at 2-8° C. (e.g., 4° C.). A composition can also be formulated for storage at a temperature below 0° C. (e.g., −20° C. or −80° C.). A composition can further be formulated for storage for up to 2 years (e.g., one month, two months, three months, four months, five months, six months, seven months, eight months, nine months, 10 months, 11 months, 1 year, 1½ years, or 2 years) at 2-8° C. (e.g., 4° C.). Thus, the compositions described herein can be stable in storage for at least 1 year at 2-8° C. (e.g., 4° C.).

The compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can be in a variety of forms. These forms include, e.g., liquid, semi-solid and solid dosage forms, such as liquid solutions (e.g., injectable and infusible solutions), dispersions or suspensions, tablets, pills, powders, liposomes and suppositories. The preferred form depends, in part, on the intended mode of administration and therapeutic application.

For example, compositions intended for systemic or local delivery can be in the form of injectable or infusible solutions. Accordingly, the compositions (such as TNALP, for example the sALP polypeptide of SEQ ID NO: 1 or a polypeptide variant having at least 95% sequence identity to the sequence of SEQ ID NO: 1, e.g., asfotase alfa) can be formulated for administration by a parenteral mode (e.g., subcutaneous, intravenous, intraperitoneal, or intramuscular injection).

The compositions including sALPs and sALP fusion polypeptides (such as TNALP, for example the sALP fusion polypeptide of SEQ ID NO: 1 or a polypeptide variant having at least 95% sequence identity to the sequence of SEQ ID NO: 1, e.g., asfotase alfa) can be formulated as a solution, microemulsion, dispersion, liposome, or other ordered structure suitable for stable storage at high concentration. Sterile injectable solutions can be prepared by incorporating a composition described herein in the required amount in an appropriate solvent with one or a combination of ingredients enumerated above, as required, followed by filter sterilization. Generally, dispersions are prepared by incorporating a composition described herein into a sterile vehicle that contains a basic dispersion medium and the required other ingredients from those enumerated above. In the case of sterile powders for the preparation of sterile injectable solutions, methods for preparation include vacuum drying and freeze-drying that yield a powder of a composition described herein plus any additional desired ingredient (see below) from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition a reagent that delays absorption, for example, monostearate salts, and gelatin.

The compositions described herein can also be formulated in immunoliposome compositions. Such formulations can be prepared by methods known in the art such as, e.g., the methods described in Epstein et al. (1985) *Proc Natl Acad Sci USA* 82:3688; Hwang et al. (1980) *Proc Natl Acad Sci USA* 77:4030; and U.S. Pat. Nos. 4,485,045 and 4,544,545.

Liposomes with enhanced circulation time are disclosed in, e.g., U.S. Pat. No. 5,013,556.

Compositions including sALPs and sALP fusion polypeptides (such as TNALP, for example the sALP polypeptide of SEQ ID NO: 1 or a polypeptide variant having at least 95% sequence identity to the sequence of SEQ ID NO: 1, e.g., asfotase alfa) can also be formulated with a carrier that will protect the composition (e.g., an sALP polypeptide or sALP fusion polypeptide) against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known in the art. See, e.g., J. R. Robinson (1978) *Sustained and Controlled Release Drug Delivery Systems*, Marcel Dekker, Inc., New York.

When compositions are to be used in combination with a second active agent, the compositions can be co-formulated with the second agent, or the compositions can be formulated separately from the second agent formulation. For example, the respective pharmaceutical compositions can be mixed, e.g., just prior to administration, and administered together or can be administered separately, e.g., at the same or different times.

Carriers/Vehicles

Preparations containing an sALP or sALP fusion polypeptide (such as TNALP, for example the sALP polypeptide of SEQ ID NO: 1 or a polypeptide variant having at least 95% sequence identity to the sequence of SEQ ID NO: 1, e.g., asfotase alfa) can be provided to HPP patients, such as an adult having HPP (e.g., an adult having HPP of about 18 years of age or older, such as an adult having pediatric-onset HPP) or an adolescent having HPP (e.g., an adolescent having HPP of about 13 years of age to about 17 years of age), in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. For example, the pharmaceutically acceptable carrier can include sodium chloride and/or sodium phosphate, in which the composition includes, e.g., about 150 mM sodium chloride and/or about 25 mM sodium phosphate, pH 7.4.

Intravenous vehicles can include fluid and nutrient replenishers, electrolyte replenishers, such as those based upon Ringer's dextrose, and the like. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, can be present in such vehicles. A thorough discussion of pharmaceutically acceptable carriers is available in *Remington's Pharmaceutical Sciences* (Mack Pub. Co., N.J. 1991).

The following examples are intended to illustrate, rather than limit, the disclosure. These studies feature the administration of asfotase alfa (SEQ ID NO: 1) to adults having HPP, such as adults having pediatric-onset HPP of about 18 years of age or older, or adolescents having HPP, an analysis of HPP symptoms in these patients after administration of asfotase alfa, and physical impairments associated therewith for an extended period of time.

Example 1. Treatment of Pediatric-Onset Hypophosphatasia (HPP) Patients with Asfotase Alfa Adolescents and adults with hypophosphatasia (HPP) of about 12 years to about 66 years of age participated in study to determine the efficacy, safety, and tolerability of treatment with a soluble alkaline phosphatase (sALP) (asfotase alfa; SEQ ID NO: 1). A subpopulation analysis of 12 adults with pediatric-onset hypophosphatasia (HPP) of about 18 years to about 66 years of age was performed to investigate biochemical and functional improvements from treatment with asfotase alfa. During an initial phase study for 6 months, 9 adults with HPP received treatment with asfotase alfa (the treatment group) and 3 adults with HPP did not receive treatment with asfotase alfa (the control group). The median age of onset of HPP symptoms in the control group was 3 years of age, with a minimum of 0.8 years of age and maximum of 4 years of age, while the median age of onset of HPP symptoms in the treatment group was 2 years of age, with a minimum of 0.1 years of age and maximum of 4 years of age (Table 2, dosage treatment groups (2.1 mg/kg/week and 3.5 mg/kg/week) were combined for all results). Data are expressed as median (min, max) unless noted otherwise). A total of 2 of the control adults were female (67%) and 7 of the treated adults were female (78%).

TABLE 2

Baseline characteristics for pediatric-onset HPP patients prior to treatment with asfotase alfa.

| | Initial group assignment | | |
|---|---|---|---|
| Characteristic | Control (n = 3) | Combined treatment (n = 9) | Overall (N = 12) |
| Age at enrollment, years | 21 (13, 58) | 55 (14, 66) | 53 (13, 66) |
| Age at enrollment, years | 54 (26, 58) | 56 (45, 66) | 55 (26, 66) |
| Age category at enrollment, n (%) Adult (age ≥18 years) | 3 (100) | 9 (100) | 12 (100) |
| Age at symptom onset, years (min, max) | 3 (0.8, 4) | 2 (0.1, 13) | 2.5 (0.1, 3) |

TABLE 2-continued

Baseline characteristics for pediatric-onset HPP patients prior to treatment with asfotase alfa.

| | Initial group assignment | | |
|---|---|---|---|
| Characteristic | Control (n = 3) | Combined treatment (n = 9) | Overall (N = 12) |
| Age category at symptom onset, n (%) <18 years of age | 3 (100) | 9 (100) | 12 (100) |
| Female, n (%) | 2 (67) | 7 (78) | 9 (75) |

HPP patients selected for treatment with asfotase alfa had serum ALP below the age-adjusted normal range, plasma pyridoxal 5'-phosphate (PLP) concentrations of at least twice the upper normal limit, and evidence of osteopenia or osteomalacia in skeletal radiographs and/or bone biopsies. Patients were excluded from the study for serum calcium or phosphate levels below the normal range, serum vitamin D levels less than 20 ng/mL, serum creatinine or parathyroid hormone levels above the upper limit of normal, or a medical condition or other extenuating circumstances that could significantly interfere with patient compliance with the study protocol.

During the initial phase of treatment with asfotase alfa for 6 months, 4 adults received asfotase alfa at a dosage of 0.3 mg/kg/day (2.1 mg/kg/week) and 5 adults received asfotase alfa at a dosage of 0.5 mg/kg/day (3.5 mg/kg/week) via subcutaneous administration. The 3 patients in the initial control group did not receive asfotase alfa treatment. Following the initial phase study, both treatment and control group patients (12 total patients) received treatment with asfotase alfa. Asfotase alfa was administered via subcutaneous administration at an initial dose of 0.5 mg/kg/day (3.5 mg/kg/week), which was increased after 1 year to 1 mg/kg/day administered via subcutaneous administration once daily over 6 days (6 mg/kg/week). The dosage of asfotase alfa was maintained at 6 mg/kg/week for the remainder of the extension phase.

Metrics used during the extension phase to assess treatment of HPP pediatric-onset adults with asfotase alfa included: 1) changes in inorganic pyrophosphate (PPi) and pyridoxal 5'-phosphate (PLP) concentrations in patient plasma samples to assess ALP activity; 2) Six Minute Walk Test (6MWT) values to assess walking ability; and 3) Bruininks-Oseretsky Test of Motor Proficiency, 2nd Edition (BOT-2) scores to assess physical function.

Example 2. Statistically Significant Median Decrease in Plasma Inorganic Pyrophosphate (PPi) and Pyridoxal 5'-Phosphate (PLP) Concentrations after Administration of Asfotase Alfa ALP activity in plasma samples collected from the HPP adults was assessed by quantifying the concentrations of the ALP substrates PPi and PLP, as described in Whyte et al., 1995 (J. Clin. Invest. 95(4): 1440-1445), hereby incorporated by reference in its entirety. The median PPi and PLP concentration in plasma samples from the control adults and adults treated with asfotase alfa were elevated at baseline from the normal range (Table 3). Similarly, ALP activity values were relatively low for the control group (21.0 U/L) and for the treatment group (18.0 U/L) compared to age- and gender-adjusted lower limit of normal (LLN) ALP activity values (31 U/L for 18 to less than 50 years of age or 35 U/L for 50 to less than 70 years of age).

TABLE 3

Measurements of alkaline phosphatase (ALP) activity and plasma inorganic pyrophosphate (PPi) and pyridoxal 5'-phosphate (PLP) concentration for adults with pediatric onset HPP prior to treatment with asfotase alfa. All data expressed as median (minimum, maximum) unless indicated otherwise.

| | Initial group assignment | | |
|---|---|---|---|
| Characteristic | Untreated control (n = 3) | Combined treatment (n = 9)[a] | Overall (N = 12)[b] |
| ALP, U/L | | | |
| LLN (age- and gender-adjusted) 18 to <50 years: 31 (M), 31 (F) ≥50 to <70 years: 35 (M), 35 (F) | 21.0 (18.0, 26.0) | 18.0 (18.0, 35.0) | 18.0 (18.0, 35.0) |
| PPi, μM | | | |
| Normal range 13-18 y: <0.75-4.78 >18 y: 1.00-5.82 | 5.9 (5.2, 6.6) | 5.5 (2.2, 8.2) | 5.7 (2.2, 8.2) |
| PLP, ng/mL | | | |
| Normal range: 5-18 y: 5.7-61.2 >18 y: 2.8-26.7 | 199.0 (196.0, 474.0) | 267.0 (28.8, 1270.0) | 233.0 (28.8, 1270.0) |

[a]Initial treatment groups are combined for analysis.
[b]Control and treatment adults combined since all adults receive treatment in extension phase.
LLN, lower limit of normal.

The median plasma PPi concentration was 5.9 μM (minimum plasma PPi concentration of 5.2 μM; maximum plasma PPi concentration of 6.6 μM) for the control group at baseline and 5.5 μM (minimum plasma PPi concentration of 2.2 μM; maximum plasma PPi concentration of 8.2 μM) for the treatment group at baseline (Table 3). Plasma PPi concentrations decreased after 6 months of treatment with asfotase alfa, as indicated by a statistically significant median change from baseline of −3.0 for patients treated with asfotase alfa compared to a change of −0.3 for the untreated control group (FIG. 1A). The P-value for the median change in PPi concentration from baseline was 0.0364 based on an exact Wilcoxon rank sum test comparing the treatment group to the control group. Analysis of plasma PPi concentrations after 6 months of treatment with asfotase alfa for the two different dosage groups showed that there was a median change from baseline of −2.870 for patients treated with 0.3 mg/kg/day asfotase alfa and −2.990 for patients treated with 0.5 mg/kg/day asfotase alfa (Table 4, P-value based on exact Wilcoxon rank sum test comparing each treatment group to the control group; estimate and exact confidence interval are from Hodges-Lehmann-Sen method for location shift in distribution between the treatment group and the control group).

TABLE 4

Statistical analysis of PPi concentration for adults with pediatric onset HPP after treatment with asfotase alfa for 6 months

| Statistic | Control Group (n = 3) | Asfotase Alfa 0.3 mg/kg/day (n = 4) | Asfotase Alfa 0.5 mg/kg/day (n = 5) | Asfotase Alfa Combined (n = 9) |
|---|---|---|---|---|
| n | 3 | 4 | 5 | 9 |
| Mean (SD) | −0.060 (1.0193) | −2.790 (1.4903) | −2.258 (1.4739) | −2.494 (1.4134) |
| 95% CI | (−2.592, 2.472) | (−5.161, −0.419) | (−4.088, −0.428) | (−3.581, −1.408) |
| Median | −0.340 | −2.870 | −2.990 | −2.990 |
| Min, Max | −0.91, 1.07 | −4.40, −1.02 | −3.18, 0.32 | −4.40, 0.32 |
| P-value | | 0.0571 | 0.1429 | 0.0364 |
| Estimate | | −2.925 | −2.270 | −2.640 |
| 95% CI$^b$ | | (NA, NA) | (−4.250, 1.230) | (−4.250, −0.110) |

Figure 1B:
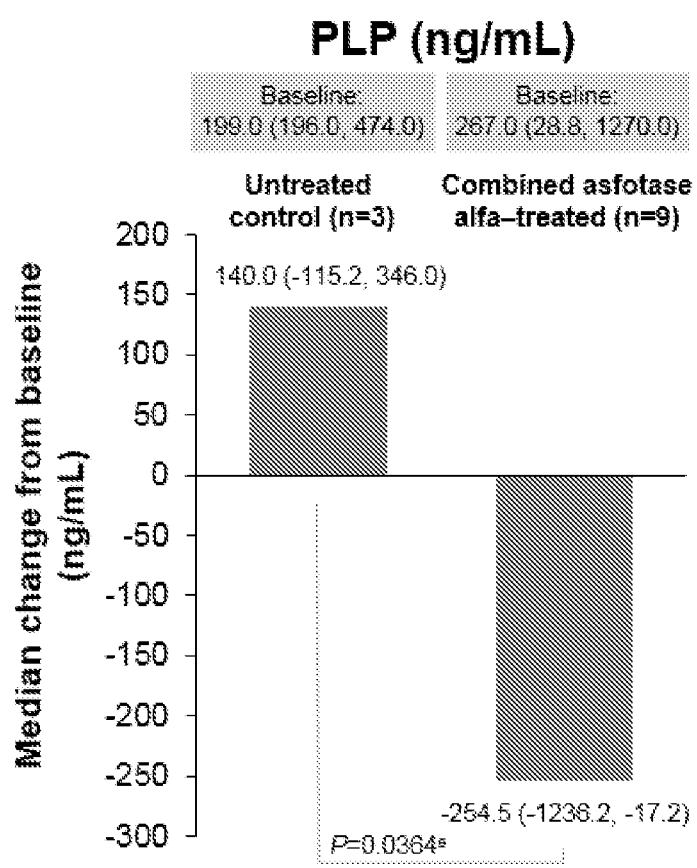

The median plasma PLP concentration was 199.0 ng/ml (minimum plasma PLP concentration of 196.0 ng/ml; maximum plasma PLP concentration of 474.0 ng/ml) for the control group at baseline and 267.0 ng/ml (minimum plasma PLP concentration of 28.8 ng/ml; maximum plasma PLP concentration of 1270.0 ng/ml) for the treatment group at baseline (Table 3). Plasma PLP concentrations decreased after 6 months of treatment with asfotase alfa, as indicated by a statistically significant median change from baseline of −254.5 for patients treated with asfotase alfa compared to a change of 140.0 for the control group (FIG. 1B). The P-value for the median change in PLP concentration from baseline was 0.0364 based on an exact Wilcoxon rank sum test comparing the treatment group to the control group. Analysis of plasma PLP concentrations after 6 months of treatment with asfotase alfa for the two different dosage groups showed that there was a median change from baseline of −298.60 for patients treated with 0.3 mg/kg/day asfotase alfa and −254.50 for patients treated with 0.5 mg/kg/day asfotase alfa (Table 5; P-value based on exact Wilcoxon rank sum test comparing each treatment group to the control group, estimate and exact confidence interval are from Hodges-Lehmann-Sen method for location shift in distribution between the treatment group and the control group).

TABLE 5

Statistical analysis of PLP concentration for adults with pediatric onset HPP after treatment with asfotase alfa for 6 months

| Statistic | Control Group (N = 3) | Asfotase Alfa 0.3 mg/kg/day (N = 4) | Asfotase Alfa 0.5 mg/kg/day (N = 5) | Asfotase Alfa Combined (N = 9) |
|---|---|---|---|---|
| n | 3 | 4 | 5 | 9 |
| Mean (SD) | 123.60 (231.037) | −301.30 (186.482) | −383.72 (492.195) | −347.09 (368.857) |
| 95% CI | (−450.33, 697.53) | (−598.03, −4.57) | (−994.86, 227.42) | (−630.62, −63.56) |
| Median | 140.00 | −298.60 | −254.50 | −254.50 |
| Min, Max | −115.2, 346.0 | −486.4, −121.6 | −1236.2, −17.2 | −1236.2, −17.2 |
| P-value | | 0.0571 | 0.1429 | 0.0364 |

TABLE 5-continued

Statistical analysis of PLP concentration for adults with pediatric onset HPP after treatment with asfotase alfa for 6 months

| Statistic | Control Group (N = 3) | Asfotase Alfa 0.3 mg/kg/day (N = 4) | Asfotase Alfa 0.5 mg/kg/day (N = 5) | Asfotase Alfa Combined (N = 9) |
|---|---|---|---|---|
| Estimate | | −419.40 | −394.50 | −394.50 |
| 95% CI | | (NA, NA) | (−1582.20, 98.00) | (−1121.00, −6.40) |

[a] P-value based on exact Wilcoxon rank sum test comparing each treatment group to the control group.
[b] Estimate and exact confidence interval are from Hodges-Lehmann-Sen method for location shift in distribution between the treatment group and the control group.

Figure 2:
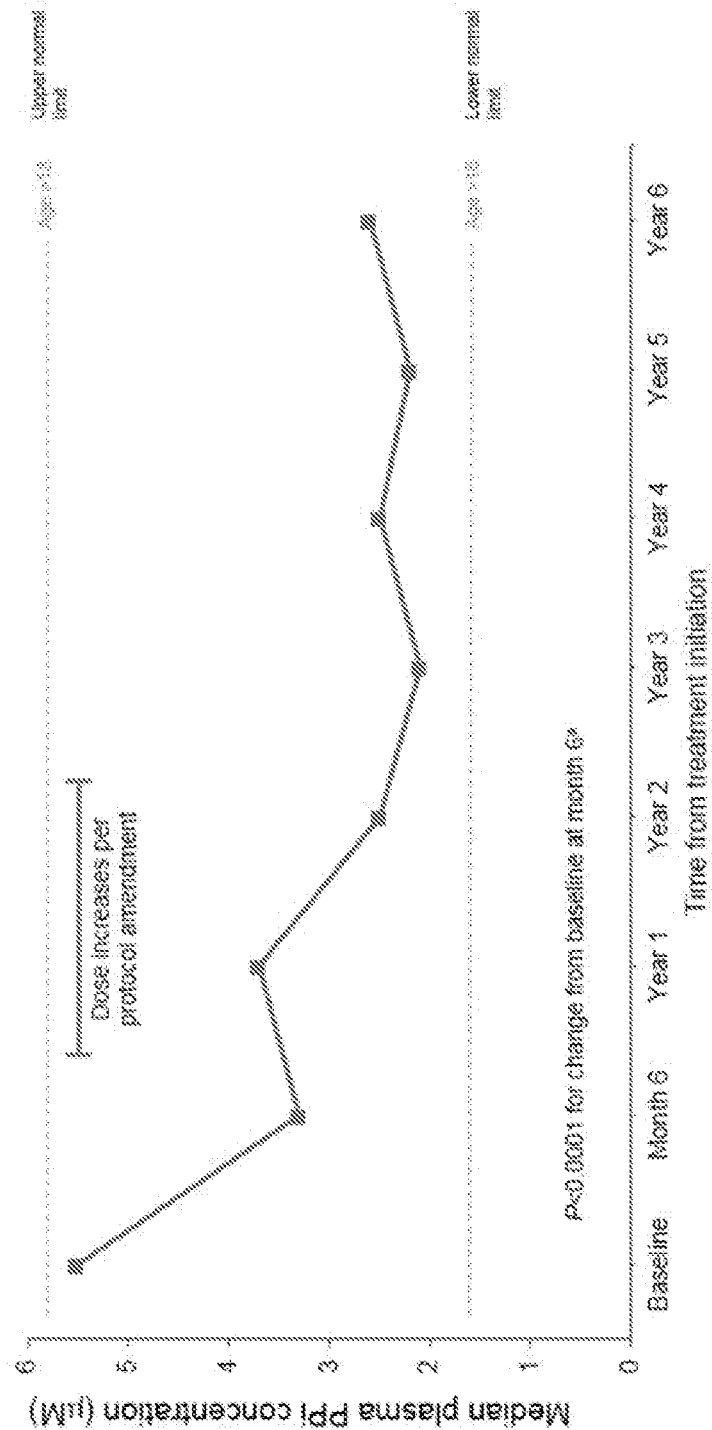
FIG. 2 is a graph showing the median PPi concentration in plasma samples from adult pediatric-onset HPP patients administered asfotase alfa over a treatment period of 6 years. The upper normal limit and lower normal limit of PPi concentration for healthy subjects older than 18 years of age are shown. The control group started treatment with asfotase alfa at six months after the combined treated group. The treatment period during which asfotase alfa was increased to a dosage of 6 mg/kg/week via protocol amendment is shown. $^a$P<0.0001 for the change in median plasma PPi concentration from baseline at six months.

For all subsequent measurements, plasma PPi and PLP concentrations were combined for the treatment group and control group at each respective time point (6 months, 1 year, 2 years, 3 years, 4 years, 5 years, and 6 years of asfotase alfa treatment), since the control group received treatment with asfotase alfa after the initial phase of 6 months. The decrease in plasma PPi concentrations was sustained throughout the extension phase of treatment with asfotase alfa (FIG. 2). The median plasma PPi concentration decreased from 5.53 µM (minimum plasma PPi concentration of 2.15 µM; maximum plasma PPi concentration of 8.20 µM) to 3.30 µM (minimum plasma PPi concentration of 0.75 µM; maximum plasma PPi concentration of 5.02 µM) after 6 months of treatment with asfotase alfa. The median PPi concentration was 3.74 µM at 1 year (minimum plasma PPi concentration of 1.62 µM; maximum plasma PPi concentration of 5.40 µM); the median PPi concentration was 2.49 µM at 2 years (minimum plasma PPi concentration of 1.32 µM; maximum plasma PPi concentration of 10.90 µM); the median PPi concentration was 2.09 µM at 3 years (minimum plasma PPi concentration of 1.24 µM; maximum plasma PPi concentration of 2.94 µM); the median PPi concentration was 2.49 µM at 4 years (minimum plasma PPi concentration of 1.09 µM; maximum plasma PPi concentration of 4.52 µM); the median PPi concentration was 2.2 µM at 5 years (minimum plasma PPi concentration of 0.92 µM; maximum plasma PPi concentration of 5.36 µM); and the median PPi concentration was 2.60 µM at 5 years (minimum plasma PPi concentration of 1.95 µM; maximum plasma PPi concentration of 4.84 µM). The sample size was 9 HPP pediatric-onset adults at 6 months, 12 HPP pediatric-onset adults at 1 year through 5 years, and 3 HPP pediatric-onset adults at 6 years.

Figure 3:
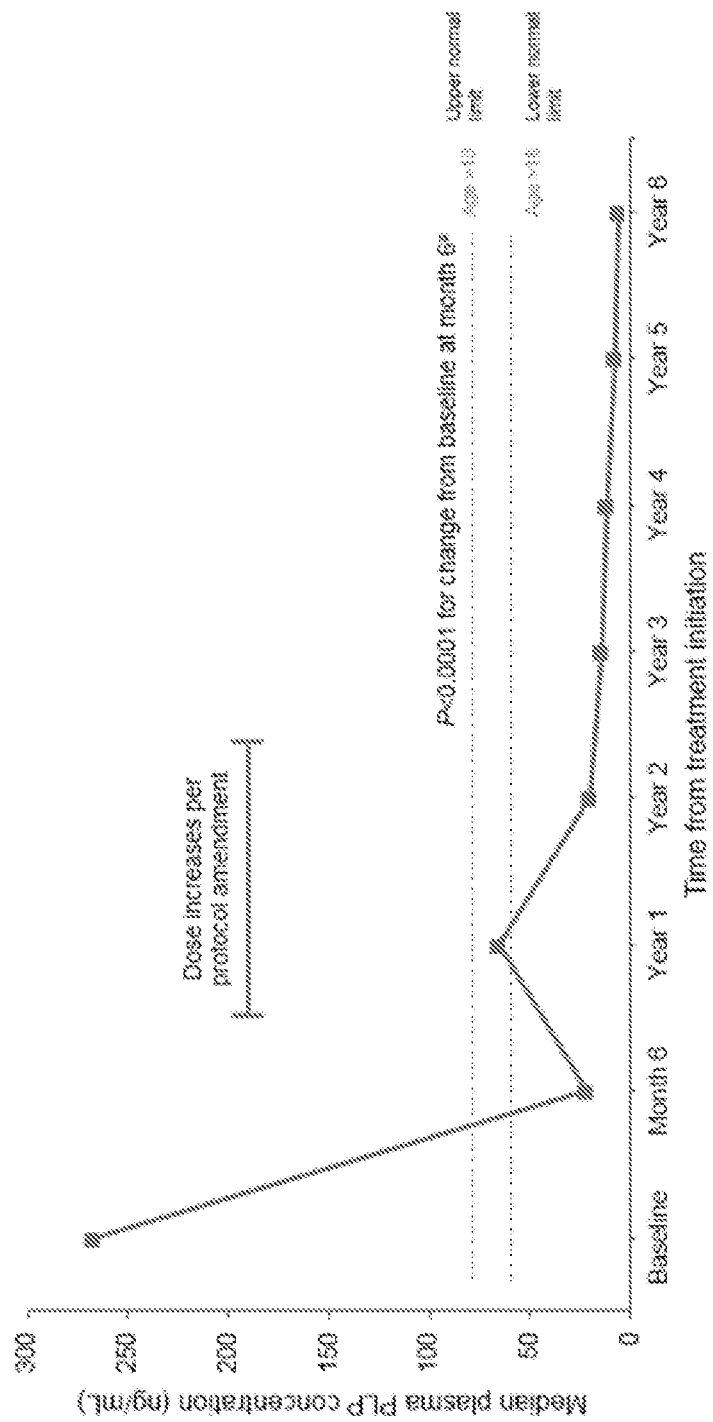
FIG. 3 is a graph showing the median PLP concentration in plasma samples from adult pediatric-onset HPP patients administered asfotase alfa over a treatment period of 6 years. The upper normal limit and lower normal limit of PLP concentration for healthy subjects older than 18 years of age are shown. The control group started treatment with asfotase alfa at six months after the combined treated group. The treatment period during which asfotase alfa was increased to a dosage of 6 mg/kg/week via protocol amendment is shown. $^a$P<0.0001 for the change in median plasma PPi concentration from baseline at six months.

Likewise, the decrease in plasma PLP concentrations was sustained throughout the extension phase of treatment with asfotase alfa (FIG. 3). The median plasma PLP concentration decreased from 267.0 ng/ml (minimum plasma PLP concentration of 28.8 ng/ml; maximum plasma PLP concentration of 1270.0 ng/ml) to 21.6 ng/ml (minimum plasma PLP concentration of 2.5 ng/ml; maximum plasma concentration of 141.0 ng/ml) after 6 months of treatment with asfotase alfa. The median PLP concentration was 65.1 ng/ml at 1 year (minimum plasma PLP concentration of 15.9 ng/ml; maximum plasma PLP concentration of 367.0 ng/ml); the median PLP concentration was 20.1 ng/ml at 2 years (minimum plasma PLP concentration of 2.7 ng/ml; maximum plasma PLP concentration of 45.7 ng/ml); the median PLP concentration was 14.0 ng/ml at 3 years (minimum plasma PLP concentration of 2.5 ng/ml; maximum plasma PLP concentration of 36.2 ng/ml); the median PLP concentration was 12.0 ng/ml at 4 years (minimum plasma PLP concentration of 2.5 ng/ml; maximum plasma PLP concentration of 38.4 ng/ml); the median PLP concentration was 7.8 ng/ml at 5 years (minimum plasma PLP concentration of 2.5 ng/ml; maximum plasma PLP concentration of 29.5 ng/ml); and the median PLP concentration was 6.0 ng/ml at 6 years (minimum plasma PLP concentration of 4.7 ng/ml; maximum plasma PLP concentration of 15.1 ng/ml). The sample size was 9 HPP pediatric-onset adults at 6 months and 1 year, 12 HPP pediatric-onset adults at 2 years through 5 years, and 3 HPP pediatric-onset adults at six years.

Example 3. Improvements in Physical Function and Walking Ability of Adult Pediatric-Onset HPP Patients Assessed with the Six Minute Walk Test (6MWT)

Physical function and walking ability of the HPP pediatric-onset patients was assessed with the Six Minute Walk Test (6MWT). Patients treated with asfotase alfa improved from an average walking distance of 315.0 meters in 6 minutes at baseline (minimum distance of 223.0, maximum distance of 540.0) to an average walking distance of 421.5 meters in 6 minutes after 1 year of treatment with asfotase alfa (minimum distance of 204.0, maximum distance of 640.0). In contrast, the untreated control group did not improve from an average walking distance of 401.0 meters in 6 minutes at baseline (minimum distance of 6.0, maximum distance of 440.0) to an average walking distance of 355.0 meters in 6 minutes after 6 months of treatment with asfotase alfa (minimum distance of 13.0, maximum distance of 420.0).

The mean change from baseline after 1 year of treatment with asfotase alfa was a distance of 88.0 meters walked in 6 minutes, while the median change from baseline in the control group was −20.0 meters walked in 6 minutes after 6 months without treatment (Table 6). This change includes the 3 patients in the control group that were unable to walk the full 6 minutes at baseline. The mean change from baseline in the 6MWT for the treated group was 17.6% with an increase from 62.8% of the predicted 6MWT value (minimum predicted 6MWT value of 42.4%, predicted 6MWT maximum value 101.3%) at baseline to 85.0% of the predicted 6MWT value (minimum predicted 6MWT value of 31.1%, maximum predicted 6MWT value of 121.3%) after 1 year of treatment with asfotase alfa. In contrast, the mean change from baseline in the 6MWT for the untreated control group was −6.2 with a decrease from 85.8% of the predicted 6MWT value (minimum predicted 6MWT value of 79.1%, predicted 6MWT maximum value 92.4%) at baseline to 79.6% of the predicted 6MWT value (minimum predicted 6MWT value of 70.4%, maximum predicted 6MWT value of 88.7%) after 1 year of treatment with asfotase alfa. Additionally, the change from baseline of the percent predicted 6MWT value at 6 months between controls and asfotase alfa-treated pediatric-onset HPP patients was statistically significant (p=0.04). Thus, HPP patients after 1 year of treatment with asfotase exhibited a statistically significant improvement in walking ability, while the walking ability of the control group patients worsened or did not improve.

TABLE 6

Distance walked in six minutes for adults with pediatric onset HPP after treatment with asfotase alfa for 6 months

|  | Untreated control | | Combined treatment | |
| --- | --- | --- | --- | --- |
|  | Meters (n = 3) | % Predicted (n = 2) | Meters$^a$ (n = 9) | % Predicted$^b$ (n = 8) |
| Baseline | 401.0 (6.0, 440.0) | 85.8 (79.1, 92.4) | 315.0 (223.0, 540.0) | 62.8 (42.4, 101.3) |
| Follow-up (control: 6 months; treated: 1 year) | 355.0 (13.0, 420.0) | 79.6 (70.4, 88.7) | 421.5 (204.0, 640.0) | 85.0 (31.1, 121.3) |
| Mean change from baseline | −20.0 (−46.0, 7.0) | −6.2 (−8.7, −3.7) | 88.0 (−123.0, 197.0) | 17.6 (−23.1, 29.8) |

$^a$n = 12 with data at 1 year.
$^b$n = 10 with data at 1 year and n = 9 with data for change from baseline.

Figure 4:
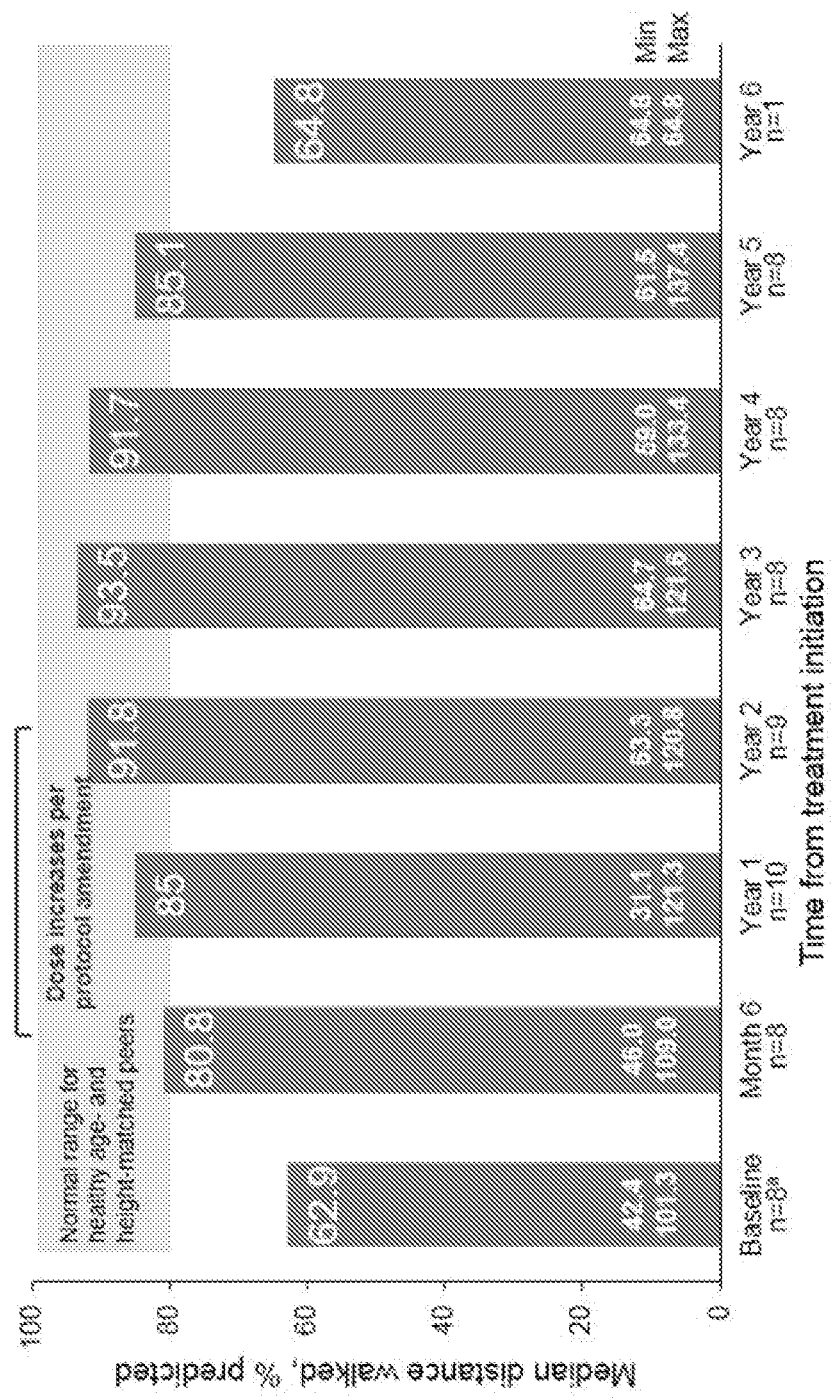
FIG. 4 is a graph showing the percent predicted median Six Minute Walk Test (6MWT) distance of adult pediatric-onset HPP patients administered asfotase alfa over a treatment period of 6 years. Median, minimum, maximum, and n values are shown for each time interval (baseline, 6 months, 1 year, 2 years, 3 years, 4 years, 5 years, and 6 years). The gray area represents the normal range for the 6MWT distance for healthy age-matched and height-matched peers. The control group started treatment with asfotase alfa at six months after the combined treated group. The treatment period during which asfotase alfa was increased to a dosage of 6 mg/kg/week via protocol amendment is shown. $^a$HPP patients receiving 0.3 mg/kg/day and 0.5 mg/kg/day of asfotase alfa prior to the protocol amendment to 6 mg/kg/week were combined for the entire treatment period.

For 6MWT values after baseline, 6MWT values were combined for the treatment group and control group at each respective time point (1 year, 2 years, 3 years, 4 years, 5 years, and 6 years of asfotase alfa treatment), since the control group received treatment with asfotase alfa after the initial phase of 6 months. The change in the 6MWT represented an increase from 62.9% of the predicted 6MWT value (minimum predicted 6MWT value of 42.4%, predicted 6MWT maximum value 101.3%; n=8) at baseline to 80.8% of the predicted 6MWT value (minimum predicted 6MWT value of 46.0%, maximum predicted 6MWT value of 109.0%; n=8) after 6 months of treatment with asfotase alfa (FIG. 4). The increase in the 6MWT value was sustained throughout treatment with asfotase alfa at 85% of the predicted 6MWT value (minimum predicted 6MWT value of 31.1%; maximum predicted 6MWT value of 121.3%; n=10) after 1 year; 91.8% of the predicted 6MWT value (minimum predicted 6MWT value of 63.3%; maximum predicted 6MWT value of 120.8%; n=9) after 2 years; 93.5% of the predicted 6MWT value (minimum predicted 6MWT value of 64.7%; maximum predicted 6MWT value of 121.6%; n=8) after 3 years; 91.7% of the predicted 6MWT value (minimum predicted 6MWT value of 59.0%; maximum predicted 6MWT value of 133.4%; n=8) after 4 years; and 85.1% of the predicted 6MWT value (minimum predicted 6MWT value of 61.5%; maximum predicted 6MWT value of 137.4%; n=8) after 5 years. In summary, the 6MWT value of the patients having HPP treated with asfotase alfa improved from 76% of the predicted 6MWT value at baseline to 80.8% of the predicted 6MWT value, which is within the normal range of healthy subjects of the same age and height, by 6 months. The improvement in the 6MWT value was sustained throughout 4 years of treatment with asfotase alfa.

Example 4. Improvements in Physical Function of Adult Pediatric-Onset HPP Patients Assessed with the Bruininks-Oseretsky Test of Motor Proficiency, 2nd Edition (BOT-2)

Physical function and impairments of the HPP patients were assessed with the running speed and agility test and strength test of the Bruininks-Oseretsky Test of Motor Proficiency, 2nd Edition (BOT-2). BOT-2 tests to assess running speed and agility of the HPP patients included the 50 foot shuttle run, sideways steps over balance beam, and one and two legged side hops. BOT-2 tests to assess strength of the HPP patients included sit-ups, v-ups, standing long jump, wall sit, and push-ups. BOT-2 speed and agility total scores and BOT-2 strength total scores were then determined from the sum of points awarded per BOT-2 tests for each time interval (baseline, 6 months, 1 year, 2 year, 3 years, 4 years, 5 years, and 6 years). For BOT-2 scores after baseline, BOT-2 scores were combined for the treatment group and control group at each respective time point (6 months, 1 year, 2 years, 3 years, 4 years, 5 years, and 6 years of asfotase alfa treatment), since the control group received treatment with asfotase alfa after the initial phase of 6 months.

Figure 5:
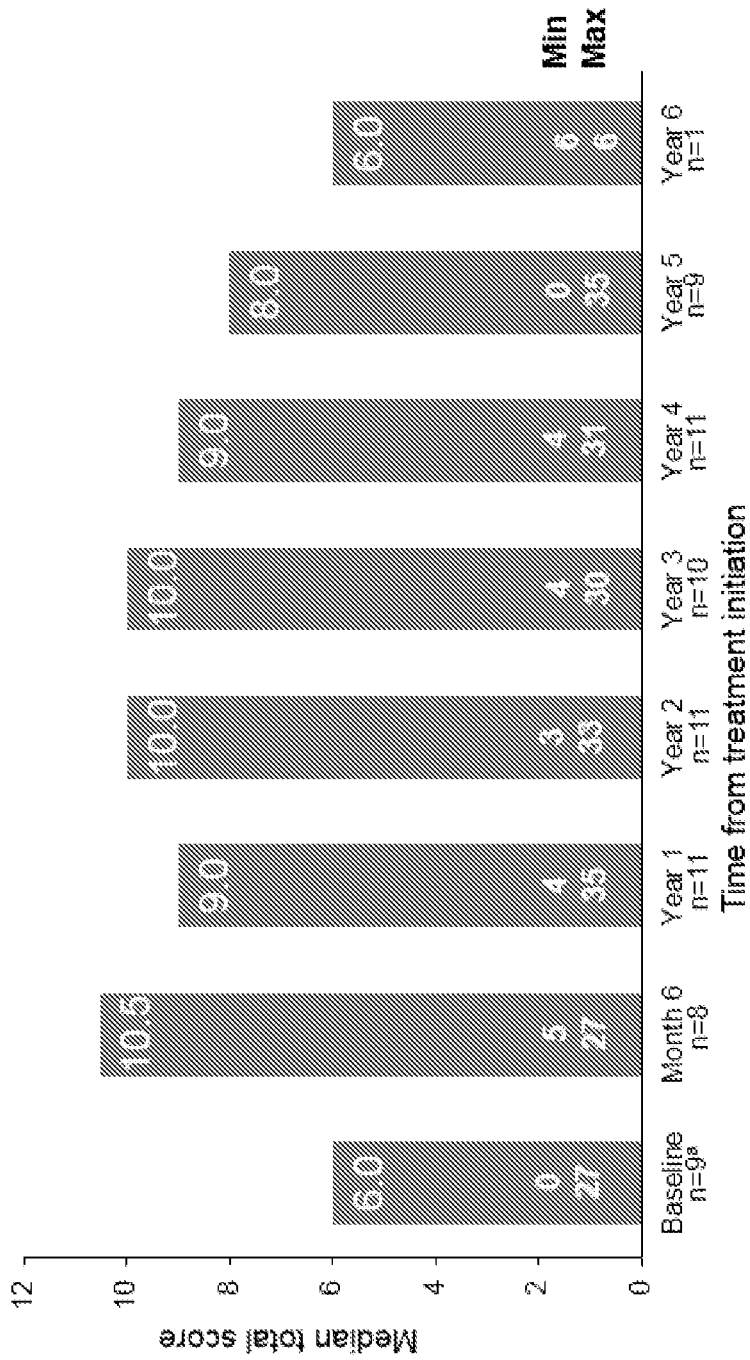
FIG. 5 is a graph showing the median total Bruininks-Oseretsky Test of Motor Proficiency, 2nd Edition (BOT-2) running speed and agility test scores for adult pediatric-onset HPP patients administered asfotase alfa over a treatment period of 6 years. Median, minimum, maximum, and n values are shown for each time interval (baseline, 6 months, 1 year, 2 years, 3 years, 4 years, 5 years, and 6 years). The control group started treatment with asfotase alfa at six months after the combined treated group. For baseline, HPP patients receiving 0.3 mg/kg/day and 0.5 mg/kg/day of asfotase alfa prior to the protocol amendment to 6 mg/kg/week were combined for the entire treatment period.
Figure 6:
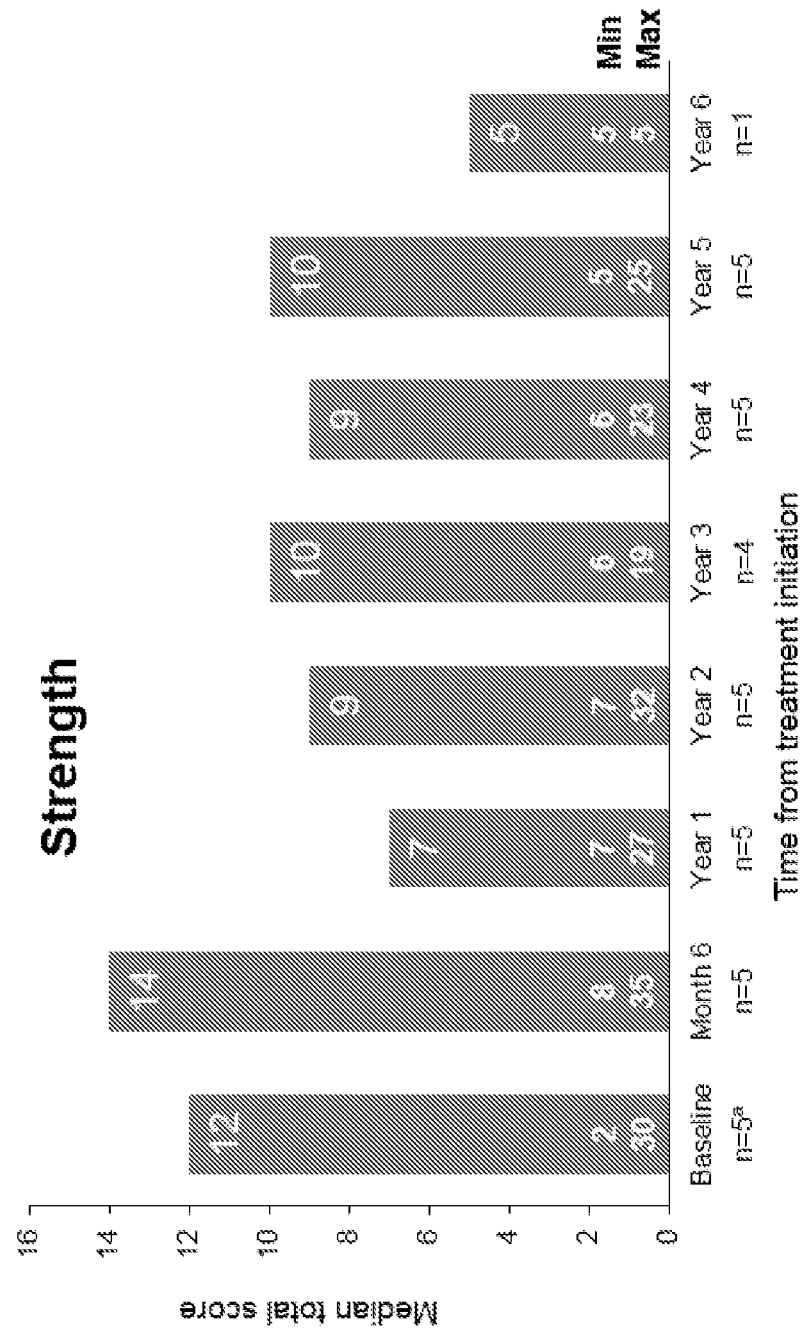
FIG. 6 is a graph showing the median total BOT-2 strength test scores for adult pediatric-onset HPP patients administered asfotase alfa over a treatment period of 6 years. Median, minimum, maximum, and n values are shown for each time interval (baseline, 6 months, 1 year, 2 years, 3 years, 4 years, 5 years, and 6 years). The control group started treatment with asfotase alfa at six months after the combined treated group. For baseline, HPP patients receiving 0.3 mg/kg/day and 0.5 mg/kg/day of asfotase alfa prior to the protocol amendment to 6 mg/kg/week were combined for the entire treatment period.

BOT-2 running speed and agility total scores improved after 6 months of treatment with asfotase alfa from a median BOT-2 running speed and agility total score of 6 (minimum BOT-2 score of 0; maximum BOT-2 score of 27; n=9) at baseline to 10.5 (minimum BOT-2 score of 5; maximum BOT-2 score of 27; n=8) at 6 months (FIG. 5). The improvement in the median BOT-2 running speed and agility total score was sustained throughout the extension phase of treatment with asfotase alfa, with a median BOT-2 running speed and agility total score of 9.0 (minimum BOT-2 score of 4; maximum score of 35; n=11) at 1 year; a median BOT-2 running speed and agility total score of 10.0 (minimum BOT-2 score of 3; maximum score of 33; n=11) at 2 years; a median BOT-2 running speed and agility total score of 10.0 (minimum BOT-2 score of 4; maximum score of 30; n=10) at 3 years; a median BOT-2 running speed and agility total score of 9 (minimum BOT-2 score of 4; maximum score of 31; n=11) at 4 years; and a median BOT-2 running speed and agility total score of 8.0 (minimum BOT-2 score of 0; maximum score of 35; n=9) at 5 years. BOT-2 strength total scores improved after 6 months of treatment with asfotase alfa from a median BOT-2 strength total score of 12 (minimum BOT-2 score of 2; maximum score of 30; n=5) at baseline to 14 (minimum BOT-2 score of 8; maximum score of 35; n=5) at 6 months (FIG. 6).

Example 5. Improvements in Bone Mineralization of Adult Pediatric-Onset HPP Patients after Administration of Asfotase Alfa Dual-energy X-ray absorptiometry (DXA) were performed at baseline and 6 months for untreated control patients and at baseline and 1 year for patients treated with asfotase alfa on the femoral neck, lumbar spine, and whole body. In adults with pediatric-onset HPP, treated patients exhibited increases from baseline in lumbar spine bone mineral density (BMD) after 6 months of asfotase alfa administration. A statistically significant increase in lumbar spine BMD was observed after six months of treatment with asfotase alfa (Table 7).

TABLE 7

Lumbar Spine Bone Mineral Density for adults with pediatric onset HPP at baseline after treatment with asfotase alfa for 12 months

| | Untreated control group (n = 3) | Combined treatment (n = 9) |
|---|---|---|
| Lumbar Spine Bone Mineral Density (g/cm$^2$) | | |
| Baseline | 1.0947 (0.39910) | 1.1853 (0.22806) |
| Follow-up (6 months) | 1.1127 (0.37064) | 1.2128 (0.21789) |
| Mean change from baseline | 0.0180 (0.02858) | 0.0262 (0.01861) |
| 95% confidence interval for mean change from baseline | (−0.053, 0.089) | (0.011, 0.042) |

Bone biopsies were also performed at baseline and 6 months for untreated control patients and at baseline and 1 year for patients treated with asfotase alfa to determine osteoid volume and thickness (Table 8) and mineralization lag time (Table 9). Statistically significant reductions in osteoid volume/bone volume (%) and osteoid thickness (μm) were observed after one year of treatment with asfotase alfa. This testing was significantly more invasive than the DXA testing.

TABLE 8

Osteoid volume/bone volume and osteoid thickness for adults with pediatric onset HPP at baseline after treatment with asfotase alfa for 12 months

| | Untreated control group (n = 3) | Combined treatment (n = 9) |
|---|---|---|
| Osteoid volume/bone volume (%) | | |
| Baseline | 9.2 (4.1) | 7.6 (4.2) |
| Follow-up (control: 6 months; treated: 1 year) | 9.4 (3.9) | 5.4 (4.5) |
| Mean change from baseline | 0.2 (3.2) | −3.8 (−0.5) |
| 95% confidence interval for mean change from baseline | (−7.7, 8.1) | (−3.8, −0.5) |
| Osteoid thickness (μm) | | |
| Baseline | 11.2 (0.6) | 10.2 (5.1) |
| Follow-up (control: 6 months; treated: 1 year) | 9.0 (1.4) | 8.3 (4.8) |
| Mean change from baseline | −2.2 (2.0) | −1.8 (1.9) |
| 95% confidence interval for mean change from baseline | (−7.1, 2.8) | (−3.3, −0.4) |

At baseline, mineralization lag time was prolonged for all HPP patients, although it included a large degree of inter-patient variability. Such variability is expected for this type of histomorphometric measurement and testing. After treatment with asfotase alfa for 1 year, mineralization lag time was reduced in the treatment group with a mean change from baseline of −696 days relative to the untreated control group with a mean change from baseline of 65 days at 6 months. These results show that administration of asfotase alfa in pediatric-onset adult HPP patients promotes bone mineralization.

TABLE 9

Mineralization lag time for adults with pediatric onset HPP at baseline after treatment with asfotase alfa for 12 months

| | Untreated control group (n = 3) | Combined treatment (n = 9) |
|---|---|---|
| Mineralization lag time (days) | | |
| Baseline | 456 (261), 2 | 964 (1212), 6 |
| Follow-up (control: 6 months; treated: 1 year) | 369 (264), 3 | 436 (486), 7 |
| Mean change from baseline | 65 (270), 2 | −696 (1069), 6 |
| 95% confidence interval for mean change from baseline | (−1506, 1460) | (−1818, 426) |

Figure 7:
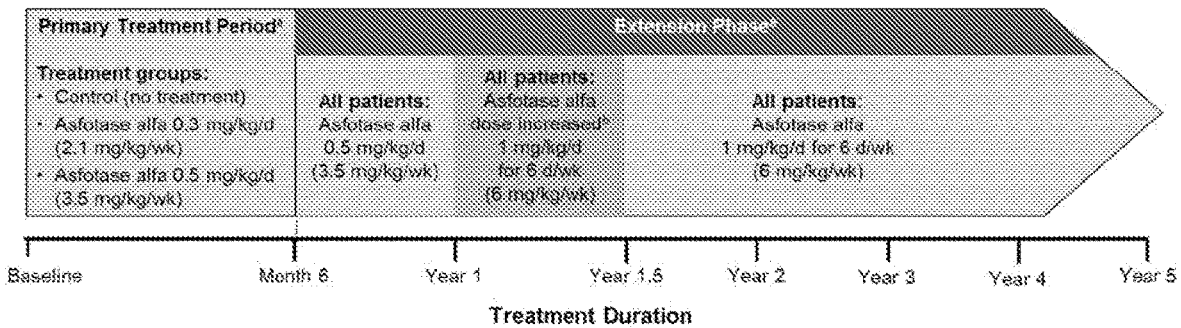
FIG. 7 is a schematic showing the study design for administering asfotase alfa to adolescents and adults having HPP over a time period of five years, including an initial phase of treatment with asfotase alfa (from baseline) to six months and an extension phase of treatment with asfotase alfa (from six months of treatment to five or more years of treatment). $^a$The dose of asfotase alfa was adjusted every 3 months for weight change; the maximum dose was 80 mg of asfotase alfa unless the investigator, after consultation of medical monitor, approved a dose of greater 80 mg. $^b$ The dose of asfotase alfa was increased by protocol amendment in all patients. During the extension phase, all patients initially received daily doses of asfotase alfa at 0.5 mg/kg/week for approximately 6 months to 1 year, which was later changed to 1 mg/kg on 6 days/week.
Figure 8:
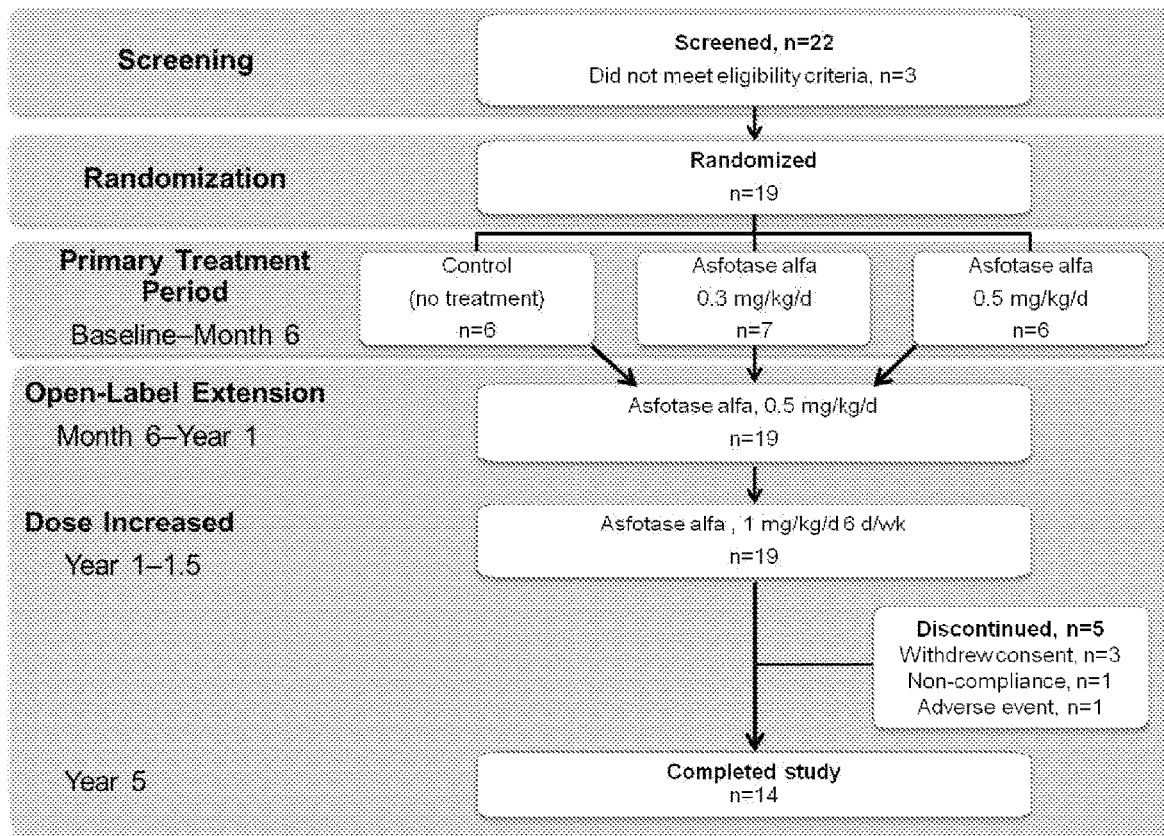
FIG. 8 is a schematic showing the number of adolescent and adult HPP patients in the different stages of the study (screening, randomization, the primary treatment period from baseline to six months of asfotase alfa treatment, the open-label extension period from six months to one year of asfotase treatment, and the period during which the dosage of asfotase alfa was increased to 1 mg/kg/day administered 6 days/week until year five of the study).

Example 6. Study Design of Treatment of HPP Adolescents and Adults with Asfotase Alfa Adolescents and adults with HPP of about 13 years to about 65 years of age participated in a study to determine the efficacy, safety, and tolerability of treatment with an sALP (asfotase alfa; FIG. 7). During the initial phase of treatment with asfotase alfa for 6 months, a total of 19 patients were randomized to receive asfotase alfa at a dosage of 0.3 mg/kg/day (2.1 mg/kg/week; n=7) via subcutaneous administration, 0.5 mg/kg/day (3.5 mg/kg/week; n=6) via subcutaneous administration, or no treatment (n=6) in the control group (FIG. 8). Following the initial phase study of 6 months, both treatment and control group patients received treatment with asfotase alfa at a dosage of 0.5 mg/kg/day (3.5 mg/kg/week) via subcutaneous administration. After the first 6 months of the extension phase, the dose was increased to 1 mg/kg/day for 6 days/week (6 mg/kg/week) for all patients under a protocol amendment. Study inclusion and exclusion criteria are described in Table 10. Patient demographics and baseline characteristics for HPP adolescents and adults, including HPP disease-related history, are summarized in Table 11.

TABLE 10

Key inclusion and exclusion criteria for study of adolescents and adults with HPP treated with asfotase alfa

| Key inclusion criteria | Key exclusion criteria |
|---|---|
| ≥13 to ≤65 years of age | Low serum calcium or phosphate |
| Pre-established clinical diagnosis of HPP, with onset at any age based on: | Low serum 25(OH) vitamin D (<20 ng/mL)$^d$ |
| Low serum alkaline phosphatase, adjusted for patient age | High serum creatinine or parathyroid hormone (PTH) or treatment with PTH |

TABLE 10-continued

Key inclusion and exclusion criteria for study of adolescents
and adults with HPP treated with asfotase alfa

| Key inclusion criteria | Key exclusion criteria |
|---|---|
| High pyridoxal-5'-phosphate PLP (≥2 × upper limit of normal)[a] | within 6 months |
| Evidence of osteopenia or osteomalacia on skeletal radiograph[b] | Use of bisphosphonates within 2 years of study entry (for any length of time) or for >2 years at any time[e] |
| Osteomalacia on bone biopsy (mineralization lag time Z-score ≥ +2)[c] | |

[a] No vitamin $B_6$ administered for ≥1 week prior to determination of PLP levels.
[b] Osteomalacia confirmed by bone biopsy
[c] Treatment was not withheld until biopsy was read, but all patients were confirmed by biopsy to have osteomalacia.
[d] Patients failing screening owing to low levels could be rescreened after supplementation at the discretion of the investigator.
[e] Patients with allowed prior bisphosphonate use must have had serum C-telopeptide and urine N-telopeptide or deoxypyridinoline levels within normal or elevated range.

TABLE 11

Demographics and baseline characteristics for adolescents
and adults with HPP treated with asfotase alfa

| | | Primary treatment period group assignment | |
|---|---|---|---|
| | Overall[a] (N = 19) | Control group (n = 6) | Asfotase alfa treatment group[b] (n = 13) |
| Demographics | | | |
| Age at enrollment, y, median (min, max) | 53 (13, 66) | 21 (13, 58) | 55 (14, 66) |
| Age category at enrollment | | | |
| Adolescent (age 13-<18 y) | 6 (32) | 3 (50) | 3 (23) |
| Adult (age ≥18 y) | 13 (68) | 3 (50) | 10 (77) |
| Age at symptom onset, y, median (min, max) | 2.0 (0, 36) | 0.9 (0.2, 4) | 2.0 (0, 36) |
| Age category at symptom onset, n (%) | | | |
| <18 y | 18 (95) | 6 (100) | 12 (92) |
| ≥18 y | 1 (5)[c] | 0 (0) | 1 (8)[c] |
| Female, n (%) | 12 (63) | 2 (33) | 10 (77) |
| White | 18 (95) | 5 (83) | 13 (100) |
| HPP-specific medical history | | | |
| Patients with fractures, n (%) | 18 (95) | 6 (100) | 12 (92) |
| Number of fractures, median (min, max) | 6.0 (1, 30) | 5.0 (1, 8) | 9.5 (1, 30) |
| Bone pain severity, n (%) | | | |
| Limit activity | 18 (95) | 5 (83) | 13 (100) |
| Require pain medications | 16 (84) | 5 (83) | 11 (85) |
| Muscle complaints, n (%) | | | |
| Weakness | 17 (90) | 5 (83) | 12 (92) |
| Pain | 14 (74) | 4 (67) | 10 (77) |
| Joint complaints, n (%) | | | |
| Pain | 17 (90) | 5 (83) | 12 (92) |
| Swelling | 7 (37) | 2 (33) | 5 (39) |
| Unusual gait, n (%) | 15 (79) | 4 (67) | 11 (85) |
| Assistive devices for ambulation, n (%) | 5 (26) | 2 (33) | 3 (23) |
| Craniosynostosis, n (%) | 3 (16) | 0 | 3 (23) |
| Premature loss of deciduous teeth, n (%) | 16 (84) | 5 (83) | 11 (85) |
| Loss of adult teeth, n (%) | 8 (42) | 1 (17) | 7 (54) |
| Adult teeth remaining, median (min, max) | 24 (0, 30) | 26 (0, 28) | 23 (0, 30) |
| Hypercalcemia, n (%) | 6 (32) | 3 (50) | 3 (23) |
| Hyperphosphatemia, n (%) | 6 (32) | 2 (33) | 4 (31) |

TABLE 11-continued

Demographics and baseline characteristics for adolescents
and adults with HPP treated with asfotase alfa

| | Overall[a] (N = 19) | Primary treatment period group assignment | |
|---|---|---|---|
| | | Control group (n = 6) | Asfotase alfa treatment group[b] (n = 13) |
| Gout, n (%) | 5 (26) | 2 (33) | 3 (23) |
| Kidney stones, n (%) | 4 (21) | 2 (33) | 2 (15) |

[a]Combined since all patients receive treatment in the extension phase.
[b]Asfotase alfa treatment groups pooled for analysis.
[c]One patient initially categorized as having adult HPP was later determined to have had signs and symptoms of HPP in childhood.
ALP = alkaline phosphatase;
HPP = hypophosphatasia.

Metrics used during the extension phase to assess treatment of HPP adolescents and adults with asfotase alfa included: 1) changes in inorganic pyrophosphate (PPi) and pyridoxal 5'-phosphate (PLP) concentrations in patient plasma samples to assess ALP activity; 2) Six Minute Walk Test (6MWT) values to assess walking ability; 3) Bruininks-Oseretsky Test of Motor Proficiency, 2nd Edition (BOT-2) scores to assess physical function; 4) Handheld Dynamometry (HHD) to assess strength; 5) Lower Extremity Functional Scale (LEFS) to assess disability; and 6) Brief Pain Inventory-Short Form (BPI-SF) to assess pain.

Efficacy analyses were performed on the full analysis set of the intent-to-treat population, which included all randomized patients; all patients received the treatment to which they were randomized. Group comparisons were made between the pooled asfotase alfa treatment group and the control group in the initial treatment period. Analyses were also performed by duration of exposure to asfotase alfa up to 5 years; for patients in the control group, asfotase alfa treatment began 6 months later at the start of the extension phase. For the outcome measures of change in plasma concentrations of PPi and PLP from Baseline to Month 6, comparisons between the pooled asfotase alfa treatment group and the control group were made using an exact Wilcoxon rank-sum test for each parameter using a 2-sided alpha of 0.05; missing values were imputed using last observation carried forward. For the 6MWT, the percentage (%) predicted value, defined as the percent of normal predicted distance walked based on age, sex, and height, was calculated if the patient walked the full 6 minutes at baseline.

Figure 9A:
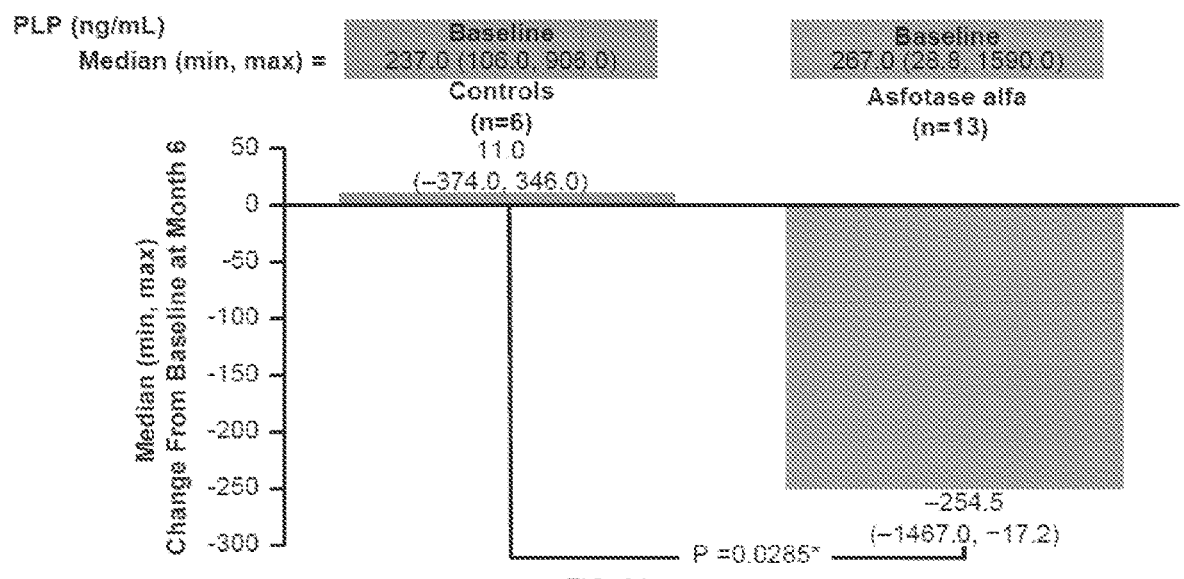
FIGS. 9A-B are graphs showing the median change in pyridoxal 5'-phosphate (PLP.
Figure 9B:
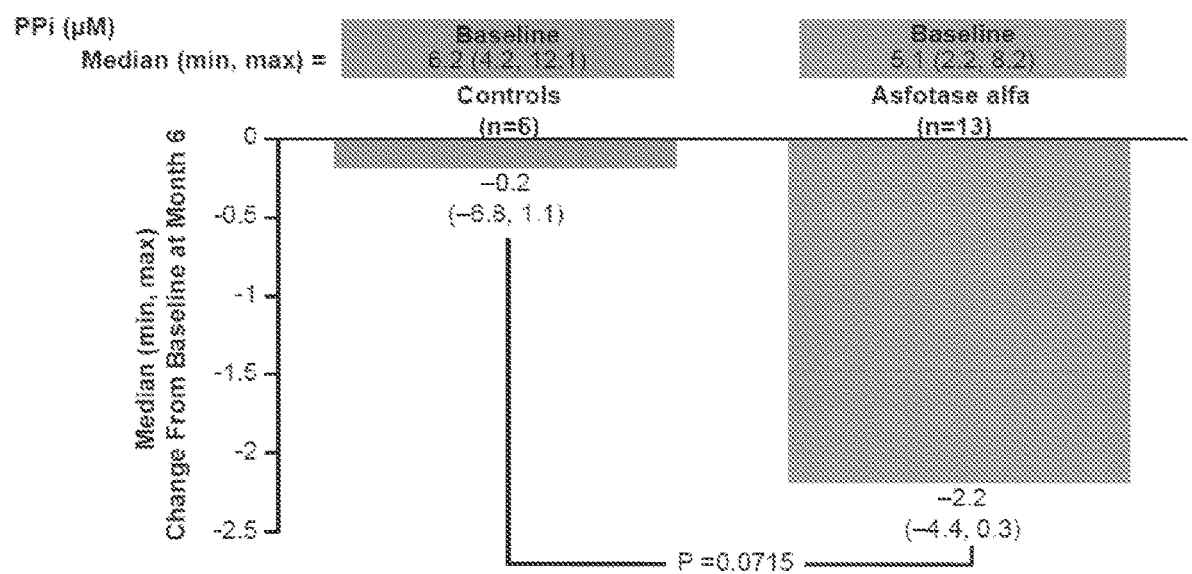
Figure 10A:
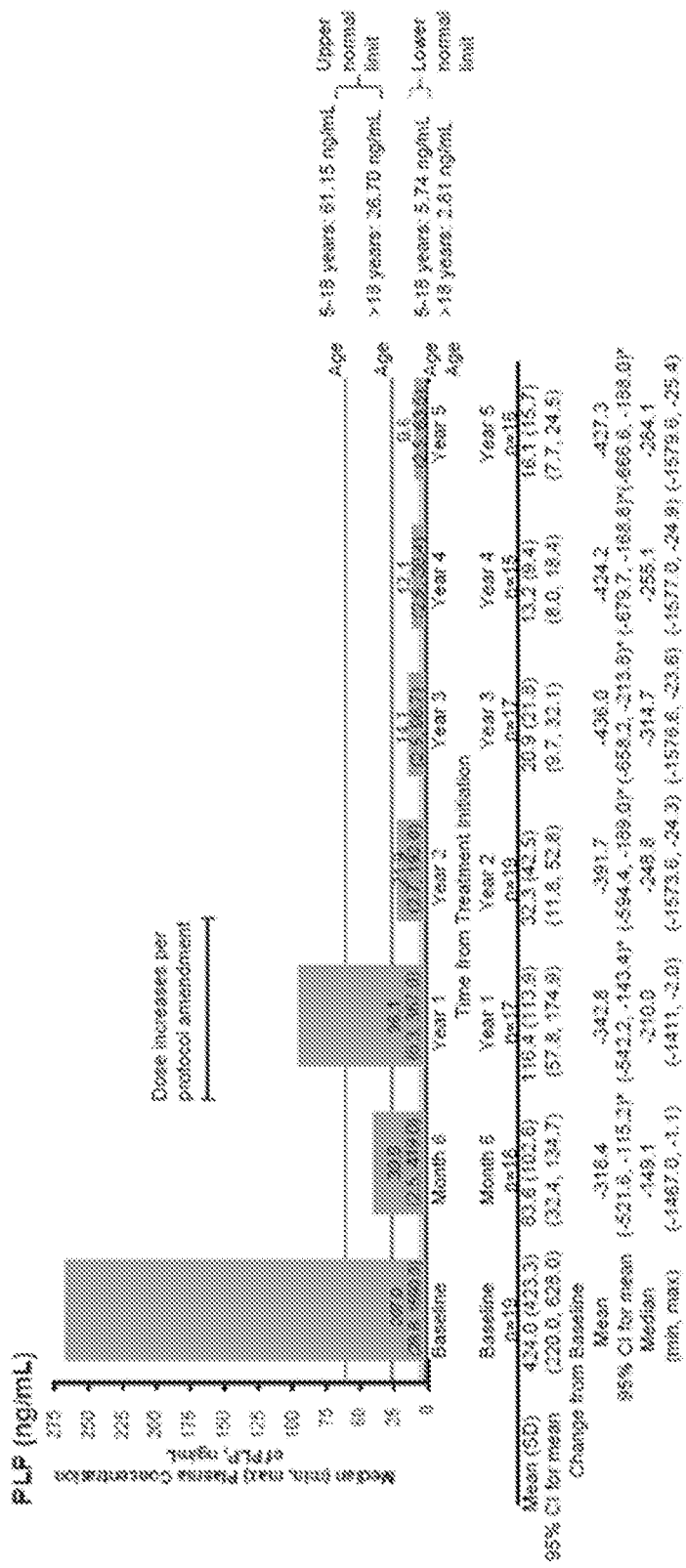
FIGS. 10A-10B are graphs showing the median PLP (FIG. 10A) and PPi (FIG. 10B) concentration in plasma samples from adolescent and adult HPP patients administered asfotase alfa over a treatment period of five years. The upper normal limit and lower normal limit of PPi and PLP concentrations for healthy subjects are also shown. The control group started treatment with asfotase alfa at six months after the combined treated group. The treatment period during which asfotase alfa was increased to a dosage of 6 mg/kg/week via protocol amendment is shown.
Figure 10B:
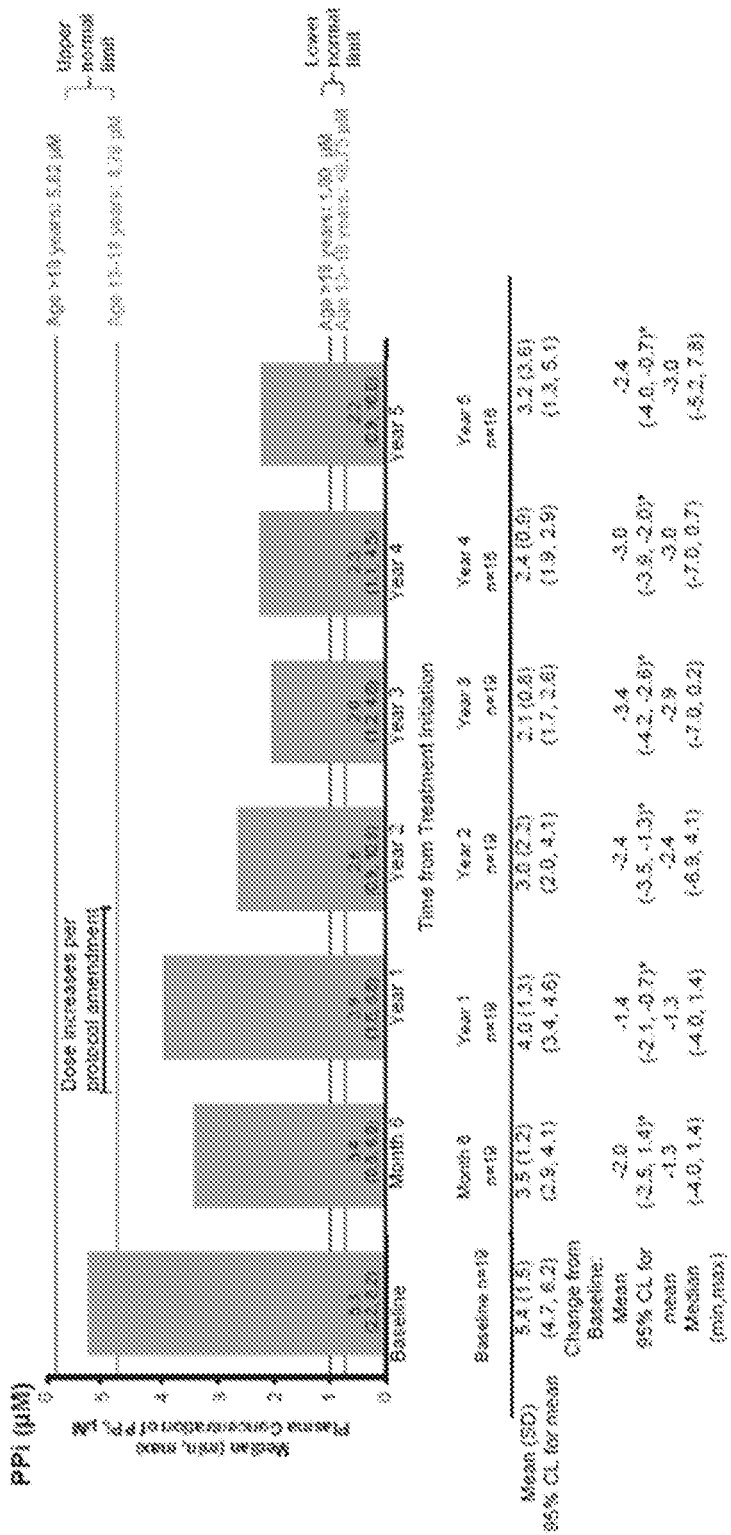

Example 7. Median Decrease in PPi and PLP Concentrations after Administration of Asfotase Alfa to HPP Adults and Adolescents ALP activity in plasma samples collected from the HPP adolescents and adults was assessed by quantifying the concentrations of the ALP substrates PPi and PLP, as described in Whyte et al., 1995 (J. Clin. Invest. 95(4): 1440-1445). There was a greater change in both PPi (−2.2 μm) and PLP (−254.5 ng/ml) plasma concentrations of adolescent and adult HPP patients treated with asfotase alfa relative to the control group after 6 months (FIGS. 9A and 9B, respectively). The difference between groups was statistically significant for changes in plasma PLP (P=0.0285) but not for changes in plasma PPi (P=0.0715). Post-hoc sensitivity analyses, which excluded one patient in the control group with a high baseline PPi concentration (12.1 μM), showed a statistically significant reduction in plasma PPi concentration at Month 6 in the asfotase alfa group compared with the control group (P=0.0044). Median decreases in adolescent and adult HPP patient plasma PPi and PLP concentrations were maintained through five years of asfotase alfa treatment (FIGS. 10A and 10B, respectively).

Example 8. Improvements in Physical Function and Walking Ability of Adolescent and Adult HPP Patients Assessed with the Six Minute Walk Test (6MWT)

Physical function and walking ability of the HPP adolescents and adults was assessed with the Six Minute Walk Test (6MWT). For 6MWT values after baseline, 6MWT values were combined for the treatment group and control group at each respective time point (1 year, 2 years, 3 years, 4 years, and 5 years of asfotase alfa treatment) because the control group was switched and began receiving treatment with asfotase alfa after the initial 6 month phase. The original control group started treatment with asfotase alfa at six months after the treated group. Baseline for all analyses was the last assessment before patients received the first dose of asfotase alfa. The predicted 6MWT value was calculated only if the patient walked the full six minutes. Three patients initially assigned to the control group were not included in the % predicted analysis, because these patients were unable to walk the full 6 minutes at baseline due to physical and/or cognitive impairment. At the baseline measurement, 5 of 19 patients were using assistive ambulatory devices (n=3, asfotase alfa group; n=2, control group).

Figure 11A:
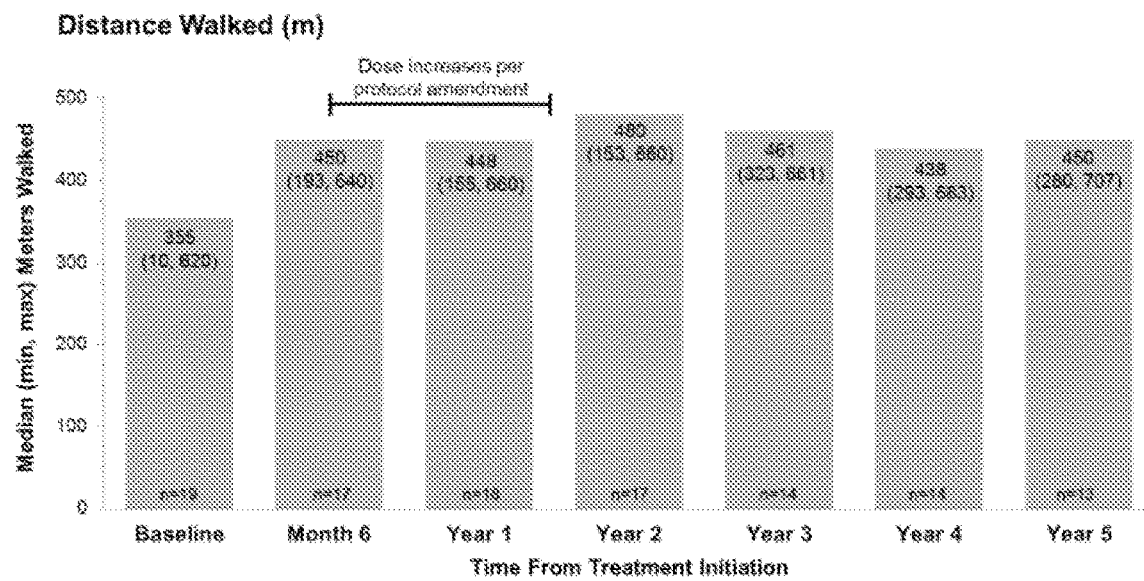
FIGS. 11A-11B are graphs showing the median distance walked in the 6MWT (FIG. 11A) and percent predicted median 6MWT distance (FIG. 11B) of adolescent and adult HPP patients administered asfotase alfa over a treatment period of 5 years. Median, minimum, maximum, and n values are shown for each time interval (baseline, 6 months, 1 year, 2 years, 3 years, 4 years, and 5 years). The gray area represents the normal range for the 6MWT distance for healthy age-matched and height-matched peers. The control group started treatment with asfotase alfa at six months after the combined treated group. The treatment period during which asfotase alfa was increased to a dosage of 6 mg/kg/week via protocol amendment is shown.
Figure 11B:
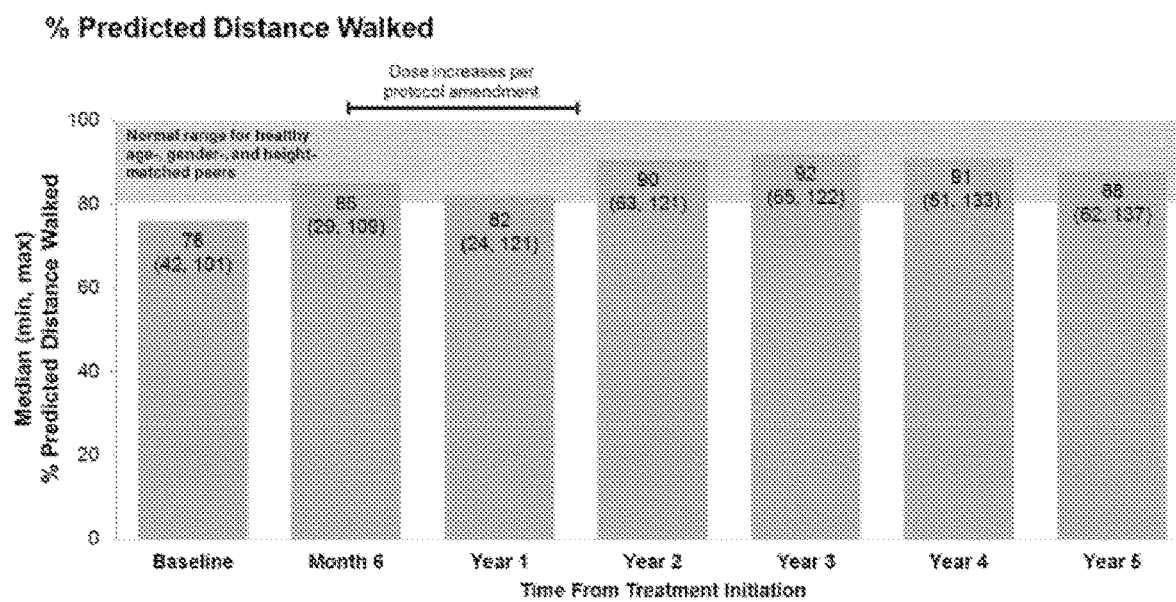

Adolescent and adult HPP patients treated with asfotase alfa improved from 355 meters (minimum distance of 10 meters; maximum distance of 620 meters) at treatment start to 450 meters (minimum distance of 280 meters; maximum distance of 707 meters) after six months of treatment with asfotase alfa (FIG. 11A). Likewise, the median % predicted 6MWT distance walked increased from 76% predicted at baseline (minimum of 42%, maximum of 101%) to 85% (minimum of 29%, maximum of 109%) after six months of treatment with asfotase alfa (FIG. 11B). The improvement in the 6MWT distance walked and % predicted 6MWT distance walked was sustained throughout five years of treatment with asfotase alfa. After two years of treatment with asfotase alfa, all five patients using assistive ambulatory devices improved: one progressed from wheelchair to crutches, one from walker to a cane, one from wheeled walker to independent ambulation, and two from cane to independent ambulation.

Figure 12A:
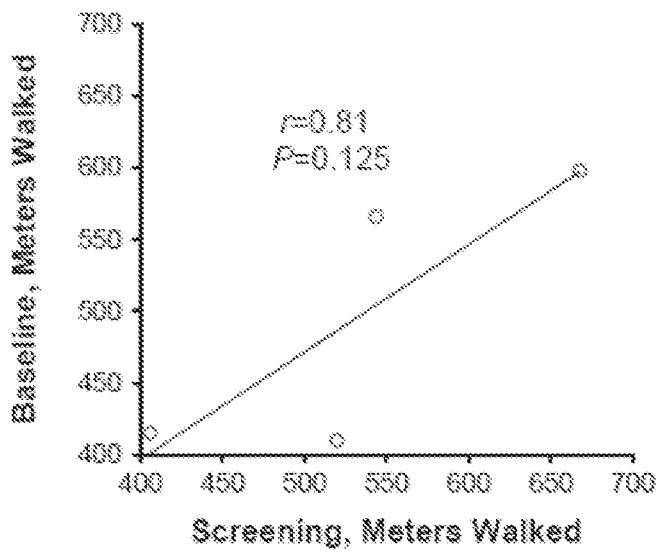
FIGS. 12A-12B are graphs showing the correlation between distance walked during the 6MWT at screening and baseline in adolescents with HPP (FIG. 12A) and adults with pediatric-onset HPP (FIG. 12B).
Figure 12B:
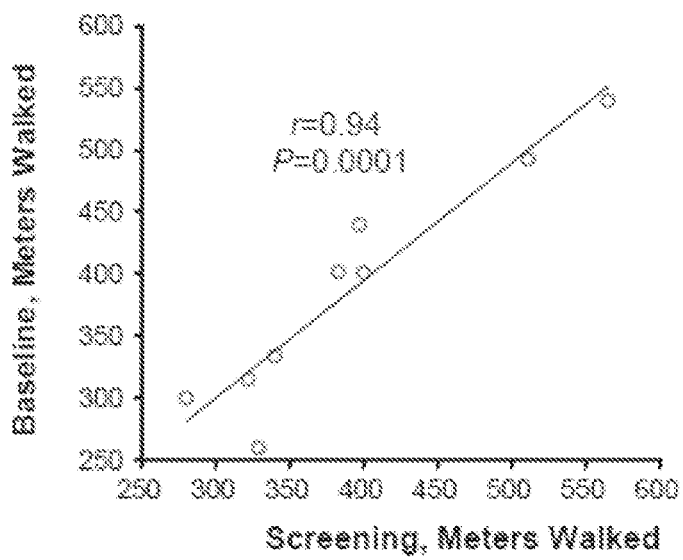

A post hoc analysis was also performed to evaluate the 6MWT results for adolescent HPP patients (n=4) and adults having pediatric-onset HPP (n=9) before and after treatment with asfotase alfa. Test-retest reliability of the 6MWT was evaluated by calculating the Pearson's correlation coefficient (r) between 6MWT distances walked at screening time points relative to baseline, and two-sided P values were calculated (exact test null hypothesis: r=0). Test-retest reliability was analyzed separately for adolescents of about 13 to about 17 years of age and adults greater than about 18 years of age. The Pearson's correlation coefficients (r) between the distance walked at screening time points relative to baseline were 0.81 (P=0.1250) for adolescent HPP patients (FIG. 12A) and 0.94 (P=0.0001) for adult pediatric-onset HPP patients (FIG. 12B). The minimal clinically important difference (MCID) for the 6MWT of adolescent HPP patients (n=4) and adults having pediatric-onset HPP (n=9) was calculated using distribution-based methods applied to screening time points and baseline 6MWT data. The current post hoc analysis used the standard error of measurement (SEM) and the ⅓ standard deviation (SD) distribution-based methodologies to estimate the MCID. The most conservative estimates of the MCID were 43 meters for adolescents (SEM method; n=4) and 31 meters for adults (SD method; n=9) with pediatric-onset HPP who completed the 6MWT at screening time points and baseline.

Example 9. Improvements in Physical Function of Adolescent and Adult HPP Patients Assessed with the Bruininks-Oseretsky Test of Motor Proficiency, 2nd Edition (BOT-2)

Figure 13:
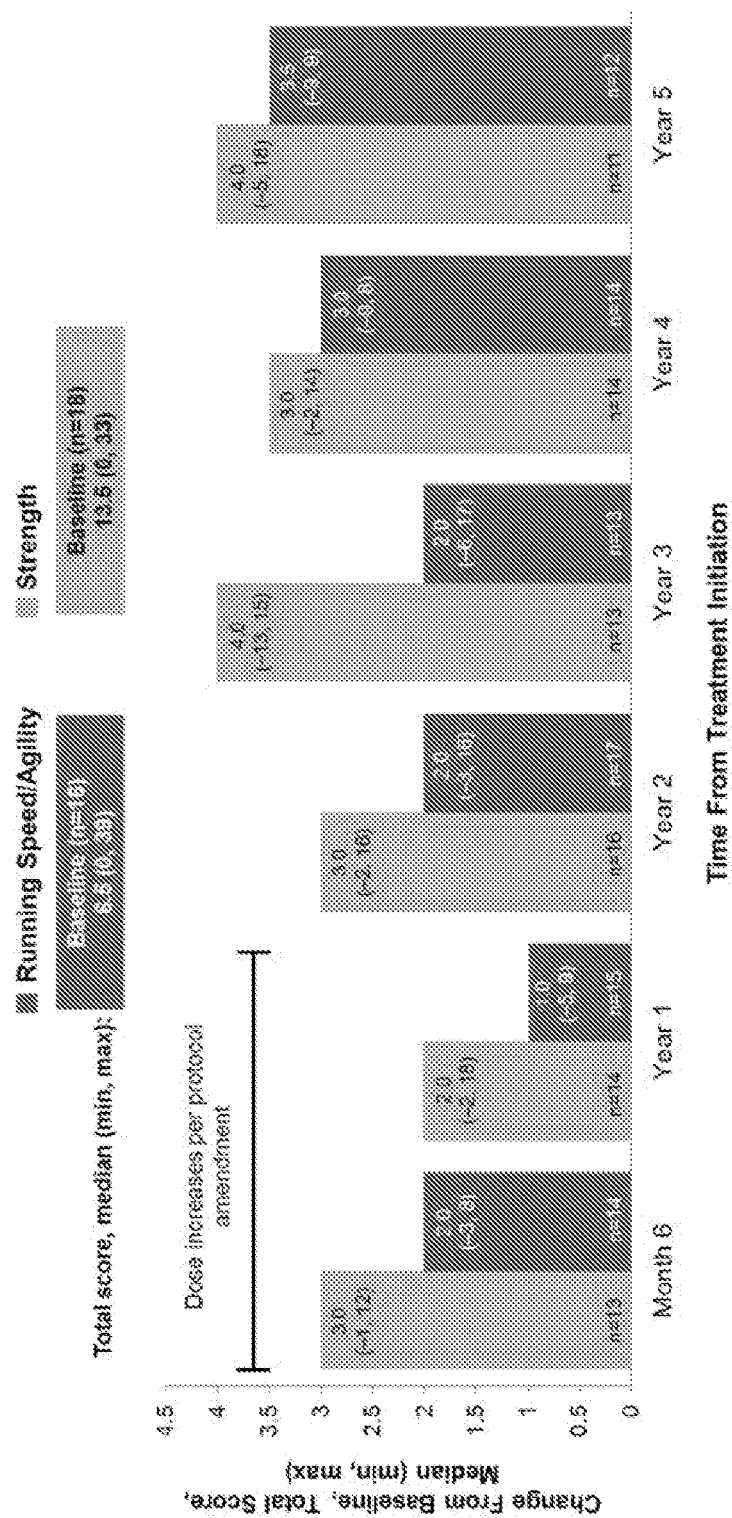
FIG. 13 is a graph showing the change from baseline in the median total BOT-2 running speed and agility test scores and the median total BOT-2 strength test scores for adolescent and adult HPP patients administered asfotase alfa over a treatment period of 5 years. Median, minimum, maximum, and n values are shown for each time interval (baseline, 6 months, 1 year, 2 years, 3 years, 4 years, and 5 years). The control group started treatment with asfotase alfa at six months after the combined treated group. For baseline, HPP patients receiving 0.3 mg/kg/day and 0.5 mg/kg/day of asfotase alfa prior to the protocol amendment to 6 mg/kg/week were combined for the entire treatment period.

Physical function and impairments of the HPP adolescents and adults were assessed with the running speed and agility test and strength test of the Bruininks-Oseretsky Test of Motor Proficiency, 2nd Edition (BOT-2). BOT-2 tests to assess running speed and agility of the HPP patients included the 50 foot shuttle run, sideways steps over balance beam, and one- and two-legged side hops. BOT-2 tests to assess strength of the HPP patients included sit-ups, v-ups, standing long jump, wall sit, and push-ups. BOT-2 speed and agility total scores and BOT-2 strength total scores were then determined from the sum of points awarded per BOT-2 tests for each time interval (baseline, 6 months, 1 year, 2 year, 3 years, 4 years, and 5 years). For BOT-2 scores after baseline, BOT-2 scores were combined for the treatment group and control group at each respective time point (6 months, 1 year, 2 years, 3 years, 4 years, and 5 years of asfotase alfa treatment) because the control group received treatment with asfotase alfa after the initial phase of 6 months. The median BOT-2 running speed and agility total score for adults and adolescents with HPP was 6.5 (minimum of 0, maximum of 39) at baseline and improved by 4.0 (minimum of –5, maximum of 18) after 5 years of treatment with asfotase alfa (FIG. 13). The median BOT-2 strength total point score was 13.5 (minimum of 0, maximum of 33) at treatment start and improved by 3.5 (minimum of –9, maximum of 9) after five years of treatment with asfotase alfa (FIG. 13).

Example 10. Improvements in Grip and Muscle Strength of Adolescent and Adult HPP Patients Assessed with Hand Held Dynamometry (HHD)

The grip and muscle strength of the HPP adolescents and adults was assessed using Hand Held Dynamometry (HHD). The following bilateral muscle groups were tested by administration of HHD: grip, knee flexors, knee extensors, hip flexors, hip extensors, and hip abductors. Strength was reported in pounds. Measurements were assessed in pounds (force), converted to Newtons (N), and torque was calculated in Newton meters (NM) using limb length. Torque was used to determine the % predicted HHD scores based on age, gender, and weight in patients less than 16 years of age and force was used for % predicted HHD scores comparisons in adults.

Median values for HHD hip abduction % predicted for HPP adolescent and adult patients (n=13) was 45.60% at baseline (minimum of 9.1%, maximum of 126.2%). Improvement in strength in the proximal muscles of the hip were observed in HPP patients treated with asfotase alfa after 24 weeks of treatment with asfotase alfa. The median change in % predicted value (dominant side) from baseline to week 24 was 11.10% (minimum of –25.7%, maximum of 20.4%) in the combined asfotase alfa treatment group compared with 6.70% (minimum of –7.1%, maximum of 12.0%) in the control group for hip abduction. The median change in % predicted value (dominant side) from baseline to week 24 was 7.95% (minimum of 12.6%, maximum of 19.5%) in the combined asfotase alfa treatment group, compared with 1.90% (minimum of 15.0%, maximum of 11.2%) in the control group for hip extension.

Adolescent and adult HPP patients treated with asfotase alfa showed improvement in hip abduction after treatment with asfotase alfa at 48 weeks (median change of 11.00% predicted (minimum of –15.0, maximum of 30.5%)), 96 weeks (median change of 11.95% predicted (minimum of –14.0%, maximum of 47.2%)), 144 weeks (median change of 17.05% predicted (minimum of –6.7%, maximum of 55.5%)), 192 weeks (median change of 19.45% predicted (minimum of –24.2%, maximum of 94.7%)), and 240 weeks (median change of 9.80% predicted (minimum of –7.2%, maximum of 155.2%)). Adolescent and adult HPP patients treated with asfotase alfa showed improvement in hip extension after treatment with asfotase alfa at 24 weeks (median change of 6.20% predicted (minimum of –12.6%, maximum of 19.5%)), 48 weeks (median change of 4.90% predicted (minimum of 1.7%, maximum of 27.7%)), 96 weeks (median change of 6.75% predicted (minimum of –24.1%, maximum of 31.2%)), 144 weeks (median change of 15.40% predicted (minimum of –15.6%, maximum of 45.2%)), 192 weeks (median change of 17.10% predicted (minimum of –3.2%, maximum of 50.2%)), and 240 weeks (median change of 12.40% predicted (minimum of –9.2%, maximum of 45.1%)). Adolescent and adult HPP patients treated with asfotase alfa showed improvement in hip abduction after 240 weeks of treatment with asfotase alfa. The adolescent and adult HPP patients had a median change in knee extension of 16.05% predicted (minimum of 7.1%, maximum of 40.7%)) and in knee flexion of 14.30% predicted (minimum of 2.1%, maximum of 68.0%)).

Example 11. Improvements in Functional Disability in the Lower Extremities of Adolescent and Adult HPP Patients Assessed with Lower Extremity Functional Scale (LEFS)

The functional disability in the lower extremities of the HPP adolescents and adults was assessed using the Lower Extremity Functional Scale (LEFS). A licensed physical therapist administered the LEFS assessment to HPP patients in interview format. Total LEFS scores range from 0 to 80 with higher scores indicative of better lower extremity functioning. Baseline mean and median LEFS score were much lower in the control group than in the combined asfotase alfa group. There was an improvement in the LEFS score of the combined asfotase alfa treatment group of adolescent and adult HPP patients compared to the untreated control group (Table 12). A clinically meaningful improvement 9 point increase) from Baseline to week 24 was observed in 1 of 5 patients (20.0%) in the control group, compared with 4 of 13 (30.8%) of HPP patients treated with asfotase alfa.

TABLE 12

Improvement in Lower Extremity Functional Scale (LEFS) Functional Disability Scores of HPP Patients from Baseline to Week 24 of Asfotase Alfa Treatment

| Visit | Parameter | Control Group (N = 6) | Asfotase Alfa 0.3 mg/kg (N = 7) | Asfotase Alfa 0.5 mg/kg (N = 6) | Asfotase Alfa Combined (N = 13/19) |
|---|---|---|---|---|---|
| Baseline | n | 5 | 7 | 6 | 13 |
| | Mean (SD) | 35.8 (4.66) | 40.0 (25.04) | 41.7 (15.62) | 40.8 (20.39) |
| | Median | 35.0 | 28.0 | 36.0 | 35.0 |
| | Min, Max | 30, 41 | 17, 78 | 29, 70 | 17, 78 |
| Week 24 | n | 4 | 7 | 6 | 13 |
| | Mean (SD) | 42.0 (12.73) | 52.3 (21.05) | 44.8 (21.07) | 48.8 (20.53) |
| | Median | 37.5 | 58.0 | 47.5 | 53.0 |
| | Min, Max | 33, 60 | 22, 78 | 22, 77 | 22, 78 |
| Change from Baseline to Week 24 | n | 4 | 7 | 6 | 13 |
| | Mean (SD) | 5.5 (13.70) | 12.3 (17.13) | 3.2 (13.09) | 8.1 (15.51) |
| | Median | 2.0 | 5.0 | 5.5 | 5.0 |
| | Min, Max | −7, 25 | −2, 40 | −15, 23 | −15, 40 |
| | p-value* | — | — | — | 0.7248 |

*P-value based on exact Wilcoxon rank sum test comparing the treatment group to the control group.

During treatment with asfotase alfa, 14 of 18 patients (77.8%) with a baseline LEFS score data had an increase (improvement) in total LEFS score from baseline to five years of treatment with asfotase alfa. In addition, 8 of the 18 total patients (44.4%) demonstrated a clinically meaningful improvement 9 points) in LEFS score at their final assessment compared to the baseline LEFS score. The mean change from baseline for all 18 patients to last overall exposure to asfotase alfa was 7.5 (standard deviation of 13.33).

Example 12. Pain in Adolescent and Adult HPP Patients Assessed with the Brief Pain Inventory-Short Form (BPI-SF)

The pain of the HPP adolescents and adults was assessed using the Brief Pain Inventory-Short Form (BPI-SF). BPI-SF scores of the HPP adolescents and adults are a composite of 11 pain assessments. There was no mean increase between baseline and week 24 in the combined BPI-SF score of the HPP adolescents and adults (Table 13). Mean and median change from baseline to week 24 in BPI-SF scores were similar between the HPP adolescents and adults treated with asfotase alfa and the control group.

During treatment with asfotase alfa for five years, BPI-SF scores for HPP adolescents and adults and control patients were consistent with those observed during the initial 24 week treatment period. By 96 weeks (N=19) and 144 weeks (N=17) of treatment with asfotase alfa, the median improvement was −4.0 (range: −13, 11) and −4.0 (range: −24, 9) for HPP adolescents and adults treated with asfotase alfa and control patients, respectively. At 192 weeks (N=15) and 240 weeks (N=16) of treatment with asfotase alfa, median improvement was −3.0 (range: −20, 8) and −3.5 (range −20, 5) for HPP adolescents and adults and control patients, respectively. Thus, HPP adolescents and adults showed no pain increase after treatment with asfotase alfa over about 5 years.

Example 13. Tolerability to Long-Term Treatment with Asfotase Alfa

Generally, treatment with asfotase alfa was well-tolerated in adolescents and adults having HPP, with most adverse events (AEs) consisting of injection-site reactions (ISRs) and arthralgia. Safety assessments included continuous monitoring of adverse events (AEs), including ISRs and injection associated reactions (IARs). ISRs were localized to

TABLE 13

No Change in Brief Pain Inventory-Short Form (BPI-SF) Scores of HPP Patients from Baseline to Week 24 of Asfotase Alfa Treatment

| Visit | Parameter | Control Group (N = 6) | Asfotase Alfa 0.3 mg/kg (N = 7) | Asfotase Alfa 0.5 mg/kg (N = 6) | Asfotase Alfa Combined (N = 13/19) |
|---|---|---|---|---|---|
| Baseline | n | 6 | 7 | 6 | 13 |
| | Mean (SD) | 12.3 (7.17) | 10.3 (10.78) | 17.8 (8.18) | 13.8 (10.07) |
| | Median | 12.0 | 8.0 | 20.0 | 15.0 |
| | Min, Max | 5, 25 | 0, 30 | 3, 25 | 0, 30 |
| Week 24 | n | 4 | 7 | 6 | 13 |
| | Mean (SD) | 10.3 (6.60) | 6.0 (7.16) | 15.2 (8.82) | 10.2 (8.98) |
| | Median | 10.0 | 3.0 | 16.0 | 7.0 |
| | Min, Max | 3, 18 | 0, 21 | 4, 26 | 0, 26 |
| Change from Baseline to Week 24 | n | 4 | 7 | 6 | 13 |
| | Mean (SD) | −4.0 (6.00) | −4.3 (7.04) | −2.7 (6.38) | −3.5 (6.51) |
| | Median | −3.0 | −3.0 | −0.5 | −2.0 |
| | Min, Max | −11, 1 | −17, 3 | −11, 4 | −17, 4 |
| | p-value* | — | — | — | 0.7315 |

*P-value based on exact Wilcoxon rank sum test comparing the treatment group to the control group.

the site of administration and occurred at any time point after initiation of asfotase alfa treatment. IARs included systemic signs, symptoms, or findings (e.g., generalized urticaria or itching, hypotension, or respiratory distress) that occurred within 3 hours after asfotase alfa administration.

No deaths occurred during asfotase alfa treatment. Only one patient withdrew because of injection site hypersensitivity and anaphylactoid reaction (1 episode each). All patients experienced at least one treatment-emergent adverse event (TEAE) during the study; most TEAEs were mild (864/1145 (75%)) or moderate (229/1145 (20%)) in intensity. The TEAEs of arthralgia, injection site erythema, pain in an extremity, back pain, injection site hematoma, bone pain, injection site discoloration, ophthalmologic calcifications, musculoskeletal pain, peripheral edema, dizziness, foot fracture, injection site reaction, joint swelling, upper respiratory tract infection, headache, injection site pain, nasopharyngitis, cough, fall, injection site atrophy, injection site pruritus, procedural pain, sinusitis, fatigue, injection site swelling, injection site hypertrophy, nausea, oropharyngeal pain, osteoarthritis, paresthesia, and post-traumatic pain were reported in more than three HPP patients (Table 14).

TABLE 14

Treatment-emergent adverse event (TEAEs) occurring in greater than three HPP patients during treatment with asfotase alfa

| TEAE (preferred term) | Patients, n (%) N = 19 |
|---|---|
| Arthralgia | 13 (68) |
| Injection site erythema | 13 (68) |
| Pain in extremity | 12 (63) |
| Back pain | 10 (53) |
| Injection site hematoma | 10 (53) |
| Bone pain | 9 (47) |
| Injection site discoloration | 9 (47) |
| Ophthalmologic calcifications[a] | 9 (47) |
| Musculoskeletal pain | 8 (42) |
| Peripheral edema | 8 (42) |
| Dizziness | 7 (37) |
| Foot fracture | 7 (37) |
| Injection site reaction | 7 (37) |
| Joint swelling | 7 (37) |
| Upper respiratory tract infection | 7 (37) |
| Headache | 6 (32) |
| Injection site pain | 6 (32) |
| Nasopharyngitis | 6 (32) |
| Cough | 5 (26) |
| Fall | 5 (26) |
| Injection site atrophy | 5 (26) |
| Injection site pruritus | 5 (26) |
| Procedural pain | 5 (26) |
| Sinusitis | 5 (26) |
| Fatigue | 4 (21) |
| Injection site swelling | 4 (21) |
| Injection site hypertrophy | 4 (21) |
| Nausea | 4 (21) |
| Oropharyngeal pain | 4 (21) |
| Osteoarthritis | 4 (21) |
| Paresthesia | 4 (21) |
| Post-traumatic pain | 4 (21) |

[a]TEAE includes preferred terms "deposit eye" and "conjunctival deposit."

The most common TEAEs were ISRs (385/1145 (34%)), which occurred in all patients; the most common ISRs (≥5% of ISRs) were erythema (121/385 (31%)), discoloration (66/385 (17%)), ISR not otherwise specified (56/385 (15%)), hematoma (33/385 (9%)), pain (26/385 (7%)), and pruritus (20/385 (5%)). A total of two patients experienced TEAES that were categorized as hypersensitivity IARs (oral hypoesthesia and chills in one patient; anaphylactoid reaction in one patient), which were all considered moderate in intensity. A total of 29 treatment-emergent serious AEs (SAEs) were reported for 9 patients, and 8 SAEs reported for two patients were assessed by the investigator as related to asfotase alfa administration (oral hypoesthesia, chills, pain in extremity, and headache in one patient and hypersensitivity reaction and anaphylactoid reaction in one patient). Overall, administration of asfotase alfa was well-tolerated in the HPP adolescents and adults.

Example 14. Pharmacodynamic Results from Phase 2a, Randomized, Multicenter, Open-Label, Dose-Ranging Study of Asfotase Alfa in Adults with Pediatric HPP In studies in patients aged 6-12 years and in adolescents and adults with HPP, asfotase alfa decreased circulating PPi and PLP levels and improved functional outcomes. Asfotase alfa has been approved in the United States, Europe, and Japan for the treatment of HPP in patients of all ages with pediatric-onset HPP at a recommended dose of 2.0 mg/kg 3 times per week or 1.0 mg/kg 6 times per week. In the United States, this dose may be increased to 3.0 mg/kg 3 times per week where a treating physician believes the efficacy to be insufficient.

The pharmacodynamics, pharmacokinetics, and safety/tolerability of asfotase alfa was evaluated in adults with pediatric-onset HPP at 3 doses over a 6-fold range bracketing a currently recommended dose of 2.0 mg/kg 3 times per week. The pharmacodynamics and safety/tolerability were measured.

Eligible patients included men and non-pregnant women aged ≥18 years with pediatric-onset HPP and diagnosis of HPP, as indicated by a documented history of HPP-related skeletal abnormalities and one or more of the following: documented TNSALP gene (ALPL) mutation(s), serum alkaline phosphatase activity below the age-adjusted normal range and PLP above the upper limit of normal at screening (historical results for PLP may be used to determine patient eligibility; the criterion for plasma PLP was not applicable for patients receiving pyridoxine treatment), plasma PPi ≥3.9 µM at screening, and no asfotase alfa treatment within 3 years of study entry.

Figure 14:
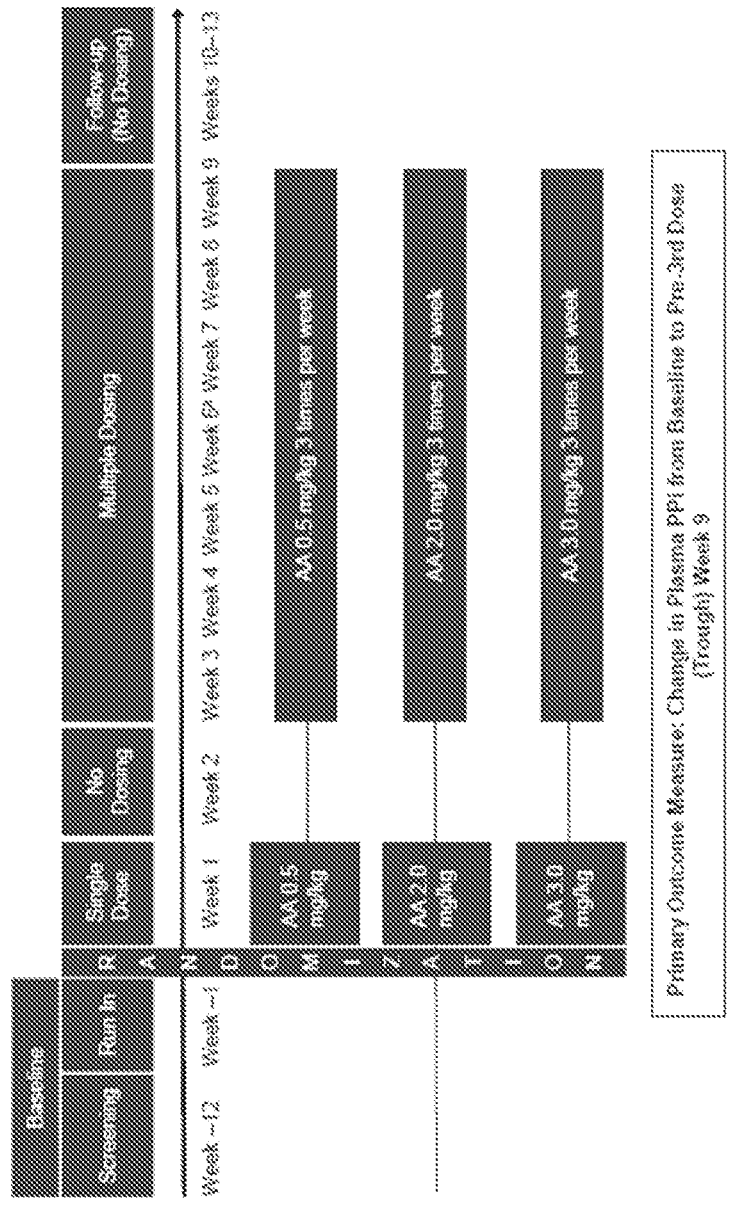
FIG. 14 is a schematic diagram showing the dosing schedule of patients receiving asfotase alfa at various concentrations during Phase 2a clinical trials.

The study design and treatment was a 13-week, Phase 2a, multicenter, randomized, open-label, dose-response study. After screening, an initial run-in period permitted sampling for substrate analysis. Patients were then randomized 1:1:1 to a single dose of asfotase alfa (0.5, 2.0, or 3.0 mg/kg) administered subcutaneously (SC) during Week 1. Patients did not receive asfotase alfa during Week 2. Asfotase alfa was then administered from Week 3 to Week 9 at a dose of 0.5, 2.0, or 3.0 mg/kg SC 3 times per week (equivalent to 1.5, 6.0, or 9.0 mg/kg/wk) (FIG. 14).

Pharmacodynamic outcome measures were changes in plasma PPi (primary) and PLP (secondary) from Baseline to pre-3rd dose (trough) Week 9, where Baseline was defined as the average of all assessments prior to first SC injection with asfotase alfa. Blood samples for measurement of plasma PPi and PLP were collected during screening, run-in, Week 1, Week 9, and Week 13 at the clinic. Blood samples for Weeks 2-8 and Weeks 10-12 could be collected at the clinic or at home. Other secondary outcome measures included safety/tolerability and pharmacokinetic parameters. Pharmacodynamic and safety/tolerability results are reported.

The primary hypotheses tested whether the differences in change from Baseline in plasma PPi between the cohorts differed from zero at pre-3rd dose Week 9. To control for multiplicity, a fixed sequence testing procedure was used to first determine the difference between the 3.0 and 0.5 mg/kg cohorts and, only if this was statistically significant, to then determine the difference between the 2.0 and 0.5 mg/kg cohorts. A 2-sided 5% Type I error was used when performing the significance testing (P<0.05). The primary outcome measure was met if the null hypothesis was rejected for both comparisons at the significance testing level of 0.05 (P<0.05 for both). The primary analysis was performed using a restricted maximum likelihood (REML)-based repeated measures mixed model to estimate the change from Baseline to Week 9 (pre-3rd dose; Day 61). This model used results from pre-dose samples obtained at Week 4 (Day 22), Week 5 (Day 29), Week 7 (Day 43), Week 8 (Day 50), Week 9 (Day 57), and Week 9 (Day 61). The Week 3 (Day 15) pre-dose time point was not included as it was collected after a 2-week washout period following the single dose and was expected to yield values similar to those at the Baseline. Following the protocol, pharmacodynamic assessments were not collected at Week 6. The analysis included covariates for the fixed, categorical effect of visit, treatment cohort, Baseline PPi, sex, Baseline weight group (≥median vs. <median), and study drug lot assignment. An unstructured covariance structure was used to model the within-patient errors, and the Kenward-Roger approximation was used to estimate denominator degrees of freedom.

Of the 35 patients screened, 27 were enrolled and completed the study. Demographic and Baseline disease characteristics are summarized in Table 15. Among the 3 dose cohorts, the median age was 45.0 years (range: 18-77) and most patients were white (96%) and female (59%).

TABLE 15

Demographic and Baseline HPP Characteristics

| | AA 0.5 mg/kg cohort (n = 8) | AA 2.0 mg/kg cohort (n = 10) | AA 3.0 mg/kg cohort (n = 9) | Total AA (N = 27) |
|---|---|---|---|---|
| Age at enrollment, year, median (range) | 44.5 (18-64) | 42.5 (24-77) | 55.0 (24-69) | 45.0 (18-77) |
| Sex, n (%) | 3 (38) | 4 (40) | 4 (44) | 11 (41) |
| Male | 5 (63) | 6 (60) | 5 (56) | 16 (59) |
| Race, n (%) | | | | |
| White | 7 (88) | 10 (100) | 9 (100) | 26 (96) |
| Multiple | 1 (13) | 0 | 0 | 1 (4) |
| Height, cm, mean (SD) | 161 (14) | 163 (7) | 163 (9) | 163 (10) |
| Weight, kg, mean (SD) | 89 (24) | 73 (13) | 85 (19) | 82 (20) |
| Form of HPP, n (%)[a] | | | | |
| Perinatal or infantile | 0 | 1 (10) | 1 (11) | 2 (7) |
| Childhood | 3 (38) | 5 (50) | 4 (44) | 12 (44) |
| Perinatal, infantile, or childhood | 5 (63) | 4 (40) | 4 (44) | 13 (48) |
| ALPL gene mutation sequence, n (%)[b] | 7 (88) | 9 (90) | 9 (100) | 25 (93) |
| Gene mutation category, n (%) | | | | |
| Homozygous | 0 | 1 (10) | 0 | 1 (4) |
| Heterozygous | 2 (25) | 3 (30) | 4 (44) | 9 (33) |
| Compound heterozygous | 5 (63) | 5 (50) | 5 (56) | 15 (56) |
| Not available | 1 (13) | 1 (10) | 0 | 2 (7) |
| History of high PLP used for HPP diagnosis at screening, n (%) | 7 (88) | 9 (90) | 8 (89) | 24 (89) |
| Baseline PPi, μM, mean (SD)[c] | 5.4 (1.6) | 5.3 (1.2) | 5.0 (0.9) | 5.2 (1.2) |
| Baseline PLP, ng/mL, mean (SD)[d] | 309.5 (349.2) | 382.1 (385.9) | 229.5 (321.4) | 309.7 (347.0) |
| Baseline ALP, U/L, mean (SD)[e] | 20.1 (4.2) | 20.4 (6.6) | 25.6 (20.5) | 22.0 (12.5) |

[a]Based on categorical collection of age at first sign/symptom.
[b]Gene mutation analysis performed as part of the study at a central laboratory.
[c]Normal range for PPi: 0.75-4.78 μM for patients aged 13-18 years and 1.00-5.82 for patients aged >18 years.
[d]Normal range for PLP: 5.74-61.15 ng/mL for patients aged 6-18 years and 2.81-26.70 ng/mL for patients aged >18 years.
[e]Normal range for ALP: 60-270 U/L for male patients aged 16-19 years, 40-120 U/L for male patients aged >19 years, and 40-120 U/L for female patients >15 years. For analysis, values below the LLOQ of 18 U/L were set to 18 U/L.
AA = asfotase alfa:
ALP = alkaline phosphatase;
HPP = hypophosphatasia;
TNSALP = tissue-nonspecific alkaline phosphatase;
PLP = pyridoxal 5'-phosphate;
PPi = inorganic pyrophosphate;
SD = standard deviation.

Figure 15:
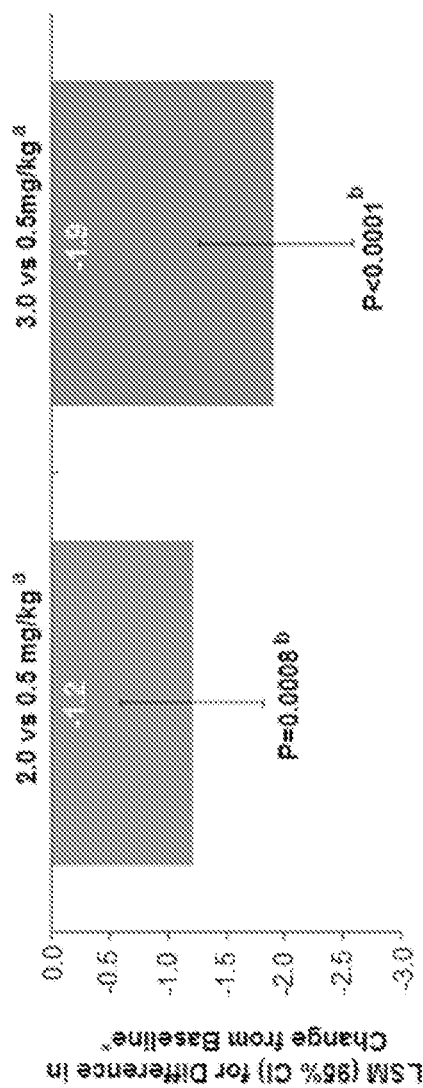
FIG. 15 is a graph showing significant differences observed between least squares mean (LSM) changes in PPi from Baseline to pre-3rd dose Week 9 during Phase 2a clinical trials.
Figure 16:
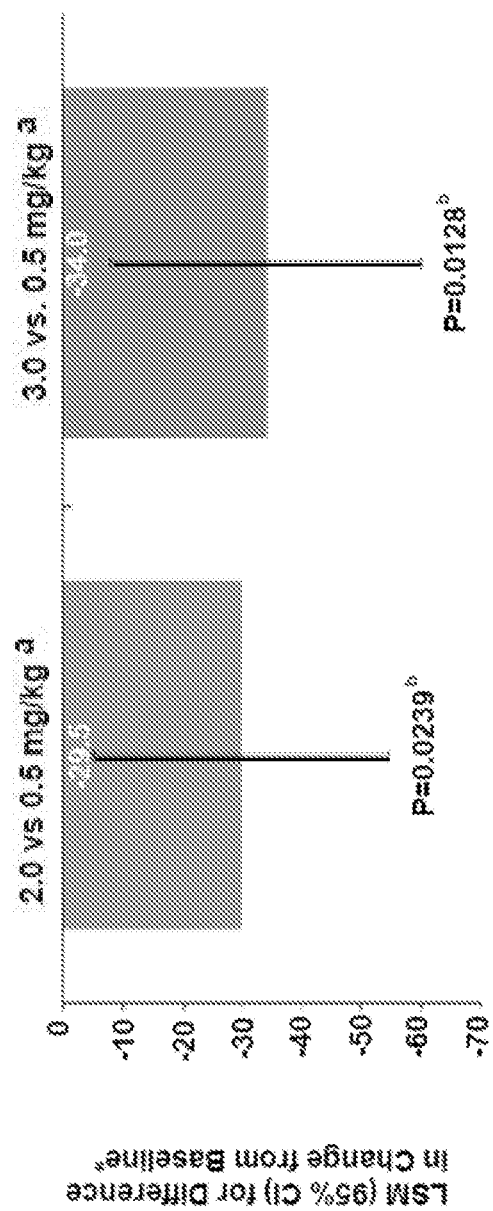
FIG. 16 is a graph showing significant differences observed between LSM changes in PLP from Baseline to pre-3rd dose Week 9 during Phase 2a clinical trials.

Significant differences were observed between least squares mean (LSM) changes in PPi from Baseline to pre-3rd dose Week 9 (Table 16 and FIG. 15). Significant differences were also observed between LSM changes in PLP from Baseline to pre-3rd dose Week 9 (Table 16 and FIG. 16).

events in 1 patient in the 2.0 mg/kg cohort). Ectopic calcifications (4 events in 4 patients; 2 each in the 2.0 and 3.0 mg/kg cohorts) were observed in the kidney (2 patients; 1 each in the 2.0 and 3.0 mg/kg cohorts), eye (1 patient in the 2.0 mg/kg cohort), and liver (1 patient in the 3.0 mg/kg cohort). Hypersensitivity reactions were also observed (4

TABLE 16

Mean Change in PPi and PLP from Baseline to Pre-$3^{rd}$ Dose at Week 9

|  | AA 0.5 mg/kg cohort (n = 8)[a] | AA 2.0 mg/kg cohort (n = 10)[a] | AA 3.0 mg/kg cohort (n = 9)[a] |
|---|---|---|---|
| PPi, μM |  |  |  |
| Baseline, mean (SD) | 5.4 (1.6) | 5.3 (1.2) | 5.0 (0.9) |
| Pre-$3^{rd}$ dose Week 9, mean (SD)[b] | 3.1 (0.7) | 1.9 (0.6) | 1.1 (0.3)[c] |
| LSM, change from Baseline (SE)[d] | −2.6 (0.2) | −3.8 (0.2) | −4.5 (0.2) |
| PLP, ng/mL |  |  |  |
| Baseline, mean (SD) | 309.5 (349.2) | 382.1 (385.9) | 229.5 (321.4) |
| Pre-$3^{rd}$ dose Week 9, mean (SD)[b] | 40.7 (45.8) | 13.0 (9.5) | 4.8 (4.4) |
| LSM change from Baseline (SE)[d] | −304.0 (0.4) | −333.4 (8.1) | −338.0 (8.5) |

[a]Doses administered 3 times per week during the multiple dosing period.
[b]Pre-3rd dose Week 9 sample was collected on Day 61.
[c]One patient had no result
[d]From primary analysis restricted maximum likelihood-based repeated measures mixed model.
AA = asfotase alfa;
CI = confidence interval;
LSM = least squares mean;
PLP = pyridoxal 5'-phosphate;
PPi = inorganic pyrophosphate;
SD = standard deviation;
SE = standard error.

With regards to safety and tolerability, treatment-emergent adverse events (TEAEs) observed in ≥5 patients overall are presented in Table 17, For example, injection site reactions (137 events in 21 patients) were more common in the 2.0 and 3.0 mg/kg cohorts. Lipodystrophy was observed (2 events in 1 patient in the 2.0 mg/kg cohort). Overall, 99% (480/485) of TEAEs were mild or moderate in severity. No serious TEAEs were reported, and no patients withdrew from the study because of TEAEs.

TABLE 17

Treatment-emergent Adverse Events in ≥5 Patients

|  | AA 0.5 mg/kg cohort (n = 8)[a] | | AA 2.0 mg/kg cohort (n = 10)[a] | | AA 3.0 mg/kg cohort (n = 9)[a] | | Overall (N = 27) | |
|---|---|---|---|---|---|---|---|---|
| TEAE | Events, n | Patients, n (%) | Events, n | Patients, n (%) | Events, n | Patients, n (%) | Events, n | Patients, n (%) |
| Pain in extremity | 17 | 4 (50) | 11 | 5 (50) | 10 | 4 (44) | 38 | 13 (48) |
| Arthralgia | 13 | 2 (25) | 12 | 4 (40) | 15 | 5 (56) | 40 | 11 (41) |
| Headache | 10 | 3 (38) | 9 | 3 (30) | 7 | 5 (56) | 26 | 11 (41) |
| Fatigue | 9 | 3 (38) | 11 | 4 (40) | 5 | 3 (33) | 25 | 10 (37) |
| Injection site erythema | 4 | 2 (25) | 4 | 3 (30) | 4 | 4 (44) | 12 | 9 (33) |
| Injection site reaction | 4 | 1 (13) | 21 | 3 (30) | 68 | 4 (44) | 93 | 8 (30) |
| Back pain | 13 | 4 (50) | 4 | 1 (10) | 2 | 2 (22) | 19 | 7 (26) |
| Bone pain | 3 | 2 (25) | 3 | 3 (30) | 3 | 2 (22) | 9 | 7 (26) |
| Erythema | 4 | 2 (25) | 7 | 3 (30) | 2 | 1 (11) | 13 | 6 (22) |
| Injection site pain | 2 | 2 (25) | 2 | 1 (10) | 4 | 3 (33) | 8 | 6 (22) |

TABLE 17-continued

Treatment-emergent Adverse Events in ≥5 Patients

| TEAE | AA 0.5 mg/kg cohort (n = 8)[a] | | AA 2.0 mg/kg cohort (n = 10)[a] | | AA 3.0 mg/kg cohort (n = 9)[a] | | Overall (N = 27) | |
|---|---|---|---|---|---|---|---|---|
| | Events, n | Patients, n (%) | Events, n | Patients, n (%) | Events, n | Patients, n (%) | Events, n | Patients, n (%) |
| Nausea | 3 | 2 (25) | 2 | 1 (10) | 2 | 2 (22) | 7 | 5 (19) |
| Upper respiratory infection | 1 | 1 (13) | 3 | 3 (30) | 1 | 1 (11) | 5 | 5 (19) |

[a]Doses administered 3 times per week during the multiple dosing period.
AA = asfotase alfa.

Adult patients with pediatric-onset HPP treated with asfotase alfa at or above the recommended dose (2.0 or 3.0 mg/kg) had statistically significant reductions from Baseline in their pre-3rd dose Week 9 PPi and PLP values compared with patients treated with the lower than recommended dose (0.5 mg/kg). Injection site reactions were more frequent with increasing dose. Otherwise, asfotase alfa was well tolerated at all doses.

Example 15. Population Pharmacokinetic and Pharmacokinetic-Pharmacodynamic Analysis of Asfotase Alpha in Adult Patients with Pediatric-Onset Hypophosphatasia from Study AA-HPP-208

We calculated asfotase alfa pharmacokinetic (PK) parameters using non-compartmental analyses (NCA) in order to describe the PK of asfotase alfa in adult patients with pediatric-onset HPP. We estimated population PK parameters, including typical values and random interindividual and residual variabilities and identified individual-specific covariate factors (e.g., weight) that are predictive of the unexplained random variability in the population PK analysis. We described the population pharmacokinetic-pharmacodynamic (PKPD) relationship between asfotase alfa exposure and PPi response. Additionally, we estimated population PK-PPi parameters, including typical values and random interindividual and residual variabilities. Also, we simulated the exposure-response (ER) relationship between PK-PPi in asfotase alfa adult patients with pediatric-onset HPP to support a recommended dose of 6 mg/kg/week. Lastly, we described the population PKPD relationship between asfotase alfa exposure and pyridoxal-50-phosphate (PLP) response in patients who did not receive treatment with Vitamin B6-containing supplements. This includes description of the PK-PLP dose or ER and estimation of typical values and random interindividual and residual variabilities.

Figure 17A:
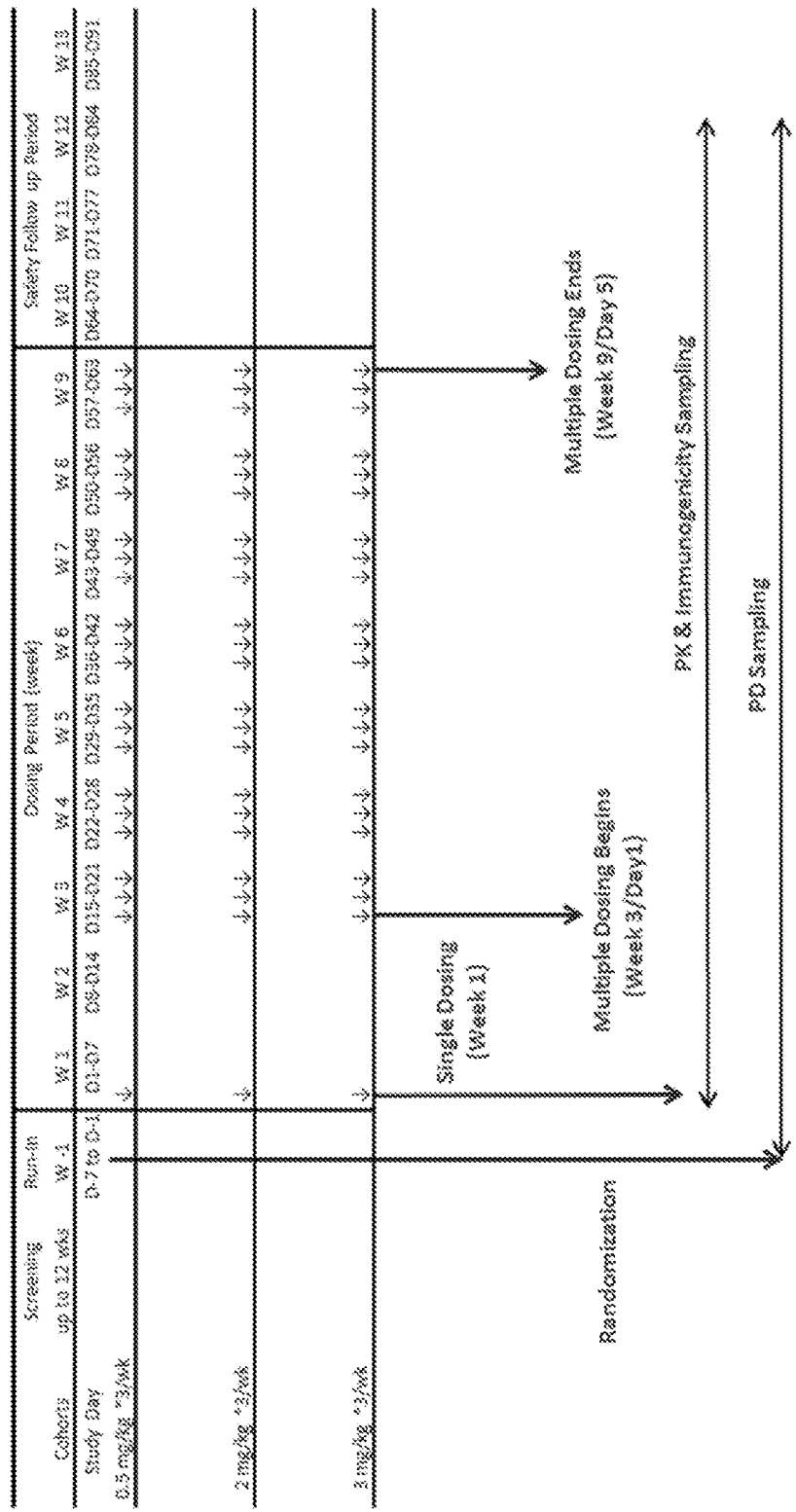

The Phase 2a study (Protocol AA-HPP-208) was a randomized, parallel group design of three escalating multiple-dosing regimens of asfotase alfa in 27 HPP patients over approximately 13 weeks (FIGS. 17A-17B). The study consisted of a screening period, a single-dose period (3 weeks), and a multiple-dose treatment period (10 weeks). The study consisted of a single dose of 0.5, 2.0 or 3.0 mg/kg of asfotase alfa followed by multiple doses of the same amounts 3×/week, starting after 2 weeks. Twenty-seven individuals (approximately 9 per cohort) were included in the study and rich PK, PPi, and PLP sampling was performed after single and multiple-dosing with sparse sampling during accumulation phase.

Figures 18A, 18B:
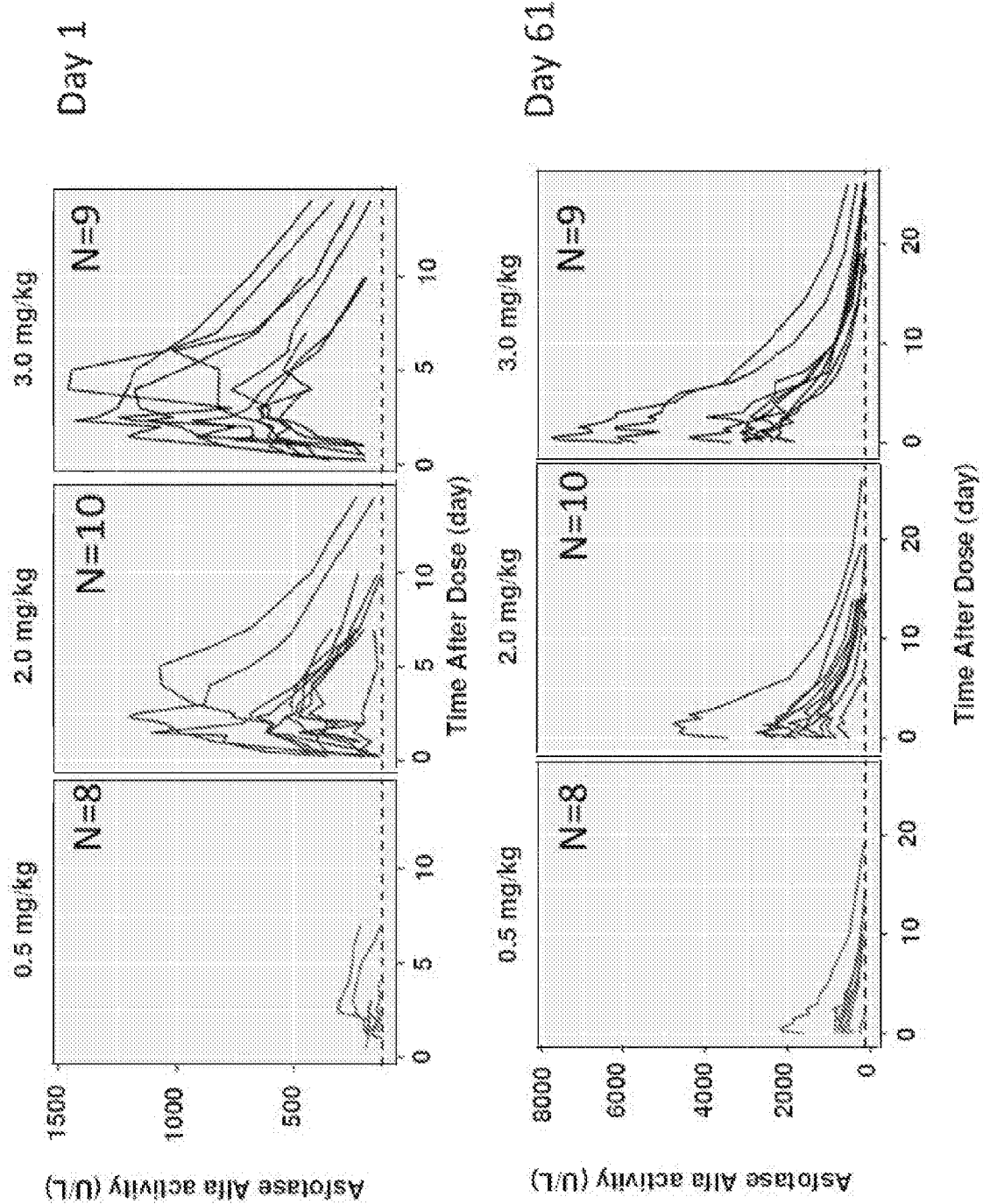
FIGS. 18A-18B are graphs showing individual PK profiles of asfotase alfa activity (U/L) in each dosage cohort (0.5 mg/kg 3×/week, 2 mg/kg 3×/week, and 2 mg/kg 3×/week) each day after the initial dose on day 1 (FIG. 18A) and after the multiple dosing event on day 61 (FIG. 18B).
Figure 19A:
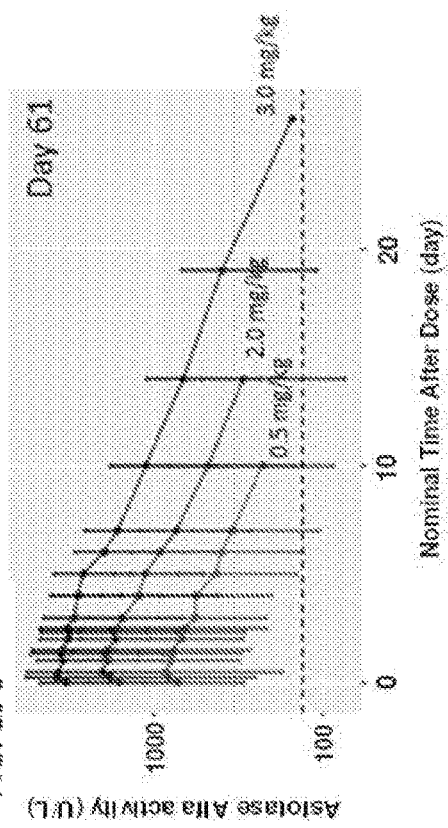
FIGS. 19A-19C are graphs showing mean±SD of PK profiles of asfotase alfa alfa activity (U/L) in each dosage cohort each day after the initial dose on day 1 (FIG. 20A), after the multiple dosing events between days 15-61 (FIG. 19B), and after the multiple dosing event on day 61 (FIG. 19C).
Figure 19B:
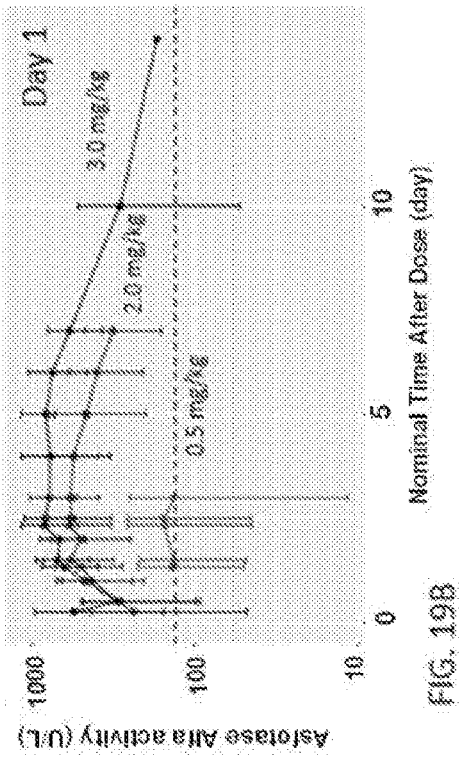
Figure 19C:
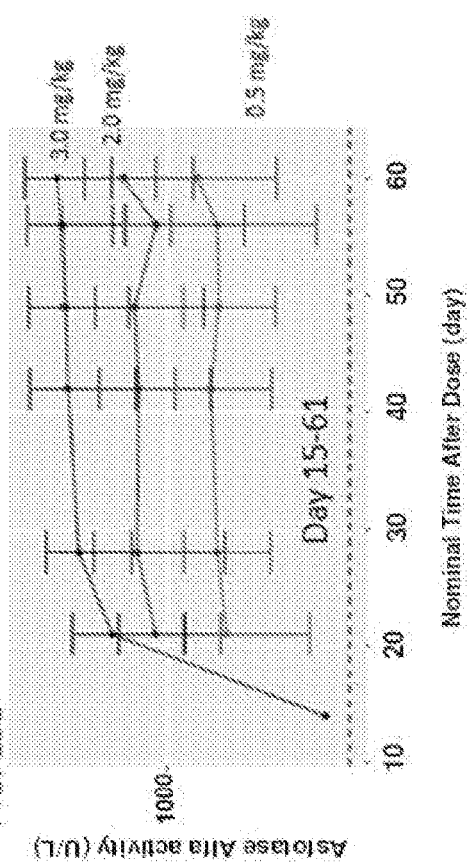
Figure 20A:
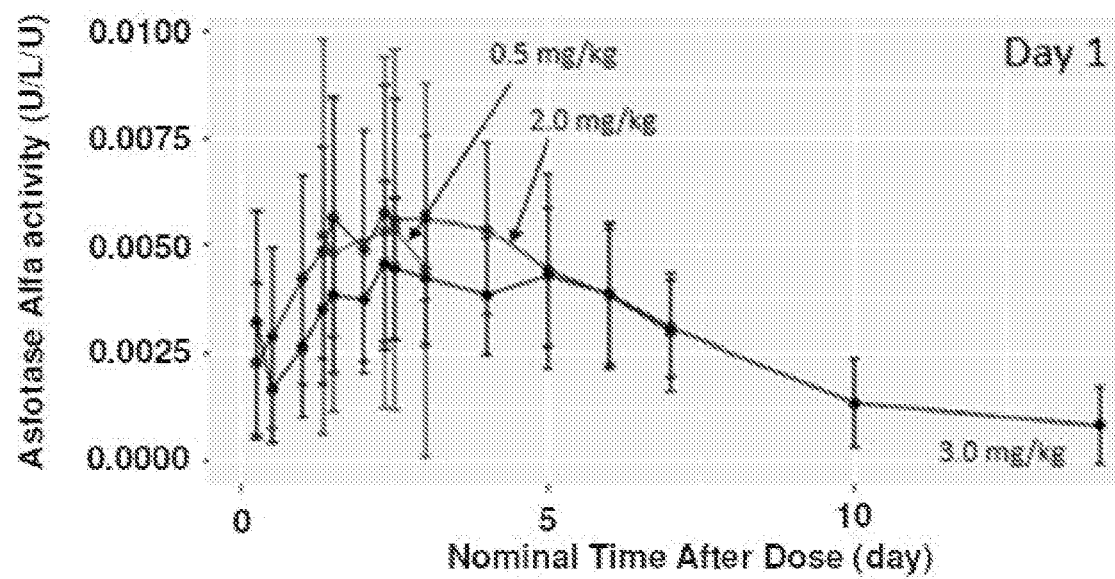
FIGS. 20A-20B are graphs showing mean±SD dose normalized asfotase alfa activity (U/L) in each dosage cohort each day after the initial dose on day 1 (FIG. 20A) and after the multiple dosing event on day 61 (FIG. 20B).
Figure 20B:
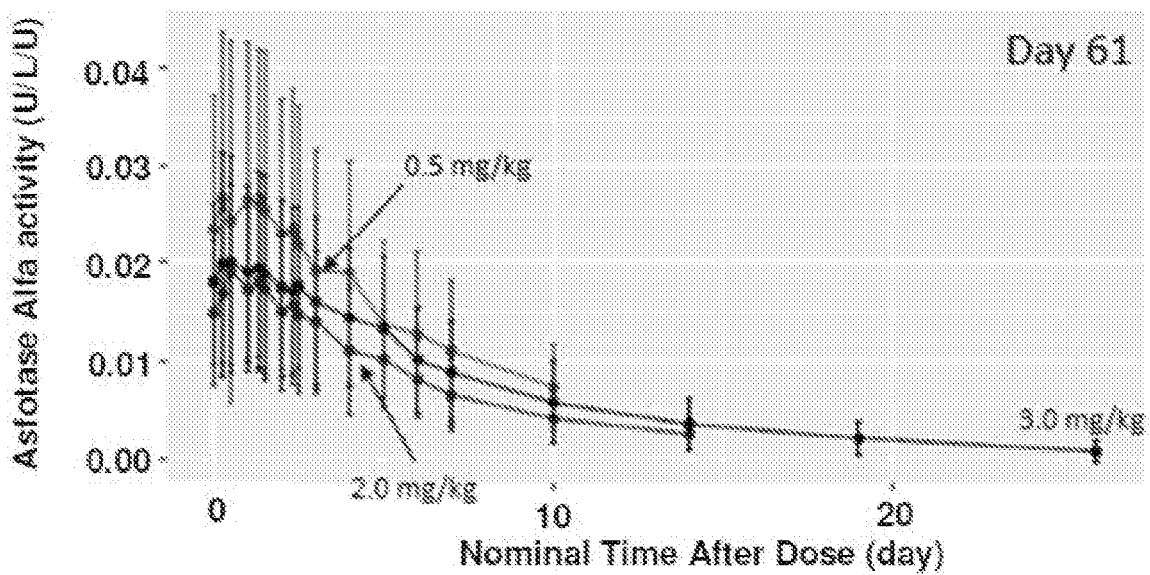

Individual and mean PK profiles were obtained for all three cohorts. The individual PK profiles indicated asfotase alfa accumulation from after single dosing events on day 1 (FIG. 18A) to after multiple dosing events on day 61 (FIG. 18B). Both single-dose and multiple-dose mean±SD PK profiles showed that asfotase alfa exhibited linear PK with increased exposure within the tested 0.5 to 3 mg/kg dose range (FIGS. 19A and 19C). Steady state was reached around day 29 (or after 4 weeks of repeated dosing) where asfotase alfa trough concentration consistently reached plateau under all three dosing regimens (FIG. 19B). Dose normalized mean±SD PK profiles showed that asfotase alfa PK increased approximately dose-proportionally (or within 2-fold of the proportionality range) from 0.5 mg/kg to 3.0 mg/kg (FIGS. 20A-20B).

Population PK data including concentration observations, dosing histories, event times, and covariate factors (age, height, weight, sex, and race) were assembled and formatted for analysis. PK parameter values were estimated using the NCA module in PhoenixWinNonlin v 7.0 (Certara, Princeton N.J., USA). The dataset for NCA was derived from the NONMEM®population PKPD dataset. PK parameters derived from concentration results were used to assess the dose proportionality of asfotase alfa. Population PKPD analyses for repeated-measures endpoints were conducted via nonlinear mixed effects modeling with a qualified installation of the nonlinear mixed effects modeling (NONMEM®) software, Version 7.3 (ICON Development Solutions, Hanover, Md.).

Previous modeling work suggested asfotase alfa follows a multi-compartmental disposition, so that initial modeling was conducted using a two-compartment model with first-order absorption parameterized in terms of clearance (CL), central volume of distribution ($V_2$), peripheral volume of distribution ($V_3$), intercompartmental clearance (Q), absolute bioavailability (F), absorption rate constant ($k_a$), and subcutaneous absorption lag time (ALAG) (ADVAN13), with appropriate random effect distributions. Model selection was guided by various goodness-of-fit criteria, including diagnostic scatter plots, convergence with at least 2 significant digits, plausibility of parameter estimates, precision of parameter estimates, correlation between model parameter estimation errors <0.95, and the AIC, given the minimum objective function value and number of estimated parameters. Final model parameter estimates were reported with a measure of estimation uncertainty including the asymptotic standard errors (obtained from the NONMEM®$COVARIANCE step).

Prior modeling work with asfotase alfa also guided covariate modeling. A full model was constructed with care to avoid correlation or collinearity in predictors. Model parameters were estimated, and assessment of any remaining trends was conducted by graphical inspection of all covariate effects. Inferences about clinical relevance of parameters were based on the resulting parameter estimates of the full model and measures of estimation precision. Individual PK parameters were also estimated, and average concentration during the dosing interval at steady-state ($C_{avg,ss}$) was calculated. A predictive check model evaluation step was performed to assess the performance of the final model and parameters.

For the PK-PPi data analyses, plasma PPi response in terms of change from baseline was plotted and summarized across exposure quartiles. The frequencies of pre-dose Study Day 61 PPi concentrations below the PPi lower limit of normal (1.33 µM) (LLN) were tabulated by interquartile range of $C_{avg,ss}$ and treatment cohort. Individual values of asfotase alfa $C_{avg,ss}$ ranging from 253-6800U/L were calculated and used to graphically and quantitatively assess this ER relationship.

The asfotase alfa PKPD data set was comprised of 27 patients contributing a total of 1140 serum asfotase alfa concentrations and 1293 plasma PPi concentrations over the entire study duration. There were 198 observations below the limit of quantification, which made up over 17% of the total number of serum asfotase alfa observations. The study population consisted of 11 males and 16 females with ages ranging from 18 to 77 years and weights ranging from 48.2 to 121.3 kg. The majority of the patients were white (96.3%). Height, sex, age, and race were included in the dataset and are summarized in tabular format for completeness but were not considered as potential covariates in the population models. Drug LOT information used in the analyses included lot activity, total sialic acid content (TSAC) content, and batch size.

The NCA analysis revealed that the relatively long half-life and frequency of dosing resulted in marked accumulation at all dose levels. Extensive inter-individual variability was observed in the concentration vs. time profiles within each cohort, though all profiles seemed to display a monoexponential decline, when viewed on a semi-log graph. Estimates of exposure (maximum concentration in the dosing interval ($C_{max}$), area under the concentration-time curve from time zero to time of the last observed concentration in a dosing interval ($AUC_{last}$), and area under the concentration-time curve from time zero to infinity ($AUC_{inf}$) increased with increasing dose and between single and multiple-dose administration. Due to limited concentrations above the lower limit of detection in the 0.5 mg/kg cohort, $AUC_{inf}$, apparent clearance after subcutaneous dosing (CL/F), apparent volume of distribution after subcutaneous dosing ($V_z/F$), and terminal half-life ($t_{1/2}$) were not evaluable. The geometric mean estimates of CL/F and $V_2/F$ were 18.8 L/day and 99.1 L for the 2.0 mg/kg cohort and 22.1 L/day and 150 L for the 3.0 mg/kg cohort, respectively. Estimates of $t_{1/2}$ had geometric mean values ranging from 3.66 to 5.54 $day^{-1}$. Median time of maximum concentration in the dosing interval ($T_{max}$) estimates ranged from 1.91 to 3.0 and 0.747 to 1.16 days in the single and multiple dose cohorts, respectively. Dose proportionality in asfotase alfa PK was assessed using the logarithmic form of the power model fit to single and multiple-dose $C_{max}$ values and single dose $AUC_{inf}$ and $AUC_{last}$ values.

Results were inconclusive for all but single dose $C_{max}$ where non-proportionality was concluded. For the single dose $C_{max}$ parameter, the threshold dose ratio to reject proportionality was 7.85. The maximal proportional dose ratios for these parameters ranged from 1.37 to 1.69, as compared with the maximum dose ratio of 18.2 in the dataset.

Our prior modeling work suggested asfotase alfa follows a multi-compartmental disposition, so that initial modeling was conducted using a two-compartment model with first-order absorption, with appropriate random effect distributions. The full covariate model from the previous analysis included the pre-specified effects of allometrically-scaled weight, TSAC and anti-drug neutralizing antibodies (NAb) on CL; allometrically-scaled weight on $V_2$, $V_3$, and Q, and manufacturing lot batch size as a covariate on F and $k_a$ since multiple batch sizes were included. The manufacturing lots for the current analysis included only the 20K batch size, therefore the observed drug substance activity for each lot was also included in the model as a direct factor of dose, but this was not an estimated covariate effect. The typical estimates (95% CI) of PK model parameters for the reference covariate effects (70 kg, 1.7 mol/mol, absence of anti-drug antibodies, 20K lot size) were 17.9 (13.7, 23.4) L/day, 36.6 (0.876, 1530) L, 95.7 (18.5, 496) L, 3490 (6.47, 1.88e+06) L/day and 1.10 (0.603, 2.02) $day^{-1}$, for CL/F, apparent (subcutaneous) central volume of distribution ($V_2/F$), apparent (subcutaneous) peripheral volume of distribution ($V_3/F$), apparent (subcutaneous) intercompartmental clearance (Q/F) and single dose absorption rate constant (kaSD), respectively. These results were consistent with those from the NCA and somewhat consistent with those from prior analyses.

The effects of covariate factors on asfotase alfa PK were also investigated. The expected impact of covariates on CL/F, $V_2/F$, $V_3/F$ and Q/F was illustrated by calculating the $C_{avg,ss}$ at values attributed to each predictor that was distinguishable from the null effect. Between extreme values for body weight (48.2 and 121.3 kg), TSAC (1.4 and 1.6 mol/mol) and in the presence or absence of anti-drug antibody, the predicted median $C_{avg,ss}$ ranged from 1750 U/L to 2769 U/L, when the normalization value for TSAC was 1.7. Unexplained random variability (% CV) was reduced for CL/F (43.9 percent coefficient of variation (CV %)), in the final model, when compared to the base model CL/F (48.8 CV %) variance estimate. The clinical relevance of this finding is that dose adjustment for known covariates is not expected to result in a meaningful reduction in response variability.

The final population PK model provided a good description of the PK data. Goodness-of-fit criteria revealed that the final model was consistent with the observed data and that no systematic bias remained. The model evaluation results provided evidence that both the fixed and random effects components of the final model were reflective of the observed data, as well.

Plasma PPi response tended to be greater with increasing asfotase alfa exposure, though extensive overlap in response was noted across exposure quartiles. The frequency of this PPi response appeared to plateau to 66.7% at concentrations above the median asfotase alfa $C_{avg,ss}$ of 2030 U/L, indicating that increasing the median $C_{avg,ss}$ over 2030 U/L appears to have no further impact on increasing the frequency of PPi response.

The asfotase alfa PK parameters were calculated using NCA and are summarized in Table 18. The relatively long half-life and frequency of dosing resulted in marked accumulation at all dose levels, however $AUC_{inf}$, CL/F, $V_z/F$, and $t_{1/2}$ were not evaluable in the 0.5 mg/kg cohort, due to limited concentrations above the lower limit of detection.

TABLE 18

Summary of PK NCA Parameters

| Parameter | Asfotase alfa 0.5 mg/kg (N = 8) | | Asfotase alfa 2.0 mg/kg (N = 10) | | Asfotase alfa 3.0 mg/kg (N = 9) | |
|---|---|---|---|---|---|---|
| | Day 1 | Day 61 | Day 1 | Day 61 | Day 1 | Day 61 |
| $C_{max}$ (U/L) | 218 (24.1) | 743 (63.6) | 617 (51.8) | 1900 (53.6) | 915 (35.3) | 3600 (43.7) |
| $t_{max}$ (day) | 1.91 | 0.747 | 2.34 | 1.16 | 3.00 | 0.990 |
| | (0.485, 3.00) | (0.00, 2.46) | (1.49, 5.04) | (0.00, 2.49) | (1.50, 6.04) | (0.254, 1.33) |
| $AUC_{last}$ (U × day/L) | 588 (77.0) | NE | 3310 (60.6) | NE | 5620 (63.3) | NE |
| $AUC_{inf}$ (U × day/L) | NE | NE | 5350 (45.6) | NE | 9030 (40.3) | NE |
| $t_{1/2}$ (day) | NE | 5.12 (10.2) | 3.66 (16.4) | 4.62 (28.0) | 4.69 (17.9) | 5.54 (18.3) |
| $\lambda_z$ (day$^{-1}$) | NE | 0.135 (10.2) | 0.189 (16.4) | 0.150 (28.0) | 0.148 (17.9) | 0.125 (18.3) |
| CL/F (U/L) | NE | NE | 18.8 (37.2) | NE | 22.1 (41.2) | NE |
| $V_z$/F (L) | NE | NE | 99.1 (25.9) | NE | 150 (36.2) | NE |
| CtroughR | NE | 4.15 (35.3) | NE | 3.14 (65.5) | NE | 4.68 (33.6) |

Geometric mean and geometric CV % were provided for all parameters except $t_{max}$, where median and range were provided.
$\lambda_z$ = terminal disposition rate constant;
$AUC_{inf}$ = area under the concentration-time curve from time zero to infinity;
$AUC_{last}$ = area under the concentration-time curve from time zero to time of the last observed concentration in a dosing interval;
CL/F = apparent clearance after subcutaneous dosing;
$C_{max}$ = maximum concentration in the dosing interval;
CtroughR = ratio of concentration 48 hours after first dose to pre-dose concentration on Day 61 after multiple dosing;
NE = not evaluable;
$t_{1/2}$ = terminal half-life;
$t_{max}$ = time of maximum concentration in the dosing interval;
$V_z$/F = apparent volume of distribution after subcutaneous dosing.

Composite and mean plots of the serum asfotase alfa concentration-time data showed increasing exposure with increasing doses, although a large portion of concentrations in the 0.5 mg/kg cohort had data that were below the limit of quantitation (BLQ) following Day 1 dosing. Extensive interpatient variability was observed in the concentration versus time profiles within each cohort, although all profiles seemed to display a mono-exponential decline when viewed on a semi-log graph.

Estimates of exposure ($C_{max}$, $AUC_{last}$, and $AUC_{inf}$) increased with increasing dose and between single and multiple-dose administration. Due to limited concentrations above the lower limit of detection in the 0.5 mg/kg cohort, $AUC_{inf}$, CL/F, $V_z$/F, and $t_{1/2}$ were not evaluable. The geometric mean estimates of CL/F and $V_z$/F were 18.8 L/day and 99.1 L for the 2.0 mg/kg cohort and 22 1 L/day and 150 L for the 3.0 mg/kg cohort, respectively. Estimates of $t_{1/2}$ had geometric mean values ranging from 3.66 to 5.54 days. Median $t_{max}$ estimates ranged from 1.91 to 3.0 days and 0.747 to 1.16 days in the single and multiple-dose cohorts, respectively.

Given the irregular time between consecutive doses (i.e. 3 times per week dosing results in 2 intervals of 2 days and 1 interval of 3 days in a 7-day period), the accumulation ratio could not be directly assessed with standard methods. An approximation of the accumulation with 3 times a week dosing was assessed by calculating the ratio of the concentration 48 hours after first dose administration to the predose concentration on Day 61 after multiple dosing. The geometric means of these ratios ranged from 3.14 to 4.68 across the 3 cohorts. The full model population PK model is shown in Table 19.

TABLE 19

Full Model: Population PK Model 30502

| PK Parameter (Unit) | NONMEM Parameter | Estimate | 95% CI* |
|---|---|---|---|
| CL/F (L/day) | $\exp(\theta_1)$ | 17.9 | (13.7, 23.4) |
| V2/F (L) | $\exp(\theta_2)$ | 36.6 | (0.876, 1530) |
| V3/F (L) | $\exp(\theta_3)$ | 95.7 | (18.5, 496) |
| Q/F (L/day) | $\exp(\theta_4)$ | 3490 | (6.47, 1.88e+06) |
| $ka_{SD}$ (day$^{-1}$) | $\exp(\theta_5)$ | 1.10 | (0.603, 2.02) |
| ALAG (day) | $\exp(\theta_6)$ | 0.0771 | (0/00939, 0.634) |
| $ka_{MD}$ (day$^{-1}$) | $\exp(\theta_7)$ | 2.09 | (1.14, 3.82) |
| CL/F~AllometricExponent | $\theta_8$ | 0.776 FIX | |
| CL/F~ADA+/Nab− | $\exp(\theta_9)$ | 1.11 FIX | |
| CL/F~TSAC | $\theta_{10}$ | −1.08 FIX | |
| IIVvar CL/F ($\omega^2_{CL/F}$) | $\Omega_{1,1}(\eta_1)$ | 0.176 (% CV = 4 3.9) | (0.00, 0.472) |
| IIVcov CL/F, V$_2$/F ($\omega_{CL/F}, \omega_{V2/F}$) | $\Omega_{2,1}$ | 0.0253 | (−0.126, 0.176) |
| IIVvar V$_2$/F ($\omega^2_{V2/F}$) | $\Omega_{2,2}(\eta_2)$ | 0.108 (% CV = 33.7) | (0.00, 1.13) |
| IIVcov CL/F, V$_3$/F ($\omega_{CL/F}, \omega_{V3/F}$) | $\Omega_{3,1}$ | 0.229 | (−0.00757, 0.465) |
| IIVcov V$_2$/F, V$_3$/F ($\omega_{V2/F}, \omega_{V3/F}$) | $\Omega_{3,2}$ | −0.0295 | (−0.502, 0.443) |
| IIVvar V$_3$/F ($\omega^3_{V3/F}$) | $\Omega_{3,3}(\eta_3)$ | 0.405 (% CV = 70.6) | (0.00, 1.07) |
| IIVcov CL/F, $k_a$ ($\omega_{CL/F}, \omega_{ka}$) | $\Omega_{4,1}$ | 0.101 | (−0.118, 0.320) |
| IIVcov V$_2$/F, $k_a$ ($\omega_{V2/F}, \omega_{ka}$) | $\Omega_{4,2}$ | 0.175 | (−0.527, 0.876) |
| IIVcov V$_3$/F, $k_a$ ($\omega_{V3/F}, \omega_{ka}$) | $\Omega_{4,3}$ | 0.104 | (−0.136, 0.344) |

TABLE 19-continued

Full Model: Population PK Model 30502

| PK Parameter (Unit) | NONMEM Parameter | Estimate | 95% CI* |
|---|---|---|---|
| IIVvar $k_a$ ($\omega^4_{ka}$) | $\Omega_{4,4}(\eta_4)$ | 0.372 (% CV = 67.1) | (0.00, 0.891) |
| $\Sigma_{1,1,\ additive}$ ($\varepsilon_1$) | $\Sigma_{1,1,\ additive}$ ($\varepsilon_1$) | 0.0488 (SD = 0.2221) | (0.0435, 0.0541) |

*95% CI derived from standard errors obtained from the NONMEM $COVARIANCE step
IIV = interindividual variability,
CV = coefficient of variation,
SD = standard deviation The population PK of asfotase alfa was described in adult patients with pediatric-onset HPP by a two compartment model with first-order absorption with an absorption lag time. Typical population parameter estimates (95% CI) of 17.9 (13.7, 23.4) L/hr, 36.6 (0.876, 1530) L, 95.7 (18.5, 496) L, 3490 (6.47, 1.88e+06) L/day and 1.10 (0.603, 2.02) day$^{-1}$ were estimated for CL/F, $V_2$/F, $V_3$/F, Q/F and ka$_{SD}$, respectively. Estimates of CL/F and $V_z$/F were consistent between the NCA and population analyses.

Individual-specific covariate factors that were predictive of the unexplained random variability in the population included allometrically-scaled weight effects on CL/F, $V_2$/F, $V_3$/F and Q/F, and effects of antibody status and TSAC on CL/F. An effect of single versus multiple dose administration was also included on $k_a$.

Figure 21:
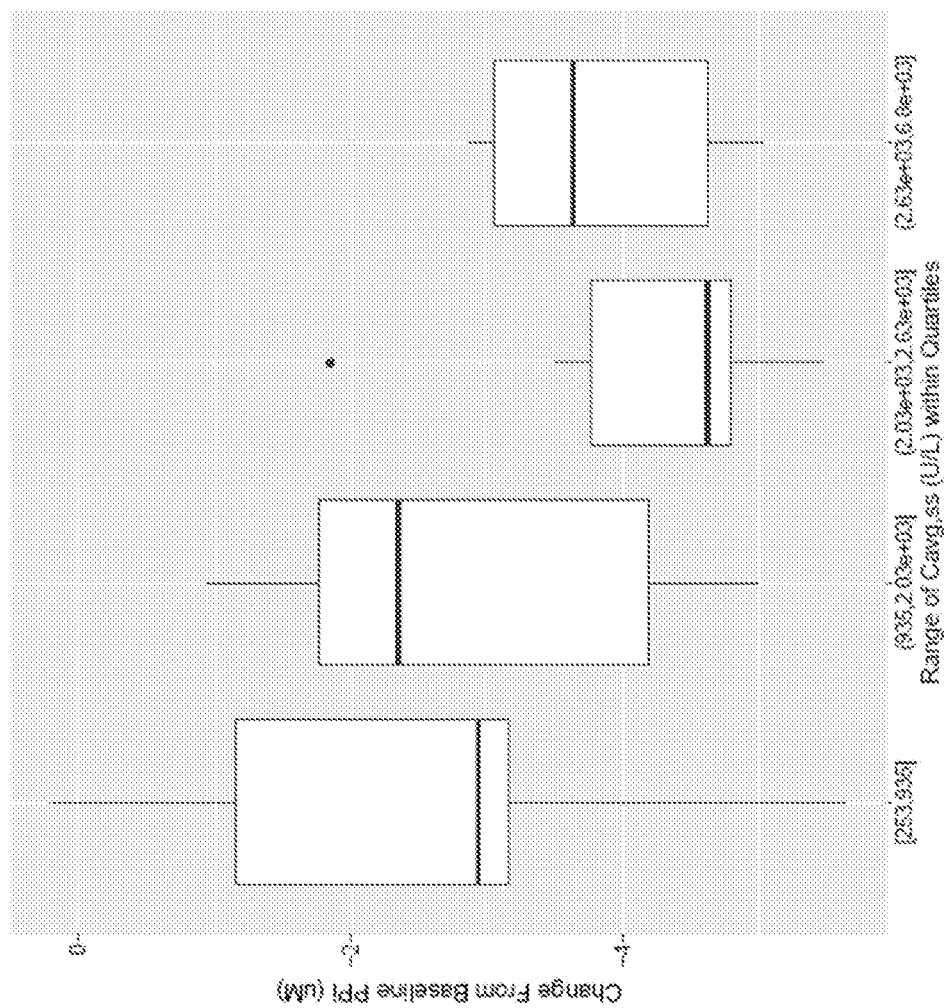
FIG. 21 is a graph showing Day 61 change from baseline (CBL) PPi by asfotase alfa $C_{avg,ss}$ exposure quartiles. Median values of CBL PPi values are designated by a line in the center of the box. Boxes indicate the inter-quartile range (IQR). Whiskers represent 1.5*IQR. Outliers are marked outside of the whiskers by solid circles.

The population PKPD relationship between asfotase alfa exposure and PPi response was tabulated by quantiles of predicted $C_{avg,ss}$ and examined graphically. Plasma PPi response tended to be greater with increasing dose and asfotase alfa exposure, though extensive overlap in response was noted across exposure quartiles (FIG. 21 and Table 20).

TABLE 20

PK-PPi Response: $C_{avg,\ ss}$ Exposure (U/L) vs. Change from Baseline PPi (μM) Response on Study Day 61

| Cavgbin (U/L) | N | Mean | Median | Min | Max |
|---|---|---|---|---|---|
| [253, 935] | 7 | −2.44 | −2.94 | −5.64 | 0.192 |
| (9.35, 2.03e+03] | 7 | −2.89 | −2.35 | −4.99 | −0.938 |
| (2.03e+03, 2.63e+03] | 6 | −4.14 | −4.62 | −5.46 | −1.85 |
| (2.63e+03, 6.8e+03] | 7 | −3.83 | −3.64 | −5.03 | −2.87 |

N = number of patients,
Cavgbin = the Cavg, ss interquartile range within which all change from baseline PPi data were summarized,
Cavg, ss = average steady-state asfotase alfa concentration calculated using individual empirical bayes estimates of CL = F and assuming the last doses (Units of activity) administered to each patient were administered 3 times over a 7-day dosing interval.

The frequency of the PPi response appeared to plateau to 66.7% at concentrations above the median asfotase alfa $C_{avg,ss}$ of 2030 U/L (Table 21).

TABLE 21

PPi < LLN By $C_{avg,\ ss}$ Quartile: Frequency of PPi < Lower Limit of Normal (1.33 μM) on study Day 61 By Exposure Quartile

| Cavgbin (U/L) | N | Frequency (%) |
|---|---|---|
| [253, 935] | 7 | 0.0 |
| (9.35, 2.03e+03] | 7 | 14.3 |
| (2.03e+03, 2.63e+03] | 6 | 66.7 |
| (2.63e+03, 6.8e+03] | 7 | 66.7 |

N = number of patients,
Cavgbin = the Cavg, ss interquartile range within which all change from baseline PPi data were summarized,
Cavg, ss = average steady-state asfotase alfa concentration calculated using individual empirical bayes estimates of CL = F and assuming the last doses (Units of activity) administered to each patient were administered 3 times over a 7-day dosing interval.
Frequency calculated using pre-dose PPi concentration on Study Day 61.

The median predicted $C_{avg,ss}$ value for the 2 mg/kg×3 days/week treatment in AA-HPP-208 adult patients (1810 U/L) approaches this threshold concentration, while the frequency of patients who achieved a PPi response (20%) is consistent with prior predictions for the adult population (17.6%) at this dose. Collectively, these results support a 2 mg/kg×3 days/week dosing regimen in adult HPP patients with pediatric phenotype.

These data from adult patients with pediatric-onset HPP confirm the efficacy of a 2 mg/kg×3 days/week dosing regimen in adolescent patients with HPP. The newly available dose-ranging and PK/PD data from Study AA-HPP-208 show effective dosing in adult HPP patients ≥18 years, a previously untested patient population, and confirm that adult patients with pediatric-onset HPP benefit from asfotase alfa treatment.

In addition, there are significant differences in the ability to confirm therapeutic effectiveness of asfotase alfa in pediatric patients versus adult patients with pediatric-onset HPP. For example, in pediatric patients, asfotase alfa efficacy can be determined using the Radiographic Impression of Change (RGI-C) scale to assess skeletal changes in pediatric patients. The RGI-C scale is limited in HPP, because it can only assess those with open growth plates (i.e., pediatric patients). Consequently, the RGI-C scale cannot be used to assess efficacy in adult patients with pediatric-onset HPP. Nonetheless, the PK/PD/efficacy results from Study AA-HPP-208 confirm the therapeutic effectiveness of asfotase alfa in these adult patients.

Finally, prior to Study AA-HPP-208, no data addressed whether asfotase alfa treatment would be well-tolerated by adult patients with pediatric-onset HPP. These data confirm that, although the side effects of asfotase alfa therapy are different in pediatric patients versus adolescent and adult patient populations, asfotase alfa therapy is well-tolerated by both groups with minimal side effects.

Other Embodiments

All publications, patents, and patent applications mentioned in the above specification are hereby incorporated by reference to the same extent as if each individual publication, patent or patent application was specifically and individually indicated to be incorporated by reference in its entirety. Various modifications and variations of the described methods, pharmaceutical compositions, and kits of the invention will be apparent to those skilled in the art without departing from the scope and spirit of the claimed invention. Although the disclosure has been described in connection with specific embodiments, it will be understood that it is capable of further modifications and that the invention as claimed should not be unduly limited to such specific embodiments.

The invention claimed is:

1. A method of treating hypophosphatasia (HPP) in a naïve, pediatric-onset HPP subject of 18 years of age or older that is characterized as having at least one symptom of adult HPP, wherein the method comprises administering a soluble alkaline phosphatase (sALP) to the subject in a treatment regimen providing about 1 mg/kg/week to about 9 mg/kg/week of the sALP for a treatment period of at least five years, wherein the sALP comprises an amino acid sequence having at least 95% sequence identity to the amino acid sequence of SEQ ID NO: 1, and wherein the method further comprises one or more of the following:

(i) determining an inorganic pyrophosphate (PPi) concentration in blood from the subject, wherein administration of the sALP for at least five years results in a sustained statistically significant decrease in the PPi concentration in the blood of the subject of at least about 1 μM;

(ii) determining a pyridoxal 5'-phosphate (PLP) concentration in the blood from the subject, wherein the administration of the sALP for at least five years results in a aid statistically significant decrease in the PLP concentration in the blood of the subject of at least about 100 ng/ml; and (iii) determining a Six Minute Walk Test (6MWT) score of the subject, wherein the administration of the sALP for at least five years results in a sustained statistically significant increase of at least 50 meters in walking distance of the subject, as assessed by the 6MWT.

2. The method of claim 1, wherein the method treats at least one symptom of adult HPP selected from elevated blood and/or urine levels of phosphoethanolamine (PEA), hypomineralization, hypercalciuria, skeletal deformity, waddling gait, bone pain, bone fracture, calcium pyrophosphate dihydrate crystal deposition, arthritis, pyrophosphate arthropathy, chondrocalcinosis, calcific periarthritis, and pseudofracture.

3. The method of claim 1, wherein at least one of:
(a) the subject does not exhibit ectopic calcification after administration of the sALP; and
(b) the subject exhibits tolerability to administration of the sALP, wherein the tolerability comprises a lack of or decreased incidence of at least one adverse event selected from the group consisting of injection site erythema, decrease in hemoglobin, pyrexia, pneumonia, upper respiratory tract infection, otitis media, vomiting, constipation, diarrhea, tooth loss, nasopharyngitis, rash, dental carries, and irritability.

4. The method of claim 1, wherein the sALP comprises or consists of the amino acid sequence of SEQ ID NO: 1.

5. The method of claim 1, wherein the sALP is administered in a composition comprising at least one pharmaceutically acceptable carrier, diluent, or excipient.

6. The method of claim 5, wherein the at least one pharmaceutically acceptable carrier, diluent, or excipient is saline or comprises sodium chloride and sodium phosphate.

7. The method of claim 6, wherein the at least one pharmaceutically acceptable carrier, diluent, or excipient comprises about 150 mM sodium chloride and about 25 mM sodium phosphate.

8. The method of claim 5, wherein the composition is administered subcutaneously, intramuscularly, intravenously, orally, nasally, sublingually, intrathecally, or intradermally.

9. The method of claim 8, wherein the composition is administered subcutaneously.

10. The method of claim 1, wherein the sALP is administered at least one of:
(a) one or more times per day, per week, or per month;
(b) in multiple doses on two days a week, three days a week, four days a week, five days a week, six days a week, or seven days a week;
(c) at an initial dosage of about 2.1 mg/kg/week to about 3.5 mg/kg/week and subsequently is increased to a dosage of about 6 mg/kg/week;
(d) at a dosage of about 1.3 mg/kg/week, about 2.7 mg/kg/week, or about 6 mg/kg/week; and
(e) at a dosage of about 2 mg/kg three times a week, about 3 mg/kg two times a week, about 3 mg/kg three times a week, or about 1 mg/kg six times a week.

11. The method of claim 1, wherein at least one of:
(a) the sALP is administered at least twice a week;
(b) the sALP is administered at an initial dosage of about 0.3 mg/kg/day to about 0.5 mg/kg/day of the sALP; and
(c) wherein the sALP is administered once daily on consecutive or alternating days.

12. The method of claim 1, wherein the method comprises administering the sALP to the subject in a treatment regimen providing about 6 mg/kg/week.

13. The method of claim 1, wherein the sALP is at least one of:
(a) physiologically active toward PEA, PPi, and PLP;
(b) catalytically competent to improve skeletal mineralization in bone; and
(c) the soluble extracellular domain of an alkaline phosphatase.

14. The method of claim 1, wherein the subject is a human.

15. The method of claim 1, wherein the treatment period is at least six years, at least seven years, at least eight years, at least nine years, or at least ten years, or the lifetime of the subject.

16. The method of claim 1, wherein at least one of:
(a) the decrease in the PPi concentration in the blood of the subject is at least about 2 µM;
(b) prior to administration of the sALP, the PPi concentration in the blood of the subject is about 6 µM;
(c) the decrease in the PPi concentration in the blood of the subject is about 2 µM to about 5 µM after administration of the sALP;
(d) the decrease in the PLP concentration in the blood of the subject is at least about 200 ng/ml;
(e) prior to administration of the sALP, the PLP concentration in the blood of the subject is up to 1300 ng/ml; and
(f) the decrease in the PLP concentration in the blood of the subject is about 2 ng/ml to about 150 ng/ml after administration of the sALP.

17. The method of claim 1, wherein at least one of:
(a) the administration of the sALP results in an increase in the walking distance in six minutes of at least 100 meters or more;
(b) prior to the administration of the sALP, the waking distance of the subject in six minutes is about 350 meters or less;
(c) the walking distance of the subject in six minutes is about 420 meters or more after the administration of the sALP;
(d) the subject exhibits a decreased reliance on an assistive mobility device after the administration of the sALP; and
(e) the subject experiences a decreased incidence of fractures after ±Q administration of the sALP.

18. The method of claim 17, wherein the assistive mobility device is at least one device selected from the group consisting of a walker, a wheelchair, braces, crutches, and orthotics.

19. A method of treating hypophosphatasia (HPP) in a subject of about 13 years of age or older, wherein said method comprises administering a soluble alkaline phosphatase (sALP) to the subject in a treatment regimen providing about 1 mg/kg/week to about 9 mg/kg/week of the sALP for a treatment period of at least five years, wherein the sALP comprises an amino acid sequence having at least 95% sequence identity to the amino acid sequence of SEQ ID NO: 1, and wherein the method further comprises one or more of the following:
(i) determining a Handheld Dynamometry (HHD) score of the subject, wherein administration of the sALP for at least five years results in a sustained change in a percentage (%) predicted HHD score of the subject of about 5% or more relative to the % predicted HHD score of the subject without the administration of the sALP;
(ii) determining a Lower Extremity Functional Scale (LEFS) score of the subject, wherein the administration of the sALP for at least five years results in a c change in the LEFS score of the subject of about 3 or more relative to the LEFS score of the subject without the administration of the sALP;

(iii) determining a Brief Pain Inventory-Short Form (BPI-SF) score of the subject, wherein the administration of the sALP for at least five years results in sustained change in the BPI-SF score score of the subject of about −2 or more relative to the BPI-SF score of the subject without the administration of the sALP;

(iv) determining a PPI concentration in blood from the subject, wherein the administration of the sALP for at least five years results in a sustained decrease in the PPi concentrations in the blood of the subject of about 25% or greater relative to the PPi concentrations in blood from the subject without the administration of the sALP;

(v) determining a PLP concentration in the blood from the subject, wherein the administration of the sALP for at least five years results in a sustained decrease in the PLP concentrations in the blood of the subject of about 50% or greater relative to the PLP concentrations in blood of the subject without the administration of the sALP; and (vi) determining a 6MWT value of the subject, wherein the administration of the sALP for at least five years results in a sustained increase in the 6MWT value of the subject to about 80% or greater than about 80% of a predicted 6MWT value of the subject relative to the 6MWT value of the subject without the administration of the sALP.

20. The method of claim 19, wherein the method comprises administering the sALP to the subject in a treatment regimen providing about 6 mg/kg/week.

* * * * *

UNITED STATES PATENT AND TRADEMARK OFFICE
CERTIFICATE OF CORRECTION

| | |
|---|---|
| PATENT NO. | : 11,224,637 B2 |
| APPLICATION NO. | : 16/498143 |
| DATED | : January 18, 2022 |
| INVENTOR(S) | : Moseley et al. |

It is certified that error appears in the above-identified patent and that said Letters Patent is hereby corrected as shown below:

In the Claims

Column 129, Line 65, replace "pvrophosphate" with --pyrophosphate--.

Column 130, Line 59, replace "aid" with --sustained--.

Column 133, Line 4, replace "score score" with --score--.

Signed and Sealed this
Twelfth Day of July, 2022

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 726
<212> TYPE: PRT
<213> ORGANISM: Artificial Sequence
<220> FEATURE:
<223> OTHER INFORMATION: Synthetic Construct

<400> SEQUENCE: 1

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
130                 135                 140

Gly Ile Val Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
210                 215                 220

Ala Arg Gly Thr Arg Leu Asp Gly Leu Asp Leu Val Asp Thr Trp Lys
225                 230                 235                 240

Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe

```
                355                 360                 365
Gly Gly Tyr Thr Pro Arg Gly Asn Ser Ile Phe Gly Leu Ala Pro Met
370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
            500                 505                 510

Lys Pro Lys Asp Thr Leu Met Ile Ser Arg Thr Pro Glu Val Thr Cys
        515                 520                 525

Val Val Val Asp Val Ser His Glu Asp Pro Glu Val Lys Phe Asn Trp
    530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Ala Pro Ile Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
    690                 695                 700

Gln Lys Ser Leu Ser Leu Ser Pro Gly Lys Asp Ile Asp Asp Asp Asp
705                 710                 715                 720

Asp Asp Asp Asp Asp
                725

<210> SEQ ID NO 2
<211> LENGTH: 524
<212> TYPE: PRT
<213> ORGANISM: Homo sapiens

<400> SEQUENCE: 2
```

```
Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
            35                  40                  45

Asn Val Ala Lys Asn Val Ile Met Phe Leu Gly Asp Gly Met Gly Val
50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
            195                 200                 205

Met His Asn Ile Arg Asp Ile Asp Val Ile Met Gly Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
            290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
            370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
```

```
            420                 425                 430
Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
        500                 505                 510

Leu Ala Leu Ala Leu Tyr Pro Leu Ser Val Leu Phe
            515                 520

<210> SEQ ID NO 3
<211> LENGTH: 524
<212> TYPE: PRT
<213> ORGANISM: Homo sapiens

<400> SEQUENCE: 3

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg His Lys His Ser His Phe Ile Trp Asn Arg
            260                 265                 270
```

```
Thr Glu Leu Leu Thr Leu Asp Pro His Asn Val Asp Tyr Leu Leu Gly
            275                 280                 285

Leu Phe Glu Pro Gly Asp Met Gln Tyr Glu Leu Asn Arg Asn Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Lys Gln Ala Leu His Glu Ala
            340                 345                 350

Val Glu Met Asp Arg Ala Ile Gly Gln Ala Gly Ser Leu Thr Ser Ser
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
            515                 520

<210> SEQ ID NO 4
<211> LENGTH: 524
<212> TYPE: PRT
<213> ORGANISM: Homo sapiens

<400> SEQUENCE: 4

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125
```

-continued

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ser Lys
450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
            500                 505                 510

Leu Ala Leu Ala Leu Tyr Pro Leu Ser Val Leu Phe
        515                 520

<210> SEQ ID NO 5
<211> LENGTH: 524

<212> TYPE: PRT
<213> ORGANISM: Homo sapiens

<400> SEQUENCE: 5

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
    290                 295                 300

Thr Asp Pro Ser Leu Ser Glu Met Val Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Arg Ala Ile Gly Gln Ala Gly Ser Leu Thr Ser Ser
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Pro Phe Thr Ala Ile Leu Tyr Gly
            405                 410                 415

Asn Gly Pro Gly Tyr Lys Val Val Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                    485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 6
<211> LENGTH: 524
<212> TYPE: PRT
<213> ORGANISM: Homo sapiens

<400> SEQUENCE: 6

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp

```
                    245                 250                 255
Lys Ser Phe Lys Pro Arg His Lys His Ser His Phe Ile Trp Asn Arg
            260                 265                 270

Thr Glu Leu Leu Thr Leu Asp Pro His Asn Val Asp Tyr Leu Leu Gly
                275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Arg Ile
            325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
                435                 440                 445

Leu Arg His Glu Thr His Gly Gly Glu Asp Val Ala Val Phe Ser Lys
            450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Ala Gly Ser Leu Ala Ala Gly Pro Leu Leu
                500                 505                 510

Leu Ala Leu Ala Leu Tyr Pro Leu Ser Val Leu Phe
            515                 520

<210> SEQ ID NO 7
<211> LENGTH: 652
<212> TYPE: PRT
<213> ORGANISM: Macaca mulatta

<400> SEQUENCE: 7

Met Pro Thr Val Lys Thr Lys Gln Glu Ser His Ala Gly Ser Gly Ser
1               5                   10                  15

Gly Pro Arg Leu Ala Glu Arg Lys Gly Arg Val Gly Ala Ala Arg Arg
            20                  25                  30

Gln Ser Pro Arg Ala Pro Gly Gly Leu Pro Gly Pro Arg Ser Gly
        35                  40                  45

Pro Ala Ala Ala Phe Ile Arg Arg Arg Gly Arg Trp Pro Gly Pro Arg
    50                  55                  60

Cys Ala Pro Ala Thr Pro Arg Pro Arg Ser Arg Leu Cys Ala Pro Thr
65                  70                  75                  80

Arg Leu Cys Leu Asp Glu Pro Ser Ser Val Leu Cys Ala Gly Leu Glu
                85                  90                  95
```

```
His Gln Leu Thr Ser Asp His Cys Gln Pro Thr Pro Ser His Pro Arg
                100                 105                 110

Arg Ser His Leu Trp Ala Ser Gly Ile Lys Gln Val Leu Gly Cys Thr
            115                 120                 125

Met Ile Ser Pro Phe Leu Val Leu Ala Ile Gly Thr Cys Leu Thr Asn
        130                 135                 140

Ser Leu Val Pro Glu Lys Glu Lys Asp Pro Lys Tyr Trp Arg Asp Gln
145                 150                 155                 160

Ala Gln Glu Thr Leu Lys Tyr Ala Leu Glu Leu Gln Lys Leu Asn Thr
                165                 170                 175

Asn Val Ala Lys Asn Val Ile Met Phe Leu Gly Asp Gly Met Gly Val
            180                 185                 190

Ser Thr Val Thr Ala Thr Arg Ile Leu Lys Gly Gln Leu His His Asn
        195                 200                 205

Pro Gly Glu Glu Thr Arg Leu Glu Met Asp Lys Phe Pro Phe Val Ala
        210                 215                 220

Leu Ser Lys Thr Tyr Asn Thr Asn Ala Gln Val Pro Asp Ser Ala Gly
225                 230                 235                 240

Thr Ala Thr Ala Tyr Leu Cys Gly Val Lys Ala Asn Glu Gly Thr Val
                245                 250                 255

Gly Val Ser Ala Ala Thr Glu Arg Ser Arg Cys Asn Thr Thr Gln Gly
            260                 265                 270

Asn Glu Val Thr Ser Ile Leu Arg Trp Ala Lys Asp Ala Gly Lys Ser
        275                 280                 285

Val Gly Ile Val Thr Thr Thr Arg Val Asn His Ala Thr Pro Ser Ala
        290                 295                 300

Ala Tyr Ala His Ser Ala Asp Arg Asp Trp Tyr Ser Asp Asn Glu Met
305                 310                 315                 320

Pro Pro Glu Ala Leu Ser Gln Gly Cys Lys Asp Ile Ala Tyr Gln Leu
                325                 330                 335

Val His Asn Ile Arg Asp Ile Asp Val Ile Met Gly Gly Gly Arg Lys
            340                 345                 350

Tyr Met Tyr Pro Lys Asn Lys Thr Asp Val Glu Tyr Glu Ile Asp Glu
        355                 360                 365

Lys Ala Arg Gly Thr Arg Leu Asp Gly Leu Asp Leu Val Asn Ile Trp
370                 375                 380

Lys Ser Phe Lys Pro Arg His Lys His Ser His Phe Ile Trp Asn Arg
385                 390                 395                 400

Thr Glu Leu Leu Thr Leu Asp Pro His Asn Val Asp Tyr Leu Leu Gly
                405                 410                 415

Leu Phe Glu Pro Gly Asp Met Glu Tyr Glu Leu Asn Arg Asn Asn Val
            420                 425                 430

Thr Asp Pro Ser Leu Ser Glu Met Val Val Ala Ile Gln Ile Leu
        435                 440                 445

Arg Lys Asn Pro Lys Gly Phe Phe Leu Leu Val Glu Gly Gly Arg Ile
450                 455                 460

Asp His Gly His His Glu Gly Lys Ala Lys Gln Ala Leu His Glu Ala
465                 470                 475                 480

Val Glu Met Asp Arg Ala Ile Gly Gln Ala Gly Ser Met Thr Ser Leu
                485                 490                 495

Glu Asp Thr Leu Thr Val Val Thr Ala Asp His Ser His Val Phe Thr
            500                 505                 510

Phe Gly Gly Tyr Thr Pro Arg Gly Asn Ser Ile Phe Gly Leu Ala Pro
```

-continued

```
                515                 520                 525
Met Leu Ser Asp Thr Asp Lys Lys Pro Phe Thr Ala Ile Leu Tyr Gly
        530                 535                 540

Asn Gly Pro Gly Tyr Lys Val Val Gly Gly Glu Arg Glu Asn Val Ser
545                 550                 555                 560

Met Val Asp Tyr Ala His Asn Asn Tyr Gln Ala Gln Ser Ala Val Pro
                565                 570                 575

Leu Arg His Glu Thr His Gly Gly Glu Asp Val Ala Val Phe Ser Lys
        580                 585                 590

Gly Pro Met Ala His Leu Leu His Gly Val His Glu Gln Asn Tyr Ile
                595                 600                 605

Pro His Val Met Ala Tyr Ala Ala Cys Ile Gly Ala Asn Leu Asp His
        610                 615                 620

Cys Ala Pro Ala Ser Ser Ala Gly Ser Leu Ala Ala Gly Pro Leu Leu
625                 630                 635                 640

Leu Pro Leu Ala Leu Phe Pro Leu Ser Ile Leu Phe
                645                 650

<210> SEQ ID NO 8
<211> LENGTH: 524
<212> TYPE: PRT
<213> ORGANISM: Rattus norvegicus

<400> SEQUENCE: 8

Met Ile Leu Pro Phe Leu Val Leu Ala Ile Gly Pro Cys Leu Thr Asn
1               5                   10                  15

Ser Phe Val Pro Glu Lys Glu Lys Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Ile Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Thr Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Thr Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Arg Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240
```

```
Lys Ala Arg Gly Thr Arg Leu Asp Gly Leu Asp Leu Ile Ser Ile Trp
            245                 250                 255
Lys Ser Phe Lys Pro Arg His Lys His Ser His Tyr Val Trp Asn Arg
        260                 265                 270
Thr Glu Leu Leu Ala Leu Asp Pro Ser Arg Val Asp Tyr Leu Leu Gly
    275                 280                 285
Leu Phe Glu Pro Gly Asp Met Gln Tyr Glu Leu Asn Arg Asn Asn Leu
290                 295                 300
Thr Asp Pro Ser Leu Ser Glu Met Val Glu Val Ala Leu Arg Ile Leu
305                 310                 315                 320
Thr Lys Asn Pro Lys Gly Phe Phe Leu Leu Val Glu Gly Gly Arg Ile
            325                 330                 335
Asp His Gly His His Glu Gly Lys Ala Lys Gln Ala Leu His Glu Ala
            340                 345                 350
Val Glu Met Asp Glu Ala Ile Gly Lys Ala Gly Thr Met Thr Ser Gln
            355                 360                 365
Lys Asp Thr Leu Thr Val Val Thr Ala Asp His Ser His Val Phe Thr
        370                 375                 380
Phe Gly Gly Tyr Thr Pro Arg Gly Asn Ser Ile Phe Gly Leu Ala Pro
385                 390                 395                 400
Met Val Ser Asp Thr Asp Lys Lys Pro Phe Thr Ala Ile Leu Tyr Gly
                405                 410                 415
Asn Gly Pro Gly Tyr Lys Val Val Asp Gly Glu Arg Glu Asn Val Ser
            420                 425                 430
Met Val Asp Tyr Ala His Asn Asn Tyr Gln Ala Gln Ser Ala Val Pro
            435                 440                 445
Leu Arg His Glu Thr His Gly Gly Glu Asp Val Ala Val Phe Ala Lys
        450                 455                 460
Gly Pro Met Ala His Leu Leu His Gly Val His Glu Gln Asn Tyr Ile
465                 470                 475                 480
Pro His Val Met Ala Tyr Ala Ser Cys Ile Gly Ala Asn Leu Asp His
                485                 490                 495
Cys Ala Trp Ala Ser Ser Ala Ser Ser Pro Ser Pro Gly Ala Leu Leu
            500                 505                 510
Leu Pro Leu Ala Leu Phe Pro Leu Arg Thr Leu Phe
        515                 520

<210> SEQ ID NO 9
<211> LENGTH: 502
<212> TYPE: PRT
<213> ORGANISM: Canis lupus familiaris

<400> SEQUENCE: 9

Glu Lys Asp Pro Lys Tyr Trp Arg Asp Gln Ala Gln Gln Thr Leu Lys
1               5                   10                  15
Tyr Ala Leu Arg Leu Gln Asn Leu Asn Thr Asn Val Ala Lys Asn Val
            20                  25                  30
Ile Met Phe Leu Gly Asp Gly Met Gly Val Ser Thr Val Thr Ala Thr
        35                  40                  45
Arg Ile Leu Lys Gly Gln Leu His His Asn Pro Gly Glu Glu Thr Arg
    50                  55                  60
Leu Glu Met Asp Lys Phe Pro Tyr Val Ala Leu Ser Lys Thr Tyr Asn
65                  70                  75                  80
Thr Asn Ala Gln Val Pro Asp Ser Ala Gly Thr Ala Thr Ala Tyr Leu
                85                  90                  95
```

-continued

```
Cys Gly Val Lys Ala Asn Glu Gly Thr Val Gly Val Ser Ala Ala Thr
            100                 105                 110

Gln Arg Thr His Cys Asn Thr Thr Gln Gly Asn Glu Val Thr Ser Ile
            115                 120                 125

Leu Arg Trp Ala Lys Asp Ala Gly Lys Ser Val Gly Ile Val Thr Thr
            130                 135                 140

Thr Arg Val Asn His Ala Thr Pro Ser Ala Ala Tyr Ala His Ser Ala
145                 150                 155                 160

Asp Arg Asp Trp Tyr Ser Asp Asn Glu Met Pro Pro Glu Ala Leu Ser
                    165                 170                 175

Gln Gly Cys Lys Asp Ile Ala Tyr Gln Leu Met His Asn Val Lys Asp
                180                 185                 190

Ile Glu Val Ile Met Gly Gly Arg Lys Tyr Met Phe Pro Lys Asn
            195                 200                 205

Arg Thr Asp Val Glu Tyr Glu Met Asp Glu Lys Ser Thr Gly Ala Arg
            210                 215                 220

Leu Asp Gly Leu Asn Leu Ile Asp Ile Trp Lys Asn Phe Lys Pro Arg
225                 230                 235                 240

His Lys His Ser His Tyr Val Trp Asn Arg Thr Glu Leu Leu Ala Leu
                    245                 250                 255

Asp Pro Tyr Thr Val Asp Tyr Leu Leu Gly Leu Phe Asp Pro Gly Asp
                260                 265                 270

Met Gln Tyr Glu Leu Asn Arg Asn Asn Val Thr Asp Pro Ser Leu Ser
            275                 280                 285

Glu Met Val Glu Ile Ala Ile Lys Ile Leu Ser Lys Lys Pro Arg Gly
            290                 295                 300

Phe Phe Leu Leu Val Glu Gly Gly Arg Ile Asp His Gly His His Glu
305                 310                 315                 320

Gly Lys Ala Lys Gln Ala Leu His Glu Ala Val Glu Met Asp Arg Ala
                    325                 330                 335

Ile Gly Lys Ala Gly Val Met Thr Ser Leu Glu Asp Thr Leu Thr Val
                340                 345                 350

Val Thr Ala Asp His Ser His Val Phe Thr Phe Gly Gly Tyr Thr Pro
            355                 360                 365

Arg Gly Asn Ser Ile Phe Gly Leu Ala Pro Met Val Ser Asp Thr Asp
            370                 375                 380

Lys Lys Pro Phe Thr Ala Ile Leu Tyr Gly Asn Gly Pro Gly Tyr Lys
385                 390                 395                 400

Val Val Gly Gly Glu Arg Glu Asn Val Ser Met Val Asp Tyr Ala His
                    405                 410                 415

Asn Asn Tyr Gln Ala Gln Ser Ala Val Pro Leu Arg His Glu Thr His
                420                 425                 430

Gly Gly Glu Asp Val Ala Val Phe Ala Lys Gly Pro Met Ala His Leu
            435                 440                 445

Leu His Gly Val His Glu Gln Asn Tyr Ile Pro His Val Met Ala Tyr
            450                 455                 460

Ala Ala Cys Ile Gly Ala Asn Gln Asp His Cys Ala Ser Ala Ser Ser
465                 470                 475                 480

Ala Gly Gly Pro Ser Pro Gly Pro Leu Leu Leu Leu Ala Leu Leu
                    485                 490                 495

Pro Val Gly Ile Leu Phe
            500
```

<210> SEQ ID NO 10
<211> LENGTH: 252
<212> TYPE: PRT
<213> ORGANISM: Sus scrofa

<400> SEQUENCE: 10

| Ala | Glu | Leu | Leu | Ala | Leu | Asp | Pro | His | Thr | Val | Asp | Tyr | Leu | Leu | Gly |
|---|---|---|---|---|---|---|---|---|---|---|---|---|---|---|---|
| 1 | | | | 5 | | | | | 10 | | | | | 15 | |

Leu Phe Glu Pro Gly Asp Met Gln Tyr Glu Leu Asn Arg Asn Asn Val
            20                  25                  30

Thr Asp Pro Ser Leu Ser Glu Met Val Glu Met Ala Ile Arg Ile Leu
        35                  40                  45

Ile Lys Asn Pro Lys Gly Phe Phe Leu Leu Val Glu Gly Gly Arg Ile
    50                  55                  60

Asp His Gly His His Glu Gly Lys Ala Lys Gln Ala Leu His Glu Ala
65                  70                  75                  80

Val Glu Met Asp Arg Ala Ile Glu Gln Ala Gly Ser Met Thr Ser Val
                85                  90                  95

Glu Asp Thr Leu Thr Val Val Thr Ala Asp His Ser His Val Phe Thr
            100                 105                 110

Phe Gly Gly Tyr Thr Pro Arg Gly Asn Ser Ile Phe Gly Leu Ala Pro
        115                 120                 125

Met Val Ser Asp Thr Asp Lys Lys Pro Phe Thr Ala Ile Leu Tyr Gly
    130                 135                 140

Asn Gly Pro Gly Tyr Lys Val Val Gly Gly Glu Arg Glu Asn Val Ser
145                 150                 155                 160

Met Val Asp Tyr Ala His Asp Asn Tyr Gln Ala Gln Ser Ala Val Pro
                165                 170                 175

Leu Arg His Glu Thr His Gly Gly Glu Asp Val Ala Ile Phe Ala Arg
            180                 185                 190

Gly Pro Met Ala His Leu Leu His Gly Val His Glu Gln Asn Tyr Ile
        195                 200                 205

Pro His Val Met Ala Tyr Ala Ala Cys Val Gly Ala Asn Arg Asp His
    210                 215                 220

Cys Ala Ser Ala Ser Ser Gly Ser Pro Ser Gly Pro Leu Leu
225                 230                 235                 240

Leu Leu Leu Ala Leu Leu Pro Leu Gly Ile Leu Phe
            245                 250

<210> SEQ ID NO 11
<211> LENGTH: 524
<212> TYPE: PRT
<213> ORGANISM: Mus musculus

<400> SEQUENCE: 11

Met Ile Ser Pro Phe Leu Val Leu Ala Ile Gly Thr Cys Leu Thr Asn
1               5                   10                  15

Ser Phe Val Pro Glu Lys Glu Arg Asp Pro Ser Tyr Trp Arg Gln Gln
            20                  25                  30

Ala Gln Glu Thr Leu Lys Asn Ala Leu Lys Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

```
Thr Gly Glu Glu Thr Arg Leu Glu Met Asp Lys Phe Pro Phe Val Ala
            85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
            115                 120                 125

Gly Val Ser Ala Ala Thr Glu Arg Thr Arg Cys Asn Thr Thr Gln Gly
130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Asp Val Ile Met Gly Gly Gly Arg Lys
    210                 215                 220

Tyr Met Tyr Pro Lys Asn Arg Thr Asp Val Glu Tyr Glu Leu Asp Glu
225                 230                 235                 240

Lys Ala Arg Gly Thr Arg Leu Asp Gly Leu Asp Leu Ile Ser Ile Trp
                245                 250                 255

Lys Ser Phe Lys Pro Arg His Lys His Ser His Tyr Val Trp Asn Arg
            260                 265                 270

Thr Glu Leu Leu Ala Leu Asp Pro Ser Arg Val Asp Tyr Leu Leu Gly
        275                 280                 285

Leu Phe Glu Pro Gly Asp Met Gln Tyr Glu Leu Asn Arg Asn Asn Leu
    290                 295                 300

Thr Asp Pro Ser Leu Ser Glu Met Val Glu Val Ala Leu Arg Ile Leu
305                 310                 315                 320

Thr Lys Asn Leu Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Lys Ala Gly Ala Met Thr Ser Gln
        355                 360                 365

Lys Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Asp Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ser Cys Ile Gly Ala Asn Leu Asp His
                485                 490                 495

Cys Ala Trp Ala Gly Ser Gly Ser Ala Pro Ser Pro Gly Ala Leu Leu
```

```
                500                 505                 510
Leu Pro Leu Ala Val Leu Ser Leu Arg Thr Leu Phe
            515                 520

<210> SEQ ID NO 12
<211> LENGTH: 524
<212> TYPE: PRT
<213> ORGANISM: Bos taurus

<400> SEQUENCE: 12

Met Ile Ser Pro Phe Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
                20                  25                  30

Ala Gln Gln Thr Leu Lys Asn Ala Leu Arg Leu Gln Thr Leu Asn Thr
            35                  40                      45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
                100                 105                 110

Thr Ala Thr Ala Tyr Leu Cys Gly Val Lys Ala Asn Glu Gly Thr Val
            115                 120                 125

Gly Val Ser Ala Ala Thr Gln Arg Ser Gln Cys Asn Thr Thr Gln Gly
            130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
                180                 185                 190

Pro Pro Glu Ala Leu Ser Gln Gly Cys Lys Asp Ile Ala Tyr Gln Leu
            195                 200                 205

Met His Asn Ile Lys Asp Ile Glu Val Ile Met Gly Gly Gly Arg Lys
        210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
            260                 265                 270

Thr Asp Leu Leu Ala Leu Asp Pro His Ser Val Asp Tyr Leu Leu Gly
        275                 280                 285

Leu Phe Glu Pro Gly Asp Met Gln Tyr Glu Leu Asn Arg Asn Asn Ala
            290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350
```

Val Glu Met Asp Gln Ala Ile Gly Gln Ala Gly Ala Met Thr Ser Val
            355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
            500                 505                 510

Leu Leu Leu Ala Leu Leu Pro Leu Gly Ser Leu Phe
        515                 520

<210> SEQ ID NO 13
<211> LENGTH: 524
<212> TYPE: PRT
<213> ORGANISM: Bos taurus

<400> SEQUENCE: 13

Met Ile Ser Pro Phe Leu Leu Leu Ala Ile Gly Thr Cys Phe Ala Ser
1               5                   10                  15

Ser Leu Val Pro Glu Lys Glu Lys Asp Pro Lys Tyr Trp Arg Asp Gln
            20                  25                  30

Ala Gln Gln Thr Leu Lys Asn Ala Leu Arg Leu Gln Thr Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Ser
65                  70                  75                  80

Pro Gly Glu Glu Thr Lys Leu Glu Met Asp Lys Phe Pro Tyr Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met His Asn Ile Lys Asp Ile Glu Val Ile Gly Gly Gly Arg Lys
210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
                260                 265                 270

Thr Asp Leu Leu Ala Leu Asp Pro His Ser Val Asp Tyr Leu Leu Gly
                275                 280                 285

Leu Phe Glu Pro Gly Asp Met Gln Tyr Glu Leu Asn Arg Asn Asn Ala
    290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Gln Ala Ile Gly Gln Ala Gly Ala Met Thr Ser Val
    355                 360                 365

Glu Asp Thr Leu Thr Val Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
    435                 440                 445

Leu Arg His Glu Thr His Gly Gly Glu Asp Val Ala Val Phe Ala Lys
    450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
                500                 505                 510

Leu Leu Leu Ala Leu Leu Pro Leu Gly Ser Leu Phe
                515                 520

<210> SEQ ID NO 14
<211> LENGTH: 124
<212> TYPE: PRT
<213> ORGANISM: Bos taurus

<400> SEQUENCE: 14

Asp Pro Lys Tyr Trp Arg Asp Gln Ala Gln Gln Thr Leu Lys Asn Ala
1               5                   10                  15

Leu Gly Leu Gln Lys Leu Asn Thr Lys Val Ala Lys Asn Val Ile Leu
                20                  25                  30

Phe Leu Gly Asp Gly Met Gly Val Ser Thr Val Thr Ala Ala Arg Ile
            35                  40                  45

Leu Lys Gly Gln Leu His His Asn Pro Gly Glu Glu Thr Arg Leu Glu

```
                50                  55                  60
Met Asp Lys Phe Pro Phe Val Ala Leu Ser Lys Thr Tyr Asn Thr Asn
 65                  70                  75                  80

Ala Gln Val Pro Asp Ser Ala Gly Thr Ala Pro His Pro Val Arg Val
                 85                  90                  95

Lys Ala Met Arg Ala Pro Trp Gly Glu Pro His Gln Arg Gln Cys Asn
            100                 105                 110

Thr Arg Arg Ala Thr Ser Thr His Leu Leu Ala Gly
            115                 120

<210> SEQ ID NO 15
<211> LENGTH: 524
<212> TYPE: PRT
<213> ORGANISM: Felis catus

<400> SEQUENCE: 15

Met Ile Ser Pro Phe Leu Val Leu Ala Ile Gly Thr Cys Leu Thr Asn
  1               5                  10                  15

Ser Leu Val Pro Glu Lys Glu Lys Asp Pro Lys Tyr Trp Arg Asp Gln
                 20                  25                  30

Ala Gln Gln Thr Leu Lys Asn Ala Leu Arg Leu Gln Lys Leu Asn Thr
             35                  40                  45

Asn Val Val Lys Asn Val Ile Met Phe Leu Gly Asp Gly Met Gly Val
 50                  55                  60

Ser Thr Val Thr Ala Ala Arg Ile Leu Lys Gly Gln Leu His His Asn
 65                  70                  75                  80

Pro Gly Glu Glu Thr Arg Leu Glu Met Asp Lys Phe Pro Tyr Val Ala
                 85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
            115                 120                 125

Gly Val Ser Ala Ala Thr Gln Arg Thr Gln Cys Asn Thr Thr Gln Gly
            130                 135                 140

Asn Glu Val Thr Ser Ile Leu Arg Trp Ala Lys Asp Ser Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
            195                 200                 205

Met His Asn Val Arg Asp Ile Glu Val Ile Met Gly Gly Gly Arg Lys
            210                 215                 220

Tyr Met Phe Pro Lys Asn Arg Thr Asp Val Glu Tyr Glu Met Asp Glu
225                 230                 235                 240

Lys Ala Arg Gly Thr Arg Leu Asp Gly Leu Asn Leu Val Asp Ile Trp
                245                 250                 255

Lys Ser Phe Lys Pro Arg His Lys His Ser His Tyr Val Trp Asn Arg
            260                 265                 270

Thr Glu Leu Leu Thr Leu Asp Pro Tyr Gly Val Asp Tyr Leu Leu Gly
            275                 280                 285

Leu Phe Glu Pro Gly Asp Met Gln Tyr Glu Leu Asn Arg Asn Ser Thr
            290                 295                 300
```

-continued

```
Thr Asp Pro Ser Leu Ser Glu Met Val Glu Ile Ala Ile Lys Ile Leu
305                 310                 315                 320

Ser Lys Asn Pro Lys Gly Phe Phe Leu Leu Val Glu Gly Gly Arg Ile
            325                 330                 335

Asp His Gly His His Glu Gly Lys Ala Lys Gln Ala Leu His Glu Ala
                340                 345                 350

Val Glu Met Asp Gln Ala Ile Gly Arg Ala Gly Ala Met Thr Ser Val
            355                 360                 365

Glu Asp Thr Leu Thr Ile Val Thr Ala Asp His Ser His Val Phe Thr
370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ser Ile Leu Tyr Gly
                405                 410                 415

Asn Gly Pro Gly Tyr Lys Val Val Gly Glu Arg Glu Asn Val Ser
            420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ala Lys
450                 455                 460

Gly Pro Met Ala His Leu Leu His Gly Val His Glu Gln Asn Tyr Ile
465                 470                 475                 480

Pro His Val Met Ala Tyr Ala Ala Cys Ile Gly Ala Asn Leu Asp His
                485                 490                 495

Cys Ala Ser Ala Ser Ser Ala Gly Gly Pro Ser Pro Gly Pro Leu Phe
            500                 505                 510

Leu Leu Leu Ala Leu Pro Ser Leu Gly Ile Leu Phe
            515                 520

<210> SEQ ID NO 16
<211> LENGTH: 532
<212> TYPE: PRT
<213> ORGANISM: Homo sapiens

<400> SEQUENCE: 16

Met Gln Gly Pro Trp Val Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160
```

```
Ser Val Gly Val Val Thr Thr Thr Arg Val Gln His Ala Ser Pro Ala
            165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
            195                 200                 205

Leu Ile Ser Asn Met Asp Ile Asp Val Ile Leu Gly Gly Arg Lys
210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
            245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
            275                 280                 285

Glu Pro Gly Asp Met Lys Tyr Glu Ile His Arg Asp Ser Thr Leu Asp
            290                 295                 300

Pro Ser Leu Met Glu Met Thr Glu Ala Ala Leu Leu Leu Leu Ser Arg
305                 310                 315                 320

Asn Pro Arg Gly Phe Phe Leu Phe Val Glu Gly Gly Arg Ile Asp His
            325                 330                 335

Gly His His Glu Ser Arg Ala Tyr Arg Ala Leu Thr Glu Thr Ile Met
            340                 345                 350

Phe Asp Asp Ala Ile Glu Arg Ala Gly Gln Leu Thr Ser Glu Glu Asp
            355                 360                 365

Thr Leu Ser Leu Val Thr Ala Asp His Ser His Val Phe Ser Phe Gly
370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
            405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
            435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
            485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Gly Thr
            515                 520                 525

Ala Thr Ala Pro
    530

<210> SEQ ID NO 17
<211> LENGTH: 535
<212> TYPE: PRT
<213> ORGANISM: Homo sapiens
```

-continued

<400> SEQUENCE: 17

```
Met Leu Gly Pro Cys Met Leu Leu Leu Leu Leu Gly Leu Arg
1               5                   10                  15

Leu Gln Leu Ser Leu Gly Ile Ile Pro Val Glu Glu Asn Pro Asp
            20                  25                  30

Phe Trp Asn Arg Glu Ala Ala Glu Ala Leu Gly Ala Ala Lys Lys Leu
            35                  40                  45

Gln Pro Ala Gln Thr Ala Ala Lys Asn Leu Ile Ile Phe Leu Gly Asp
50                  55                  60

Gly Met Gly Val Ser Thr Val Thr Ala Ala Arg Ile Leu Lys Gly Gln
65                  70                  75                  80

Lys Lys Asp Lys Leu Gly Pro Glu Ile Pro Leu Ala Met Asp Arg Phe
                85                  90                  95

Pro Tyr Val Ala Leu Ser Lys Thr Tyr Asn Val Asp Lys His Val Pro
            100                 105                 110

Asp Ser Gly Ala Thr Ala Thr Ala Tyr Leu Cys Gly Val Lys Gly Asn
            115                 120                 125

Phe Gln Thr Ile Gly Leu Ser Ala Ala Arg Phe Asn Gln Cys Asn
130                 135                 140

Thr Thr Arg Gly Asn Glu Val Ile Ser Val Met Asn Arg Ala Lys Lys
145                 150                 155                 160

Ala Gly Lys Ser Val Gly Val Val Thr Thr Thr Arg Val Gln His Ala
                165                 170                 175

Ser Pro Ala Gly Thr Tyr Ala His Thr Val Asn Arg Asn Trp Tyr Ser
            180                 185                 190

Asp Ala Asp Val Pro Ala Ser Ala Arg Gln Glu Gly Cys Gln Asp Ile
            195                 200                 205

Ala Thr Gln Leu Ile Ser Asn Met Asp Ile Asp Val Ile Leu Gly Gly
210                 215                 220

Gly Arg Lys Tyr Met Phe Arg Met Gly Thr Pro Asp Pro Glu Tyr Pro
225                 230                 235                 240

Asp Asp Tyr Ser Gln Gly Gly Thr Arg Leu Asp Gly Lys Asn Leu Val
                245                 250                 255

Gln Glu Trp Leu Ala Lys Arg Gln Gly Ala Arg Tyr Val Trp Asn Arg
            260                 265                 270

Thr Glu Leu Met Gln Ala Ser Leu Asp Pro Ser Val Thr His Leu Met
            275                 280                 285

Gly Leu Phe Glu Pro Gly Asp Met Lys Tyr Glu Ile His Arg Asp Ser
290                 295                 300

Thr Leu Asp Pro Ser Leu Met Glu Met Thr Glu Ala Ala Leu Arg Leu
305                 310                 315                 320

Leu Ser Arg Asn Pro Arg Gly Phe Phe Leu Phe Val Glu Gly Gly Arg
                325                 330                 335

Ile Asp His Gly His His Glu Ser Arg Ala Tyr Arg Ala Leu Thr Glu
            340                 345                 350

Thr Ile Met Phe Asp Asp Ala Ile Glu Arg Ala Gly Gln Leu Thr Ser
            355                 360                 365

Glu Glu Asp Thr Leu Ser Leu Val Thr Ala Asp His Ser His Val Phe
370                 375                 380

Ser Phe Gly Gly Tyr Pro Leu Arg Gly Ser Ser Ile Phe Gly Leu Ala
385                 390                 395                 400

Pro Gly Lys Ala Arg Asp Arg Lys Ala Tyr Thr Val Leu Leu Tyr Gly
                405                 410                 415
```

```
Asn Gly Pro Gly Tyr Val Leu Lys Asp Gly Ala Arg Pro Asp Val Thr
            420                 425                 430

Glu Ser Glu Ser Gly Ser Pro Glu Tyr Arg Gln Gln Ser Ala Val Pro
            435                 440                 445

Leu Asp Glu Glu Thr His Ala Gly Glu Asp Val Ala Val Phe Ala Arg
            450                 455                 460

Gly Pro Gln Ala His Leu Val His Gly Val Gln Glu Gln Thr Phe Ile
465                 470                 475                 480

Ala His Val Met Ala Phe Ala Ala Cys Leu Glu Pro Tyr Thr Ala Cys
                    485                 490                 495

Asp Leu Ala Pro Pro Ala Gly Thr Thr Asp Ala Ala His Pro Gly Arg
                500                 505                 510

Ser Val Val Pro Ala Leu Leu Pro Leu Leu Ala Gly Thr Leu Leu Leu
            515                 520                 525

Leu Glu Thr Ala Thr Ala Pro
            530                 535

<210> SEQ ID NO 18
<211> LENGTH: 532
<212> TYPE: PRT
<213> ORGANISM: Homo sapiens

<400> SEQUENCE: 18

Met Gln Gly Pro Trp Val Leu Leu Leu Leu Gly Leu Arg Leu Gln Leu
1               5                   10                  15

Ser Leu Gly Ile Ile Pro Val Glu Glu Glu Asn Pro Asp Phe Trp Asn
            20                  25                  30

Arg Gln Ala Ala Glu Ala Leu Gly Ala Ala Lys Lys Leu Gln Pro Ala
        35                  40                  45

Gln Thr Ala Ala Lys Asn Leu Ile Ile Phe Leu Gly Asp Gly Met Gly
    50                  55                  60

Val Ser Thr Val Thr Ala Ala Arg Ile Leu Lys Gly Gln Lys Lys Asp
65                  70                  75                  80

Lys Leu Gly Pro Glu Thr Phe Leu Ala Met Asp Arg Phe Pro Tyr Val
                85                  90                  95

Ala Leu Ser Lys Thr Tyr Ser Val Asp Lys His Val Pro Asp Ser Gly
            100                 105                 110

Ala Thr Ala Thr Ala Tyr Leu Cys Gly Val Lys Gly Asn Phe Gln Thr
        115                 120                 125

Ile Gly Leu Ser Ala Ala Ala Arg Phe Asn Gln Cys Asn Thr Thr Arg
    130                 135                 140

Gly Asn Glu Val Ile Ser Val Met Asn Arg Ala Lys Lys Ala Gly Lys
145                 150                 155                 160

Ser Val Gly Val Val Thr Thr Thr Arg Val Gln His Ala Ser Pro Ala
                165                 170                 175

Gly Ala Tyr Ala His Thr Val Asn Arg Asn Trp Tyr Ser Asp Ala Asp
            180                 185                 190

Val Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Asp Asp Tyr
225                 230                 235                 240

Ser Gln Gly Gly Thr Arg Leu Asp Gly Lys Asn Leu Val Gln Glu Trp
```

245                 250                 255

Leu Ala Lys His Gln Gly Ala Arg Tyr Val Trp Asn Arg Thr Glu Leu
            260                 265                 270

Leu Gln Ala Ser Leu Asp Pro Ser Val Thr His Leu Met Gly Leu Phe
        275                 280                 285

Glu Pro Gly Asp Met Lys Tyr Glu Ile His Arg Asp Ser Thr Leu Asp
290                 295                 300

Pro Ser Leu Met Glu Met Thr Glu Ala Leu Leu Leu Leu Ser Arg
305                 310                 315                 320

Asn Pro Arg Gly Phe Phe Leu Phe Val Glu Gly Gly Arg Ile Asp His
                325                 330                 335

Gly His His Glu Ser Arg Ala Tyr Arg Ala Leu Thr Glu Thr Ile Met
                340                 345                 350

Phe Asp Asp Ala Ile Glu Arg Ala Gly Gln Leu Thr Ser Glu Glu Asp
            355                 360                 365

Thr Leu Ser Leu Val Thr Ala Asp His Ser His Val Phe Ser Phe Gly
    370                 375                 380

Gly Tyr Pro Leu Arg Gly Ser Ser Ile Phe Gly Leu Ala Pro Gly Lys
385                 390                 395                 400

Ala Arg Asp Arg Lys Ala Tyr Thr Val Leu Leu Tyr Gly Asn Gly Pro
                405                 410                 415

Gly Tyr Val Leu Lys Asp Gly Ala Arg Pro Asp Val Thr Glu Ser Glu
            420                 425                 430

Ser Gly Ser Pro Glu Tyr Arg Gln Gln Ser Ala Val Pro Leu Asp Gly
        435                 440                 445

Glu Thr His Ala Gly Glu Asp Val Ala Val Phe Ala Arg Gly Pro Gln
450                 455                 460

Ala His Leu Val His Gly Val Gln Glu Gln Thr Phe Ile Ala His Val
465                 470                 475                 480

Met Ala Phe Ala Ala Cys Leu Glu Pro Tyr Thr Ala Cys Asp Leu Ala
                485                 490                 495

Pro Arg Ala Gly Thr Thr Asp Ala Ala His Pro Gly Pro Ser Val Val
            500                 505                 510

Pro Ala Leu Leu Pro Leu Leu Ala Gly Thr Leu Leu Leu Leu Gly Thr
        515                 520                 525

Ala Thr Ala Pro
        530

<210> SEQ ID NO 19
<211> LENGTH: 528
<212> TYPE: PRT
<213> ORGANISM: Homo sapiens

<400> SEQUENCE: 19

Met Gln Gly Pro Trp Val Leu Leu Leu Gly Leu Arg Leu Gln Leu
1               5                   10                  15

Ser Leu Gly Val Ile Pro Ala Glu Glu Asn Pro Ala Phe Trp Asn
            20                  25                  30

Arg Gln Ala Ala Glu Ala Leu Asp Ala Ala Lys Lys Leu Gln Pro Ile
        35                  40                  45

Gln Lys Val Ala Lys Asn Leu Ile Leu Phe Leu Gly Asp Gly Leu Gly
    50                  55                  60

Val Pro Thr Val Thr Ala Thr Arg Ile Leu Lys Gly Gln Lys Asn Gly
65                  70                  75                  80

```
Lys Leu Gly Pro Glu Thr Pro Leu Ala Met Asp Arg Phe Pro Tyr Leu
                85                  90                  95

Ala Leu Ser Lys Thr Tyr Asn Val Asp Arg Gln Val Pro Asp Ser Ala
            100                 105                 110

Ala Thr Ala Thr Ala Tyr Leu Cys Gly Val Lys Ala Asn Phe Gln Thr
        115                 120                 125

Ile Gly Leu Ser Ala Ala Arg Phe Asn Gln Cys Asn Thr Thr Arg
    130                 135                 140

Gly Asn Glu Val Ile Ser Val Met Asn Arg Ala Lys Gln Ala Gly Lys
145                 150                 155                 160

Ser Val Gly Val Val Thr Thr Arg Val Gln His Ala Ser Pro Ala
                165                 170                 175

Gly Thr Tyr Ala His Thr Val Asn Arg Asn Trp Tyr Ser Asp Ala Asp
            180                 185                 190

Met Pro Ala Ser Ala Arg Gln Glu Gly Cys Gln Asp Ile Ala Thr Gln
        195                 200                 205

Leu Ile Ser Asn Met Asp Ile Asp Val Ile Leu Gly Gly Gly Arg Lys
    210                 215                 220

Tyr Met Phe Pro Met Gly Thr Pro Asp Pro Glu Tyr Pro Ala Asp Ala
225                 230                 235                 240

Ser Gln Asn Gly Ile Arg Leu Asp Gly Lys Asn Leu Val Gln Glu Trp
                245                 250                 255

Leu Ala Lys His Gln Gly Ala Trp Tyr Val Trp Asn Arg Thr Glu Leu
            260                 265                 270

Met Gln Ala Ser Leu Asp Gln Ser Val Thr His Leu Met Gly Leu Phe
        275                 280                 285

Glu Pro Gly Asp Thr Lys Tyr Glu Ile His Arg Asp Pro Thr Leu Asp
    290                 295                 300

Pro Ser Leu Met Glu Met Thr Glu Ala Ala Leu Arg Leu Leu Ser Arg
305                 310                 315                 320

Asn Pro Arg Gly Phe Tyr Leu Phe Val Glu Gly Gly Arg Ile Asp His
                325                 330                 335

Gly His His Glu Gly Val Ala Tyr Gln Ala Leu Thr Glu Ala Val Met
            340                 345                 350

Phe Asp Asp Ala Ile Glu Arg Ala Gly Gln Leu Thr Ser Glu Glu Asp
        355                 360                 365

Thr Leu Thr Leu Val Thr Ala Asp His Ser His Val Phe Ser Phe Gly
    370                 375                 380

Gly Tyr Thr Leu Arg Gly Ser Ser Ile Phe Gly Leu Ala Pro Ser Lys
385                 390                 395                 400

Ala Gln Asp Ser Lys Ala Tyr Thr Ser Ile Leu Tyr Gly Asn Gly Pro
                405                 410                 415

Gly Tyr Val Phe Asn Ser Gly Val Arg Pro Asp Val Asn Glu Ser Glu
            420                 425                 430

Ser Gly Ser Pro Asp Tyr Gln Gln Ala Ala Val Pro Leu Ser Ser
        435                 440                 445

Glu Thr His Gly Gly Glu Asp Val Ala Val Phe Ala Arg Gly Pro Gln
    450                 455                 460

Ala His Leu Val His Gly Val Gln Glu Gln Ser Phe Val Ala His Val
465                 470                 475                 480

Met Ala Phe Ala Ala Cys Leu Glu Pro Tyr Thr Ala Cys Asp Leu Ala
                485                 490                 495

Pro Pro Ala Cys Thr Thr Asp Ala Ala His Pro Val Ala Ala Ser Leu
```

```
                    500                 505                 510
Pro Leu Leu Ala Gly Thr Leu Leu Leu Gly Ala Ser Ala Ala Pro
            515                 520                 525

<210> SEQ ID NO 20
<211> LENGTH: 227
<212> TYPE: PRT
<213> ORGANISM: Artificial Sequence
<220> FEATURE:
<223> OTHER INFORMATION: Synthetic Construct

<400> SEQUENCE: 20

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```